(12) United States Patent
Lal et al.

(10) Patent No.: US 7,964,628 B2
(45) Date of Patent: Jun. 21, 2011

(54) FIBRINOGEN RECEPTOR ANTAGONISTS AND THEIR USE

(75) Inventors: Bansi Lal, Maharashtra (IN); Ashok Kumar Gangopadhyay, Maharashtra (IN); Vadlamudi V. S. V. Rao, Maharashtra (IN); Ravindra Dattatraya Gupte, Maharashtra (IN); Gopal Vishnu Gole, Maharashtra (IN); Asha Kulkarni-Almeida, Maharashtra (IN); Sridevi Krishnan, Maharashtra (IN); Radha Bhaskar Panicker, Maharashtra (IN); Eleanor Pinto De Souza, Maharashtra (IN)

(73) Assignee: Piramal Life Sciences Limited, Mumbai (IN)

( * ) Notice: Subject to any disclaimer, the term of this patent is extended or adjusted under 35 U.S.C. 154(b) by 0 days.

(21) Appl. No.: 12/795,824

(22) Filed: Jun. 8, 2010

(65) Prior Publication Data

US 2010/0256161 A1 Oct. 7, 2010

Related U.S. Application Data

(62) Division of application No. 10/574,982, filed as application No. PCT/IB2004/051922 on Sep. 30, 2004, now Pat. No. 7,759,387.

(30) Foreign Application Priority Data

Oct. 8, 2003 (IN) .......................... 1054/MUM/2003

(51) Int. Cl.
*A61K 31/40* (2006.01)
*C07D 209/44* (2006.01)

(52) U.S. Cl. ........................................ 514/416; 548/482
(58) Field of Classification Search .................. 514/416; 548/482
See application file for complete search history.

(56) References Cited

U.S. PATENT DOCUMENTS

| 3,997,572 | A | 12/1976 | Cusic et al. |
|---|---|---|---|
| 7,759,387 | B2 * | 7/2010 | Lal et al. .................. 514/416 |

FOREIGN PATENT DOCUMENTS

| DE | 66175 | 4/1969 |
|---|---|---|
| EP | 0540334 | 5/1993 |
| EP | 0655439 | 5/1995 |
| EP | 1391451 | 2/2004 |
| GB | 989917 | 4/1965 |
| WO | 02085855 | 10/2002 |

OTHER PUBLICATIONS

New, J. S. et al., "Buspirone analogues .2. Structure-activity relationships of aromatic imide derivatives," J. Med. Chem. Amer. Chem. Soc. Washington, US, vol. 29, (8), 1986, pp. 1476-1482.

Sugimoto, H. et al., "Synthesis and structure-activity relationships of acetylcholinesterase inhibitors: 1-benzyl-4-(2-phthalimidoethyl)piperidine and related derivaties," J. Med. Chem. Amer. Chem Soc., Washington, US, vol. 34 (24), 1992, pp. 4542-4548.

* cited by examiner

*Primary Examiner* — Joseph R Kosack
(74) *Attorney, Agent, or Firm* — Volpe and Koenig, P.C.

(57) ABSTRACT

This invention relates to novel fused bicyclic compounds of the general formula (I):

$$(R^A)_s \underset{(R^B)_s}{\overset{Y_1 \; Y_2}{A}} \underset{W}{\overset{Z}{\underset{}{\bigg\langle}}} (CH_2)_n \underset{R^D \; R^E}{\overset{R^F}{\bigg\langle}} R^G \quad (I)$$

wherein the symbols are defined herein, to pharmaceutical compositions containing the compounds, processes for preparing the compounds, and to methods of using the compounds, alone or in combination with other therapeutic agents. The compounds are antagonists of the platelet glycoprotein IIb/IIIa fibrinogen receptor complex, and are therefore useful for the inhibition of platelet aggregation, and for the treatment of thrombotic diseases and other diseases.

23 Claims, 10 Drawing Sheets

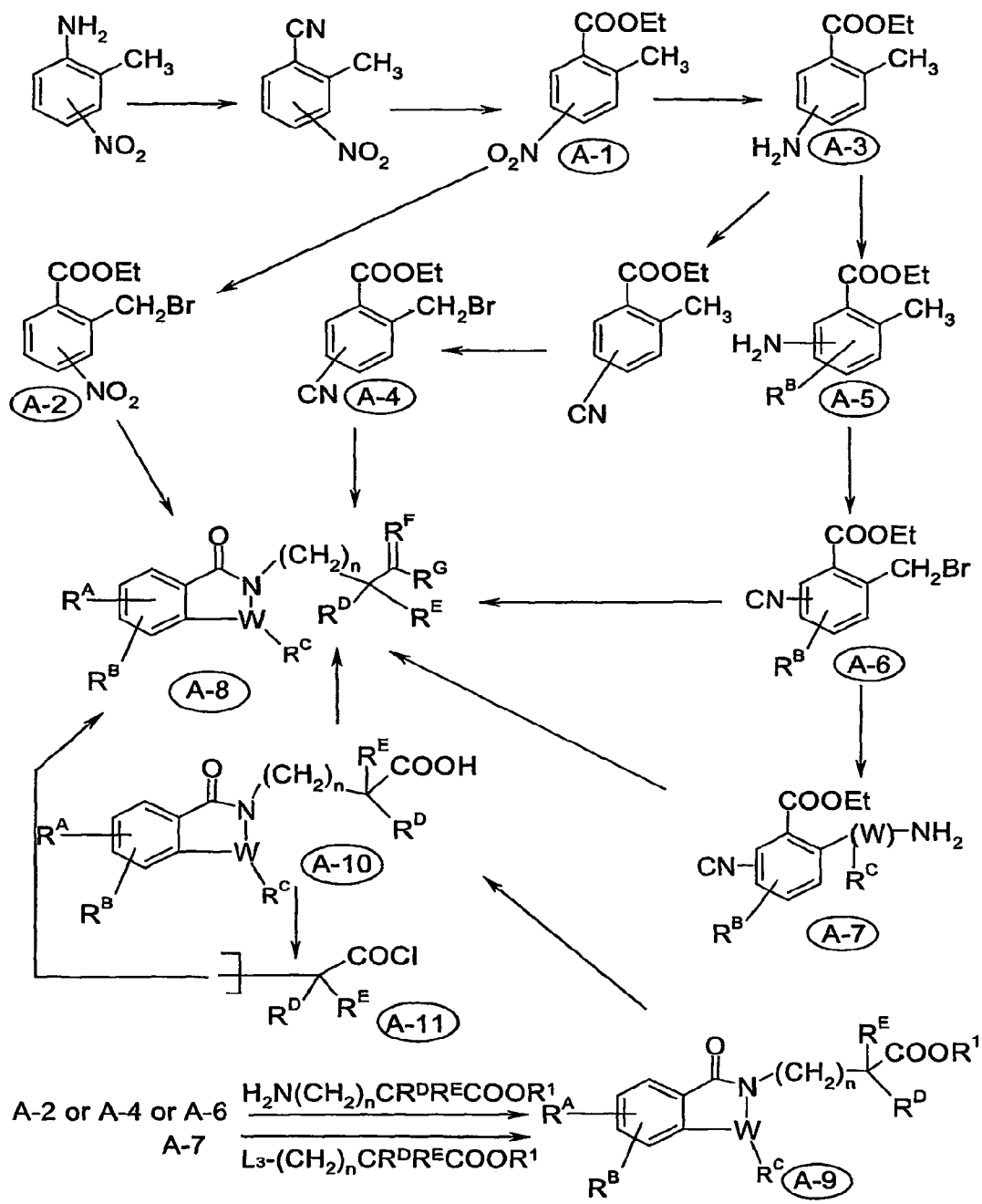
Figure A

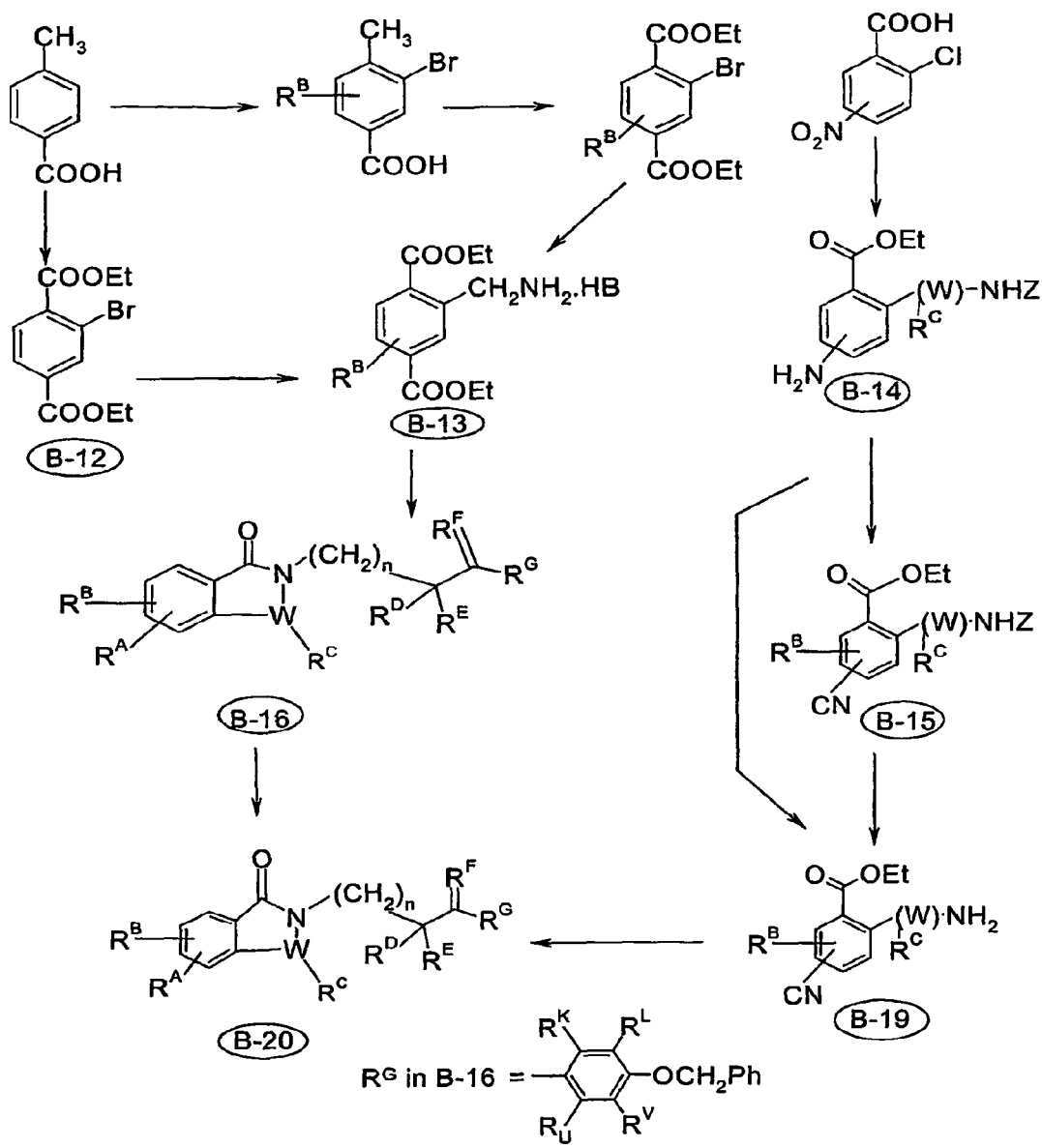
Figure B

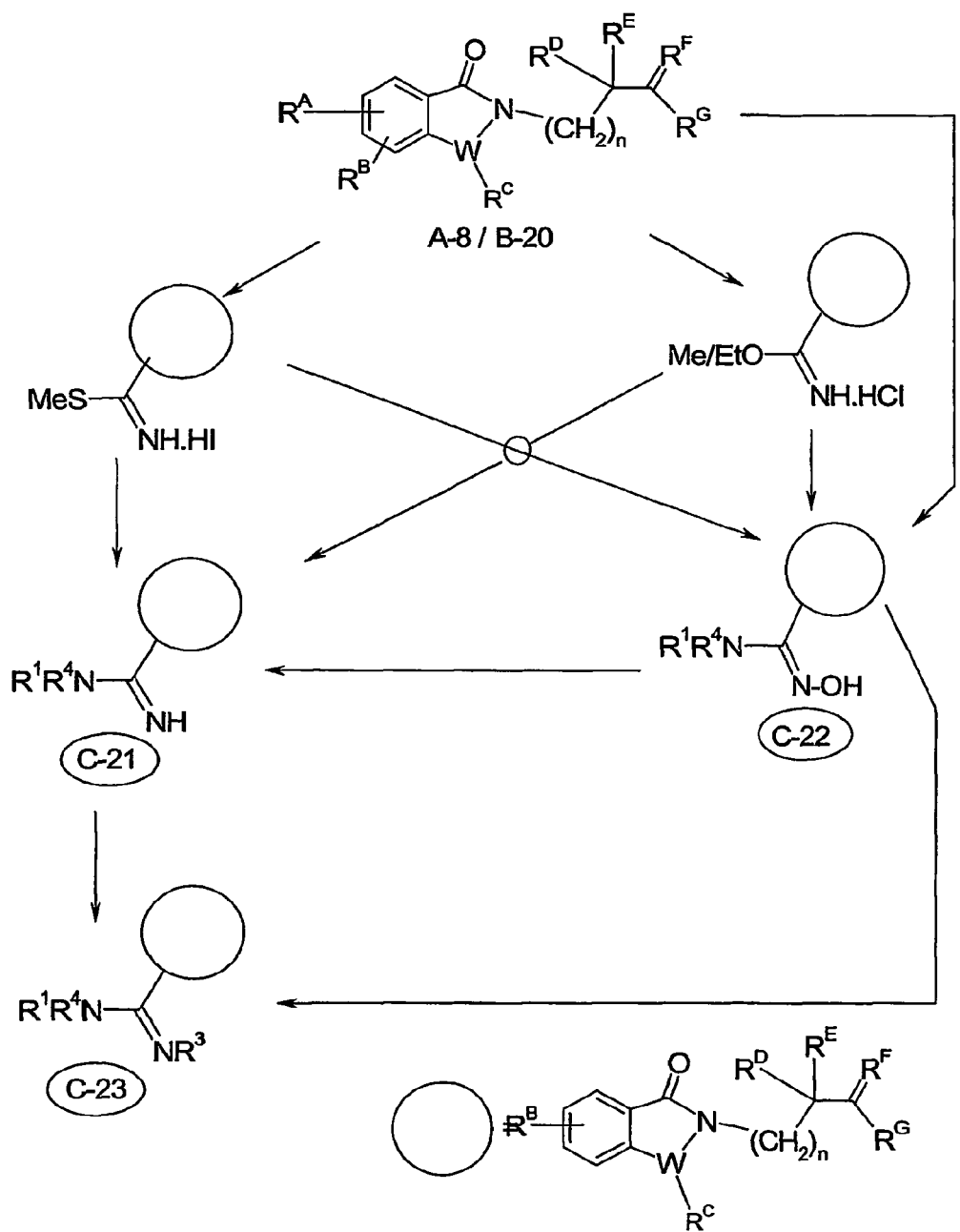

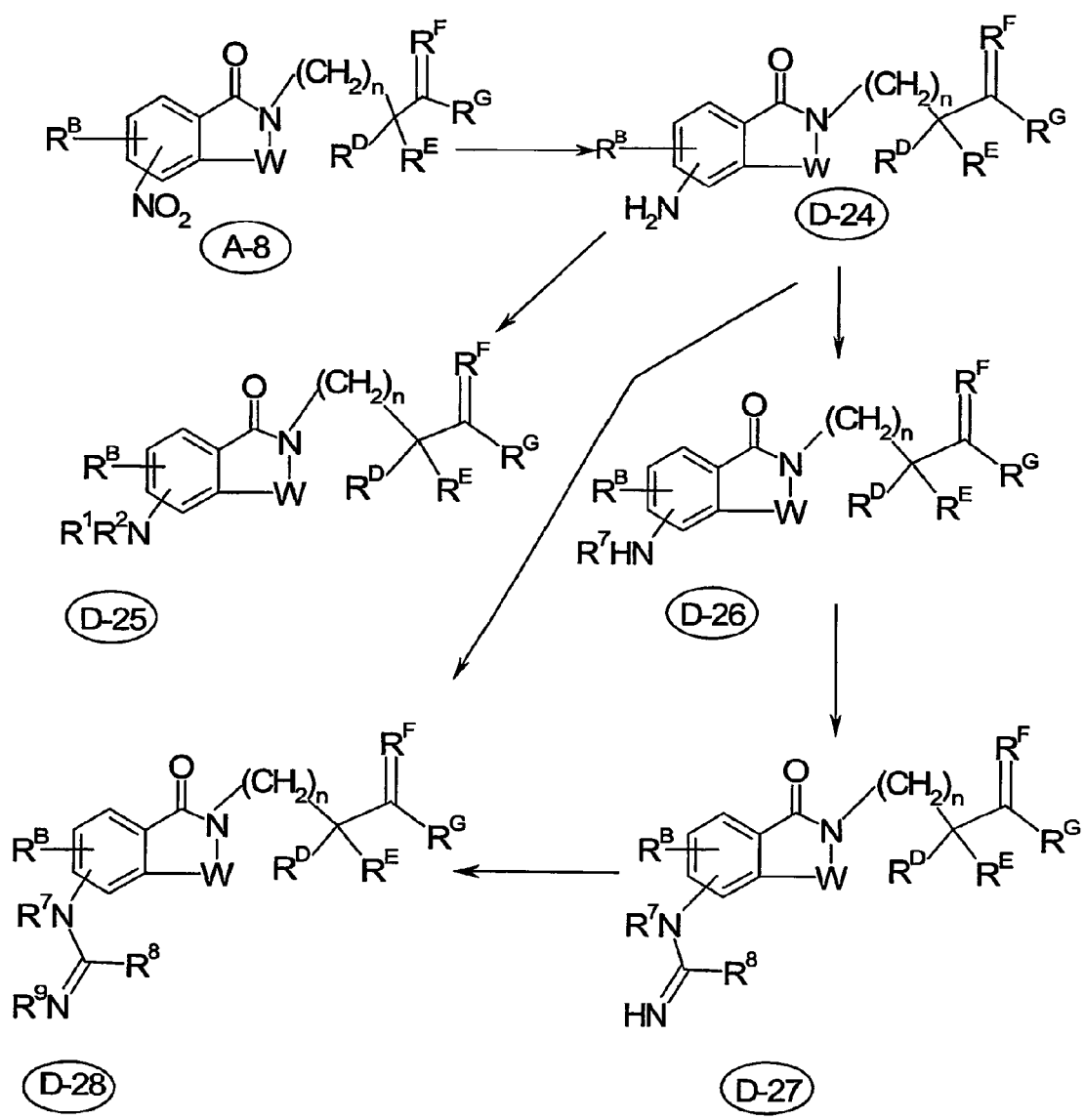
Figure D

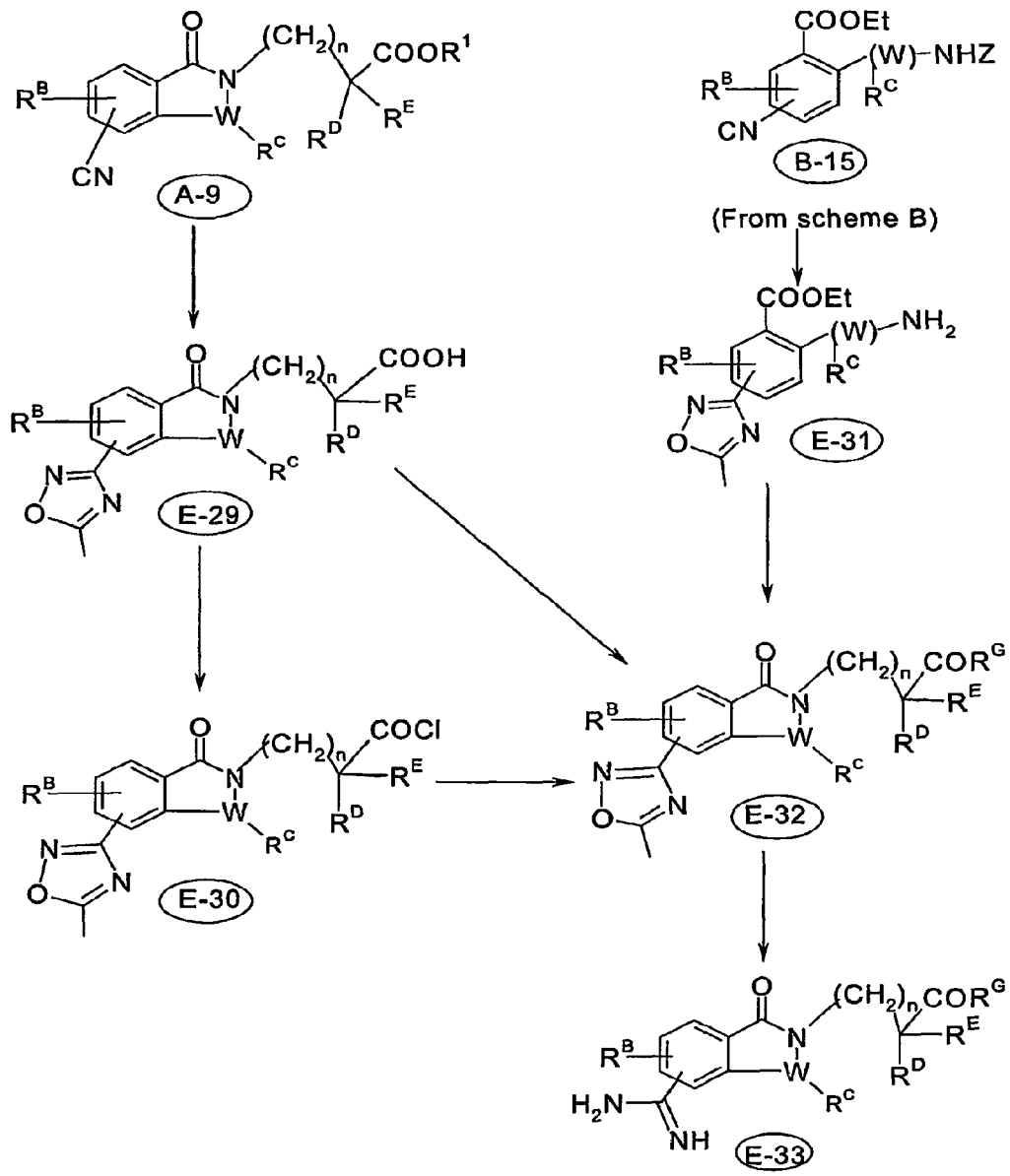
Figure E

Figure F
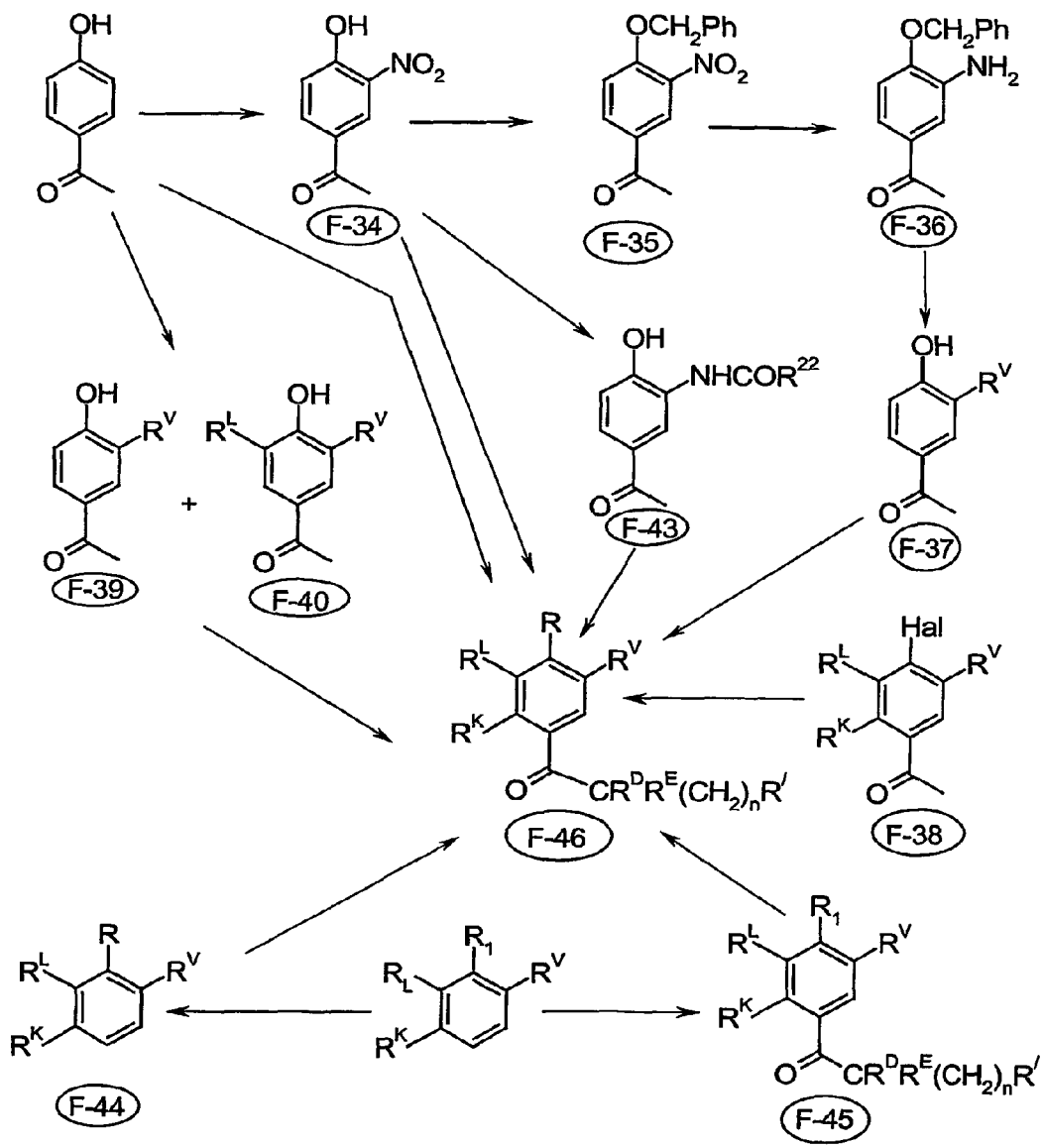

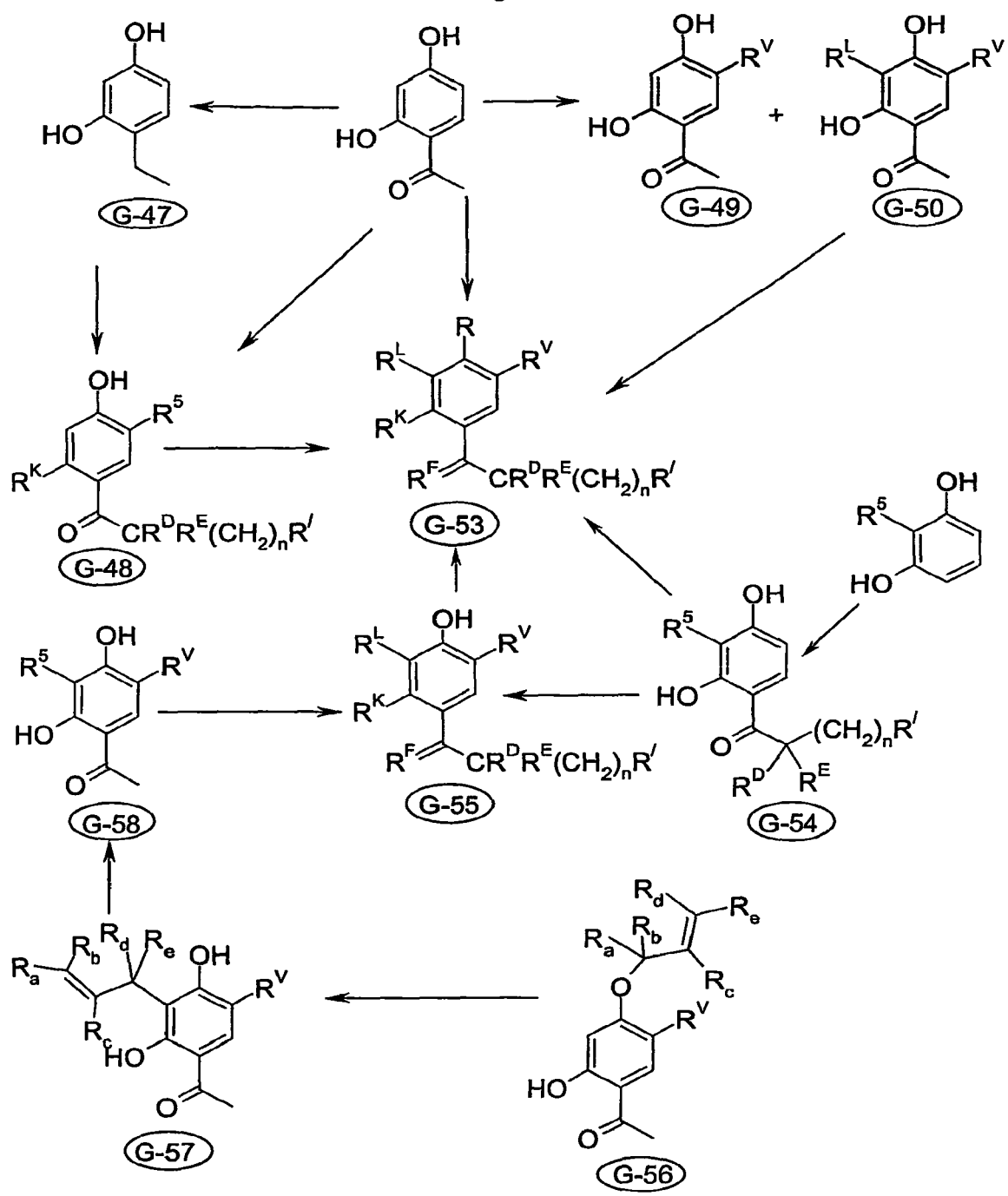
Figure G

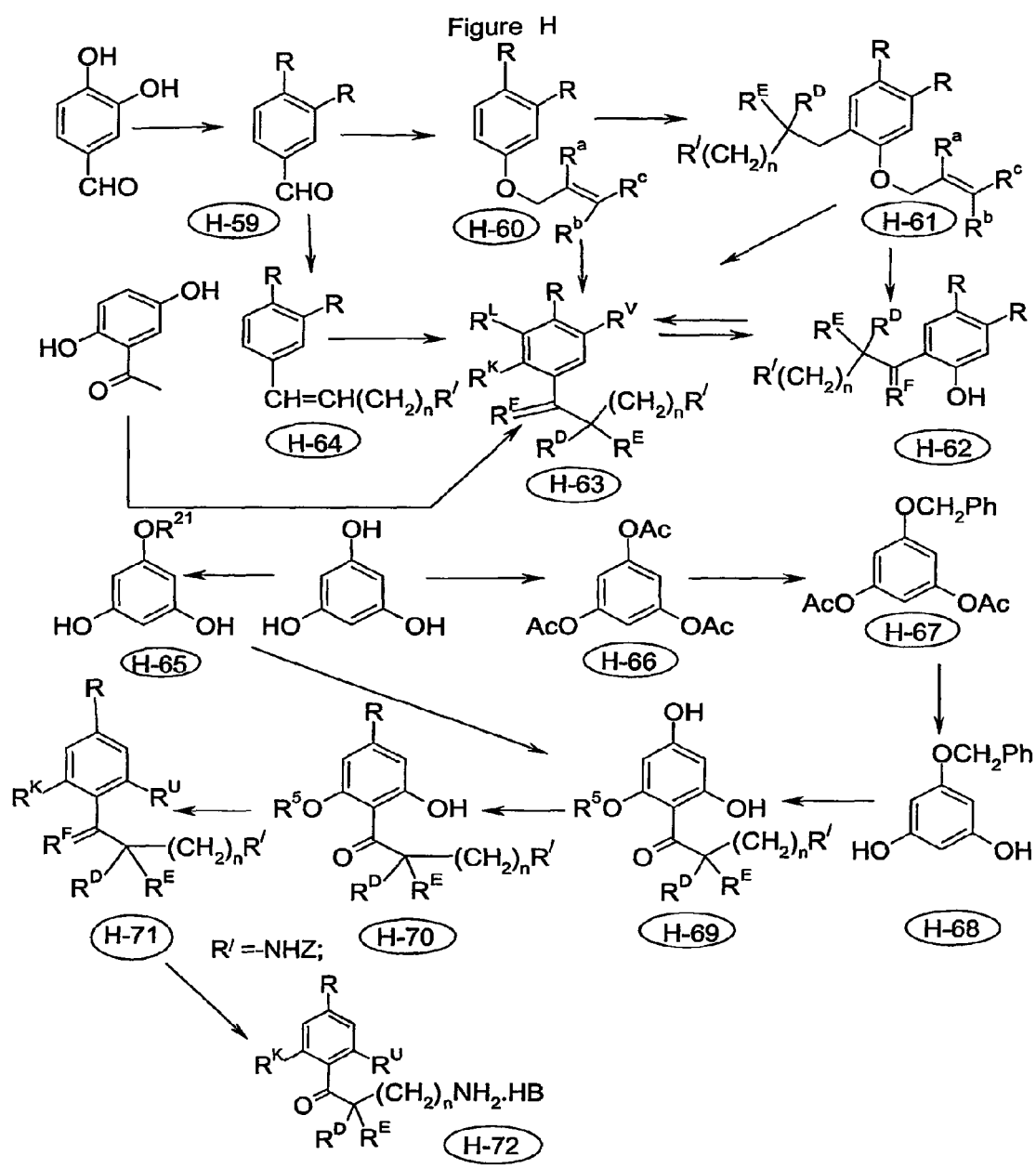
Figure H

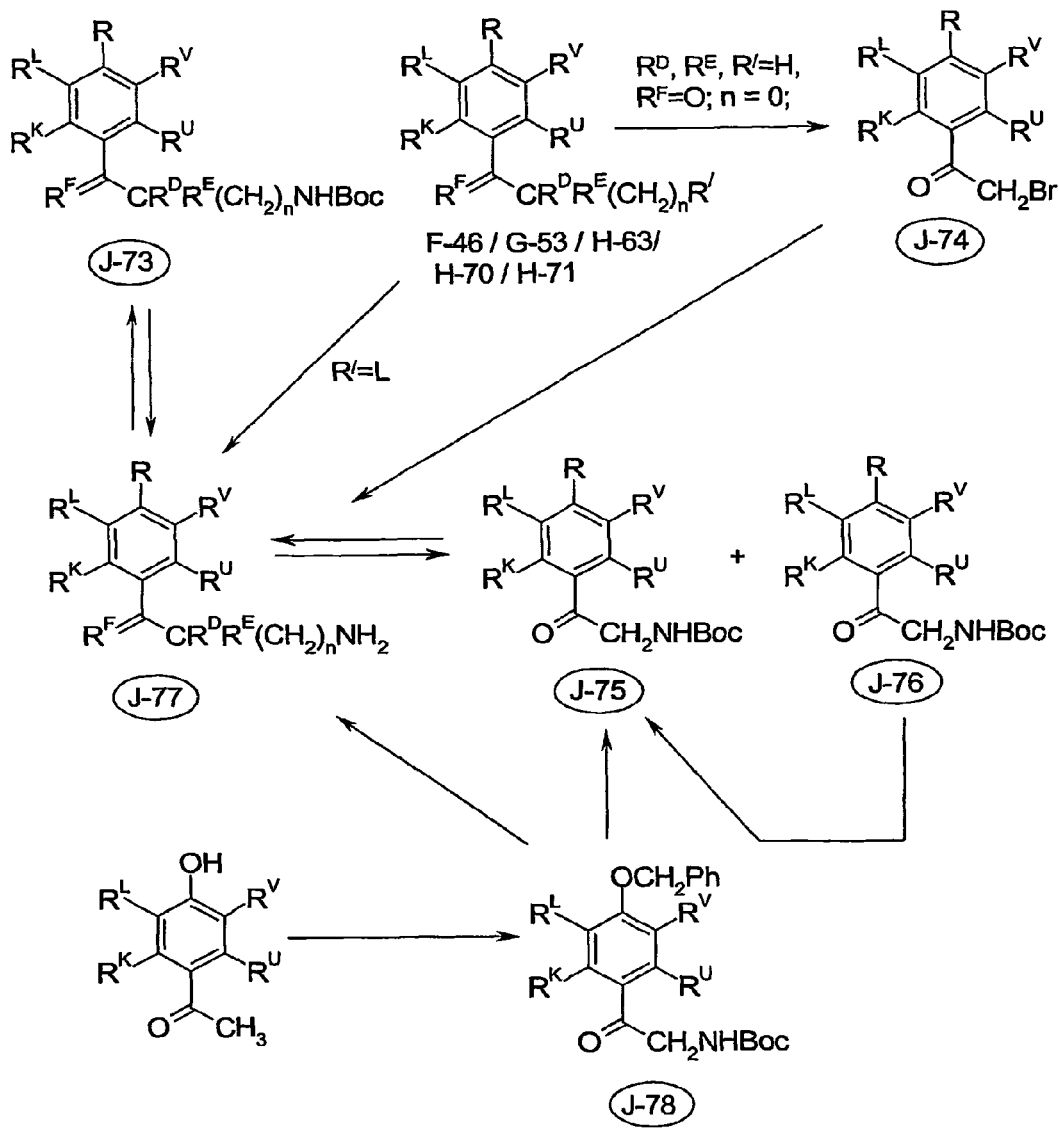
Figure J

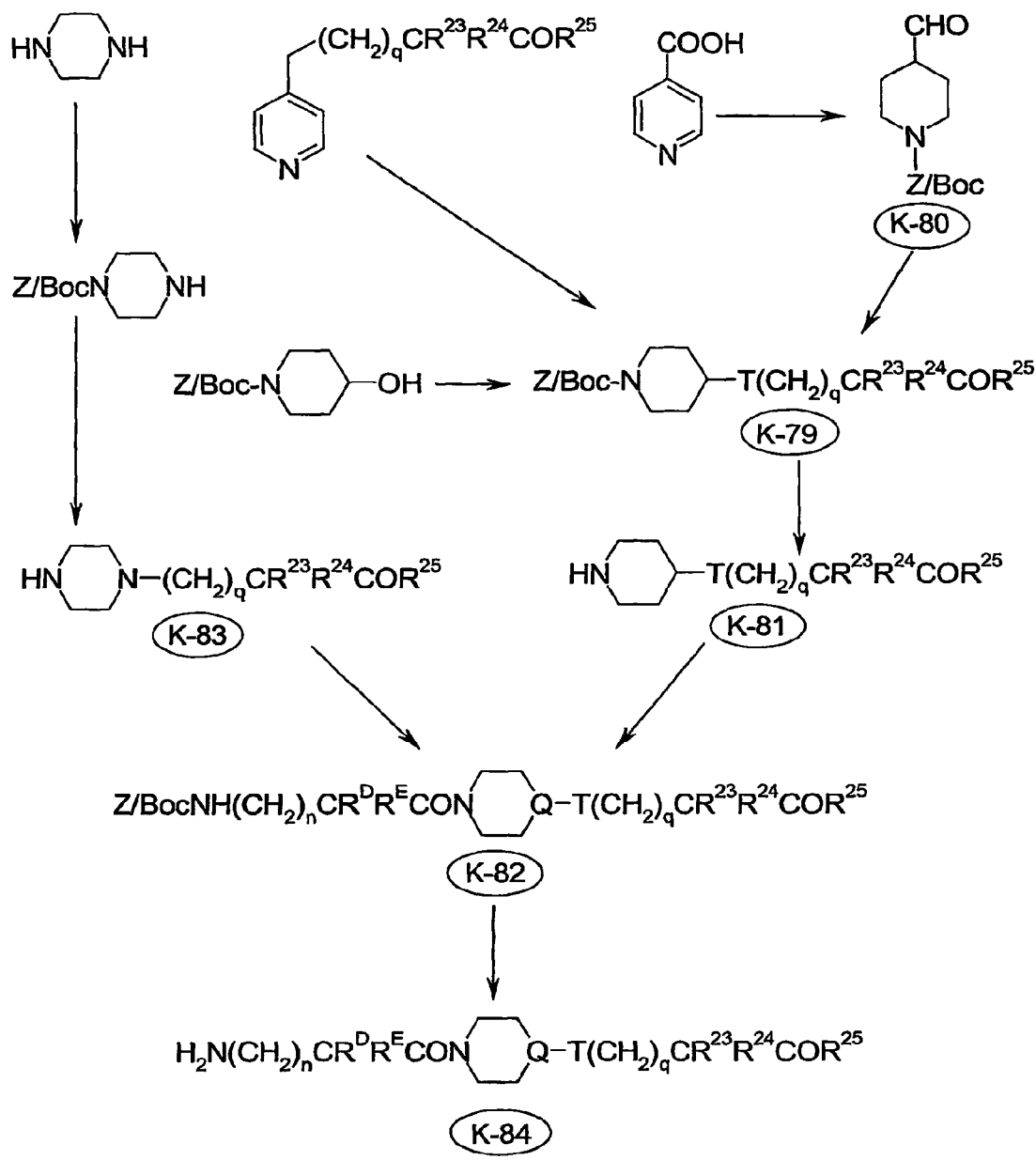
Figure K

US 7,964,628 B2

FIBRINOGEN RECEPTOR ANTAGONISTS AND THEIR USE

This application is a divisional application of U.S. application Ser. No. 10/574,982, which was filed Apr. 7, 2006 and was a 35 U.S.C. §371 national phase application of international application PCT/IB2004/051922 filed Sep. 30, 2004, both of which are incorporated herein by reference as if fully set forth.

FIELD OF THE INVENTION

The present invention relates to novel compounds, which are antagonists of fibrinogen receptors (FRAs), to pharmaceutical preparations comprising them, to processes for their preparation, and to their use as active ingredients in pharmaceuticals, alone or in combination with other therapeutic agents, in particular for the inhibition of platelet aggregation and for the treatment of thrombotic disorders.

BACKGROUND OF THE INVENTION

Platelets are cell-like anucleated fragments, found in the blood of all mammals that support primary hemostasis by forming hemostatic plugs at sites of vascular injury. Thrombosis is the pathological condition wherein improper activity of the hemostatic mechanism results in intravascular thrombus formation. Activation of platelets and the resulting platelet aggregation has been associated with a variety of pathophysiological conditions including cardiovascular and cerebrovascular thromboembolic disorders, for example, the thromboembolic disorders associated with unstable angina, myocardial infarction, transient ischemic attack, stroke, thrombotic disorders such as peripheral arterial disease, and diabetes.

Glycoprotein IIb/IIIa receptors (hereinafter referred to as GP IIb/IIIa receptors) are found on the surface of platelets and belong to a superfamily of adhesion receptors known as integrins, which are composed of transmembrane glycoproteins containing α and β subunits. Fibrinogen, fibronectin, vitronectin and von Willebrand factor (vWF) are proteins that bind to and crosslink GP IIb/IIIa receptors on adjacent activated platelets and thereby effect aggregation of platelets.

The binding of fibrinogen is mediated in part by the Arginine-Glycine-Aspartic acid (RGD) recognition sequence which is common to the adhesive proteins that bind GP IIb/IIIa receptors (Ferguson, J. J. and Zaqqa, M., Drugs, 1999, 58, 965-982; Mousa, S. A and Bennett, J. S., Drugs of the future 1996, 21, 1141-1154; Ojima, I., Chakravarty, S, and Dong, Q., Bioorganic and Medicinal Chemistry 1995, 3, 337-360).

Platelets are activated by a number of agonists that include adenosine diphosphate (ADP), thrombin, serotonin, arachidonic acid, collagen and adrenaline among others, which are released in the body as a result of various physiological reactions. Regardless of the nature of the stimuli involved in the activation of platelets, the final step of platelet aggregation is the binding of fibrinogen to the activated GP IIb/IIIa receptors on the surface of platelets thereby cross-linking platelets. (J. Lefkovits, E. F. Plow, E. J. Topol 1995, New England Journal of Medicine, 332, 1553-1559). This makes GP IIb/IIIa receptors ideal targets for inhibiting platelet aggregation. The development of GP IIb/IIIa receptor antagonists would, therefore, provide an effective strategy for the control of platelet aggregation and hence thrombi formation (Bennett, J. S, Annual Reviews of Medicine, 2001, 52, 161-184).

Cardiovascular diseases are among those that cause the highest mortality throughout the world. Thus, in order to prevent the cardiovascular diseases caused by platelet aggregation, there is an increased necessity for efficient anti-platelet aggregating treatment with drugs possessing specific characteristics namely efficacy, negligible side effects and fast onset of action.

Current antiplatelet drugs are effective against only one type of agonist; these include aspirin, which acts against arachidonic acid; ticlopidine, which acts against ADP; and hirudin, which acts against thrombin.

Until recently, aspirin has been widely used as an inhibitor of platelet function (New England Journal of Medicine, 1994, 330, 1287). While the benefits of aspirin have been demonstrated, there are clinical limitations of this drug. These limitations have provided the impetus for the development of newer antithrombotic agents having therapeutic advantages over aspirin.

Ticlopidine, a thienopyridine derivative, has also been effectively used in patients suffering cardiovascular diseases. However, this drug is associated with a number of serious side effects.

Recently, a common pathway for all known agonists has been identified, namely the platelet GP IIb/IIIa complex, which is the membrane protein mediating platelet aggregation (Phillips et al. Cell 1991, 65, 359-362). The development of GP IIb/IIIa receptor antagonists represents a promising new approach for antiplatelet therapy.

A fibrinogen receptor antagonist (hereinafter referred to as FRA) is an agent that inhibits the binding of fibrinogen to the platelet bound fibrinogen receptor GP IIb/IIIa and thereby prevents platelet aggregation and thrombus formation. Inhibition of platelet aggregation is a major target for the prevention and treatment of cardiovascular diseases.

Known fibrinogen receptor antagonists are:
1. Monoclonal antibodies—e.g. abciximab
2. Parenteral compounds
    a) Synthetic peptides—e.g. eptifibatide
    b) Non peptide peptidomimetics—e.g. tirofiban
3. Oral compounds—e.g. roxifiban, gantofiban
1. Monoclonal Antibodies:

In 1985, a mouse monoclonal antibody against GP known as c7E3, was generated. Subsequently, the Fab fragment of a chimeric human-mouse genetic reconstruction of c7E3 (c7E3 Fab), known as abciximab, was used in clinical trials (Drugs of the Future, 1995, 20, 457-463). Abciximab was launched in 1995 on the US market, as an intravenous preparation.

2. Parenteral Compounds:
a) Eptifibatide, a synthetic cyclic peptide (J. Med. Chemistry, 2000, 43, 3453-3473) was designed as a mimic of a snake venom peptide namely barbourin. Eptifibatide is effectively used for the inhibition of platelet aggregation.
b) Based on the observation that peptides containing the tripeptide Arginine-Glycine-Aspartic acid (RGD) sequence function as fibrinogen receptor antagonists, scientists attempted the development of non-peptide peptidomimetics as inhibitors of platelet aggregation (Hartman et. al. J. Med. Chemistry 1992, 35, 4640-4642).

A number of non-peptide fibrinogen receptor antagonists are known and are disclosed in the patents and other publications, which follow:

JP 10-017469 discloses oxyisoindole derivatives possessing fibrinogen receptor antagonistic activity.

EP-A-712844 discloses condensed ring carboxylic acid compounds having platelet GP IIb/IIIa receptor antagonist activity that are useful for the prophylaxis and treatment of thrombotic diseases.

EP-A-540334 discloses isoindolinone compounds as fibrinogen receptor antagonists, which are used in inhibiting the binding of fibrinogen to blood platelets and for inhibiting the aggregation of blood platelets.

WO 96/26187 discloses a series of 3,4-dihydro-1(1H)-isoquinolinone based compounds as fibrinogen receptor antagonists useful for inhibiting platelet aggregation with oral activity.

Tirofiban, a non-peptide antagonist, developed by Merck & Co. is the first agent of this class to be used for the treatment of cardiovascular diseases (Hartman G. D. et. al., J. Med. Chemistry, 1992, 35, 4640-4642).

U.S. Pat. No. 5,726,185 describes acetic acid derivatives useful for the treatment or prophylaxis of illnesses which are caused by the binding of adhesive proteins to blood platelets and by blood platelet aggregation and cell-cell adhesion.

U.S. Pat. No. 5,378,712 describes N-acyl-alpha-aminocarboxylic acid derivatives and N-acyl-alpha-amino acid derivatives which are useful for the treatment or control of illnesses which are caused by the binding of adhesive proteins to blood platelets and by blood platelet aggregation and cell-cell adhesion.

WO 93/07867 discloses substituted beta amino acid derivatives as platelet aggregation inhibitors.

3. Oral Compounds:

There are currently no oral preparations on the market. Many compounds that had reached Phase III clinical trials had to be withdrawn due to lack of efficacy or adverse effects such as major bleeding episodes and thrombocytopenia.

EP-A-483667 describes cyclic imino derivatives having aggregation inhibiting effects.

WO 95/18619 describes bicyclic fibrinogen antagonists as inhibitors of platelet aggregation.

WO 95/14683 discloses isoxazolines and isoxazoles that are useful as antagonists of the platelet GP IIb/IIIa fibrinogen receptor complex for the inhibition of platelet aggregation, as thrombolytics and/or for the treatment of thromboembolic disorders.

Gantofiban is a platelet GPIIb/IIIa antagonist for the treatment of various thrombotic diseases, such as acute coronary syndromes (J. Gante et al. Bioorganic and Medicinal Chemistry letters, 1996, 6:20, 2425-2430); Cromafiban is an orally active GP IIb/IIIa antagonist, which was being developed by COR Therapeutics as a potential treatment for thromboembolic disorders, acute coronary syndromes and stroke (Scarborough R. M., et. al, J Med. Chemistry, 2000, 43:19, 3453-3473).

Even though several FRAs are described in the prior art, there is still a need to develop specific agents having fibrinogen receptor antagonistic activity in the advent of the increased mortality rate among patients suffering from cardiovascular diseases.

The FRAs currently available are all intravenous preparations, limiting their use to a hospital environment. A clear clinical need and market exists for FRAs that can be administered by more patient-compliant routes.

A focused research on FRAs by the present inventors has resulted in the discovery of novel compounds. These compounds are effective inhibitors of GP IIb/IIIa receptors. Moreover, the compounds of the invention inhibit GP IIb/IIIa receptors with an efficacy comparable to the known FRAs, which are under clinical trials. Therefore, the compounds of the present invention are candidate agents for the treatment of thrombotic diseases.

SUMMARY OF INVENTION

As a result of the various studies made to solve the aforementioned problems, the present invention provides compounds general formula (I) (as described hereinafter).

The present invention further provides processes for the preparation of the compounds of general formula (I) and intermediates thereof.

The present invention also provides pharmaceutical compositions comprising as an active ingredient, compounds of the general formula (I), or pharmaceutically acceptable salts or prodrugs thereof, together with a pharmaceutically acceptable carrier, diluent or vehicle.

The present invention further provides for the use of compounds of the general formula (I), or pharmaceutically acceptable salts or prodrugs thereof for the manufacture of a medicament for the inhibition of platelet aggregation in a mammal.

Accordingly, the present compounds can be used for the prevention or treatment of cardiovascular diseases, such as unstable angina, myocardial infarction and stroke, and thrombotic diseases in mammals, especially humans, where antagonism of the binding of fibrinogen to the platelet membrane glycoprotein complex GP IIb/IIIa receptor is desired.

These and other objectives and advantages of the present invention will be apparent to those skilled in the art from the following description.

BRIEF DESCRIPTION OF THE DRAWINGS OF THE INVENTION

Figures A to H, J and K represent schemes of preferred processes for the preparation of example compounds of the present invention.

DETAILED DESCRIPTION OF THE INVENTION

The present invention discloses novel compounds that inhibit platelet aggregation. The compounds of the present invention are believed to inhibit the binding of fibrinogen to the platelet-bound fibrinogen receptor GP MAIM and find use in antithrombotic therapies for diseases such as cardiovascular (arterial and/or venous) and cerebrovascular thromboembolic diseases.

The compounds of the present invention are compounds of the general formula (I):

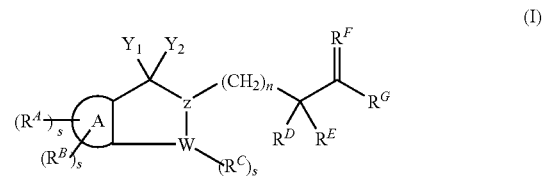

wherein:

ring A is selected from: aryl and 5- or 6-membered heteroaryl;

$R^A$ is selected from: $-NO_2$, $-(CH_2)pCN$, $-C(=O)-NR^1R^2$, $-C(=S)NR^1R^2$, $-C(=NR^1)-SMe$ and $-C(=NR^1)-OMe$, or $R^A$ is selected from one of the following groups of formula (2), formula (3) and formula (4):

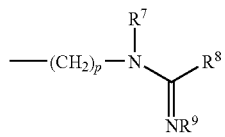
(4)

wherein p is 0, 1, 2, 3, 4 or 5;
s is 1, 2 or 3, and when s is 2 or 3 the groups $R^A$ are independent of each other and can be the same or different;
$R^1$ and $R^2$ are independently selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle; or $R^1$ and $R^2$, together with the nitrogen atom to which they are attached, form a saturated, partially saturated or aromatic heterocycle, optionally containing at least one additional hetero atom selected from: N, O and S;
$R^3$ and $R^4$ are independently selected from: H, alkyl, partially or fully fluorinated alkyl, alkenyl, alkynyl, —C(=O)OR$^5$, cycloalkyl, cycloalkylalkyl, aryl, arylalkyl, heterocycle, —OR$^5$, —SR$^5$, —NR$^5$R$^6$, —S(=O)$_2$NR$^5$R$^6$, —S(=O)$_2$R$^5$, —C(=O)R$^5$, —C(=O)NR$^5$R$^6$, —C(=O)OR$^5$, —C(=O)SR$^5$, —OC(=O)R$^5$, —OC(=O)OR$^5$, —OC(=O)NR$^5$R$^6$, —OS(=O)$_2$R$^5$, —S(C=O)NR$^5$ and —OS(=O)$_2$NR$^5$R$^6$, or $R^3$ and $R^1$ or $R^4$, together with the respective nitrogen atoms to which they are attached, form an unsubstituted or substituted 5-, 6- or 7-membered partially saturated or aromatic heterocycle, optionally having one or more additional heteroatoms selected from: N, O and S, wherein the substituents are selected from: hydroxy, halogen, alkyl, alkoxy, alkenyl, alkynyl, oxo, carboxy and —C(=O)OR$^5$;
$R^5$ and $R^6$ are independently selected from: H, alkyl, alkenyl, alkynyl, cycloalkyl, cycloalkylalkyl, aryl, arylalkyl and heterocycle, wherein each of said alkyl, alkenyl, alkynyl, cycloalkyl and cycloalkylalkyl group optionally contains at least one hetero atom selected from: N, S and O anywhere in the chain, including the terminal position;
$R^7$ and $R^9$ have the same meaning as $R^3$ and $R^4$, defined above;
$R^8$ is selected from: H, alkyl, alkenyl, alkynyl, cycloalkyl, cycloalkylalkyl, aryl, arylalkyl and heterocycle, wherein said heterocycle is saturated, partially saturated or aromatic and contains at least one hetero atom selected from: N, O and S, with its point of attachment either through C or N, and wherein each of said alkyl, alkenyl, alkynyl, cycloalkyl and cycloalkylalkyl groups optionally contains at least one hetero atom selected from: N, O and S, anywhere in the chain, including the terminal position;
$R^B$ is selected from: H, halogen, —CN, —NO$_2$, alkyl, partially or fully fluorinated alkyl, alkenyl, alkynyl, cycloalkyl, cycloalkylalkyl, aryl, arylalkyl, heterocycle, —NR$^{10}$R$^{11}$, —OR$^{10}$, —SR$^{10}$, S(O)R$^{10}$, S(O)$_2$R$^{10}$, —NHC(=O)R$^{10}$, —NHOR$^{10}$, —OC(=O)R$^{10}$, SC(=O)R$^{10}$, —NHC(=O)OR$^{10}$, —OC(=O)OR$^{10}$, —C(=O)NR$^{10}$R$^{11}$, —C(=O)R$^{10}$, and —C(=O)OR$^{10}$;
$R^{10}$ and $R^{11}$ have the same meaning as $R^5$ or $R^6$, defined above;
s is 1, 2 or 3 and when s is 2 or 3 the groups $R^B$ are independent of each other and can be the same or different;
$Y^1$ and $Y^2$ are independently selected from: H, $R^{12}$, $R^{13}$, NR$^{12}$R$^{13}$, OR$^{12}$, SR$^{12}$, CH$_2$(OR$^{12}$), CH$_2$(SR$^{12}$), CH$_2$S(=O)R$^{12}$ and CH$_2$S(=O)$_2$R$^{12}$, or $Y^1$ and $Y^2$, together, are selected from: =O, =S, =CR$^{12}$R$^{13}$, =NR$^{12}$ and =N—OR$^{12}$;
$R^{12}$ and $R^{13}$ are selected from: H, OR$^5$, alkyl, alkenyl, alkynyl, cycloalkyl, cycloalkylalkyl and aryl;
Z is CH or N;
W is (CH$_2$)$_u$, wherein u is the integer 1 or 2;
$R^C$ is selected from: $R^5$, =O, =NR$^{14}$, =S, CN, NR$^{14}$R$^{15}$, OR$^{14}$, SR$^{14}$, S(=O)$_2$R$^{16}$ and COR$^{16}$;
$R^{14}$ and $R^{15}$ have the same meaning as $R^5$ and $R^6$, defined above;
s is 1, 2 or 3 and when s is 2 or 3 the groups $R^C$ are independent of each other and can be same or different;
$R^{16}$ is selected from: H, OR$^{14}$, N(R$^{14}$)$_2$, NR$^{14}$R$^{15}$, SR$^{14}$ and $R^5$, wherein $R^5$, $R^{14}$ and $R^{15}$ are as defined above;
n is 0, 1, 2, 3, 4 or 5;
$R^D$ and $R^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy, —C(=O)OR$^5$, —OR$^{17}$, —SR$^{17}$, —NR$^{17}$R$^{18}$, —NHC(=O)R$^{17}$, —NHC(=O)OR$^{17}$, —OC(=O)R$^{17}$, —SC(=O)R$^{17}$, —OS(=O)$_2$R$^{17}$ and —NHS(=O)$_2$R$^{17}$;
$R^{17}$ and $R^{18}$ have the same meaning as $R^5$ and $R^6$, defined above;
$R^F$ is selected from: (H, H), (—H, —OH), O, S, N(OR$^{19}$), N[OC(=O)OR$^{19}$], N[OC(=O)R$^{19}$] and N[OS(=O)$_2$NR$^{19}$R$^{20}$];
$R^{19}$ and $R^{20}$ have the same meaning as $R^5$ and $R^6$, defined above;
$R^G$ is selected from: aryl, heteroaryl, and partially or fully saturated heterocycle, where said aryl, heteroaryl and heterocycle are substituted in each case by one or more groups independently selected from: —$R^5$, halogen, —CN, —SCN, —CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —SC(=O)H, —SC(=O)OR$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$, —S(=O)$_2$OR$^{21}$ and a group of formula (5):

$$T-(CH_2)_q-CR^{23}R^{24}-COR^{25} \quad (5)$$

$R^{21}$ and $R^{22}$ have the same meaning as $R^1$ and $R^2$, defined above;
T is selected from: —CH$_2$, O, S and NH;
q is 0, 1, 2, 3, 4, 5 or 6;
$R^{23}$ and $R^{24}$ are independently selected from: H, alkyl, alkenyl, alkynyl, cycloalkyl, cycloalkylallyl, aryl, arylalkyl, heterocycle and C(=O)R$^{25}$, wherein said alkyl and alkenyl optionally contain at least one hetero atom selected from: O, S and N, in any position of the alkyl or alkenyl chain, and said alkyl and alkenyl are unsubstituted or substituted with at least one group selected from: —OR$^1$, —OC(=O)R$^1$, —OS(=O)$_2$R$^1$, —S(=O)$_2$NR$^1$R$^2$, —OC(=O)OR$^1$, —OC(=O)SR$^1$, —OC(=O)NR$^1$R$^2$, —SR$^1$, —S(=O)R$^1$, —SC(=O)H, —SC(=O)OR$^1$, —NR$^1$(OR$^2$), —NR$^1$R$^2$, —NR$^1$C(=O)R$^2$, —N(R$^1$)C(=O)OR$^2$, —NR$^1$S(=O)$_2$R$^2$, C(=O)OR$^1$, —S(=O)$_2$R$^1$ and —S(=O)$_2$OR$^1$;
$R^{25}$ is selected from: OR$^5$, SR$^5$, —OCR$^3$R$^4$ and —NR$^5$R$^6$, wherein $R^3$, $R^4$, $R^5$ and $R^6$ are as defined above and wherein, optionally, $R^3$ and $R^4$, together with the carbon to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy and —C(=O)OR$^5$; and the group NR$^5$R$^6$ is, optionally, a heterocycle containing at least one additional heteroatom selected from: O, S, and N;

in all its stereoisomeric and tautomeric forms and mixtures thereof in all ratios, and its pharmaceutically acceptable salts, pharmaceutically acceptable solvates and prodrugs.

In a first embodiment of the invention, there are provided novel compounds of the general formula (I), or prodrugs, tautomeric forms, stereoisomers, pharmaceutically acceptable salts, pharmaceutically acceptable solvates, or polymorphs thereof;

wherein
ring A is aryl;
p is 0, 1 or 2;
s is 1;
Y$^1$ and Y$^2$, together, are selected from: =O, =S, =CR$^{12}$R$^{13}$, =NR$^{12}$ and =N—OR$^{12}$;
Z is N;
R$^F$ is selected from: (H, H), (H, OH), O and S;
R$^G$ is selected from: aryl, heteroaryl and partially or fully saturated heterocycle, wherein said aryl, heteroaryl and heterocycle are substituted by one or more groups independently selected from: —R$^5$, halogen, —CN, SCN, CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —NO$_2$, —NR$^{21}$(OR$^{22}$), —NR$^{21}$R$^{22}$—NR$^{21}$C(=O)R$^{22}$, —N(R$^{21}$)C(=O)OR$^{22}$, —N[S(=O)$_2$R$^{21}$]R$^{23}$, —C(=O)OR$^{21}$, —S(=O)$_2$R$^{21}$, —S(=O)$_2$OR$^{21}$ and a group of the formula (5);
q is 0, 1, 2 or 3; and
R$^1$-R$^{18}$, R$^{21}$-R$^{25}$, W, T, R$^B$, R$^C$, R$^D$, R$^E$ and n are as defined in general formula (I) above.

In a second embodiment of the invention, there are provided novel compounds of the general formula (I), or prodrugs, tautomeric forms, stereoisomers, pharmaceutically acceptable salts, pharmaceutically acceptable solvates or polymorphs thereof;

wherein
ring A is phenyl;
p is 0, 1 or 2;
s is 1;
Y$^1$ and Y$^2$, together, are selected from: =O and =S;
Z is N;
R$^C$ is selected from: H, alkyl, aryl, heterocycle, =O, =NR$^{14}$, =S, CN, NR$^{14}$R$^{15}$, OR$^{14}$, SR$^{14}$, S(=O)$_2$R$^{16}$ and COR$^{16}$;
n is 0, 1, 2 or 3;
R$^G$ is selected from: aryl, heteroaryl and partially or fully saturated heterocycle, wherein said aryl, heteroaryl and heterocycle are substituted by one or more groups of the formula (5) and, optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(O)$_2$R$^{21}$]R$^{23}$, C(=O)OR$^{21}$, —S(=O)$_2$R$^{21}$ and —S(=O)$_2$OR$^{21}$;
q is 0, 1, 2 or 3; and
R$^1$-R$^{11}$, R$^{14}$-R$^{25}$, W, T, R$^A$, R$^B$, R$^D$, R$^E$, R$^F$ and u are as defined in general formula (I) above.

In a third embodiment of the invention, there are provided novel compounds of the general formula (I), or prodrugs, tautomeric forms, stereoisomers, pharmaceutically acceptable salts, pharmaceutically acceptable solvates or polymorphs thereof;

wherein
ring A is phenyl;
R$^G$ is selected from: phenyl, piperidinyl and piperazinyl, substituted with one or more groups selected from: a group of the formula (5), OCH$_2$Phenyl and —CH$_2$C(O)R$^{25}$, and, optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —SC(=O)H, —SC(=O)OR$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —NR$^{21}$S(=O)$_2$R$^{22}$, —N[S(=O)$_2$R$^{21}$]R$^{23}$, C(=O)OR$^{21}$, —S(=O)$_2$R$^{21}$ and —S(=O)$_2$OR$^{21}$;
W is (CH$_2$)$_u$, wherein u is 1; and
R$^1$-R$^{25}$, T, Z, Y$_1$ and Y$_2$, R$^A$, R$^B$, R$^C$, R$^D$, R$^E$, R$^F$, n, s, p and q are as defined in general formula (I) above.

In a fourth embodiment of the invention, there are provided novel compounds of the general formula (I), or prodrugs, tautomeric forms, stereoisomers, pharmaceutically acceptable salts, pharmaceutically acceptable solvates or polymorphs thereof;

wherein
R$^A$ is a group of the formula (3);
R$_1$ is hydrogen;
R$_3$ and R$_4$ are independently selected from: H, OH, —C(O)OH and —C(O)Oalkyl;
R$^B$=R$^C$=R$^D$=R$^E$=hydrogen;
Z is N;
Y$^1$ and Y$^2$, together are =O;
n is the integer 0 or 1;
R$^G$ is phenyl, substituted with one or more groups selected from: hydroxy, halogen, alkyl, alkoxy, alkenyl, alkynyl, oxo, carboxy, —C(=O)OR$^5$, SR$^{21}$, S(=O)$_2$R$^{21}$, —N(R$^{21}$)—C(O)CH$_3$, —CH$_2$C(O)R$^{25}$ and -T-(CH$_2$)$_q$—CH$_2$—C(O)R$^{25}$;
q is 0, 1, 2 or 3;
R$^{25}$ is selected from: OR$^5$, OCR$^3$R$^4$ and NR$^5$R$^6$, wherein R$^3$ and R$^4$, together with the carbon to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy, —C(D)OR$^5$; and
R$^5$, R$^6$ and R$^{21}$ are independently selected from: H, alkyl and phenyl.
W is (CH$_2$)$_u$, wherein u is 1; and
R$^3$, R$^{19}$, R$^{20}$, R$^{22}$, R$^F$, T, p and q are as defined in general formula (I) above.

In a fifth embodiment of the invention, there are provided novel compounds of the general formula (I), or prodrugs, tautomeric forms, stereoisomers, pharmaceutically acceptable salts, pharmaceutically acceptable solvates or polymorphs thereof;

wherein
R$^A$ is a group of the formula (3);
R$_1$ is hydrogen;
R$_3$ and R$_4$ are independently selected from: H, OH, —C(O)OH and —C(O)Oallyl;
R$^B$=R$^C$=R$^D$=R$^E$=hydrogen;
Z is N;
Y$^1$ and Y$^2$, together are =O;
n is the integer 0 or 1;
R$^G$ is selected from: piperidinyl and piperazinyl, wherein said piperidinyl and piperazinyl are substituted with one or more groups selected from: hydroxy, halogen, alkyl, alkoxy, alkenyl, alkynyl, oxo, carboxy, —C(=O)OR$^5$ and -T-(CH$_2$)q-CH$_2$—C(O)R$^{25}$;

q is 0, 1, 2 or 3;

R$^{25}$ is OR$^5$, wherein R$^5$ is selected from: H, alkyl and phenyl; and

R$^1$, R$^3$-R$^6$, T and p are as defined in general formula (I).

Yet other embodiments of the present invention provide processes for the preparation of compounds of general formula (I), and their use as active ingredients in pharmaceuticals, alone or in combination with other therapeutic agents, in particular for the inhibition of platelet aggregation and for the treatment of thrombotic disorders in mammals, especially humans.

Listed below are definitions of various terms used to describe the compounds of the present invention. These definitions apply to the terms as they are used throughout the specification (unless they are otherwise limited in specific instances) either individually or as part of a larger group. They should not be interpreted in the literal sense. They are not general definitions and are relevant only for this application.

The term "heterocycle" or "heterocyclic" can be defined as a stable J-7 membered monocyclic or bicyclic, for example 7-10 membered bicyclic, ring which may be saturated, partially saturated or aromatic in nature. Besides carbon atoms, the ring contains 1-4 heteroatoms. The term "heteroatom" as used herein means an atom of any element other than carbon or hydrogen. Preferred heteroatoms are nitrogen (N), oxygen (O), sulfur (S) and phosphorous (P). The atoms N and S can exist in oxidized form and N can be quaternized. The terms "heterocycle" and "heterocyclic" include a bicyclic ring comprising a heterocyclic ring as defined above fused to a benzene ring. The attachment of above defined heterocyclic ring to the main structure may be through a carbon atom or a heteroatom provided that a stable structure results.

The above defined heterocyclic ring may be substituted anywhere in the ring provided that a stable structure is obtained. Examples of such heterocycles include, but are not limited to, acridinyl, azocinyl, benzofuranyl, benzimidazolyl, benzothiophenyl, carbazolyl, chromenyl, chromenyl, cinnolinyl, decahydroquinolinyl, furanyl (furyl), furazanyl, imidazolyl, imidazolinyl, indolenyl, indolizinyl, indolyl, indolinyl, 1H-indazolyl, isobenzofuranyl, isoindolinyl, isooxazolyl, isooxazolinyl, isoquinolinyl, isothiazolyl, morpholinyl, octahydroisoquinolinyl, oxazolidinyl, phenoxathinyl, phenazinyl, piperidinyl, piperazinyl, 4-piperidonyl, pteridinyl, purinyl, pyranyl, pyrazolinyl, pyrazolyl, pyrazolidinyl, pyrazinyl, pyridyl (pyridinyl), pyrimidinyl, pyridazinyl, pyrrolyl, pyrrolidinyl, pyrrolinyl, quinolinyl, 4H-quinolizinyl, quinoxalinyl, quinazolinyl, tetrahydrofuranyl, tetrahydroisoquinolinyl, tetrahydroquinolinyl, tetrazolyl, thiazolyl, triazinyl, thienyl, 6H-1,2,5-thiadiazinyl and xanthenyl.

It should be noted that any heteroatom with unsatisfied valences is assumed to have the hydrogen atom to satisfy the valences.

Halogen is fluorine, chlorine, bromine or iodine, preferably fluorine, chlorine or bromine.

As used herein, the term "alkyl" includes both branched and straight chain saturated aliphatic hydrocarbons having C$_1$-C$_{15}$ carbon atom(s), preferably C$_1$-C$_{12}$ carbon atom(s), most preferred C$_1$-C$_6$ carbon atom(s); examples of such groups include, but are not limited to, methyl, ethyl, propyl, butyl, isopentyl, neopentyl, and hexyl; the term "cycloalkyl" is intended to include a saturated mono-, bi- or poly-cyclic ring system having C$_3$-C$_{15}$ carbon atom(s), preferably C$_3$-C$_{12}$ carbon atom(s); examples of such groups include, but are not limited to, cyclopropyl, cyclobutyl, cyclohexyl, adamantyl, [3,3,0]bicyclooctantyl and [4,4,0]bicyclodecanyl; the term "cycloalkylalkyl" is intended to include connection of a cycloalkyl group defined above via an alkyl group defined above; examples of such groups include, but are not limited to, 2-cyclopropylethyl and 3-cyclohexyl-2-methylpropyl.

As used herein, the term "alkoxy" is alkyl-O—, wherein the alkyl group is as defined above; examples of such groups include, but are not limited to: methoxy, ethoxy, propyloxy, butyloxy, iso-propyloxy.

Unless stated otherwise, and irrespective of any specific substituents bonded to alkyl groups that are indicated in the definition of the compounds of the general formula (I), alkyl groups may be optionally substituted by at least one, for example 1, 2, 3, 4 or 5, identical or different substituents. Any kind of substituents present in substituted alkyl residues can be present in any desired position provided that the substitution does not lead to an unstable molecule. A substituted alkyl refers to an alkyl residue in which at least one, for example, 1, 2, 3, 4 or 5, hydrogen atoms are replaced with substituents, for example, halogen, hydroxyl, carbonyl, such as oxo, alkoxyl, ester, ether, cyano, amino, amido, imino, sulfhydryl, alkylthio, thioester, sulfonyl, nitro, heterocyclic, aralkyl, or an aryl or heteroaryl group. The carbon backbone of the alkyl group may be interrupted by heteroatoms such as oxygen, sulphur or nitrogen. Examples of substituted acyclic alkyls are: hydroxymethyl, hydroxyethyl, 2-hydroxyethyl, aminoethyl or morpholinoethyl. Examples of substituted cycloalkyl groups are: cycloalkyl groups which carry as substituent at least one, for example 1, 2, 3, 4 or 5, identical or different acyclic alkyl groups, for example acyclic (C$_1$-C$_4$)-alkyl groups like methyl groups. Examples of substituted cycloalkyl groups are 4-methylcyclohexyl, 4-tert-butylcyclohexyl and 2,3-dimethylcyclopentyl.

It will be understood by those skilled in the art that the moieties substituted on the hydrocarbon chain can themselves be substituted, if appropriate. For example, the substituents of a substituted alkyl may include substituted and unsubstituted forms of amino, imino, amido, sulfonyl (including sulfonate and sulfonamide), as well as ether, alkylthio, carbonyl (including ketones, aldehydes, carboxylates, and esters), —CF$_3$, —CN and the like. Cycloalkyls can be further substituted with alkyl, alkenyl, alkoxyl, alkylthio, aminoalkyls, carbonyl-substituted alkyl, —CF$_3$, cyano (CN), and the like.

The term "alkenyl" as used herein can be defined as a straight or branched hydrocarbon chain having C$_2$-C$_{15}$ carbon atoms, preferably C$_2$-C$_{11}$ carbon atoms containing one or more carbon-carbon double bonds present anywhere in the carbon chain provided that a stable compound is formed; examples of such a group include, but are not limited to: ethenyl, propenyl and pent-2-enyl.

As used herein the term "alkynyl" is defined as a straight or branched chain hydrocarbon chain having C$_2$-C$_{15}$ carbon atoms, preferably C$_2$-C$_{11}$ carbon atoms which contain one or more carbon-carbon triple bonds present anywhere in the chain provided that a stable compound results; examples of such a group include, but are not limited to: ethynyl and propynyl.

The terms "alkylene", "alkenylene" and "phenylene" are intended to refer to alkyl, alkenyl and phenyl groups, respectively, which are connected by two bonds to the rest of the structure as indicated in the structure of general formula (I) or substructures or partial structures thereof, wherever applicable.

The term "aryl" as used herein refers to monocyclic or polycyclic hydrocarbon groups having up to 14 ring carbon atoms in which at least one carbocyclic ring is present that has a conjugated pi electron system. Examples of $(C_6-C_{14})$-aryl residues are phenyl, naphthyl, biphenyl, fluorenyl and anthracenyl. The term "arylalkyl" indicates an aryl group as defined above which is attached to the indicated position through an alkyl bridge.

As used herein the terms "substituted", "substitution" or substituent" have the meaning that one or more hydrogens on the specified atom are replaced with an atom or group selected from a defined atom or group, such that the normal valence of the atom involved is not exceeded and a stable compound is provided. When a bond to a substituent is shown drawn across the bond connecting any two given atoms in a ring, then such substituent may be connected to any atom in the ring; an example of such a group, without intending to be limiting, is $R^4$ in the general formula (I) which may be connected to any ring member; similarly when a bond between an atom or group to another atom or group is not specifically shown, such bond may be formed with any atom or group and other such atom or group. When a substituent is listed without mention of its mode of connection i.e., the atom through which the bond is formed, then such substituent is considered to be connected via any atom in such substituent; for example a substituent shown as —O—CH=CH-includes both the substituents —O—CH=CH— and —CH=CH—O—.

The double bond $=R^F$ in general formula (I) is intended to mean both a double bond and two single bonds at the designated point of attachment. Thus, $C=R^F$ can be defined as, for example, C=O, CH(OH), $CH_2$, $C=N-OR^{19}$ and the like.

$(R^C)s$ is bonded to W in general formula (I) and s can be 1, 2 or 3. Therefore, when W is —$CH_2$—, one or two $R^C$ groups can be bonded to C, replacing one or two hydrogens, respectively, and when W is —$CH_2CH_2$—, up to three $R^C$ groups can be bonded to the two carbon atoms in W, replacing a hydrogen with each bond.

A combination of substituent(s) and/or variable(s) leading to stable compound is permissible in the present invention. As used herein a stable compound can be defined as one, which can sustain the steps involved in its isolation from the reaction mixture to a useful degree of purity and subsequent formulation into an efficacious therapeutic agent.

"Activation" refers to the change in conformation and the subsequent exposure of the otherwise inactive and unexposed GP IIb/IIIa receptors.

"Platelet aggregation" refers to the formation of clumps of platelets, which occur when fibrinogen molecules bind to the activated GP IIb/IIIa receptors and cross-link platelets.

"Thrombi" are clusters of cross-linked platelets, sometimes containing trapped red blood cells.

"GP IIb/IIIa receptors" are glycoprotein receptors on the surface of platelets, which when activated recognize the Arginine-Glycine-Aspartic acid (RGD) sequence in the fibrinogen molecules.

"Thrombocytopenia" is defined as a reduction in the number of circulating free platelets.

It is also to be understood that compounds of the present invention may have asymmetric centers; all enantiomers, diastereomers and racemic forms are included within the scope of the present invention. It is further understood that geometric isomers of olefins, C=N and conformational isomers or isomers arising out of restricted rotation, as well understood by those familiar to the art of organic chemistry, are also included within the scope of the present invention. Thus, racemic, R and S configurations of the compounds, as well as geometrical E/Z or syn/anti isomers, arising from any asymmetric centre in the compounds are included. The present invention also includes all possible enantiomers and diastereomers in pure or substantially pure form and mixtures of two or more stereoisomers, for example mixtures of enantiomers and/or diastereomers, in all ratios.

Prodrugs are considered to be any covalently bonded carriers that release the active parent drug in vivo. In other words, a prodrug when absorbed in the blood stream cleaves in such a manner as to release the drug molecule to generate desired therapeutic efficacy. Prodrugs include compounds of general formula (I) wherein hydroxyl, amino, amidino, sulfhydryl or carboxylic groups are bonded to any group, which cleaves to form a free hydroxyl, amino, sulfhydryl or carboxyl group, respectively, on administration to a mammalian subject. Thus, the present invention also includes those compounds produced in vivo after administration of a different compound (or prodrug of the compound). The in vivo effects of compounds described herein, may not be exerted by those compounds as such, but by one or more degradation products.

Compounds of general formula (I) which contain one or more basic groups, i.e. groups which can be protonated, can be present and can be used according to the invention in the form of their addition salts with non-toxic inorganic or organic acids. Examples of suitable inorganic acids include: boric acid, perchloric acid, hydrochloric acid, hydrobromic acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, ketoglutaric acid, benzenesulfonic acid, glycerophosphoric acid and other organic acids known to the person skilled in the art.

The compounds of general formula (I) which contain acidic groups can be used according to the invention, for example, as alkali metal salts like Li, Na, and K salts, as alkaline earth metal salts like Ca, Mg salts, as aluminium salts, as salts of organic bases such as lysine, arginine, guanidine, diethanolamine, choline, tromethamine, or as salts with ammonia.

The pharmaceutically acceptable salts of the present invention can be synthesized from the subject compound, which contains a basic or acidic moiety by conventional chemical methods. Generally the salts are prepared by contacting the free base or acid with stoichiometric amounts or with an excess of the desired salt-forming inorganic or organic acid or base in a suitable solvent or dispersant or by anion exchange or cation exchange with other salts. Suitable solvents are, for example, ethyl acetate, ether, alcohols, acetone, THF, dioxane or mixture of these solvents.

The present invention furthermore includes all solvates of compounds of general formula (I), for example hydrates or adducts with alcohols.

Various polymorphs of compounds of general formula (I) forming part of this invention may be prepared by crystallization of compounds of general formula (I) under different conditions. For example, using different commonly used solvents or their mixtures for crystallization; crystallization at different temperatures; various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

Specifically preferred compounds of this invention are compounds that belong to the examples cited below, or pharmaceutically acceptable salts or solvates thereof, selected from but not limited to:

(4-{2-[5-Carbamimidoyl-1-oxo-1,3-dihydro-isoindol-2-yl]-acetyl}-phenoxy)-acetic acid methyl ester;
(4-{2-[5-(N-Hydroxycarbamimidoyl)-1-oxo-1,3-dihydro-isoindol-2-yl]-acetyl}-phenoxy)-acetic acid methyl ester;
(4-{2-[5-Carbamimidoyl-1-oxo-1,3-dihydro-isoindol-2-yl]-acetyl}-phenoxy)-acetic acid ethyl ester;
(4-{2-[5-(N-Hydroxycarbamimidoyl)-1-oxo-1,3-dihydro-isoindol-2-yl]-acetyl}-phenoxy)-acetic acid ethyl ester;
4-(2-{5-Carbamimidoyl-1-oxo-1,3-dihydro-isoindol-2-yl}-acetyl]-phenoxy)-acetic acid isopropyl ester;
(4-{2-[5-(Imino-methoxycarbonylamino-methyl)-1-oxo-1,3-dihydro-isoindol-2-yl]-acetyl}-phenoxy)-acetic acid isopropyl ester;
(4-{2-[5-(Imino-isobutoxycarbonylamino-methyl)-1-oxo-1,3-dihydro-isoindol-2-yl]-acetyl}-phenoxy)-acetic acid isopropyl ester;
(4-{2-[5-(Benzyloxycarbonylamino-imino-methyl)-1-oxo-1,3-dihydro-isoindol-2-yl]-acetyl}-phenoxy)-acetic acid isopropyl ester;
(4-{2-[5-(N-Hydroxycarbamimidoyl)-1-oxo-1,3-dihydro-isoindol-2-yl]-acetyl}-phenoxy)-acetic acid isopropyl ester;
(4-{2-[5-Carbamimidoyl-1-oxo-1,3-dihydro-isoindol-2-yl]-acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;
(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxy-imino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;

2-(4-{2-[5-Carbamimidoyl-1-oxo-1,3-dihydro-isoindol-2-yl]-acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-acetyl}-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;
(4-{2-[5-(N-Hydroxycarbamimidoyl)-1-oxo-1,3-dihydro-isoindol-2-yl]-acetyl}-3-methoxy-phenoxy)-acetic acid ethyl ester;
(4-{2-[5-(N-Hydroxycarbamimidoyl)-1-oxo-1,3-dihydro-isoindol-2-yl]-acetyl}-3-propoxy-phenoxy)-acetic acid ethyl ester;
(4-{2-[5-Carbamimidoyl-1-oxo-1,3-dihydro-isoindol-2-yl]-acetyl}-3-ethoxy carbonylmethoxy-phenoxy)-acetic acid ethyl ester;

(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;

(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;

(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;

(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;

(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;

(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;

(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;

(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;

(3-Hydroxy-4-{2-[5-(N-hydroxycarbamimidoyl)-1-oxo-1,3-dihydro-isoindol-2-yl]acetyl}-2-propyl-phenoxy)-acetic acid benzyl ester;

(4-{2-[5-Carbamimidoyl-1-oxo-1,3-dihydro-isoindol-2-yl]-acetyl}-3-hydroxy-2-propyl-phenoxy)-acetic acid;

(4-Hydroxy-3-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;

(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;

(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;

(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;

(4-{2-[5-Carbamimidoyl-1-oxo-1,3-dihydro-isoindol-2-yl]-acetyl}-piperazine-1-yl)-acetic acid ethyl ester;

(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;

(1-{2-[5-(N-Hydroxycarbamimidoyl)-1-oxo-1,3-dihydro-isoindol-2-yl]-acetyl}-piperidin-4-yloxy)-acetic acid ethyl ester;

(1-{3-[5-(N-Hydroxycarbamimidoyl)-1-oxo-1,3-dihydro-isoindol-2-yl]-propionyl}-piperidin-4-yloxy)-acetic acid ethyl ester;

(1-{2-[5-(5-Methyl-isoxazol-3-yl)-1-oxo-1,3-dihydro-isoindol-2-yl]-acetyl}-piperidin-4-yloxy)-acetic acid ethyl ester;

(1-{2-[5-Carbamimidoyl-1-oxo-1,3-dihydro-isoindol-2-yl]-acetyl}-piperidin-4-yloxy)-acetic acid ethyl ester;

(1-{2-[5-(tert-Butoxycarbonylamino-imino-methyl)-1-oxo-1,3-dihydro-isoindol-2-yl]-acetyl}-piperidin-4-yloxy)-acetic acid ethyl ester;

(1-{2-[5-Carbamimidoyl-1-oxo-1,3-dihydro-isoindol-2-yl]-acetyl}-piperidin-4-yloxy)-acetic acid;

(4-{2-[5-Acetimidoylamino-1-oxo-1,3-dihydro-isoindol-2-yl]-acetyl}-3-hydroxy-phenoxy)-acetic acid ethyl ester;

(3-Ethoxy-4-{2-[5-(N-hydroxycarbamimidoyl)-1-oxo-1,3-dihydro-isoindol-2-yl]-acetyl}-phenoxy)-acetic acid ethyl ester;

(4-[2-(5-carbamimidoyl-1-oxo-1,3-dihydro-isoindol-2-yl)-acetyl]-3-ethoxy-phenoxy}-acetic acid ethyl ester;

(4-{2-[5-Carbamimdoyl-1-oxo-1,3-dihydro-isoindol-2-yl]-acetyl}-3-ethoxy-phenoxy)-acetic acid;

(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester;

(4-{2-[5-(Acetylamino-imino-methyl)-1-oxo-1,3-dihydro-isoindol-2-yl]-acetyl}-3-hydroxy-phenoxy)-acetic acid ethyl ester;

(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;

(4-{2-[5-Carbamimidoyl-1-oxo-1,3-dihydro-isoindol-2-yl]-acetyl}-3-hydroxy-2-propyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid; and (3-Allyloxy-4-{2-[5-(N-hydroxycarbamimidoyl)-1-oxo-1,3-dihydro-isoindol-2-yl]-acetyl}-phenoxy)-acetic acid ethyl ester.

According to a further aspect of the invention, there are provided processes for the preparation of the compounds of the general formula (I).

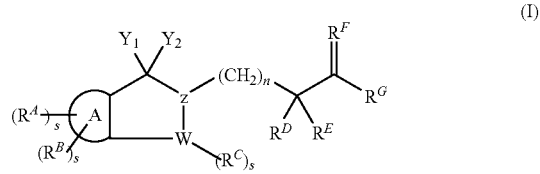

wherein ring A is phenyl;

$R^A$ is selected from: $-NO_2$, $-(CH_2)_pCN$, $-C(=O)-NR^1R^2$, $-C(=S)NR^1R^2$, $-C(=NR^1)-SMe$ and $-C(=NR^1)-OMe$, or $R^A$ is selected from one of the following groups of formula (2), formula (3) and formula (4):

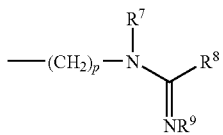
(4)

wherein p is 0, 1, 2, 3, 4 or 5;

s is 1, 2 or 3, and when s is 2 or 3 the groups $R^A$ are independent of each other and can be the same or different;

$R^1$ and $R^2$ are, independently, selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle; or $R^1$ and $R^2$, together with the nitrogen atom to which they are attached, form a saturated, partially saturated, or aromatic heterocycle, optionally containing at least one additional hetero atom selected from: N, O and S;

$R^3$ and $R^4$ are independently selected from: H, alkyl, partially or fully fluorinated alkyl, alkenyl, alkynyl, —C(=O)OR$^5$, cycloalkyl, cycloalkylalkyl, aryl, arylalkyl, heterocycle; —OR$^5$, —SR$^5$, —NR$^5$R$^6$, —S(=O)$_2$NR$^5$R$^6$, —S(=O)$_2$R$^5$, —C(=O)R$^5$, —C(=O)NR$^5$R$^6$, —C(=O)OR$^5$, —C(=O)SR$^5$, —OC(=O)R$^5$, —OC(=O)OR$^5$, —OC(=O)NR$^5$R$^6$, —OS(=O)$_2$R$^5$, —S(C=O)NR$^5$ and —OS(=O)$_2$NR$^5$R$^6$, or $R^3$ and $R^1$ or $R^4$, together with the respective nitrogen atoms to which they are attached, form an unsubstituted or substituted 5-, 6- or 7-membered partially saturated or aromatic heterocycle, optionally having one or more heteroatoms selected from: N, O and S, wherein the substituents are selected from: hydroxy, halogen, alkyl, alkoxy, alkenyl, alkynyl, oxo, carboxy and —C(=O)OR$^5$;

$R^5$ and $R^6$ are independently selected from: H, alkyl, alkenyl, alkynyl, cycloalkyl, cycloalkylalkyl, aryl, arylalkyl and heterocycle, wherein each of said alkyl, alkenyl, alkynyl, cycloalkyl and cycloalkylalkyl group optionally contains at least one hetero atom selected from: N, S and O anywhere in the chain, including the terminal position;

$R^7$ and $R^9$ have the same meaning as $R^3$ and $R^4$, defined above;

$R^8$ is selected from: H, alkyl, alkenyl, alkynyl, cycloalkyl, cycloalkylalkyl, aryl, arylalkyl, and heterocycle, wherein said heterocycle is saturated, partially saturated or aromatic and contains at least one hetero atom selected from: N, O and S, with its point of attachment either through C or N, and wherein each of said alkyl, alkenyl, alkynyl, cycloalkyl and cycloalkylalkyl groups optionally contains at least one hetero atom selected from: N, O and S anywhere in the chain, including the terminal position;

$R^B$ is selected from: H, halogen, —CN, —NO$_2$, alkyl, partially or fully fluorinated alkyl, alkenyl, alkynyl, cycloalkyl, cycloalkylalkyl, aryl, arylalkyl, heterocycle, —NR$^{10}$R$^{11}$, —OR$^{10}$, —SR$^{10}$, S(O)R$^{10}$, S(O)$_2$R$^{10}$, —NHC(=O)R$^{10}$, —NHOR$^{10}$, —OC(=O)R$^{10}$, —SC(=O)R$^{10}$, —NHC(=O)OR$^{10}$, —OC(=O)OR$^{10}$, —C(=O)NR$^{10}$R$^{11}$, —C(=O)R$^{10}$, and —C(=O)OR$^{10}$;

$R^{10}$ and $R^{11}$ have the same meaning as $R^5$ or $R^6$, defined above;

s is 1, 2 or 3 and when s is 2 or 3 the groups $R^B$ are independent of each other and can be same or different;

$Y^1$ and $Y^2$ are independently selected from: H, $R^{12}$, $R^{13}$, NR$^{12}$R$^{13}$, OR$^{12}$, SR$^{12}$, CH$_2$(OR$^{12}$), CH$_2$(SR$^{12}$), CH$_2$S(=O)R$^{12}$ and CH$_2$S(=O)$_2$R$^{12}$, or $Y^1$ and $Y^2$, together, are selected from: =O, =S, =CR$^{12}$R$^{13}$, =NR$^{12}$ and =N—OR$^{12}$;

$R^{12}$ and $R^{13}$ are selected from: H, OR$^5$, alkyl, alkenyl, alkynyl, cycloalkyl, cycloalkylalkyl and aryl;

Z is CH or N;

W is (CH$_2$)$_u$, wherein u is the integer 1 or 2;

$R^C$ is selected from: $R^5$, =O, =NR$^{14}$, =S, CN, NR$^{14}$R$^{15}$, OR$^{14}$, SR$^{14}$, S(=O)$_2$R$^{16}$ and COR$^{16}$;

$R^{14}$ and $R^{15}$ have the same meaning as $R^5$ and $R^6$, defined above;

s is 1, 2 or 3 and when s is 2 or 3 the groups $R^C$ are independent of each other and can be same or different;

$R^{16}$ is selected from: H, OR$^{14}$, N(R$^{14}$)$_2$, NR$^{14}$R$^{15}$, SR$^{14}$ and $R^5$, wherein $R^5$, $R^{14}$ and $R^{15}$ are as defined above;

n is 0, 1, 2, 3, 4 or 5;

$R^D$ and $R^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy, —C(=O)OR$^5$, —OR$^{17}$, —SR$^{17}$, —NR$^{17}$R$^{18}$, —NHC(=O)R$^{17}$, —NHC(=O)OR$^{17}$, —OC(=O)R$^{17}$, —SC(=O)R$^{17}$, —OS(=O)$_2$R$^{17}$ and —NHS(=O)$_2$R$^{17}$;

$R^{17}$ and $R^{18}$ have the same meaning as $R^5$ and $R^6$, defined above;

$R^F$ is selected from: (H, H), (—H, —OH), O, S, N(OR$^{19}$), N[OC(=O)OR$^{19}$], N[OC(=O)R$^{19}$] and N[OS(=O)$_2$NR$^{19}$R$^{20}$], wherein $R^{19}$ and $R^{20}$ have the same meaning as $R^5$ and $R^6$, defined above;

$R^G$ is selected from: aryl, heteroaryl, and partially or fully saturated heterocycle, wherein said aryl, heteroaryl, and heterocycle are substituted by one or more groups independently selected from: —R$^5$, halogen, —CN, —SCN, —CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —SC(=O)H, —SC(=O)OR$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$, —S(=O)$_2$OR$^{21}$ and a group of formula (5):

T-(CH$_2$)$_q$—CR$^{23}$R$^{24}$—COR$^{25}$ (5)

$R^{21}$ and $R^{22}$ have the same meaning as $R^1$ and $R^2$, defined above;

T is selected from: —CH$_2$, O, S and NH;

q is 0, 1, 2, 3, 4, 5 or 6;

$R^{23}$ and $R^{24}$ are independently selected from: H, alkyl, alkenyl, alkynyl, cycloalkyl, cycloalkylalkyl, aryl, arylalkyl, heterocycle, and C(=O)R$^{25}$, wherein said alkyl and alkenyl optionally contain at least one hetero atom selected from: O, S and N, in any position of the alkyl or alkenyl chain, and said alkyl and alkenyl are unsubstituted or substituted with at least one group selected from: —OR$^1$, —OS(=O)$_2$R$^1$, —S(=O)$_2$NR$^1$R$^2$, —OC(=O)OR$^1$, —OC(=O)SR$^1$, —OC(=O)NR$^1$R$^2$, —SR$^1$, —S(=O)R$^1$, —SC(=O)H, —SC(=O)OR$^1$, —NR$^1$(OR$^2$), —NR$^1$R$^2$, —NR$^1$C(=O)R$^2$, —N(R$^1$)C(=O)OR$^2$, —NR$^1$S(=O)$_2$R$^2$, C(=O)OR$^1$, —S(=O)$_2$R$^1$ and —S(=O)$_2$OR$^1$;

$R^{25}$ is selected from: OR$^5$, SR$^5$, —OCR$^3$R$^4$ and —NR$^5$R$^6$, wherein $R^3$, $R^4$, $R^5$ and $R^6$ are as defined above and wherein, optionally, $R^3$ and $R^4$, together with the carbon atom to which they are attached, form an unsubstituted or substituted 5-, 6- or 7-membered saturated, partially saturated or aromatic heterocycle, having one or more heteroatoms selected from: N, O and S, wherein the substituents are selected from: hydroxy, halogen, alkyl, alkoxy, alkenyl, alkynyl, oxo, carboxy and —C(=O)OR$^5$; and the group NR$^5$R$^6$ is, optionally, a heterocycle containing at least one additional heteroatom selected from: O, S, and N;
which process comprises
reacting compound of formula (II):

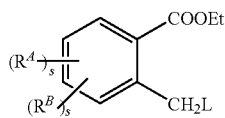

(II)

wherein
L is a leaving group, such as halogen, for example Br; and all other symbols are as defined above; with
a compound of the formula (III):

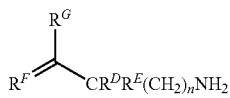

(III)

wherein all symbols are as defined above; in the presence of an organic base such as dimethylaminopyridine, purine base, pyridine, triethylamine, or inorganic base such as sodium bicarbonate, sodium carbonate, lithium carbonate, lithium hydroxide, potassium bicarbonate, potassium carbonate, in an organic solvent such as dichloromethane, chloroform, N,N-dimethylformamide, tetrahydrofuran, dioxan, methanol, ethanol, isopropanol or a mixture of at least two different organic solvents, at a temperature ranging from −40° C. to 150° C., for 0.5 to 16 h, to effect in situ cyclization to form a compound of the general formula (I) above, and, optionally, converting the compound into a physiologically tolerable salt or prodrug.

Another aspect of the present invention provides an alternative process for the preparation of a compound of the general formula (I),
which process comprises reacting a compound of the formula (IV)

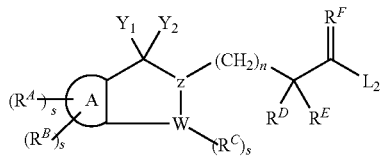

(IV)

wherein
L$_2$ is a leaving group such as halogen, preferably chlorine; and all other symbols are as defined above;
with a compound of the formula (V):

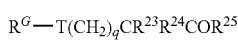

(V)

where R$^G$ is selected from: piperidinyl, piperazinyl and phenyl, wherein said piperidinyl, piperazinyl and phenyl, are optionally substituted with 1, 2, 3 or 4 hydroxyl groups, for example 2 hydroxyl groups, and all other symbols are as defined above, in the presence of an organic base such as dimethylaminopyridine, purine base, pyridine, triethylamine, or inorganic base such as sodium bicarbonate, sodium carbonate, lithium carbonate, lithium hydroxide, potassium bicarbonate, potassium carbonate in an organic solvent such as dichloromethane, chloroform, N,N-dimethylformamide, tetrahydrofuran, dioxan, methanol, ethanol, isopropanol, ethyl acetate or water at a temperature ranging from 0° C. to 150° C., for 0.5 to 12 h, to form a compound of the general formula (I), and,
optionally, converting one or more of the hydroxyl groups into a different group selected from the substituents for R$^G$ as defined in general formula (I) and, optionally, converting the resultant compound of general formula (I) into a physiologically tolerable salt or prodrug;
alternatively,
activating a compound of the formula (IV) above, wherein L$_2$ is —OH, by treatment with a mixed anhydride to form a peptide coupling with a compound of the formula (V), wherein R$^G$ is piperidinyl or piperazinyl, and thereby provide a compound of the general formula (I), wherein R$^G$ is piperidinyl or piperazinyl, substituted with at least a group of the formula 5; and, optionally, converting the resultant compound of general formula (I) into a physiologically tolerable salt or prodrug.

Yet another aspect of the present invention provides a process for the preparation of a compound of the general formula (I), wherein R$^G$ is phenyl substituted with a group of the formula (5) or —OCH$_2$Phenyl, and, optionally, substituted with at least one further group selected from: —R$^5$, halogen, —CN, —SCN, —CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —SC(=O)H, —SC(=O)OR$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$, —S(=O)$_2$OR$^{21}$ and a group of the formula 5;
W is —(CH$_2$)$_u$ wherein u is 2; and all other symbols are as defined above;
which process comprises alkylating a compound of the formula (VI):

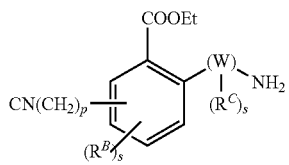

(VI)

wherein all symbols are as defined above;
with a compound of the formula (VII)

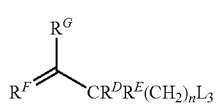

(VII)

wherein
L$_3$ is a leaving group; and all other symbols are as defined above;
in the presence of an organic base such as dimethylaminopyridine, purine base, pyridine, triethylamine, or inorganic base such as sodium bicarbonate, sodium carbonate, lithium carbonate, lithium hydroxide, potassium bicarbonate, potassium carbonate, in an organic solvent such as dichloromethane, chloroform N,N-dimethylformamide, tetrahydrofuran, dioxan, methanol, ethanol, isopropanol, or a mixture of at least two different organic solvents, at a temperature ranging from −40° C. to 150° C., for 0.5 to 16 h, to effect in situ cyclization to form a compound of the general formula (I) as defined above, and when $R^G$ is substituted with —OCH$_2$Phenyl, optionally converting the —OCH$_2$Phenyl into hydroxyl and subsequently coupling the hydroxyl with the group $L_4$-(CH$_2$)$_q$—CR$^{23}$R$^{24}$—COR$^{25}$, wherein $L_4$ is a leaving group, such as halogen, OMes or OTs; and all the other symbols are as defined in general formula (I);

optionally converting the —(CH$_2$)pCN group into a group of the formula 3; and, optionally, converting the resultant compound into a physiologically tolerable salt or prodrug.

Yet another aspect of the present invention provides a process for the preparation of a compound of the general formula (I), wherein $R^G$ is phenyl, having at least one substituent which is OCH$_2$Phenyl, and optionally at least one further substituent selected from: —R$^5$, halogen, —CN, —SCN, —CNO, —OR$^{21}$, —OC(=O)R$^{21}$, —OS(=O)$_2$R$^{21}$, —OS(=O)$_2$NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —SC(=O)H, —SC(=O)OR$^{21}$, —NO$_2$, —NR$^{21}$OH, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$ and —S(=O)$_2$OR$^{21}$; and W is —(CH$_2$)$_u$ where u is 1;

which process comprises, alkylating a compound of the formula (VIII)

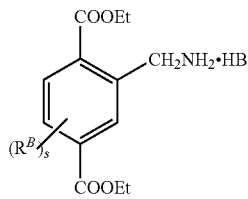

(VIII)

wherein B is halogen, acetate, formate; and all other symbols are as defined above;

with a compound of the formula (VII):

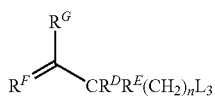

(VII)

wherein $L_3$ is a leaving group, such as halogen, tosyl, mesyl; and all other symbols are as defined above;

in the presence of an organic base such as dimethylaminopyridine, purine base, pyridine, triethylamine, or inorganic base such as sodium bicarbonate, sodium carbonate, lithium carbonate, lithium hydroxide, potassium bicarbonate, potassium carbonate, in an organic solvent such as dichloromethane, chloroform, N,N-dimethylformamide, tetrahydrofuran, dioxan, methanol, ethanol, isopropanol, or a mixture of at least two different organic solvents, at a temperature ranging from −40° C. to 150° C., for 0.5 to 16 h, to effect in situ cyclization to form the compound of general formula (I), wherein $R^A$ is —COOEt and s is 2;

optionally converting one or both of the —COOEt groups into the cyano group —(CH$_2$)pCN, wherein p is as defined;

optionally, subsequently converting at least one of the cyano groups into a group of the formula 3, as defined; and, optionally, converting the resultant compound into a physiologically tolerable salt or prodrug.

The present invention further relates to novel process for the preparation of intermediates H63, G48, G54 and H69 identified below, required for the synthesis of the compounds of general formula (I).

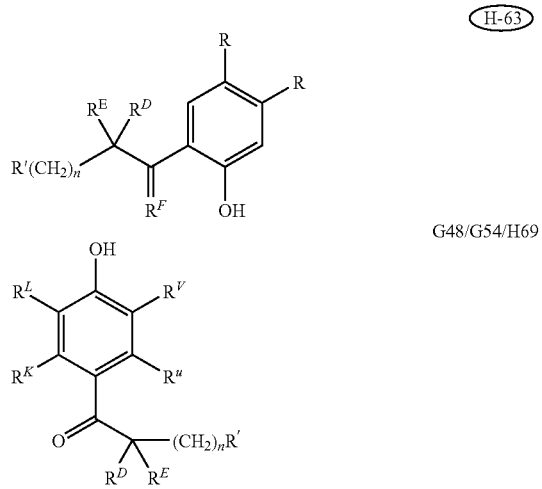

Accordingly, there is provided a process for the preparation of intermediate H-63:

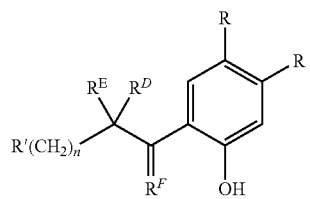

wherein R is a group of formula (5), below:

$$T(CH_2)_qCR^{23}R^{24}COR^{25} \quad (5)$$

wherein

T is selected from: —CH$_2$, O, S and NH;

q is 0, 1, 2, 3, 4, 5 or 6;

$R^{23}$ and $R^{24}$ are independently selected from: H, alkyl and alkenyl, alkynyl, cycloalkyl, cycloalkylalkyl, aryl, arylalkyl, heterocycle and C(=O)R$^{25}$, wherein said alkyl and alkenyl optionally contain at least one hetero atom selected from: O, S and N, in any position of the alkyl or alkenyl chain, and said alkyl and alkenyl are unsubstituted or substituted with at least one group selected from: —OR$^1$, —OC(=O)R$^1$, —OS(=O)$_2$R$^1$, —S(=O)$_2$NR$^1$R$^2$, —OC(=O)OR$^1$, —OC(=O)SR$^1$, —OC(=O)NR$^1$R$^2$, —SR$^1$, —S(=O)R$^1$, —SC(=O)H, —SC(=O)OR$^1$, —NR$^1$(OR$^2$), —NR$^1$R$^2$, —NR$^1$C(=O)R$^2$, —N(R$^1$)C(=O)OR$^2$, —NR$^1$S(=O)$_2$R$^2$, C(=O)OR$^1$, —S(=O)$_2$R$^1$ and —S(=O)$_2$OR$^1$;

$R^1$ and $R^2$ are as defined in general formula (I) above;

$R^{25}$ is selected from: $OR^5$, $SR^5$, —$OCR^3R^4$ and —$NR^5R^6$, wherein $R^3$, $R^4R^5$ and $R^6$ are as defined in general formula (I), and wherein, optionally, $R^3$ and $R^4$, together with the carbon atom to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy and —$C(=O)OR^5$; and the group $NR^5R^6$ is, optionally, a heterocycle containing at least one additional heteroatom selected from: O, S, and N;

R' is H, a protected amino group, such as NHZ, or L, wherein L is a leaving group, such as halogen, OMes or OTs;

$R^D$ and $R^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy, —$C(=O)OR^5$, —$OR^{17}$, —$SR^{17}$, —$NR^{17}R^{18}$, —$NHC(=O)R^{17}$, —$NHC(=O)OR^{17}$, —$OC(=O)R^{17}$, —$SC(=O)R^{17}$, —$OS(=O)_2R^{17}$ and —$NHS(=O)_2R^{17}$;

$R^{17}$ and $R^{18}$ have the same meaning as $R^5$ and $R^6$;

$R^F$ is =O; and n is 0, 1, 2, 3, 4 or 5;

which process comprises reacting the O-allylic compound H-60

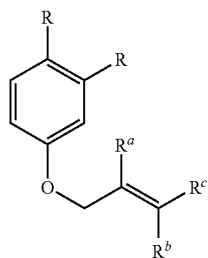

(H-60)

wherein $R^a$, $R^b$ and $R^c$ are independently selected from: alkyl and alkylaryl, and R has the meaning defined above, with the compound R'(CH$_2$)$_n$CR$^D$R$^E$COCl, wherein R', $R^D$, $R^E$ and n are as defined above, in the presence of a Lewis acid catalyst such as Zn, BF$_3$.etherate, FeCl$_3$, AlCl$_3$ and ZnCl$_2$, preferably Zn, in the presence of an organic solvent or mixture of at least two organic solvents selected from, for example: toluene, benzene, heptane, kerosene, CS$_2$, CCl$_4$ and nitrobenzene, preferably toluene, at a temperature ranging from room temperature to 120° C., for a period of 2 to 12 h and, optionally, isolating the intermediate H-63 from the reaction mixture. This is a single step process in which the O-allylic compound H60 may undergo cleavage during the reaction.

There is also provided a novel process for the preparation of novel intermediates G48, G54 and H69 required for the synthesis of a compound of the general formula (I):

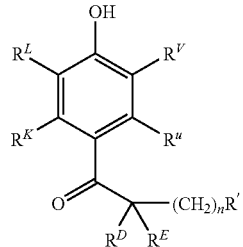

G48/G54/H69 wherein $R^K$, $R^L$, $R^V$ and $R^U$, are independently selected from: H, alkyl, alkenyl, alkynyl, cycloalkyl, cycloalkylalkyl, aryl, arylalkyl, halogen, —CN, —SCN, —CNO, —$OR^{21}$, —$OC(=O)R^{21}$, —$OS(=O)_2R^{21}$, —$OS(=O)_2NR^{21}R^{22}$, —$OC(=O)OR^{21}$, —$OC(=O)SR^{21}$, —$OC(=O)NR^{21}R^{22}$, —$SR^{21}$, —$S(=O)R^{21}$, —$SC(=O)H$, —$SC(=O)OR^{21}$, —$NO_2$, —$NR^{21}(OR^{22})$, —$NR^{21}R^{22}$, —$NR^{21}C(=O)OR^{22}$, —$N(R^{21})C(=O)OR^{22}$, —$N[S(=O)_2R^{21}]R^{23}$, $C(=O)OR^{21}$, —$S(=O)_2R^{21}$, —$S(=O)_2OR^{21}$ and a group of formula (5):

$$T-(CH_2)_q-CR^{23}R^{24}-COR^{25} \qquad (5)$$

wherein

T is selected from: —CH$_2$, O, S and NH;

q is 0, 1, 2, 3, 4, 5 or 6;

$R^{23}$ and $R^{24}$ are independently selected from: H, alkyl, alkenyl, alkynyl, cycloalkyl, cycloalkylalkyl, aryl, arylalkyl, heterocycle and $C(=O)R^{25}$, wherein said alkyl and alkenyl optionally contain at least one hetero atom selected from: O, S and N, in any position of the alkyl or alkenyl chain, and said alkyl or alkenyl are unsubstituted or substituted with at least one group selected from: —$OR^1$, —$OC(=O)R^1$, —$OS(=O)_2R^1$, —$S(=O)_2NR^1R^2$, —$OC(=O)OR^1$, —$OC(=O)SR^1$, —$OC(=O)NR^1R^2$, —$SR^1$, —$S(=O)R^1$, —$SC(=O)H$, —$SC(=O)OR^1$, —$NR^1(OR^2)$, —$NR^1R^2$, —$NR^1C(=O)R^2$, —$N(R^1)C(=O)OR^2$, —$NR^1S(=O)_2R^2$, $C(=O)OR^1$, —$S(=O)_2R^1$ and —$S(=O)_2OR^1$;

wherein $R^1$, $R^2$, $R^{21}$ and $R^{22}$ are as defined in general formula (I);

$R^{25}$ is selected from: $OR^5$, $SR^5$, —$OCR^3R^4$ and —$NR^5R^6$, wherein $R^3$, $R^4$, $R^5$ and $R^6$ are as defined in general formula (I), and wherein, optionally, $R^3$ and $R^4$, together with the carbon atom to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy and —$C(=O)OR^5$; and the group $NR^5R^6$ is, optionally, a heterocycle containing at least one additional heteroatom selected from: O, S, and N; with the proviso that at least one of the groups $R^K$, $R^L$, $R^V$ and $R^U$ is OH;

$R^D$ and $R^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy, —$C(=O)OR^5$, —$OR^{17}$, —$SR^{17}$, —$NR^{17}R^{18}$, —$NHC(=O)R^{17}$, —$NHC(=O)OR^{17}$, —$OC(=O)R^{17}$, —$SC(=O)R^{17}$, —$OS(=O)_2R^{17}$ and —$NHS(=O)_2R^{17}$;

$R^{17}$ and $R^{18}$ have the same meaning as $R^5$ and $R^6$;

R' is H, a protected amino group, such as NHZ, NHTroc or NHFmoc, preferably NHZ, or a leaving group; and n is 0, 1, 2, 3, 4 or 5;

which process comprises reacting a mono- or polyhydroxy phenol of the formula (IX):

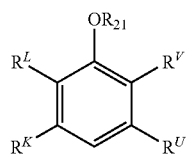

wherein
R$^{21}$ is selected from H, alkyl or aralkyl; and
R$^K$, R$^L$, R$^V$ and R$^U$ have the meaning defined above, preferably R$^K$ and/or R$^U$=—OH
with a compound of the formula X:

$$R'(CH_2)_nCR^DR^ECN \qquad (X),$$

in which R', R$^D$ and R$^E$ & n have the meaning defined hereinabove;

in the presence of an inorganic acid, such as HCl or HBr, and a Lewis acid catalyst, such as Zn, BF$_3$.etherate, FeCl$_3$, AlCl$_3$ or ZnCl$_2$, preferably ZnCl$_2$, and, optionally, isolating the resultant intermediate from the reaction mixture.

The reaction may be carried out at 0° C. to 60° C., preferably at 0° C. to ambient temperature, for a period of 2 to 12 h. in at least one solvent selected from, for example: ether, benzene, THF and dioxane, preferably ether.

Examples of the polyhydroxy phenol that may be used in the process of the present invention are the intermediates G-47, H-65 and H-68, given below:

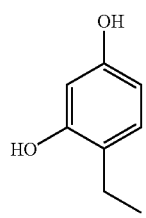

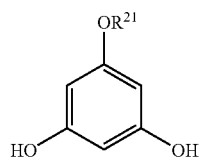

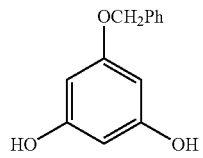

wherein R$^{21}$ is as defined in respect of general formula (I). Specific examples of the polyhydroxy phenol include: 2 or 4 substituted resorcinol; 1,2,3 trihydroxyphenol; 1,2,4 trihydroxyphenol; and 1,3,5 trihydroxyphenol.

Synthesis

The compounds of the present invention can be synthesized by the methods described below, with reference to the schemes in Figures A-H, J and K. Some steps in the methods may include synthetic methods known in the art of synthetic organic chemistry or a modification thereof, as appreciated by those skilled in the art. However, the methods of preparation of the compounds of the present invention are not limited to those methods described below. The reactants and intermediates used in the processes described are either commercially available or can be prepared according to standard literature procedures.

All references cited here are hereby incorporated in their entirety herein by reference.

The following abbreviations are used herein:
AcOH: acetic acid
Ac$_2$O: acetic anhydride
AIBN: 2,2'-azobis-(2-methylpropionitrile)/2,2'-azobisisobutyronitrile
β-Ala: 3-aminopropionic acid
Boc: tert-butyloxycarbonyl
Boc$_2$O: di-tert-butyl dicarbonate
DCC: 1,3-dicyclohexylcarbodiimide
DCU: 1,3-dicyclohexyl urea
DEA: diethyl amine
DIEA diisopropylethyl amine
DMAP: 4-dimethylaminopyridine
DMF: N,N-dimethylformamide
DMSO: dimethylsulfoxide
EtOAc: ethyl acetate
EtOH: ethyl alcohol
Fmoc: Fluorenyl methyloxy carbonyl
HOBt: 1-hydroxybenzotriazole
IBCF: iso-butylchloroformate
IPA: iso-propyl alcohol
MCPBA: meta-chloroperbenzoic acid
MeOH: methanol
NBS: N-bromosuccinimide
NCS: N-chlorosuccinimide
NIS: N-iodosuccinimide
NMM: N-methylmorpholine
NMP: N-methylpyrrolidine
PPh$_3$: triphenylphosphine
PTSA: 4-toluenesulfonic acid
Pyr: pyridine
TEA: triethylamine
TFA: trifluoroacetic acid
THF: tetrahydrofuran
Troc 2,2,2-trichloroethoxycarbonyl
Tyr: L-tyrosine
Z: benzyloxycarbonyl The symbols used herein R$^1$ to R$^{25}$, R$^A$, R$^B$, R$^C$, R$^D$, R$^E$, R$^F$, R$^G$, n, q, Z, W and T have the same meaning as described for the general formula (I), unless otherwise indicated; L is a leaving group such as halogen, OMes or OTs; Q is CH or N. For the purpose of describing the synthesis, Y$^1$ and Y$^2$ together, are =O; R is T(CH$_2$)$_q$CR$^{23}$R$^{24}$COR$^{25}$; and R' is H, a leaving group (L) or a protected amine, such as —NHZ.

A convenient method for the synthesis of compounds of the present invention involves alkylation of an appropriately substituted amino compound with a suitable alkylating agent and in situ cyclization followed by reaction steps involving functional group modification. Examples of similar cyclization steps have been described in U.S. Pat. No. 5,719,144.

Compounds of general formula (I) above may be derived from key intermediates designated as A-8/B-20 and B-19. The preparation of these intermediates by alternative reaction sequences is depicted in the schemes shown in Figures A (compound A-8) and B (compounds B-19 and B-20), which are provided in the accompanying drawings.

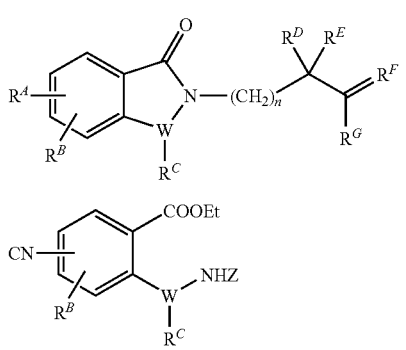

Figure A

The preparation of variants of the key intermediate A-8 by alternative reaction sequences are described in the following processes designated herein as processes 1-1, 1-2, 1-3 and 1-4, which are schematically presented in Figure A.

Process 1-1 for the Preparation of Compound A-8 ($R^A$ is $NO_2$, $R^B$ and $R^C$ are H)

(i) An appropriately substituted o-tolylamine may be subjected to a Sandmeyer reaction (Vogel's Textbook of Practical Org. Chem., 5$^{th}$ edition, 938) to obtain the corresponding cyano compound, which may be hydrolysed with 50-75% aqueous $H_2SO_4$ at 100°-150° C. for 12-24 hrs in accordance with a known procedure (Vogel's Textbook of Practical Org. Chem., 5$^{th}$ edition, 1063). The resulting acid may further be converted to its corresponding ester designated as A-1 by any standard procedure known in the art. Alternatively, ester A-1 may also be obtained from the cyano compound by alcoholysis in presence of a mineral acid under reflux.

(ii) The methyl group in A-1 may be converted to $CH_2L$ (wherein L represents a leaving group, e.g. Br), by any conventional method known in the art. One suitable method for said conversion involves treating the ester A-1 with NBS in presence of AIBN or dibenzoyl peroxide under reflux in an organic solvent, such as carbon tetrachloride, chloroform or carbon disulphide, for 2-24 h to obtain the compound designated as A-2.

(iii) The resulting compound A-2 may then be converted to the desired compound A-8 ($R^A$ is $NO_2$, $R^B$ and $R^C$ are H, W is $CH_2$) by alkylation followed by in situ cyclization with compounds designated herein as H-72, J-77 and K-84. Said cyclization step may be carried out in presence of an organic base, such as TEA, DMA or pyridine, or an inorganic base, such as $NaHCO_3$, $Na_2CO_3$, $KHCO_3$, $K_2CO_3$, $Cs_2CO_3$, or CsOH, in an organic solvent, such as $CH_2Cl_2$, $CHCl_3$, MeOH, EtOH, iPrOH, THF, dioxane or DMF, or a mixture of at least two of said solvents, at a temperature ranging from −40° C. to reflux; preferably at −25° C. to ambient temperature.

The synthesis of the compounds H-72, J-77 and K-84 are described hereinafter in processes 8-2, 9-1 and 10-1, respectively.

Process 1-2 for the Preparation of Compound A-8 ($R^A$ is CN, $R^B$ and $R^C$ are H):

(i) The nitro group in the ester A-1 may be reduced to the corresponding amine designated as A-3 by catalytic hydrogenation or transfer hydrogenation with ammonium formate in presence of a catalyst, such as Pd, Pt, Pd—C or Pt—C, or with Raney Ni, in an organic solvent such as EtOAc, MeOH, EtOH, iPrOH, DMF, or a combination of at least two of said solvents. This reduction may also be carried out by various conventional methods known in the art for converting a nitro group to an amino group. One suitable method uses Zn and $CoCl_2 \cdot 6H_2O$ as described in a reported procedure (Ind. J. Chem., 1994, 33B 758).

(ii) The amino group in compound A-3 may then be converted to a cyano group by a Sandmeyer reaction (Vogel's Textbook of Practical Org. Chem., 5$^{th}$ edition, 938). The resulting compound may be subsequently converted to compound A-4 in a manner similar to that described hereinabove for the conversion of compound A-1 to compound A-2.

(iii) The compounds H-72, J-77 and K-84 may be subjected to alkylation and in situ cyclization with compound A-4 by a procedure as described hereinabove for the conversion of compound A-2 to the desired compound A-8 ($R^A$ is CN).

Process 1-3 for the Preparation of Variants of Compound A-8 ($R^A$ is CN; $R^B$ is $COR^{10}$, $OR^{10}$, $C_1$-$C_{15}$-alkyl, hologen, $SR^{10}$, $S(O)R^{10}$, $S(O)_2R^{10}$, $NHCOR^{10}$, $NHCOOR^{10}$, $NO_2$, or NHZ/NHTroc; and $R^C$ is H):

(i) Preparation of Variants of Compound A-5:

a) The compound A-5 ($R^B$ is $COR^{10}$) may be prepared by first protecting the amino group in compound A-3 with an appropriate protecting group (eg. phthaloyl) and then subjecting the resulting compound to Friedel-Crafts acylation with a suitable acylating agent, such as an acid chloride or an anhydride, followed by deprotection of the amino group by any conventional method known in the art.

b) The compound A-5 ($R^B$ is $C_1$-$C_{15}$-alkyl) may be prepared by first protecting the amino group in compound A-3 with an appropriate protecting group (eg. phthaloyl) and then subjecting the resulting compound to Friedel-Crafts alkylation followed by deprotection of the amino group. Alternatively, said compound A-5 may be prepared by reducing the carbonyl group in the compound of the type A-5 (wherein $R^B$ is CO $C_1$-$C_{14}$-alkyl), which after reduction results in $CH_2C_1$-$C_{14}$-alkyl, according to a reported procedure (Synthesis, 763, 1978; Tetrahedron, 23, 2235, 1967).

c) The compound A-5 ($R^B$ is halogen, such as Cl, Br, I) may be prepared by treating compound A-3 with N-halosuccinimide in an organic solvent, such as DMF, acetonitrile, AcOH, $CHCl_3$, $CS_2$, $CH_2Cl_2$ or a mixture of at least two of said solvents, at a temperature ranging from 0°-100° C.

d) The compound A-5 ($R^B$ is $OR^{10}$) may be prepared by first protecting the amino group in the compound A-5 ($R^B$ is Cl, Br or I) with a suitable protecting group, such as Boc or Z, and subsequently treating the resulting compound with an alkali metal alkoxide in the presence of CuCl, CuBr or CuI in accordance with a reported procedure (Tetrahedron, 48, 3633, 1992; J. Org. Chem., 62, 5413, 1997), followed by deprotection of the amino group.

e) Compound A-5 ($R^B$ is $SR^1$) may be prepared by treating the compound A-5 ($R^B$ is Cl, Br or I) with $CuSR^{10}$ in accordance with a reported procedure (J. Am. Chem. Soc, 81, 4927, 1959). The resulting compound A-5 ($R^B$ is $SR^{10}$) may be converted to its corresponding sulfoxide or sulfone [$R^B$ is $S(O)R^{10}$ or $S(O)_2R^{10}$] by subjecting it to oxidation.

f) Compound A-5 ($R^B$ is $NO_2$) may be prepared by first protecting the amino group in compound A-3 with a suitable protecting group (e.g. phthaloyl) and subjecting the resulting compound to a standard nitration reaction followed by deprotection of the amino group by any conventional method known in the art.

Alternatively, prior to deprotection, the nitro group in the resulting compound may be reduced to the corresponding amino group by following the same procedure as described hereinabove for the conversion of compound A-1 to compound A-3. The newly formed amino group may be protected with a different protecting group, such as Z or Troc, so that it is compatible with the phthaloyl group and does not interfere at the time of deblocking the phthaloyl protecting group. The phthaloyl group may then be removed to obtain the corresponding compound A-5 ($R^B$ is NHZ or NHTroc).

Alternatively, the amino compound prior to deprotection of phthaloyl group may be treated with an appropriate acid chloride or a choloroformate using a standard procedure in the art to obtain the desired compound A-5 ($R^B$ is NHCOR$^{10}$ or NHCOOR$^{10}$).

(ii) The thus obtained variants of compound A-5 may be converted to the corresponding compound A-6 by a procedure as described hereinabove for the conversion of compound A-3 to compound A-4.

(iii) The compounds H-72, J-77 and K-84 may be subjected to alkylation and in situ cyclization with compound A-6 by a procedure as described above in process 1-1, to obtain the desired compound A-8 ($R^A$ is CN, $R^B$ is as defined above and $R^C$ is absent).

(iv) Alternatively, the compound A-8 may also be obtained from compound A-7, which in turn can be obtained from compound A-6. The —CH$_2$Br group in compound A-6 may be converted to —CH$_2$CN or —CH$_2$CH$_2$NO$_2$ by using any conventional method. One such method for converting the —CH$_2$Br group to —CH$_2$CN is by treating the halide with an alkali metal cyanide or Zn(CN)$_2$ in a suitable solvent, such as DMF, DMSO or alcohol. One method for converting the —CH$_2$Br group to —CH$_2$CH$_2$NO$_2$ is by treating the halide with nitro methane in the presence of a suitable base, such as NaOEt or NaH. The nitrile or nitro group is then reduced to an amino group by any conventional method known in the art. One such method involves catalytic hydrogenation as described hereinabove to obtain the compound A-7.

The resulting compound A-7 may then be converted to the desired variants of compound A-8, wherein W is CH$_2$CH$_2$ ($R^C$ is H) and other symbols are as defined earlier, by alkylation followed by in situ cyclization with compounds designated herein as F-46, G-53, H-63, wherein R' is a leaving group, such as Cl, Br, I, OMes and OTs, and J-74. The synthesis of the compounds F-46, G-53, H-63 and J-74 are described hereinafter in processes 6-1, 7-1, 8-1 and 9-1, respectively.

Process 1-4 for the Preparation of Other Variants of Compound A-8:

(i) The intermediates A-2, A-4 and A-6 may alkylate amines of the type H$_2$N(CH$_2$)$_2$CR$^D$R$^E$COOR$^1$ (wherein R$^1$ is Me/Et/CH$_2$Ph) followed by cyclization to obtain a compound designated as A-9. Likewise, the intermediate A-7 may undergo alkylation with L$_3$(CH$_2$)$_n$CR$^D$R$^E$COOR$^1$ to obtain the compound A-9.

(ii) The compound A-9 may be hydrolysed with aqueous LiOH in an organic solvent, such as MeOH, EtOH, iPrOH, THF, dioxane and DMF, to obtain the corresponding acid A-10. The protecting group (R$^1$) of the ester, such as the benzyl group, may also be removed by catalytic hydrogenolysis of A-9 to obtain the corresponding acid A-10.

(iii) The acid thus obtained may then be coupled with compounds designated as K-81 or K-83 via a standard peptide coupling procedure, preferably with DCC, by a mixed anhydride method or by using any other method for activation of the acid to give further variants of compound A-8.

(iv) Alternatively, the acid A-10 may further be converted to its acid chloride A-11 by any conventional method, for example, by treating said acid with SOCl$_2$. The thus obtained acid chloride may be coupled with compounds designated as K-81 or K-83 in the presence of organic bases, such as TEA, pyridine or DIPEA and inorganic bases such as NaOH, Na$_2$CO$_3$, or CsCO$_3$. The synthesis of the compounds K-81 and K-83 are described hereinafter in process 10-1.

(v) Alternatively, a suitably substituted mono or polyhydroxy phenol derivative, such as H65, H68 and G47, may be subjected to a Friedel-Crafts acylation with the acid chloride A-11 using a Lewis acid catalyst or by using activated Zn as reported in the literature (Synth. Commun, 28, 2203, 1998), to obtain yet another variant of compound A-8.

Figure B

The preparation of variants of the key intermediate B-19 and B-20 by alternative reaction sequences is described below by the processes designated as processes 2-1, 2-2, 2-3 and 2-4, which are schematically presented in Figure B:

Process 2-1 for the Preparation of Compounds B-20 ($R^B$ is H):

(i) 4-Methylbenzoic acid may be treated with bromine in presence of AgNO$_3$ according to a reported method (J. Org. Chem., 25, 1024, 1960) to obtain 3-bromo-4-methylbenzoic acid. The methyl group in the resulting compound may be oxidized by any conventional oxidizing agent, for example, alkaline potassium permanganate at a temperature ranging from 50°-100° C. for 2-6 hr to obtain the corresponding dicarboxylic acid. The resulting dicarboxylic acid (Beil, 9, IV, 3335) may be esterified by refluxing with an appropriate alcohol (e.g. EtOH) in presence of a mineral acid or by treatment with SOCl$_2$ followed by addition of an appropriate alcohol (e.g. EtOH) to give a compound designated as B-12.

(ii) The bromo compound B-12 may then be converted to a cyano compound by treating it with a reagent, such as CuCN, alkali metal cyanide or Zn(CN)$_2$, in a solvent, such as pyridine, DMF, a lower alcohol, or pyrrolidone; at a temperature ranging from 50°-150° C. for 3-24 hr. The resulting cyano compound may then be subjected to catalytic hydrogenation in a solvent, such as an alcohol, AcOH, chloroform, DMF, or a mixture of at least two of said solvents, at 200-500 psi, preferably in an alcohol and chloroform mixture over PtO$_2$ at 400 psi for 2-8 hr to obtain a compound designated as B-13, wherein B is, for example, halogen, acetate or formate.

(iii) The compound B-13 may then be subjected to alkylation with $R^G$(C=$R^F$)CR$^D$R$^E$(CH$_2$)$_n$L$_3$ and in situ cyclization to obtain a compound designated as B-16, wherein the groups R$^K$, R$^L$, R$^U$ and R$^V$ are the same as the ring substituents in the definition of R$^G$. In compound B-16, R$^G$ is not substituted with a —COOR group. The ester group (R$^A$=—COOEt) in compound B-16 may be converted to a cyano group by any conventional method, for example, through amide formation followed by dehydration by a number of reagents well known in the art, to obtain a compound designated as B-17, wherein R$^A$=—CN.

Alternatively, the ester group (R$^A$) in the compound B-16 may be converted to a —(CH$_2$)$_p$CN group by a number of synthetic steps. These steps involve hydrolysis of an ester to an acid, reduction of the resulting acid to an alcohol by any conventional reducing agent, such as $NaBH_4$— mixed anhydride (except in cases in which $R^F$ is O and S). The resulting alcohol is converted to a leaving group such as halide, mesyl or tosyl, by a standard procedure well known to those skilled in the art. This is followed by treatment with alkali metal cyanide by a known procedure. (Vogel's Textbook of Practical Org. Chem., $5^{th}$ edition, 714).

The benzyl group of B-16 to B-18 can be removed by a known method such as catalytic hydrogenolysis or by treatment with silyl iodide particularly in those compounds wherein $R^F$ is O, in a solvent such as $CH_2Cl_2$, $CHCl_3$, DMF, benzene, toluene, THF or dioxane, at ambient to reflux temperature for 2-18 hr.

(iv) The phenolic OH group formed by the removal of the benzyl group in B-16 to B-18 may be finally coupled with L-$(CH_2)_q CR^{23}R^{24}COR^{25}$ by a standard procedure to afford the desired key intermediate B-20 (where $R^A$=—$(CH_2)_p CN$).

Process 2-2 for the Preparation of Variants of Compound B-20 ($R^B$ is $COR^{10}$, $C_1$-$C_{15}$-alkyl, halogen, $OR^{10}$, $SR^{10}$, $S(O)R^{10}$ or $S(O)_2R^{10}$, $NO_2$, NHC(O)$R^{10}$, NHC(O)O$R^{10}$, NHZ or NHTroc):

(i) The preparation of variants of compound B-13 ($R^B$ is $COR^{10}$, $OR^{10}$, $SR^{10}$, $S(O)R^{10}$ or $S(O)_2R^{10}$)

The variants of compound B-13 may be prepared by functionalising 3-bromo-4-methylbenzoic acid by $R^B$, wherein $R^B$ has the meaning as described above, in a manner similar to that described in process 1-3 for the preparation of variants of compound A-5.

(ii) The variants of compound B-13 may then be converted to the desired variants of compound B-20 in a manner similar to that described in the above process 2-1.

Process 2-3 for the Preparation of Compound B-20 Starting from nitro 2-halobenzoic acid:

(i) Nitro substituted 2-halobenzoic acid may be esterified in a manner similar to that described in the above process 2-1(i).

(ii) The halo group in the resulting ester may then be converted to the cyano group according to the procedure described in process 2-1(ii). Both the nitro and the cyano groups may then be reduced under acidic conditions by any conventional method known in the art, for example, catalytic hydrogenation as described in the above process 2-1. The primary amino group can selectively be protected using a suitable protecting group, such as Z, Boc, Fmoc or Troc, to give B-14.

(iii) In yet another variation, the substituted 2-halo benzoate ester may be treated with a reagent, such as ZNH—$CH_2CR^8$=$CR^C$-L, in the presence of a Pd- or Ni-based catalyst. This can be followed by reduction of the nitro group and double bond to give another variant of B-14. The reduction of the double bond is optional.

(iv) Similarly, the substituted 2-halo benzoate ester may be treated with $R^P$O—$CR^8$=$CR^C$-L. Removal of the protecting group ($R^P$) from the resulting enol ether will give a keto compound. The keto compound may undergo reductive amination to obtain a diamine. The amino group in the side chain may be protected selectively, using reagents such as Z, Fmoc or Troc, to give further variants of compound B-14.

(v) The variants of compound B-14 thus obtained may be subjected to a Sandmeyer reaction in a manner similar to that described in process 1-2 with the minor modification of carrying out said reaction in a solvent medium of an organic solvent, such as THF, dioxane or DMF, and water to obtain a compound designated as B-15.

(vi) The compound B-15 may then be reacted with TFA-thioanisole (J. C. S. Chem. Commun. 101, 1980) or any other standard reagent used for deprotection such as 2N HBr in AcOH for the removal of the Z group to obtain a compound designated as B-19.

(vii) The resulting compound B-19 may then be converted to the desired key compound B-20 by alkylation followed by in situ cyclization with compounds F-46 (R' is L), G-53 (R' is L), H-63(R' is L), H-71(R' is L), and J-74. The symbol L represents a leaving group, such as Cl, Br, I, OMes or OTs.

The synthesis of said fragments F-46, G-53, H-63, H-71 and J-74 are provided hereinafter in processes 6-1, 7-1, 8-1 and 9-1, respectively.

Process 2-4 for the Preparation Variants of Compound B-20 Starting from nitro 2-halobenzoic acid ($R^B$ is $C(O)R^{10}$, $OR^{10}$, halogen, $SR^{10}$, $NO_2$, $NHCOR^{10}$ or $NHCOOR^{10}$)

(i) The compound B-14 described above may be substituted with $R^8$ (which is as described above) by the method described in process 1-3. For this, B-14 may be used in which the amino group substituted on the phenyl ring may be in the unprotected or protected (with groups, such as phthaloyl, Fmoc or Troc, which are compatible with Z) form. (Protecting groups in Org Synthesis, Ed, III, Green. T. W. and Wuts. P. G. M., John Wiley & Sons Inc., p 494). Subsequent to the substitution of compound B-14 with $R^B$, any protecting group, such as phthaloyl, Fmoc or Troc, may be removed by any conventional method.

(ii) The resulting amine may be subjected to a Sandmeyer reaction as described in process 1-1 to obtain a cyano derivative which on deprotection would result in another variant of B-19.

(iii) The resulting compound may then be converted to the desired variant of compound B-20 by alkylation with compounds F-46 (R' is L), G-53 (R' is L), H-63 (R' is L), H-71 (R' is L), and J-74, followed by in situ cyclization. The symbol L is as described earlier.

The synthesis of said compounds F-46, G-53, H-63, H-71 and J-74 are provided hereinafter in processes 6-1, 7-1, 8-1 and 9-1, respectively.

The key compounds A-8, B-20, A-9 and B-15 thus obtained may be subjected to further reaction steps to obtain the compounds designated herein as C-22 and C-23; D-25, D-26, D-27 and D-28; and E-32 and E-33; which correspond to the compounds of general formula (I), as described below by the processes 3-1 to 5-1 and as schematically presented in Figures C, D and E, respectively.

Figure C

The preparation of compounds C-22 and C-23 by alternative reaction sequences is described below by the processes designated as process 3-1 and process 3-2, which are schematically presented in Figure C:

Process 3-1 for the Preparation of Compounds C-22 and C-23:

(i) The cyano group in compound A-8 ($R^A$=—CN) or B-20 ($R^A$=NC$(CH_2)_p$, where p is 0, 1-5) may be subjected to a Pinner reaction to obtain the corresponding hydrochloride salt of an imino ether which may then be treated with an appropriate amino compound (substituted or unsubstituted) to obtain the substituted or unsubstituted amidine compound designated as C-21. Likewise the imino ether may be treated with a substituted or unsubstituted hydroxylamine to obtain the corresponding substituted or unsubstituted oxime designated as C-22.

Alternatively, the cyano group in compound A-8 ($R^4$=CN) or B-20 ($R^4$=NC($CH_2$)$_p$, where p is 0, 1-5) may be subjected to a known reaction (Daniel. J., Sall. et. al. Bioorg. Med. Chem. Lett. 6, 81, 1996 and reference therein) to obtain the corresponding thioimidate compound which may then be treated with an appropriate amino compound (substituted or unsubstituted) or hydroxylamine to obtain the respective substituted or unsubstituted amidino compound C-21 or the oxime C-22.

Compounds of the present invention wherein the group $R^G$ in the compound C-23 (corresponding to compounds of general formula (I)) is substituted by a group of formula 5 (defined hereinabove) in which $R^{25}$ is OH may be obtained as follows: (1) by subjecting an appropriately substituted oxime C-22 ($R^{25}$ is OCH$_2$Ph) to acylation with Ac$_2$O($R^{25}$ is OMe/OEt) followed by hydrogenation ($R^{25}$ is OH) in accordance with a known procedure (D. C., Batt. et. al. J. Org. Chem. 65, 8100, 2000), (2) by hydrogenolysis of an appropriately substituted amidine C-21 ($R^{25}$ is OCH$_2$Ph), or (3) by first protecting the amidino group with an appropriate group, preferably a Boc group, to give the compound C-23 ($R^{25}$ is OMe/OEt, $R^3$ is Boc) which may be subjected to hydrolysis followed by deprotection of the amidino group ($R^{25}$ is OH; $R^3$ is H) using any conventional method known in the art.

A variant of compound C-22 ($R^1$ &/or $R^4$ is H, and $R^{25}$ is OH) may be obtained by hydrolysis of an appropriately substituted hydroxy amino compound C-22 ($R^1$ &/or $R^4$ is H, and $R^{25}$ is OMe or OEt) by LiOH in aqueous THF or NaOH or KOH in MeOH or a lower alcohol.

Yet another variant of compound C-23 ($R^1/R^3/R^4$ is COOR$^5$ or COSR$^5$) may be prepared by treating a suitably substituted amidine C-21 (in which at least one of $R^1$, $R^3$ and $R^4$ in formula 3 as defined under general formula (I) represents H) with a suitable chloroformate ($R^5$OCOCl or $R^5$SCOCl) or dicarbonate (($R^5$OCO)$_2$O or ($R^5$SCO)$_2$O).

Yet another variant of compound C-23, namely the N-sulphonyl or N-acyl derivative of said compound, may be obtained by treating a suitably substituted amidine C-21 (in which at least one of $R^1$, $R^3$ and $R^4$ in formula 3 as defined under general formula (I) represents H) with a suitable sulfonyl chloride or acyl chloride, respectively.

Yet another further variant of compound C-23, namely the carbonate, O-acyl or O-sulfonyl derivative of said compound, may be prepared by treating the oxime C-22 (in which at least one of $R^1$ or $R^4$ in formula 3 as defined under general formula (I) represents OH) with an appropriate reagent such as chloroformate, acyl chloride or sulfonyl chloride.

Process 3-2 for the Preparation of Compounds C-22 and C23, wherein the $R^4$ Group Represents a Heterocyclic Ring:

The compound C-23 ($R^4$ is 1,2,4-oxadiazole) may be prepared by cyclizing compound C-22 ($R^1$ &/or $R^4$ is H) with a suitable acid anhydride, such as acetic anhydride, in accordance with a reported procedure (Joachim Gante et al, Bioorg. Med. Chem. Lett. 6, 2425, 1996) followed by hydrolysis.

Likewise, another compound corresponding to compound C-22 ($R^4$ is 5-oxo-4,5-dihydro-[1,2,4]oxadiazole) may be prepared by treating the compound C-22 ($R^1$ &/or $R^4$ is H) with a reagent such as diethyl carbonate, carbonyl diimidazole, triphosgene or phosgene by using a standard procedure known in the art.

Figure D

The preparation of compounds D-25 and D-28 by alternative reaction sequences is described below by the processes designated as process 4-1, which are schematically presented in Figure D:

Process 4-1 for the Preparation of Compounds Designated as D-25 to D-28

(i) The nitro group in the compound A-8 ($R^4$ is NO$_2$) may be subjected to reduction as described hereinbefore by using Zn and CoCl$_2$ (Baruah. R. N., Ind. J. Chem., 33B, 758, 1994) to obtain the corresponding amino compound designated as D-24.

(ii) The amino compound D-24 may be treated with a suitable co-di-halogen compound under standard conditions known in the art to give the compound designated as D-25, which corresponds to a cyclic amino derivative.

(iii) The amino compound D-24 may also be substituted with a desired alkyl group to give a compound designated as D-26.

(iv) The amino compound D-24 may further be treated with a suitably substituted thioimidate salt (Ting Su et al, J. Med. Chem., 40, 4308, 1997) to obtain a variant of the amidine compound designated as D-28, in which $R^4$ represents the group of formula 4 (defined hereinabove).

The amidine compound D-28 wherein at least one of the groups $R^7$ and $R^9$ in formula 4 represents H, may further be functionalised with groups such as urethan, N-acyl or N-sulfonyl by treating with a suitable chloroformate, acyl chloride or sulfonyl chloride, respectively, to obtain the desired variants of the compound D-28.

Figure E

The preparation of compounds E-32 and E-33 by alternative reaction sequences is described below by the processes designated as process 5-1 and process 5-2 which are schematically presented in Figure E:

Process 5-1 for the Preparation of Compounds Designated as E-32 and E-33 Starting from Compound A-9:

(i) The 1,2,4-oxadiazole derivative designated as E-29 can be obtained from compound A-9 by a procedure which is described in process 3-2 above. The 1,2,4-oxadiazole derivative E-29 may be treated with a compound designated as K-81 or K-83 using a standard peptide coupling method, such as a DCC, mixed anhydride method, to give the compound designated as E-32, wherein $R^G$ represents a heterocyclic ring.

(The preparation of compounds K-81 and K-83 are described hereinafter in process 10).

(ii) Alternatively, the compound E-32 may be prepared by first converting the derivative E-29 to an acid chloride designated as E-30 and coupling the resulting acid chloride with compounds designated as K-81 or K-83 in a manner similar to that described in process 1-4.

(iii) Alternatively, a suitably substituted mono or polyhydroxy phenol derivative may be subjected to a Friedel-Crafts acylation with the acid chloride E-30 in a manner similar to that described in process 1-4 to obtain yet another variant of compound E-32 in which $R^G$ represents an aryl or aromatic heterocycle.

(iv) The variants of compound E-32 may be subjected to hydrogenolysis to obtain an amidine designated as E-33.

Process 5-2 for the Preparation of Variants of Compounds E-32 and E-33 from the Compound B-15:

The cyano group in compound B-15 may be converted to 1,2,4-oxadiazole by the method described in the above process 3-2. The resulting compound is then subjected to a standard deprotection procedure known in the art to remove the Z group to obtain a compound designated as E-31. The resulting compound E-31 may then be subjected to alkylation with F-46, G-53, H-62, H-63 (wherein R' is a leaving group, such as Cl, Br, I, OMes or OTs) and J-74, followed by in situ cyclization to obtain another variant of compound E-32. The resulting compound E-32 may be subjected to hydrogenation to obtain the amidine E-33.

Figure F

The preparations of variants of compound F-46 (used in the synthesis of key intermediates A-8 and B-20) via different synthetic routes are described below by the processes designated as process 6-1, 6-2 and 6-3, which are schematically presented in Figure F. The groups $R^K$, $R^L$ and $R^V$ in said compound F-46 represent substituents having the same meaning as the ring substituents in the definition of $R^G$. The group R represents T $(CH_2)_q CR^{23}R^{24}COR^{25}$; R' represents a H atom, a leaving group L, such as halogen, OMes or OTs, or a protected amino group, such as NHZ; Hal is the halogen F, Cl, Br or I and the remaining groups are as defined earlier.

Process 6-1 for the Preparation of Variants of Compound F-46
(i) An appropriately substituted 1-(hydroxy-phenyl)ethanone may be treated with L $(CH_2)_q CR^{23}R^{24}COR^{25}$ to obtain a compound designated as F-46.
(ii) The compound F-46 thus obtained may then be treated with chlorosulfonic acid followed by treatment with a suitable amine $R^{21}R^{22}NH$ to get a variant of compound F-46 in which $R^L$ and/or $R^V$ is $SO_2NR^{21}R^{22}$, wherein $R^L$ and $R^V$ are as defined above.
(iii) The compound I-(hydroxy-phenyl)-ethanone may be functionalised with a halogen through a standard nuclear halogenation method; preferably using N-halosuccinimide in solvents such as chloroform, dichloromethane, DMF, dioxane, THF, acetonitrile or acetic, or a mixture of at least two of these solvents, at from 0° C. to reflux temperature to obtain compounds designated as F-39 and F-40, wherein $R^L$ and $R^V$ each represent a halogen, independently selected from, for example: Cl, Br and I.
(iv) The halogen substituted compounds F-39 and F-40 may be converted to ether or thio ether derivatives designated herein as F-41, wherein $R^L/R^V$ are $OR^{21}$ or $SR^{21}$, according to a reported procedure (Tetrahedron, 48, 3633, 1992; J. Org. Chem., 62, 5413, 1997 and R. Adams et. al. J. Amer. Chem. Soc., 81, 4927, 1959).
(v) The thio ether F-41($R^L/R^V$ are $SR^{21}$), may be oxidized to the sulfoxide or sulfone designated as F-42 ($R^L/R^V$ are $S(O)R^{21}$ or $S(O)_2R^{21}$) with a suitable oxidizing agent well known to those skilled in the art, preferably mCPBA, OXONE®, hydrogen peroxide or $NaIO_4$—Ru (IV).
(vi) The compounds F-39 to F-42 thus obtained may independently be alkylated with $L(CH_2)_q CR^{23}R^{24}COR^{25}$ (wherein the groups $R^{23}$, $R^{24}$, $R^{25}$ and the integer q are as defined earlier), using standard reaction conditions to obtain variants of compound F-46, wherein R is $O(CH_2)_q CR^{23}R^{24}COR^{25}$, $R^K$ is H, and the remaining groups are as defined earlier.

Process 6-2 for the Preparation of Variants of Compound F-46 in which the Substituent $R^V$ Contains a Nitrogen Atom and is Connected to the Aromatic Ring through N.
(i) An appropriately substituted 1-(hydroxy-phenyl)-ethanone is nitrated by a standard procedure known in the literature or a modification thereof, to give a compound designated as F-34, which may be treated with $L(CH_2)_q CR^{23}R^{24}COR^{25}$ to obtain a variant of the compound F-46, wherein R is $O(CH_2)_q CR^{23}R^{24}COR^{25}$; $R^K$ is H; $R^V$ is $NO_2$; and the remaining groups are as defined earlier.
(ii) The nitro group in compound F-34 may be subjected to reductive acylation using catalytic hydrogenation in the presence of an appropriate acid anhydride and a catalyst, such as Raney Ni, or a noble metal (such as Pd or Pt) based catalyst, to give a compound designated as F-43. F-43 may be subjected to alkylation with $L(CH_2)_q CR^{23}R^{24}COR^{25}$ to obtain a variant of the compound F-46, wherein R is $O(CH_2)_q CR^{23}R^{24}COR^{25}$; $R^K$ and $R^L$ are H; $R^V$ is $NHCOR^{22}$; and the remaining groups are as defined earlier.
(iii) Alternatively, the OH group in compound F-34 may be protected with a suitable protecting group (Protecting groups in Org Synthesis, Ed, III, Green T. W. and Wuts. P. G. M, John Wiley & Sons Inc., p 246), such as a benzyl group, to obtain a compound designated as F-35. The compound F-35 may then be subjected to nitro group reduction using any conventional reduction method known in the art, for example, catalytic reduction using Raney Ni or Zn—$CoCl_2$ in DMF (Baruah. R. N. Ind. J. Chem., 33B, 758, 1994) to obtain an amino compound designated as F-36. The amino compound F-36 may be treated with an appropriate acyl chloride ($R^{21}COCl$), sulfonyl chloride ($R^{21}SO_2Cl$), or chloroformate ($R^{21}OCOCl$) followed by deblocking of the benzyl group using any conventional method known in the art to obtain a compound designated as F-37 in which $R^V$ is $NHCOR^{21}$, $NHSO_2NR^{21}R^{22}$, or $NHCOOR^2$, respectively. The compound F-37 may then be subjected to alkylation with $L(CH_2)_q CR^{23}R^{24}COR^{25}$ to obtain yet another variant F-46, wherein R is $O(CH_2)_q CR^{23}R^{24}COR^{25}$; $R^V$ is $NHCOR^{21}$, $NHSO^2NR^{21}R^{22}$ or $NHCOOR^{21}$; $R^K$ and $R^L$ are H; and the remaining groups are as defined earlier.

Process 6-3 for the Preparation of Variants of Compound F-46 from the Compound F-38:
(i) An appropriate 1-(halo-phenyl)-ethanone designated as F-38 may be subjected to nucleophilic displacement utilizing $HS(CH_2)_q CR^{23}R^{24}COR^{25}$ either directly or through Cu(I)-thiolate using a suitable modification of a reported procedure (R. Adams et. al., J. Amer. Chem. Chem., 81, 4927, 1959) to obtain a variant of compound F-46, wherein R is $S(CH_2)_q CR^{23}R^{24}COR^{25}$; and the remaining groups are as defined earlier.
(ii) Alternatively, the compound F-38 may be subjected to a C—C bond forming reaction, preferably vinyl coupling with $L-CH=CH(CH_2)_q CR^{23}R^{24}COR^{25}$, wherein L is a halogen and q is 0-5, using a Pd- or Ni-based catalyst to give compound F-46. F-46 may be hydrogenated to provide another variant of compound F-46, wherein R is $CH_2(CH_2)_q CR^{23}R^{24}COR^{25}$; q is 1-6; and the remaining groups are as defined earlier.

These variants of compound F-46 as prepared herein correspond to the compounds of the present invention of the general formula (I), wherein T in $T-(CH_2)_q CR^{23}R^{24}COR^{25}$ (formula 5) represents $CH_2$ or S.

Process 6-4 for the Preparation of Variants of Compound F-46 from Compound F-44 or F-45
(i) An appropriately substituted di- or tri-hydroxy benzene may be subjected to a Friedel-Crafts acylation with an anhydride, such as $R'(CH_2)_n CR^P R^E CO)_2O$, or an acid chloride such as $R'(CH_2)CR^P R^E COCl$, in the presence of a Lewis acid, such as $ZnCl_2$, $AlCl_3.HClO_4$, $BF_3.$etherate, $TiCl_4$, $FeCl_3$ or $I_2$, and in a solvent, such as $CHCl_3$, $CH_2Cl_2$, nitrobenzene or a $C_6$-$C_{14}$ hydrocarbon, at a temperature ranging from an ambient temperature to 150° C., to obtain a compound designated as F-45. Alternatively, the appropriately substituted di- or tri-hydroxy benzene may be subjected to a Fries rearrangement with a phenol ester of the type ArOCOCR$^D$R$^E$(CH$_2$)$_n$R' or a Houben-Hoesch acylation using a suitably substituted or unsubstituted nitrile R'(CH$_2$)$_n$, CR$^D$R$^E$CN according to a reported procedure (Junkichi Murai, Chem. Abstr. 50 981c, 1950) to obtain the compound F-45, wherein two or three of the groups R$^1$, R$^K$, R$^L$ and K are OH and the remaining groups are as defined earlier.

(ii) The resulting compound F-45 may be subjected to alkylation with L(CH$_2$)$_q$CR$^{23}$R$^{24}$COR$^{25}$ to give the desired mono-, di- or tri-alkylated products representing another variant of compound F-46 wherein two or three of the groups selected from: R$^1$, R$^K$, R$^L$ and R$^V$ are —O(CH$_2$)$_q$CR$^{23}$R$^{24}$COR$^{25}$ and the remaining groups are as defined earlier.

(iii) In an alternative approach, the appropriately substituted polyhydroxy phenol may be alkylated first with LCH$_2$CR$^{23}$R$^{24}$COR$^{25}$ to obtain a compound designated as F-44, wherein two or three of the groups selected from: R, R$^K$, R$^L$ and R$^V$ are —O(CH$_2$)$_q$CR$^{23}$R$^{24}$COR$^{25}$, and the remaining groups are as defined earlier. The intermediate F-44 may be subjected to a Friedel-Crafts acylation with [R'(CH$_2$)$_n$CR$^D$R$^E$CO)$_2$O] or acid chloride [R'(CH$_2$)CR$^D$R$^E$COCl] in presence of a catalyst, such as ZnCl$_2$, I$_2$, HClO$_4$ or, most preferably, Zn powder (see Synth. Commun. 28, 2203, 1998) to obtain the desired variants of the compound F-46.

These variants of compound F-46 as prepared herein correspond to the compounds of the present invention of the general formula (I), in which the aromatic ring in R$^G$ is substituted with at least two T-(CH$_2$)CR$^{23}$R$^{24}$COR$^{25}$ groups.

Figure G

The preparation of variants of compound G-53 (used in the synthesis of key compounds A-8, E-32 and B-20) via different synthetic routes is described below by the processes designated as process 7-1, which is schematically presented in Figure G. The groups R, R$^K$, R$^L$ and R$^V$ in said compound G-53 and the remaining groups are as defined earlier.

Process 7-1 for the Preparation of Compound G-53:

(i) Unsubstituted or substituted 1-(2,4-dihydroxyphenyl) ethanone may be subjected to various reactions similar to those described in the above process 6-1, such as halogenation of the compound 1-(2,4-dihydroxyphenyl) ethanone to obtain the mono-substituted compound designated as G-49 and the di-substituted compound G-50 (R$^L$/R$^V$=Cl/Br/I).

(ii) The compounds G-49 and G-50 may be converted into a ether or a thioether derivative where R$^L$/R$^V$=OR$^{21}$/SR$^{21}$ in a manner similar to that described in process 6-1 for the conversion of compounds F-39 and F-40 to the compound designated as F-41.

(iii) The thioether may be oxidized to a sulfoxide or sulfone where R$^L$/R$^V$ is S(=O)R$^{21}$ or S(=O)$_2$R$^{21}$ with a suitable oxidizing agent.

(iv) The unsubstituted or appropriately substituted 1-(2,4-dihydroxy-phenyl)ethanone may be subjected to a Friedel-Crafts alkylation to obtain the compound designated as G-48, wherein R$^K$ is OH.

(v) Friedel-Crafts acylation of G-47 (which is obtained by the reduction of 1-(2,4-dihydroxy-phenyl)ethanone by a standard procedure) or an appropriately substituted polyhydroxy phenol, such as substituted resorcinol or trihydroxy phenol, with a suitable anhydride, such as (R'(CH$_2$)$_n$, CR$^D$R$^E$CO$_2$)O, or a suitable acid chloride, such as R'(CH$_2$)$_n$CR$^D$R$^E$COCl, gives the compounds designated as R'-48 and G-54. Alternatively, the compound G-47 or an appropriately substituted polyhydroxy phenol may be subjected to a Houben-Hoesch acylation with R'(CH$_2$)$_n$CR$^D$R$^E$CN to give the compounds designated as G-48 or G-54, wherein R$^K$ is OH and the remaining groups are as defined earlier.

(vi) The Claisen rearrangement of phenolic allyl ether G-56, wherein R$^a$, R$^b$, R$^c$, R$^d$ and R$^e$ are independently selected from: C$_1$-C$_5$ alkyl and C$_7$-C$_{12}$ alkylaryl, resulted in G-57. The double bond reduction of G-57 according to a standard procedure well known in the art gives compound G-58, wherein its groups are as defined earlier.

(vii) The compounds G-54 and G-58 may be reduced partially or fully by a standard procedure to give the compound designated as G-55, wherein R$^F$ is (H, OH) or (H, H) and the remaining symbols are as defined.

(viii) All the compounds G-48 to G-52, G-54, G-55, G-58 as well as 1-(2,4-dihydroxy-phenyl)ethanone, are treated with L-(CH$_2$)$_q$CR$^{23}$R$^{24}$COR$^{25}$ using a standard procedure to give a variant of compound G-53, wherein R$^K$ is OH; one or more of the groups R, R$^L$ and R$^V$ represent O(CH$_2$)$_q$CR$^{23}$R$^{24}$COR$^{25}$; and the remaining groups are as defined earlier.

(ix) The compounds G-53 in which R$^K$ is OH, may be further subjected to substitution reactions using an appropriate alkyl halide, acyl halide, sulfonyl chloride or chloroformate, to obtain variants of compound G-53, wherein R$^K$ is OCOR$^{21}$, OS(=O)$_2$R$^{21}$ or —OCOOR$^{21}$; one or more of the groups R, R$^L$ and R$^V$ are O(CH$_2$)$_q$CR$^{23}$R$^{24}$COR$^{25}$; and the remaining symbols are as defined earlier.

Figure H

The preparation of variants of compounds H-63, H-71 and H-72, wherein R$^K$ and/or R$^U$ are/is OH or substituted OH (used in the synthesis of key intermediates A-8, B-20 and E-32) via different synthetic routes is described below in the processes designated as 8-1 and 8-2, which are schematically presented in Figure H.

Process 8-1 for the Preparation of Compound H-63 and its Variants:

(i) An appropriately substituted dihydroxy benzaldehyde, such as 3,4-dihydroxy benzaldehyde, may be subjected to a sequence of reaction steps such as alkylation with L(CH$_2$)$_q$CR$^{23}$R$^{24}$COR$^{25}$ to obtain the compound designated as H-59, wherein R is O(CH$_2$)$_q$R$^{23}$R$^{24}$COR$^{25}$. The compound H-59 may then be subjected to a Baeyer-Villiger oxidation (I. M. Godfrey et. al, J. C. S. Perkin I, 1353, 1974) followed by hydrolysis of the resulting formyl ester and subsequent alkylation of phenolic OH to obtain the compound designated as H-60, wherein R$^a$, R$^b$ and R$^c$ are independently selected from: C$_1$-C$_5$ alkyl and C$_7$-C$_{12}$ alkyl aryl.

(ii) The compound H-60 may be subjected to a Friedel-Crafts acylation (H. M. Meshram. et. al., Synth. Commun, 28, 2203, 1998) with R'(CH$_2$)$_n$CR$^D$R$^E$COCl in the presence of a Lewis acid catalyst, such as Zn, BF$_3$.etherate, FeCl$_3$, AlCl$_3$ and ZnCl$_3$, preferably Zn, in the presence of at least one organic solvent selected from, for example: toluene, benzene, heptane, kerosene, CS$_2$, CCl$_4$, and nitrobenzene, preferably toluene, and in situ cleavage of the allyl group to obtain the desired compound H-63, wherein R and R$^V$ are O(CH$_2$)$_q$CR$^{23}$R$^{24}$COR$^{25}$; R$^K$ is OH; R$^L$ is H; R$^F$ is O; and the remaining groups are as defined earlier.

(iii) A variant of compound H-63 (wherein R$^K$ represent OR$^{21}$, OCOR$^{21}$, OS(=O)$_2$R$^{21}$ or OCOOR$^{21}$, and the remaining groups are as defined earlier) may be obtained by treatment of the compound H-63, wherein R$^K$ is OH, with an appropriate alkyl halide, acyl halide, sulfonyl halide or chloroformate under standard reaction conditions well known in the art.

(iv) Yet another variant of compound H-63, wherein R and $R^V$ represent $O(CH_2)_q CR^{23}R^{24}COR^{25}$; $R^F$ is (H, H); $R^D$ and $R^E$ are H; and the remaining groups are as defined earlier, may be prepared by subjecting the compound H-59 to a Wittig reaction to obtain the compound designated as H-64 which on hydrogenation gives the desired variant.

(v) An appropriately substituted 1-(2,5-dihydroxy-phenyl)-ethanone may be alkylated with L-$(CH_2)_q$ $CR^{23}R^{24}COR^{25}$ to give a variant of compound H-63 (wherein R is H; $R^V$ is $O(CH_2)_q CR^{23}R^{24}COR^{25}$; $R^F$ is O; and the remaining groups are as defined earlier).

(vi) Another variant of compound H-63 may be obtained by subjecting the compound H-60 to a Friedel-Crafts alkylation with R'$(CH_2)_n CR^D R^E CH_2L$, wherein R' is H, NHZ or L and L is a leaving group, such as halogen, OMes or OTs, to obtain the compound designated as H-61, followed by the removal of the allyl group from the resulting compound H-61 to obtain another variant of compound H-63, wherein $R^F$ represents (H, H); R and $R^V$ are $O(CH_2)_q CR^{23}R^{24}COR^{25}$; $R^K$ is OH; and the remaining groups are as defined earlier.

(vii) Yet another variant of compound H-63 may be obtained by reducing the carbonyl group in compound H-63 (wherein $R^F$ is O) by a standard procedure known in the art to give compound H-63, wherein $R^F$ represents (H, OH) or (H, H), and the remaining groups are as defined earlier.

(viii) The allyl group in compound H-61 may be removed by a standard method to give the compound designated as H-62, wherein $R^F$ is (H, H). The compound H-62 may be subjected to a substitution reaction with an appropriate alkyl halide, acyl halide or chloroformate leading to the formation of a variant of the compound H-63, wherein $R^F$ is (H, H); $R^K$ represents $OR^{21}$; $OCOR^{21}$; $OCOR^{21}$; $OS(=O)_2R^{21}$ or $OCOOR^{21}$; and the remaining groups are as defined earlier.

Process 8-2 for the Preparation of Variants of Compound H-71 and H-72 (wherein $R^K$ and/or $R^U$ are/is OH or Substituted OH):

(i) Phloroglucinol may be subjected to O-alkylation (Chem. Abstr., 50, 977d, 1956) to obtain 5-methoxy-1, 3-benzenediol, designated as H-65.

(ii) Alternatively, phlororoglucinol may be converted to 5-benzyloxy-1,3-benzenediol designated as H-68 by following a sequence of reactions according to a reported procedure (Haruo. Kawamoto. et. al., Synth. Commun. 26, 531, 1996).

(iii) The compounds H-65 and H-68 thus obtained may be subjected to a novel modification of the Houben-Hoesch reaction in which a suitably protected amino nitrile of the type R'$(CH_2)_n CR^D R^E CN$, wherein R' is H, NHZ or L, and L is a leaving group, such as halogen, OMes or OTs, may be treated with dry HCl in presence of a Lewis acid, such as $ZnCl_2$ or $BF_3$.etherate, in a solvent, such as ether, THF or dioxane, followed by hydrolysis of the resulting imine hydrochloride to obtain the compound designated as H-69, wherein its groups are as defined earlier.

(iv) The compound H-69 may be subjected to selective alkylation with L-$(CH_2)_q CR^{23}R^{24}COR^{25}$, wherein L is a leaving group, such as halogen, OMe-s or OTs, to give the compound designated as H-70, wherein R is $O(CH_2)_q CR^{23}R^{24}COR^{25}$, and the remaining groups are as defined earlier.

(v) The compound H-70 may be subjected to further reactions such as O-alkylation, O-sulphonation, O-acylation or carbonate formation reaction as described earlier resulting in variants of the compound H-70 designated as H-71, wherein $R^U$ represents $OR^{21}$, $OCOR^{21}$, $OS(=O)_2R^{21}$ or $OCOOR^{21}$; and the remaining groups are as defined earlier.

(vi) The compound H-71 in which R' is NHZ and optionally $R^K$ is $OCH_2Ph$ may be subjected to a standard deblocking reaction known in the art, to obtain the amino compound designated as H-72, wherein B is halogen, acetate or formate.

Figure J

The preparation of compounds J-74 and J-77 (used in the synthesis of key intermediates A-8, B-20 and E-32) via different synthetic routes is described below by the processes designated as process 9-1, which is schematically presented in Figure J. In the compounds referred to below, the groups R', $R^F$, $R^D$, $R^E$, and n are as described earlier. R is $T(CH_2)_q$ $CR^{23}R^{24}COR^{25}$ or $OCH_2$Phenyl and $R^K$, $R^L$, $R^U$ and $R^V$ are independently selected from the substituent groups provided in the definition of $R^G$.

Process 9-1 for the Preparation of Compounds J-74 and J-77

(i) Appropriately substituted compounds F-46, G-53, H-63, H-70 and H-71 (in all these compounds n is 0, R'=$R^D$=$R^E$=H) (prepared by processes described hereinabove) may be subjected to a standard α-bromination reaction, most preferably by using bromine in an appropriate solvent, for example, an organic solvent such as, optionally in the presence of a catalyst, such as $AlCl_3$ or other Lewis acid, to obtain the mono-bromo compound designated as J-74. Alternatively, the bromination may be carried out using $CuBr_2$ according to a known precedure (L C. King. et. al., J. Org. Chem., 29, 3459, 1964), leading to the formation of the mono bromo compound J-74.

(ii) The mono-bromo derivative J-74 may then be converted to a hexamine salt according to a reported procedure (L. M. Long. et al J. Amer. Chem. Soc., 71, 2473, 1949) which may in turn be subjected to a cleavage reaction using an aqueous acid optionally in presence of a lower alcohol, such as MeOH, EtOH, or iPrOH, to obtain the amine hydrochloride designated as J-77, and a small amount of acid ($R^{25}$ is OH) as a side product, wherein $R^F$ is O; $R^D$ and $R^E$ are H; n is 0; and the remaining groups are as described.

(iii) The compound J-77, if required, may be purified by treating the mixture of the compound and the residual acid with a suitable reagent, such as $(Boc)_2O$, for protecting the amino group in an alkaline condition to obtain the separated compounds designated as J-75 (wherein $R^F$ is O; $R^D$ and $R^E$ are H; n is 0) and J-76, (wherein $R^F$ is O; $R^D$ and $R^E$ are H; n is 0; and R and/or $R^V$=$T(CH_2)_q CR^{23}R^{24}COOH$). Deprotection of the compound J-75 may be carried out using a standard deprotecting reagent known in the art of peptide synthesis to obtain the desired compound J-77.

(iv) Likewise, the other compound J-76 (wherein $R^{25}$ is OH) may be converted to its corresponding ester by treatment with $R^5OH$ or $R^5SH$, in the presence of DCC and DMAP according to a reported procedure (Alfred. Hassner. et. al. Tetrahedron Lett. 4475, 1978) to obtain a variant of the compound J-75, wherein R is $O(CH_2)_q$ $CR^{23}R^{24}COR^{25}$, and $R^{25}$ is OH.

(v) Alternatively, the compound J-76 in which $R^{25}$ is OH may be converted to an amide by treatment with an appropriate amine of formula $R^5R^6NH$ in which $R^5$ and $R^6$ are as defined, using a standard peptide coupling procedure resulting in a variant of the compound J-75.

(vi) Deprotection of the Boc group of the compound J-75 may be carried out using formic acid, TFA or HCl in an organic solvent in presence of anisole or thioanisole to give the compound J-77, wherein $R^F$ is O; $R^D$ and $R^E$ are H; n is 0; and the remaining groups are as defined earlier.

(vii) Alternatively, the compounds F-46, G-53, H-63, H-70 and H-71 [wherein R' is L and $R^F$ is O or (H, H)] may be converted to a hexamine salt (see L. M. Long. et al J. Amer. Chem. Soc., 71, 2473, 1949), which may be subjected to cleavage using aqueous acid, optionally in presence of a lower alcohol, such as MeOH, EtOH or iPrOH, to obtain the corresponding amine hydrochloride J-77. Purification of said amine hydrochloride, if required, may be carried out by treating the mixture of compound J-77 and acid with a suitable reagent such as $(Boc)_2O$ for protecting the amino group in an alkaline condition to obtain the compound J-73, wherein $R^F$ is O or (H, H); and the remaining groups are as defined earlier.

(viii) Deprotection of the compound J-73 may be carried out using a standard deprotecting reagent known in the art of peptide synthesis to obtain the compound J-77, wherein $R^F$ is O or (H, H) and the remaining groups are as defined earlier.

(ix) Further, if required, functional group modification such as alkylation, acylation, sulphonation or carbonate formation may be carried out on the OH, SH and/or $NHR^{21}$ group(s) of the compound J-75, wherein one or more of the groups $R^K$, $R^L$, $R^U$ and $R^V$ independently represent OH, SH or $NHR^{21}$ to obtain the desired variant of the compound, wherein one or more of the groups $R^K$, $R^U$ and $R^V$ independently represent $OR^{21}$, $SR^{21}$ or $NR^{21}R^{22}$.

(x) The thus obtained intermediate J-75 may be subjected to deprotection of the Boc group leading to the formation of the variant of compound J-77, wherein all its groups are as defined earlier.

(xi) Variants of the compound J-75, wherein one or more of the groups $R^K$, $R^L$ $R^V$ and $R^U$ represent $SR^{21}$, may be subjected to functional group modification, such as oxidation of the thiol ether to give a variant of compound J-75, wherein one or more of the groups $R^K$, $R^L$ $R^V$ and $R^U$ represent $S(=O)R^{21}$ or $S(=O)_2R^{21}$, which may further be subjected to Boc deblocking leading to the formation of variant J-77, wherein all its groups are as defined earlier.

(xii) Variants of the compound J-75, wherein one or more of the groups $R^K$, $R^L$ $R^V$ and $R^U$ represent $NO_2$, may be subjected to reduction to obtain the corresponding amine, which may further be treated with an appropriate acyl halide, sulfonyl halide or chloroformate to give a variant of compound J-75, wherein one or more of the groups $R^K$, $R^L$ $R^V$ and $R^D$ represent $NHCOR^{21}$, $NHSO_2R^{21}$ or $NHCOOR^{21}$, which in turn may be subjected to removal of the Boc group leading to the formation of variant compound J-77, wherein all its groups are as defined earlier.

(xiii) Yet another approach for the preparation of a variant of the compound J-77, wherein $R^F$ is O; $R^D$ and $R^E$ are H; n is 0; R is $OCH_2Ph$; and the remaining symbols are as defined earlier, may involve the preparation of a compound designated as J-78 from an appropriately substituted 1-(hydroxy-phenyl)ethanone through phenolic OH group protection (preferably by a benzyl group) followed by the similar sequence described earlier. After deprotection of the benzyl group, the phenolic OH group may be alkylated with $L-(CH_2)_qCR^{23}R^{24}COR^{25}$ to obtain the compound J-75. Finally, both compounds J-75 and J-78 may be subjected to removal of the Boc group to obtain variants of the compound J-77. The compound J-77 in which R is $OCH_2Ph$ is used in the synthesis of fragment B-20.

Figure K

The preparation of compounds K-81, K-83, and K-84 (used in the synthesis of key intermediates A-8 and E-32) via different synthetic routes is described below by the process designated as process 10-1, which is schematically presented in Figure K. The groups n, $R^D$, $R^E$, q and T in said compounds have the same meaning as described for the general formulae (I) and Q represents CH or N.

Process 10-1 for the Preparation of Compounds K-81, K-83 and K-84:

(i) N-Protected 4-hydroxy piperidine may be treated with $L(CH_2)_qCR^{23}R^{24}COR^{25}$ in which L and q are as defined earlier, to obtain a compound designated as K-79, wherein T is O.

(ii) The hydroxy group of the N-protected 4-hydroxy piperidine may be converted into a suitable leaving group, such as OMes or OTs, followed by treatment with an amine of the type $H_2N(CH_2)_qCR^{23}R^{24}COR^{25}$ or a thiol of the type $HS(CH_2)_qCR^{23}R^{24}COR^{25}$ to give a variant of compound K-79, wherein T is NH or S.

(iii) Another variant of the compound K-79, wherein T is $-CH_2-$, may be obtained by catalytic hydrogenation of the corresponding pyridine derivative, preferably using $PtO_2$ in acetic acid, to obtain an amine followed by protection of the resulting amine with a suitable protecting group such as Boc or Z.

(iv) Alternatively, isonicotinic acid may be reduced to isonipecotic acid according to a reported procedure (U.S. Pat. No. 7,399,68), which after N-protection with a suitable protecting group, preferably Z or Boc, may be converted to an aldehyde designated as K-80 according to a reported procedure (M. S. Egbertson et al, J. Med. Chem., 37, 2537, 1994). The aldehyde may then be treated with an appropriate Wittig reagent to obtain a variant of compound K-79, wherein $T(CH_2)_q$ represents $-CH=CH(CH_2)_{q-1}$. The double bond may be subjected to any conventional reduction method known in the art, preferably hydrogenation resulting in a variant of compound K-79, wherein T is $-CH_2-$.

(v) The removal of the Z or Boc group may be carried out using a standard procedure known in the art to obtain a compound designated as K-81, wherein all its groups are as defined earlier.

(vi) Commercially available piperazine or its derivatives may be converted to a compound designated as K-83, in a similar manner as described above in this process. A final deprotection step to remove the Boc or Z group with an appropriate deprotecting reagent known in the art provides the amino compound K-83.

(vii) Compounds K-83 and K-81 may be coupled with a suitably protected amino acid, such as Z- or Boc-NH $(CH_2)_nCR^DR^ECOOH$ (wherein the symbols are as defined earlier), using a standard peptide coupling method, preferably DCC-HOBt or IBCF-NMM, to obtain the compound designated as K-82, which may be further subjected to a standard Boc or Z deprotection to obtain the compound K-84, wherein Q is CH or N; and the remaining groups are as defined earlier.

The compounds K-81, K-83, and K-84 obtained by the above process are required for the preparation of compounds of general formula (I), in which $R^G$ represents substituted piperidine and substituted piperazine.

Compounds according to the general formula (I) can be used to antagonize the activity of GP IIb/IIIa receptors and are beneficial pharmaceutical compounds for the treatment of various thrombotic diseases. In the context of the present invention, compounds of this invention may be administered to patients, where prevention of thrombosis by inhibiting the binding of fibrinogen to the platelet membrane glycoprotein complex GPIIb/IIIa receptor is desired. This would include patients with cardiovascular (arterial and/or venous) and cerebrovascular thromboembolic diseases, under which the following can be included (though are not limited to):
1. arterial thromboembolism
2. cerebral thromboembololism
3. cerebral arterial thrombosis
4. coronary thrombosis
5. deep vein thrombosis
6. diabetes-related thromboembolic disorders
7. sudden ischemic emergencies
8. myocardial infarction
9. pulmonary thromboembolisms
10. stroke
11. thrombophlebitis
12. transient ischemic attack
13. unstable angina and venous thrombosis
14. kidney thromboembolism These compounds are useful during surgery on peripheral arteries (arterial grafts, carotid endarterectomy) and cardiovascular surgery where manipulation of arteries and organs, and/or the interaction of platelets with artificial surfaces, such as surgical instruments and the heart-lung machine leads to platelet aggregation. The aggregated platelets may form thrombi and thromboemboli. Compounds of this invention may be administered to these surgical patients to prevent such complications. (S. D. Berkowitz, American Heart Journal, 2001, 142, 7-13).

Extracorporeal circulation is routinely used for cardiovascular surgery in order to oxygenate blood. Platelets adhere to surfaces of the extracorporeal circuit. Adhesion is dependent on the interaction between GP IIb/IIIa receptors on the platelet membranes and fibrinogen adsorbed to the surface of the circuit (Gluszko et al., Am. J. Physiol., 1987, 252(H), 615-621,). Platelets released from an artificial surface show impaired hemostatic function. Compounds of this invention may be administered to prevent this adhesion.

Other applications of these compounds include (though are not limited to):
1. prevention of platelet thrombosis
2. thromboembolism and reocclusion during and after thrombolytic therapy and prevention of platelet thrombosis
3. thromboembolism and reocclusion after angioplasty or coronary artery bypass surgery
4. prevention of myocardial infarction
5. prevention of blood clots after orthopedic surgery Cell adhesion (cell-cell or cell-matrix) involves processes that require proteins like fibrinogen, fibronectin, vitronectin and vWF. These proteins bind to the integrin superfamily of receptors to produce their action. Thus, GP IIb/IIIa antagonists which antagonize the integrin superfamily of receptors may be useful in diseases, other than the above, which involve cell adhesion processes. Such diseases include (though are not limited to):
1. adult respiratory distress syndrome
2. allergies
3. asthma
4. rupture of atherosclerotic plaques
5. autoimmune diseases
6. inflammation,
7. bone degradation
8. contact dermatitis
9. diabetic retinopathy
10. eczema
11. graft versus host disease
12. inflammatory bowel disease
13. metastasis
14. organ transplantation rejection
15. osteoarthritis
16. osteoporosis
17. psoriasis
18. rheumatoid arthritis
19. septic shock
20. tumors The present invention therefore also relates to the compounds of the general formula (I) and/or their pharmaceutically acceptable salts and/or their pro-drugs for use as pharmaceuticals (or medicaments), to the use of the compounds of the general formula (I) and/or their physiologically tolerable salts and/or their pro-drugs for the manufacture of medicaments for the production of pharmaceuticals for the inhibition of GP IIb/IIIa receptors or for the therapy or prophylaxis of the diseases and conditions mentioned above, for example for the production of pharmaceuticals for the therapy and prophylaxis of cardiovascular (arterial and/or venous) and cerebrovascular thromboembolic diseases, etc., and to methods of treatment aiming at such purposes including methods for said therapies and prophylaxes. The methods of treatment comprise administering a compound of general formula (I) and/or its physiologically tolerable salts and/or its pro-drugs to a mammal, especially a human. The present invention furthermore relates to pharmaceutical compositions that contain an effective amount of at least one compound of the general formula (I) and/or its physiologically tolerable salts and/or its prodrugs in addition to a customary pharmaceutically acceptable carrier, and to a process for the production of a pharmaceutical, which comprises bringing at least one compound of general formula (I) into a suitable administration form using a pharmaceutically suitable and physiologically tolerable excipient and, if appropriate, further suitable active compounds, additives or auxiliaries. The pharmaceutical preparation comprises the compound of general formula (I) in an amount adequate to antagonize GP IIb/IIIa receptors. The present invention also relates to a method for the preparation of a medicament for the treatment or prevention of disorders associated with activation of GP IIb/IIIa receptors, characterized in that at least one compound of the general formula (I) is used as the pharmaceutically active substance.

The pharmaceuticals can be administered orally, for example in the form of pills, tablets, coated tablets, capsules, granules or elixirs. Administration, however, can also be carried out rectally, for example in the form of suppositories, or parentally, for example intravenously, intramuscularly or subcutaneously, in the form of injectable sterile solutions or suspensions, or topically, for example in the form of solutions or transdermal patches, or in other ways, for example in the form of aerosols or nasal sprays or as precoated stents.

The pharmaceutical preparations according to the invention are prepared in a manner known per se and familiar to one skilled in the art. Pharmaceutically acceptable inert inorganic and/or organic carriers and/or additives can be used in addition to the compound(s) of the general formula (I) and/or its (their) physiologically tolerable salts and/or its (their) prodrugs. For the production of pills, tablets, coated tablets and hard gelatin capsules it is possible to use, for example, lactose, corn starch or derivatives thereof gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, preferably about 5 to 70%, most preferably from about 10 to about 30% by weight of the compounds of the general formula (I) and/or their physiologically tolerable salts and/or their prodrugs. The amount of the active ingredient of the general formula (I) and/or its physiologically tolerable salts and/or its prodrugs in the oral pharmaceutical preparations normally is from about 5 to 200 mg. The dose of the compounds of this invention, which is to be administered, can cover a wide range. The dose to be administered orally daily is to be selected to suit the desired effect. About 10 to 100 mg are preferably administered orally daily per patient. If required, higher or lower daily doses can also be administered. For intravenous administration the most preferred dose will range from about 0.01 to 3 mg per patient. Actual dosage levels of the active ingredients in the pharmaceutical compositions of this invention may be varied so as to obtain an amount of the active ingredient that is effective in achieving the desired therapeutic response for a particular patient, composition and mode of administration without being toxic to the patient. The effective amount of a compound of the present invention, which may be administered in a single dose or in the form of individual divided doses, may be determined by one of ordinary skilled in the art. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredients of the general formula (I) and/or their physiologically acceptable salts and/or prodrugs and to carrier substances, the pharmaceutical preparations can contain additives such as, for example, fillers, antioxidants, dispersants, emulsifiers, defoamers, flavor corrigants, preservatives, solubilizers or colorants. They can also contain two or more compounds of the general formula (I) and/or their physiologically tolerable salts and/or their prodrugs. Furthermore, in addition to at least one compound of the general formula (I) and/or its physiologically tolerable salts and/or its prodrugs, the pharmaceutical preparations can also contain one or more other therapeutically or prophylactically active ingredients.

The compounds of the present invention may be used as drugs in the treatment of thrombotic diseases either alone or as part of combined therapies. For instance, the compounds of the present invention may be used in combination with known antithrombotic agents. If formulated as a fixed dose, such combination products employ the compounds of the present invention within the dosage range described above and the other pharmaceutically active agent within its approved dosage range. For example, in the $2^{nd}$ SYMPHONY trial patients were treated with sibrafiban and aspirin. In the NICE-4 trial, a combination of abciximab and enoxaparin was studied (Bhatt, D. L. and Topol, E. J., JAMA, 2000, 284, 1549-1558).

It is understood that modifications that do not substantially affect the activity of the various embodiments of this invention are included within the invention disclosed herein. Accordingly, the following examples are intended to illustrate but not to limit the present invention.

The examples as described below are given by way of illustration only and are not to be construed as limiting the invention in any way in as much as many variations of the invention are possible within the meaning of the invention.

EXAMPLE 1

(4-{2-[5-Carbamimidoyl-1-oxo-1,3-dihydro-isoindol-2-yl]-acetyl}-phenoxy)-acetic acid methyl ester, acetic acid salt A solution of the compound of example 1i (1.49 g; 2.76 mmol) in MeOH (40 ml) was treated with ammonium acetate (0.86 g; 11 mmol), refluxed for 1 h, concentrated, purified using flash chromatography (RP-18 column, MeOH: 0.2% AcOH in water/1:1) and crystallized using dry MeOH-ether to obtain the title compound. Yield, 0.08 g (6.6%); mp, 181-182° C.; MS (ESI): 404 ($M^+$+$Na^+$), 382 ($M^+$+1); analysis: $C_{22}H_{23}N_3O_7$, $0.5H_2O$ requires, C, 58.66; H, 5.55; N, 9.33. found: C, 58.31; H, 5.23; N, 9.72%.

EXAMPLE 1a

2-Methyl-4-nitro-benzoic acid ethyl ester

Thionyl chloride (48 ml) was added slowly to 2-methyl-4-nitro-benzoic acid (85 g; 0.469 mol) and the reaction mixture was refluxed (4-6 h) to give a clear solution. It was brought to room temperature then chilled to 0° C. Dry alcohol (150 ml) was added slowly with vigorous stirring and the reaction mixture was refluxed for 30 min. It was concentrated, treated with crushed ice, $NaHCO_3$ and extracted with EtOAc. The EtOAc layer was washed with water, brine, dried ($Na_2SO_4$), concentrated, purified using flash chromatography (silica gel, 10% EtOAc-PE 60-80° C.) and crystallized using EtOAc-PE 60-80° C. to obtain the title compound as light yellow crystals. Yield, 83.8 g (85.4%); mp, 68-71° C.; IR: 2950, 1720, 1525; MS (EI): 209($M^+$), 192. 181, 163 (100%), 89.

EXAMPLE 1b

4-Amino-2-methyl-benzoic acid ethyl ester

Compound of example 1a (41 g; 196 mmol) in MeOH (500 ml) was hydrogenated using Raney Ni (2 g) at 50 psi for 2 h. The solution was filtered free off the catalyst, concentrated and purified using flash chromatography (silica gel, 10%

EtOAc-PE 60-80° C., 30% EtOAc-PE 60-80° C.) to obtain the title compound. Yield, 33 g (93.94%); mp, 77-80° C., MS (EI): 179 (M$^+$), 134 (100%), 106, 77; analysis: $C_{10}H_{13}NO_2$ requires, C, 67.02; H, 7.31; N, 7.82. found, C, 67.25; H, 7.26; N, 7.57%.

EXAMPLE 1c

4-Cyano-2-methyl-benzoic acid ethyl ester

Compound of example 1b (32 g; 178 mmol) was treated with conc. HCl (64 ml) and water (320 ml), cooled to 0° C., then treated to a dropwise addition of an aqueous solution of $NaNO_2$ (12.33 g; 178 mmol, 320 ml) over a period of 1 h at 0-5° C. The diazonium salt solution was neutralized with $Na_2CO_3$ and added slowly to an aqueous solution of KCN and CuCN (13.38 g; 204.4 mmol, 19.34 g; 204.4 mmol, 500 ml), maintained at 0-5° C., with vigorous stirring over a period of 1 h. The reaction mixture was stirred for 30 min. at 0-5° C. and left stirring overnight at room temperature. It was subsequently heated on steam bath for 30 min., treated with an aqueous 10% $FeCl_3$ solution and extracted with EtOAc (3×500 ml). The organic layer was washed with water, brine, dried ($Na_2SO_4$), concentrated, purified using flash chromatography (silica gel, 5% EtOAc-PE 60-80° C.) and crystallized using EtOAc-PE 60-80° C. to obtain the title compound as a pure white solid. Yield, 20 g (59.2%); mp, 64-65° C.; MS (EI): 189 (M$^+$), 144 (100%), 116, 89; analysis: $C_{11}H_{11}NO_2$, $0.5H_2O$ requires C, 66.70; H, 6.06; N, 7.07. found: C, 67.11; H, 5.88; N, 6.88%.

EXAMPLE 1d

2-Bromomethyl-4-cyano-benzoic acid ethyl ester

NBS (22.8 g; 128 mmol) was added to a solution of the compound of example 1c (22 g; 116.4 mmol) in $CCl_4$ (1 lit.), followed by a catalytic amount of AIBN (~10 mg). The reaction mixture was refluxed (6-7 h), cooled to room temperature, washed with water, brine, dried ($Na_2SO_4$), concentrated, purified using flash chromatography (5% EtOAc-PE 60-80° C.) and crystallized using EtOAc-PE 60-80° C. to obtain the title compound. Yield, 15.8 g (50.64%); mp, 70-72° C.; analysis: $C_{11}H_{10}BrNO_2$, $0.5H_2O$ requires C, 49.25; H, 3.73; N, 5.22. found: C, 49.27; H, 3.62; N, 4.79%.

EXAMPLE 1e (4-{2-Amino-acetyl}-phenoxy)-acetic acid methyl ester, hydrochloride

EXAMPLE 1f (4-{2-tert-Butoxycarbonylamino-acetyl}-phenoxy)-acetic acid

Hexamine (7.56 g; 54 mmol) was added with stirring to a solution of (4-{2-Bromo-acetyl}-phenoxy)-acetic acid methyl ester (15 g; 52.3 mmol) in dry chloroform (300 ml) and the reaction mixture was stirred overnight. Dry ether (250 ml) was added and the white solid that separated was filtered, washed with $CHCl_3$-Ether 1:1 (2×30 ml), dried (22 g), treated with MeOH (35 ml), conc.HCl (17.5 ml) and stirred overnight at room temperature. The reaction mixture was concentrated, filtered and the solid obtained was washed with cold water (5 ml), ether, ethyl acetate and dried to obtain the title compound of example 1e (5.2 g, 39%). The filtrate was diluted with water (100 ml) and neutralised with $NaHCO_3$ at 0° C. A solution of $(Boc)_2O$ (8.7 g) in dioxane (100 ml) was added and the mixture was stirred for 2 h, concentrated and extracted with EtOAc. The organic layer was washed with water, brine, dried ($Na_2SO_4$) and concentrated to obtain the crude product, which was hydrolysed with 1N methanolic NaOH for 1 h. The reaction mixture was processed as is routinely done and crystallised using EtOAc-PE 60-80° C. to obtain the title compound of example 1f (8.1 g, 50%); mp, 51-53° C.; MS (ESI$^+$): 332 (M$^+$+Na$^+$) 310 (M$^+$+1), (ER) 308 (M$^+$-1).

EXAMPLE 1g (4-{2-[5-Cyano-1-oxo-1,3-dihydro-isoindol-2-yl]-acetyl}-phenoxy)-acetic acid methyl ester $NaHCO_3$ (4.6 g; 54.8 mmol) was added with stirring to a solution of the compound of example 1e (5 g; 16.44 mmol) in dry DMF (50 ml) at −25° C. Subsequently compound of example 1d (3.673 g; 13.7 mmol) in dichloromethane (50 ml) was added drop wise over a period of 1 h. The reaction mixture was maintained at −25° C. for an additional 30 min., gradually brought to room temperature and stirred overnight. It was diluted with water and extracted with EtOAc (3×30 ml). The combined organic layers was washed with water, dilute aqueous HCl, brine, dried ($Na_2SO_4$), concentrated and purified using flash chromatography (silica gel, 5-10% $CH_3CN$ in $CHCl_3$) to obtain the title compound. Yield, 1.5 g (30.12%); mp, 185-187° C.; MS (EI): 364 (M$^+$), 193 (100%), 171, 116; analysis: $C_{20}H_{16}N_2O_5$ requires, C, 65.93; H, 4.43; N, 7.69. found, C, 65.64; H, 4.44; N, 7.22%.

EXAMPLE 1h (4-{2-[1-Oxo-5-thiocarbamoyl-1,3-dihydro-isoindol-2-yl]-acetyl}-phenoxy)acetic acid methyl ester $H_2S$ gas was passed through a solution of the compound of example 1g (0.6 g, 1.65 mmol) in pyridine/$Et_3N$::5/1(50 ml) for 30 min. to obtain an amber coloured solution which was stirred at room temperature till the starting material was consumed. It was concentrated and purified using flash chromatography (silica gel, 3% MeOH in $CHCl_3$) to obtain the title compound as a pale yellow solid. Yield, 0.628 g (95.73%); $^1$H-NMR (DMSO-D$_6$): 3.72 (3H, s, OC$\underline{H}_3$), 4.56, 4.98, 5.13 (6H, 3×s, 3×C$\underline{H}_2$), 7.12 (2H, d, J=8.7, H-$\overline{2'}$ & H-5'), 7.75 (1H, d, J=7.75, H-$\overline{7}$), 7.96 (1H, dd, J=7.75, 2.0, H-6), 8.10 (1H, d, J=2.0, H-4), 8.05 (2H, d, J=8.72, H-3' & H-5'), 9.70, 10.10 (2H, 2×s, N$\underline{H}_2$).

EXAMPLE 1i (4-{2-[5-Methylsulfanylcarbonimidoyl-1-oxo-1,3-dihydro-isoindol-2-yl]-acetyl}-phenoxy)-acetic acid methyl ester, hydro iodide A solution of the compound of example 1h (0.628 g; 15.78 mmol) and iodomethane (1 ml) in dry acetone (45 ml) was refluxed for 3 h. It was concentrated to obtain the title compound as a yellow solid. Yield, 0.8 g (93.89%); $^1$H-NMR (DMSO-D$_6$): 2.84 (3H, s, SC$\underline{H}_3$), 3.72 (3H, s, OC$\underline{H}_3$), 4.64, 4.98. 5.17 (6H, 3×s, 3×C$\underline{H}_2$), 7.12 (2H, d, J=9.15, H-2' & H-6'), 7.98 (2H, m, H-6 & $\overline{H}$-7), 8.04 (2H, d, J=9.15, H-3' & H-5'), 8.15 (1H, br, H-4).

EXAMPLE 2

(4-{2-[5-(N-Hydroxycarbamimidoyl)-1-oxo-1,3-dihydro-isoindol-2-yl]-acetyl}-phenoxy)-acetic acid methyl ester, hemihydrate A mixture of the compound of example 1g (0.3 g; 0.824 mmol), hydroxylamine hydrochloride (0.22 g; 3.3 mmol) and $NaHCO_3$ (0.3 g; 3.3 mmol) in MeOH (25 ml) was stirred at room temperature for 3 h. It was concentrated, purified using flash chromatography (silica gel, 5-10% MeOH+1% AcOH in $CHCl_3$) and crystallized from MeOH-ether to obtain the title compound. Yield, 0.135 g (40.3%); mp, 175-176° C.; analysis: $C_{20}H_{19}N_3O_6$, 0.5 $H_2O$ requires, C, 59.19; H, 4.96; N, 10.33. found: C, 58.32; H, 4.72; N, 10.12%.

EXAMPLE 3

(4-{2-[5-Carbamimidoyl-1-oxo-1,3-dihydro-isoindol-2-yl]-acetyl}-phenoxy)-acetic acid ethyl ester The title compound was obtained from the compound of example 3d using the procedure described in Example 1. The crude product was purified using flash chromatography (RP-18, MeOH: 0.2% AcOH (1:1)) and crystallized from dry MeOH-ether. Yield, 44%; mp, 185-87° C.; MS (ESI$^+$): 396 (M$^+$+1); analysis: $C_{23}H_{25}N_3O_7$ requires: C, 60.65; H, 5.53; N, 9.23. found: C, 60.27; H, 5.49; N, 9.20%.

EXAMPLE 3a (4-{2-Amino-acetyl}-phenoxy)-acetic acid ethyl ester, hydrochloride The title compound was obtained from (4-{2-Bromo-acetyl}-phenoxy)-acetic acid ethyl ester (9.03 g; 30 mmol) using the procedure described in example 1e and example 1f. Yield, 2.9 g (35.5%); $^1$H-NMR (CDCl$_3$): 1.33 (3H, t, J=7.3, CH$_2$CH$_3$), 4.30 (2H, q, J=7.3, CH$_2$CH$_3$), 4.60, 4.83 (4H, 2×s, 2×$\overline{CH_2}$), 7.15 (2H, d, J=8.7, H-$\overline{3}$ & H-5), 8.08 (2H, d, J=8.7, H-2 $\overline{\&}$ H-6). Compound of example 1f was also obtained. Yield, 4.17 g (45%)

EXAMPLE 3b (4-{2-[5-Cyano-1-oxo-1,3-dihydro-isoindol-2-yl]-acetyl}-phenoxy)acetic acid ethyl ester The title compound was obtained from the compound of example 3a using the procedure described in example 1g. Yield, 1.47 g (51%); mp, 186-87° C. (CHCl$_3$-PE 60-80° C.); MS (ESI): 377 (M–1).

EXAMPLE 3c (4-{2-[1-Oxo-5-thiocarbamoyl-1,3-dihydro-isoindol-2-yl]-acetyl}-phenoxy)-acetic acid ethyl ester The title compound was obtained from the compound of example 3b using the procedure described in example 1h. The crude product was purified using flash chromatography (silica gel, 10% CH$_3$CN+0.5% MeOH in CHCl$_3$). Yield, 81%; mp, 185-186° C.; MS (ESI$^-$): 411 (M–1), analysis: $C_{21}H_{20}N_2O_5S$ requires C, 61.17; H, 4.85; N, 6.80, S, 7.77. found: C, 61.24; H, 4.68; N, 6.68; S, 8.09%.

EXAMPLE 3d (4-{2-[5-Methylsulfanylcarbonimidoyl-1-oxo-1,3-dihydro-isoindol-2-yl]-acetyl}-phenoxy)-acetic acid ethyl ester, hydroiodide The title compound was obtained from the compound of example 3c using the procedure described in example 1i. Yield, 85.8%; mp, 180-183° C.; MS (ESI$^+$): 449 (M$^+$+Na$^+$); analysis: $C_{22}H_{24}IN_2O_5S$ requires C, 47.65; H, 4.15; N, 5.05; S, 5.78. found: C, 48.06; H, 4.02; N, 4.73; S, 5.40%.

EXAMPLE 4

(4-{2-[5-(N-Hydroxycarbamimidoyl)-1-oxo-1,3-dihydro-isoindol-2-yl]-acetyl}-phenoxy)-acetic acid ethyl ester, hemihydrate Hydroxylamine hydrochloride (0.05 g; 0.75 mmol) was added to a solution of the compound of example 3d (0.277 g; 0.5 mmol) in ethanol (10 ml), followed by the addition of NaHCO$_3$ (0.063 g; 0.75 mmol). The reaction mixture was stirred at room temperature for 1 h, concentrated and purified using flash chromatography (silica gel, 3% MeOH in chloroform). Yield, 60%; mp, 175-78° C.; MS (ESI): 412 (M$^+$+1); analysis $C_{21}H_{21}N_3O_6$, 0.5 $H_2O$ requires C, 59.96; H, 5.23; N, 10.0. found: C, 60.34, H, 5.16; N, 9.64%.

EXAMPLE 5

(4-{2-[5-Carbamimidoyl-1-oxo-1,3-dihydro-isoindol-2-yl]-acetyl}-phenoxy)-acetic acid isopropyl ester, hemihydrate The title compound was obtained from the compound of example 5e using the procedure described in example 1 (propane-2-ol was used instead of methanol). Yield, 46%, mp, 162° C.; MS (ESI$^+$): 410 (M$^+$+1); analysis: $C_{24}H_{27}N_3O_7$, 0.5$H_2O$ requires C, 60.23; H, 5.90; N, 8.76. found: C, 59.92; H, 5.62; N, 8.61%.

EXAMPLE 5a (4-{2-tert-Butoxycarbonylamino-acetyl}-phenoxy)-acetic acid isopropyl ester A solution of DCC (2.06 g; 10 mmol) in EtOAc (10 ml) was added with stirring, at 0° C. to a mixture of the compound of example 1f (2.78 g; 9 mmol) and propane-2-ol (2 ml) in EtOAc (20 ml). DMAP (1.1 g; 9 mmol) was added after 10 min and stirring continued for 2 h at 0° C. The reaction mixture was stored in a freezer overnight. The precipitated DCU was filtered and the filtrate was washed with brine, dried (Na$_2$SO$_4$), concentrated and purified using flash chromatography (silica gel, 5% CH$_3$CN in CHCl$_3$) to obtain the title compound. Yield, 3.0 g (94.9%); mp, 62-64° C. (EtOAc-PE 60-80° C.); analysis: $C_{18}H_{25}NO_6$ requires C, 61.53; H, 7.17; N, 3.99. found: C, 61.94; H, 7.19; N, 3.95%.

EXAMPLE 5b (4-{2-Amino-acetyl}-phenoxy)-acetic acid isopropyl ester, hydrochloride A mixture of the compound of example 5a (2.5 g; 7.12 mmol), formic acid (12 ml) and anisole (0.4 ml) was stirred at room temperature for 4 h. Ethereal HCl (1 ml) was added and the reaction mixture was well stirred. It was concentrated, triturated with dry ether, decanted free of ether and thoroughly dried to obtain the title compound. Yield, 1.88 g (91.8%); $^1$H NMR (D$_2$O): 1.24 [6H, d, J=7.0, CH(CH$_3$)$_2$], 4.61 (2H, s, NHCH$_2$), 4.86 (2H, s, OCH$_2$CO), 5.08 (1H, hep, J=7.0, CHMe$_2$), 7.05, 7.94 (4H, 2×d, J=8.1, ArH).

EXAMPLE 5c (4-{2-[5-Cyano-1-oxo-1,3-dihydro-isoindol-2-yl]-acetyl}-phenoxy)-acetic acid isopropyl ester The title compound was obtained from the compound of example 5b using the procedure described in example 1g. It was purified using flash chromatography (silica gel, 5% CH$_3$CN—CHCl$_3$). Yield, 30%; mp, 147-49° C.; analysis: C$_{22}$H$_{20}$N$_2$O$_5$, 0.25H$_2$O requires C, 66.51; H, 5.03; N, 7.05. found: C, 66.94; H, 5.14; N, 7.14%.

EXAMPLE 5d (4-{2-[1-Oxo-5-thiocarbamoyl-1,3-dihydro-isoindol-2-yl]-acetyl}-phenoxy)-acetic acid isopropyl ester The title compound was obtained from the compound of example 5c using the procedure described in example 1h. Yield, 96.77%; mp, 165° C.; MS (ESI): 425 (M−1); analysis: C$_{22}$H$_{22}$N$_2$O$_5$S requires C, 61.96; H, 5.29; N, 6.57. found: C, 62.37; H, 5.39; N, 6.50%.

EXAMPLE 5e (4-{2-[5-Methylsulfanylcarbonimidoyl-1-oxo-1,3-dihydro-isoindol-2-yl]-acetyl}-phenoxy)-acetic acid isopropyl ester, hydroiodide The title compound was obtained from the compound of example 5d using the procedure described in Example 1i. Yield, 79%; mp, 190 (d); MS (ESI$^+$): 463 (M$^+$+Na).

EXAMPLE 6

(4-{2-[5-(Imino-methoxycarbonylamino-methyl)-1-oxo-1,3-dihydro-isoindol-2-yl]-acetyl}-phenoxy)-acetic acid isopropyl ester Methyl chloroformate (0.023 ml; 0.29 mmol) was added with stirring at 0° C. to a mixture of the compound of example 5 (0.114 g; 0.28 mmol), 0.1N aqueous NaOH (2.80 ml; 0.28 mmol) and NaHCO$_3$ (0.024 g; 0.28 mmol) in water (3 ml) and dioxan (6 ml). After 1 h, the reaction mixture was extracted with EtOAc. The organic layer was washed with brine, dried (Na$_2$SO$_4$), concentrated and purified using flash chromatography (silica gel, 3% MeOH—CHCl$_3$). Crystallization was carried out using EtOAc-PE 60-80° C. to obtain the title compound. Yield, 0.12 g (94.2%); mp, 183-84° C.; MS (ESI$^+$): 490 (M$^+$+Na$^+$), 468 (M$^+$+1); analysis: C$_{24}$H$_{25}$N$_3$O$_7$ requires C, 61.66; H, 5.39; N, 8.99. found: C, 61.20; H, 5.23; N, 8.83%.

EXAMPLE 7

(4-{2-[5-(Imino-isobutoxycarbonylamino-methyl)-1-oxo-1,3-dihydro-isoindol-2-yl]-acetyl}-phenoxy)-acetic acid isopropyl ester, hemihydrate The title compound was obtained from the compound of example 5 using the procedure described in example 6 Isobutyl chloroformate was used instead of methyl chloroformate. Yield, 40%; mp, 155-57° C.; MS (ESI$^+$): 532 (M$^+$+Na$^+$), 510 (M$^+$+1); analysis: C$_{27}$H$_{31}$N$_3$O$_7$, 0.5H$_2$O requires, C, 62.48; H, 6.17; N, 8.11. found, C, 62.62; H, 6.09; N, 7.95%.

EXAMPLE 8

(4-{2-[5-(Benzyloxycarbonylamino-imino-methyl)-1-oxo-1,3-dihydro-iso indol-2-yl]-acetyl}-phenoxy)-acetic acid isopropyl ester, hemihydrate The title compound was obtained from the compound of example 5 using the procedure described in example 6. Benzyl chloroformate was used instead of methyl chloroformate. Yield, 56%; mp, 156-58° C.; MS (ESI$^+$): 566 (M$^+$+Na$^+$), 544 (M$^+$+1); analysis: C$_{30}$H$_{29}$N$_3$O$_7$, 0.5H$_2$O requires C, 65.22; H, 5.48; N, 7.60. found, C, 65.56; H, 5.42; N, 7.58%.

EXAMPLE 9

(4-{2-[5-(N-Hydroxycarbamimidoyl)-1-oxo-1,3-dihydro-isoindol-2-yl]-acetyl}-phenoxy)-acetic acid isopropyl ester, hemihydrate The title compound was obtained from the compound of example 5e using the procedure described in example 4. Propane-2-ol was used instead of ethanol. Yield, 75.3%; mp, 164-66° C.; MS (ESI$^+$): 448 (M$^+$+Na$^+$), 426 (M$^+$+1); analysis: C$_{22}$H$_{25}$N$_3$O$_5$, H$_2$O requires C, 61.50; H, 5.82; N, 9.79. found, C, 61.70; H, 5.39; N, 10.06%.

EXAMPLE 10

(4-{2-[5-Carbamimidoyl-1-oxo-1,3-dihydro-isoindol-2-yl]-acetyl}-phenoxy)-acetic acid isobutyl ester, hydroiodide The title compound was obtained from the compound of example 10e using the procedure described in example 1. Isobutanol was used instead of methanol. Yield, 46%; mp, 105° C.; MS (CI): 435 (M$^+$+29), 407 (M$^+$+1); analysis: C$_{23}$H$_{26}$N$_3$O$_5$I, requires C, 50.10; H, 4.75; N, 7.62; I, 23.01. found: C, 50.11; H, 5.06; N, 7.28; I, 22.78%.

EXAMPLE 10a (4-{2-[tert-Butoxycarbonylamino]-acetyl}-phenoxy)-acetic acid isobutyl ester The title compound was obtained from the compound of example 1f using the procedure described in example 5a. 2-methyl-1-propanol was used instead of propane-2-ol. Yield, 93.44%; oil; MS (ESI$^+$): 388 (M$^+$+Na), 366 (M$^+$+1), $^1$H NMR (CDCl$_3$): 0.91 (6H, d, J=7.1, CH(CH$_3$)$_2$], 1.49 [9H, s, (CH$_3$)$_3$], 1.96 (1H, m, CHMe$_2$), 4.0 (2H, d, J=7.6, C H$_2$CHMe$_2$), 4.56 (2H, d, J=5.5, NHCH$_2$), 4.73 (2H, s, OC H$_2$CO), 5.57 (1H, br, NH), 6.96 (2H, d, J=8.2, H-2 & H-6), 7.96 (2H, d, J=8.2, H-3 & H-5).

EXAMPLE 10b (4-{2-Amino-acetyl}-phenoxy)-acetic acid isobutyl ester, hydrochloride The title compound was obtained from the compound of example 10a using the procedure described in example 5b. Yield, 89%.

EXAMPLE 10c (4-{2-[5-Cyano-1-oxo-1,3-dihydro-isoindol-2-yl]-acetyl}-phenoxy)-acetic acid isobutyl ester The title compound was obtained from the compound of example 10b using the procedure described in example 1g. The crude product was purified using flash chromatography (silica gel, 5% $CH_3CN$—$CHCl_3$). Yield, 25%; mp, 144-45° C.; MS (ESI$^+$): 429 (M$^+$+Na); analysis: $C_{23}H_{22}N_2O_5$, $H_2O$ requires C, 65.02; H, 5.65; N, 6.59. found: C, 65.45; H, 5.32; N, 6.51%.

EXAMPLE 10d (4-{2-[1-Oxo-5-thiocarbamoyl-1,3-dihydro-isoindol-2-yl]-acetyl}-phenoxy)-acetic acid isobutyl ester The title compound was obtained from the compound of example 10c using the procedure described in example 1h. The crude product was purified using flash chromatography (silica gel, 1% MeOH in $CHCl_3$). Yield, 95.7%; MS (ESI$^-$): 439 (M−1); analysis: $C_{23}H_{24}N_2O_5S$, requires C, 62.71; H, 5.49; N, 6.36. found: C, 62.90; H, 5.72; N, 6.45%.

EXAMPLE 10e (4-{2-[5-Methylsulfanylcarbonimidoyl-1-oxo-1,3-dihydro-isoindol-2-yl]-acetyl}-phenoxy)-acetic acid isobutyl ester, hydroiodide The title compound was obtained from the compound of example 10d using the procedure described in example 11 in 73% yield. MS (ESI: 478 (M$^+$+Na), 456 (M$^+$+1); $^1$H NMR (DMSO-D$_6$): 0.87 [6H, d, J=7.03, $CH(CH_3)_2$], 1.96 [1H, m, $CH_2CH(CH_3)_2$], 2.85 (3H, s, $SCH_3$), 3.94 (2H, d, J=6.4, C$\overline{H_2CH(CH_3)_2}$], 4.64, 4.99, 5.17 ($\overline{6H}$, 3xs, 3×$CH_2$), 7.14 (2H, $\overline{d}$, J=8.3, H-2' & H-6'), 7.98 (2H, br, H-6, H-7), 8.05 (2H, d, J=8.5, H-3', H-5'), 8.16 (1H, br, H-4).

EXAMPLE 11

(4-{2-[5-(Imino-methoxycarbonylamino-methyl)-1-oxo-1,3-dihydro-isoindol-2-yl]-acetyl}-phenoxy)-acetic acid isobutyl ester The title compound was obtained from the compound of example 10 using the procedure described in example 6. The crude product was purified using flash chromatography (silica gel with 3% MeOH—$CHCl_3$). Crystallization was carried out using hot EtOAc-PE60-80° C. Yield, 42%; mp, 162-63° C.; MS (ESI$^+$): 504 (M$^+$+Na$^+$), 482 (M$^+$+1); analysis: $C_{25}H_{27}N_3O_7$ requires C, 62.36; H, 5.65; N, 8.73. found: C, 62.41; H, 5.77; N, 9.08%.

EXAMPLE 12

(4-{2-[5-(Imino-isobutoxycarbonylamino-methyl)-1-oxo-1,3-dihydro-isoindol-2-yl]-acetyl}-phenoxy)-acetic acid isobutyl ester, sesquihydrate The title compound was obtained from the compound of example 10 using the procedure described in example 6 Isobutyl chloroformate was used instead of methyl chloroformate. The crude product was purified using flash chromatography (silica gel, ether/dichloromethane [1:1]) and crystallised using $CHCl_3$-PE60-80° C. Yield, 59%; mp, 140-41° C.; MS (ESI$^+$): 546 (M$^+$+Na$^+$), 524 (M$^+$+1); analysis: $C_{28}H_{33}N_3O_7$, requires C, 61.03; H, 6.54; N, 7.63. found, C, 61.16; H, 6.35; N, 7.49%.

EXAMPLE 13

(4-{2-[5-(Benzyloxycarbonylamino-imino-methyl)-1-oxo-1,3-dihydro-isoindol-2-yl]-acetyl}-phenoxy)-acetic acid isobutyl ester The title compound was obtained from the compound of example 10 using the procedure described in example 6. Benzyl chloroformate was used instead of methyl chloroformate. Yield, 50%; mp, 139-40° C. ($CHCl_3$-PE 60-80° C.); MS (ESL): 580 (M$^+$+Na$^+$), 558 (M$^+$+1); analysis: $C_{31}H_{31}N_3O_7$, requires C, 66.78; H, 5.60; N, 7.54. found, C, 66.44; H, 5.58; N, 7.22%.

EXAMPLE 14

(4-{2-[5-(Imino-methanesulfonylamino-methyl)-1-oxo-1,3-dihydro-iso indol-2-yl]-acetyl}-phenoxy)-acetic acid isobutyl ester Aqueous 0.1 N NaOH (2.7 ml; 0.27 mmol) was added with stirring over a period of 10 min. to an aqueous solution of the compound of example 10 (0.138 g; 0.25 mmol, 4 ml) chilled in an ice bath at 0° C. The reaction mixture was extracted with dichloromethane and dried ($Na_2SO_4$). The dichloromethane layer (10 ml) was decanted, cooled to 0° C., treated with $NaHCO_3$ (0.06 g; 0.7 mmol) and subsequently with freshly distilled methanesulfonyl chloride (0.05 ml; 0.64 mmol) under vigorous stirring conditions which was continued for 30 min at 0° C. and for 2 h at room temperature. The reaction mixture was concentrated and the residue was purified using flash chromatography (silica gel, 2.5% MeOH in chloroform). Crystallisation was carried out using 5% MeOH—$CHCl_3$ and dry ether. Yield, 0.05 g (40%); mp, 177-78° C.; MS (ESI$^+$): 524 (M$^+$+Na$^+$), 502 (M$^+$+1); analysis: $C_{24}H_{27}N_3O_7S$, requires C, 57.47; H, 5.43; N, 8.38, S, 6.39. found, C, 57.88; H, 5.50; N, 8.32; S, 6.78%.

EXAMPLE 15

(4-{2-[5-(N-Hydroxycarbamimidoyl)-1-oxo-1,3-dihydro-isoindol-2-yl]-acetyl}-phenoxy)-acetic acid isobutyl ester The title compound was obtained from the compound of example 10e using the procedure described in example 4. Isobutanol was used instead of EtOH. The crude product was purified using flash chromatography (silica gel, 2.5% MeOH in chloroform). Yield, 74.3%; mp, 153-54° C.; MS (ESI$^+$): 462 (M$^+$+Na$^+$), 440 (M$^+$+1); analysis: $C_{23}H_{25}N_3O_6$, requires C, 62.86; H, 5.73; N, 9.56. found, C, 62.58; H, 5.61; N, 9.29%.

EXAMPLE 16

(4-{2-[5-Carbamimidoyl-1-oxo-1,3-dihydro-isoindol-2-yl]-acetyl}-phenoxy)-acetic acid benzyl ester, acetic acid salt, monohydrate The title compound was obtained from the compound of example 16e using the procedure described in example 1.

Isobutanol was used instead of methanol. Yield, 38%; mp, 190° C. (d); MS (ESI$^+$): 480 (M$^+$+Na), 458 (M$^+$+1); analysis: $C_{28}H_{27}N_3O_7$, $H_2O$ requires C, 63.81; H, 5.57; N, 7.97. found: C, 63.59; H, 5.28; N, 7.70%.

EXAMPLE 16a (4-{2-[tert-Butoxycarbonylamino]-acetyl}-phenoxy) acetic acid benzyl ester A solution of hexamine (7.1 g; 50.7 mmol) in chloroform (100 ml) was added to (4-{2-bromo-acetyl}-phenoxy)-acetic acid benzyl ester (18.2 g; 50.13 mmol) with stirring at room temperature over a period of 1 h. Dry ether (100 ml) was added and the solid hexamine salt obtained was filtered, dried (19 g; 37.77 mmol) and hydrolysed with 1.5N HCl (300 ml) for 16 h. The mixture was concentrated to a volume of 100 ml, cooled to 0° C. and neutralized with NaHCO$_3$. A solution of di-tert-butyldicarbonate (12 g; 55 mmol) in dioxane (100 ml) was added with stirring and the reaction mixture was allowed to stir, at 0° C. for 1 h and subsequently at room temperature for 1 h. It was concentrated and extracted with EtOAc. The EtOAc layer was washed with brine, dried (Na$_2$SO$_4$), concentrated and purified using flash chromatography (silica gel) to obtain the title compound. Yield, 5.4 g (27%); MS (CI): 400 (M$^+$+1), 344, 300, 196, 152; $^1$H NMR (CDCl$_3$): 1.49 [9H, s, (CH$_3$)$_3$], 4.61 (2H, d, J=5.5, NHCH$_2$), 4.76 (2H, s, OCH$_2$CO), 5.26 (2H, s, CH$_2$Ph) 5.57 (1H, br, NH), 6.94, 7.90 (4H, 2×d, J=8.02, ArH), 7.32-7.40 (5H, br, CH$_2$PhH).

The acid compound of example 1f was obtained in 58% yield.

EXAMPLE 16b (4-{2-Amino-acetyl}-phenoxy)-acetic acid benzyl ester, hydrochloride The title compound was obtained from the compound of example 16a using the procedure described in example 5b. Yield, 78%; MS (ESI: 300 (M$^+$+1); $^1$H NMR (DMSO-D$_6$): 4.51, 5.05, 5.21 (6H, 3×s, 3×CH$_2$), 7.12, 7.97 (4H, 2×d, J=8.01, Ar—H), 7.38 (5H, m, CH$_2$PhH).

EXAMPLE 16c (4-{2-[5-Cyano-1-oxo-1,3-dihydro-isoindol-2-yl]-acetyl}-phenoxy)-acetic acid benzyl ester The title compound was obtained from the compound of example 16b using the procedure described in example 1g. The crude product was purified using flash chromatography (silica gel, 5% CH$_3$CN—CHCl$_3$). Yield, 25.4%; mp, 159-60° C.; MS (ESI$^+$): 463 (M$^+$+Na); analysis: C$_{26}$H$_{20}$N$_2$O$_5$ requires C, 70.90; H, 4.58; N, 6.36. found: C, 70.61; H, 4.49; N, 5.98%.

EXAMPLE 16d (4-{2-[1-Oxo-5-thiocarbamoyl-1,3-dihydro-isoindol-2-yl]-acetyl}-phenoxy)-acetic acid benzyl ester The title compound was obtained from the compound of example 16c using the procedure described in example 1h. The crude product was purified using flash chromatography (silica gel, 1% MeOH in CHCl$_3$). Yield, 93%; mp, 137-38° C.; MS (ESI$^+$): 473 (M–1); analysis: C$_{26}$H$_{22}$N$_2$O$_5$S, H$_2$O requires C, 64.75; H, 4.62; N, 5.62. found: C, 64.52; H, 4.96; N, 5.79%

EXAMPLE 16e (4-{2-[5-Methylsulfanylcarbonimidoyl-1-oxo-1,3-dihydro-isoindol-2-yl]-acetyl}-phenoxy)-acetic acid benzyl ester, hydroiodide The title compound was obtained from the compound of example 16d using the procedure described in example 11. Yield, 84.2%; $^1$H NMR (DMSO-D$_6$): 2.84 (3H, s, SCH$_3$), 4.64, 5.05, 5.17, 5.23 (8H, 4×s, 4×CH$_2$), 7.13 (2H, d, J=8.7, H-2'& H-6'), 7.39 (5H, br, PhH), 7.98 (2H, br, H-6, H-7), 8.04 (2H, d, J=8.7, H-3', H-5'), 8.25 (1H, br, H-4).

EXAMPLE 17

(4-{2-[5-Carbamimidoyl-1-oxo-1,3-dihydro-isoindol-2-yl]-acetyl}-phenoxy)-acetic acid hydrochloride, monohydrate The compound of example 16 (0.1 g) was dissolved in glacial acetic acid (30 ml) at 80° C. and the hot solution was hydrogenated using 10% Pd—C (0.01 g) for 40 min. The catalyst was filtered off and the filtrate was concentrated to obtain the title compound, which was purified using flash chromatography (RP-18, MeOH-1% AcOH [1:1]). Yield, 0.03 g; mp, 302° C.; MS: 390 (M$^+$+Na), 368 (M$^+$+1); $^1$H NMR (TFA): 2.2 (3H, s), 4.77, 4.85, 5.32 (6H, 3×s, 3×CH$_2$), 7.05 (2H, d, J=8.02), 8.1 (5H, m).

Alternative Method:

The crude compound of example 17 (b) (0.12 g) was dissolved in a mixture of formic acid (3 ml) and anisole (0.13 ml). The clear solution was kept at room temperature for 4 h. It was stirred with ethereal HCl (0.5 ml) for 2 min., evaporated to dryness and treated with dry ether. The solid obtained was filtered and washed with dry ether. Purification was effected by trituration with MeOH, filtration and drying to obtain the title compound of as a white solid. Yield, 0.04 g; mp>250° C. (d); MS (ESI$^+$): 368 (M$^+$+1); analysis: C$_{19}$H$_{18}$ClN$_3$O$_5$, H$_2$O requires C, 56.05; H, 4.74; N, 9.96; Cl, 8.42. found: C, 54.11; H, 4.66; N, 9.46; Cl, 8.41%.

EXAMPLE 17a (4-{2-[5-(tert-Butoxycarbonylamino-imino-methyl)-1-oxo-1,3-dihydro-isoindol-2-yl]-acetyl}-phenoxy)-acetic acid ethyl ester Aqueous 0.1N NaOH (1.2 ml; 1.2 mmol) was added to a solution of the compound of example 3 (0.6 g; 1.2 mmol) in dioxane (15 ml) and water (15 ml) at 0° C., with stirring, followed by the addition of NaHCO$_3$ (0.11 g; 1.2 mmol) and di-tert-butyl-dicarbonate (0.35 g; 1.44 mmol). The reaction mixture was stirred at 0-10° C. for 3 h, concentrated, treated with water and extracted with EtOAc. The EtOAc layer was washed with water, dried (Na$_2$SO$_4$), concentrated and purified using flash chromatography (silica gel, 20% CH$_3$CN in chloroform, 2% MeOH in chloroform). Yield, 0.51 g (78.3%); $^1$H NMR (DMSO-D$_6$): 1.23 (3H, t, J=7.3, CH$_2$C H$_3$), 1.48 [9H, s, C(CH$_3$)$_3$], 4.17 (2H, q, J=7.3, CH$_2$CH$_3$), 4.57, 4.95, 5.14 (6H, 3×s, 3×CH$_2$), 7.11 (2H, d, J=8.6, H-2'& H-6'), 7.81 (1H, d, J=7.3, H-7), 8.05 (3H, m, H-6, H-3', H-5'), 8.2 (1H, br, H-4), 9.1 (2H, br, 2×NH); MS (ESI$^+$): 519 (M$^+$+ Na), 496 (M$^+$+1).

EXAMPLE 17b (4-{2-[5-(tert-Butoxycarbonylamino-imino-methyl)-1-oxo-1,3-dihydro-isoindol-2-yl]-acetyl}-phenoxy)-acetic acid Aqueous 0.1N NaOH (11.4 ml; 1.14 mmol) was added to a solution of the compound of example 17a (0.375 g; 0.756 mmol) in MeOH (10 ml), The reaction mixture was stirred at room temperature for 30 min., acidified with AcOH and concentrated. The crude title compound obtained was filtered, washed with cold water and dried under vacuum. Yield, 140 mg.

EXAMPLE 18

(4-{2-[5-(Imino-methoxycarbonylamino-methyl)-1-oxo-1,3-dihydro-isoindol-2-yl]-acetyl}-phenoxy)-acetic acid benzyl ester, hemihydrate The title compound was obtained from the compound of example 16 using the procedure described in example 6. The crude product was purified using flash chromatography (silica gel, 3% MeOH—CHCl$_3$). Crystallization was carried out using hot EtOAc-PE 60-80° C. Yield, 40%; mp, 184-86° C.; MS (ESI$^+$): 538 (M$^+$+Na$^+$), 516 (M$^+$+1); analysis: C$_{28}$H$_{25}$N$_3$O$_7$, 0.5H$_2$O requires C, 64.12; H, 4.96; N, 8.02. found: C, 64.36; H, 4.92; N, 8.18%.

EXAMPLE 19

(4-{2-[5-(Imino-isobutoxycarbonylamino-methyl)-1-oxo-1,3-dihydro-isoindol-2-yl]-acetyl}-phenoxy)-acetic acid benzyl ester, monohydrate The title compound was obtained from the compound of example 16 using the procedure described in example 6. Isobutyl chloroformate was used instead of methyl chloroformate. The crude product was purified using flash chromatography (silica gel, 10% CH$_3$CN in CHCl$_3$). Crystallization was carried out using CHCl$_3$-PE 60-80° C. Yield, 29%; mp, 162-63° C.; MS (ESI$^+$): 580 (M$^+$+Na$^+$), 558 (M$^+$+1); analysis: C$_{31}$H$_{31}$N$_3$O$_7$, H$_2$O requires C, 65.95; H, 5.65; N, 7.42. found, C, 65.94; H, 5.64; N, 7.59%.

EXAMPLE 20

(4-{2-[5-Carbamimidoyl-1-oxo-1,3-dihydro-isoindol-2-yl]-acetyl}-2-ethoxycarbonyl methoxy-phenoxy)-acetic acid ethyl ester; acetic acid salt, hydrate The title compound was obtained from the compound of example 20i using the procedure described in example 1. Ethanol was used instead of methanol. mp, 168-69° C.; MS (ESI$^+$): 520 (M$^+$+Na); analysis: C$_{27}$H$_{31}$N$_3$O$_{10}$, H$_2$O requires C, 56.35; H, 5.74; N, 7.3. found: C, 56.29; H, 5.40; N, 6.97%.

EXAMPLE 20a
(2-Ethoxycarbonylmethoxy-phenoxy)-acetic acid ethyl ester

Ethyl 2-bromoacetate (36.5 ml; 165 mmol) was added slowly with stirring at room temperature over a period of 1.5 to a mixture of catechol (16.5 g; 150 mmol) and anhydrous K$_2$CO$_3$ (55 g) in dry DMF (150 ml). The reaction mixture was poured over crushed ice and extracted with EtOAc. The EtOAc layer was washed with water, dried (Na$_2$SO$_4$), concentrated and purified using flash chromatography (silica gel, 5% CH$_3$CN in chloroform) to obtain the title compound. Yield, 38.07 g (90%), oil; analysis: C$_{14}$H$_{18}$O$_6$ requires C, 59.57; H, 6.43. found: C, 59.48; H, 6.34%.

EXAMPLE 20b (4-Acetyl-2-ethoxycarbonylmethoxy-phenoxy)-acetic acid ethyl ester Perchloric acid (70% aq.; 1.0 ml) was added slowly to freshly distilled Ac$_2$O (25 ml) at 0° C. The compound of example 20a (31.8 g; 125 mmol) in CH$_2$Cl$_2$ (13 ml) was added drop wise at 10-15° C. The reaction mixture was heated on steam bath for 1 h, concentrated, poured over crushed ice and NaHCO$_3$ (~25 g) and extracted with ether. The ether layer was washed with brine, dried (Na$_2$SO$_4$), concentrated and purified using flash chromatography (silica gel, 5% CH$_3$CN in CHCl$_3$) to obtain the title compound. Yield, 24.6 g (61.5%), semisolid; analysis: C$_{16}$H$_{20}$O$_7$: requires C, 59.25; H, 6.22. found: C, 59.57; H, 6.28%.

EXAMPLE 20c (4-{2-Bromo-acetyl}-2-ethoxycarbonylmethoxy-phenoxy)-acetic acid ethyl ester Bromine (4.25 ml; 85 mmol) in AcOH:CHCl$_3$ (1:1; 10 ml) was added to a vigorously stirred solution of the compound of example 20b (25.92 g; 80 mmol) in AcOH:CHCl$_3$ (1:1; 110 ml) at 55-60° C. for 15 min. The mixture was stirred at room temperature for 5 min. and poured over crushed ice and NaHCO$_3$ and extracted with EtOAc. The EtOAc layer was washed with water, dried (Na$_2$SO$_4$), concentrated and purified using flash chromatography (silica gel, 3% CH$_3$CN in chloroform) to obtain the title compound. Yield, 19.34 g, (60%); mp, 84-85° C. (EtOAc-PE 60-80° C.); analysis: C$_{16}$H$_{19}$O$_7$Br: requires C, 47.66; H, 4.75; Br, 19.82. found: C, 48.08; H, 4.82; Br, 19.40%.

EXAMPLE 20d (4-{2-tert-Butoxycarbonylamino-acetyl}-2-ethoxycarbonylmethoxy-phenoxy)-acetic acid ethyl ester

EXAMPLE 20e (4-{2-tert-Butoxycarbonylamino-acetyl}-2-carboxymethoxy-phenoxy)-acetic acid The compound of example 20d (oil) and the compound of example 20e were obtained from the compound of example 20c using the procedure described in example 16a. Yield, (40%); MS (ESI$^+$): 462 (M$^+$+Na); $^1$H NMR (CDCl$_3$): 1.30, (6H, m, 2×CH$_2$CH$_3$), 1.46 [9H, s, C(CH$_3$)$_3$], 4.26 (4H, q, J=7.3, 2×CH$_2$CH$_3$), 4.60 (2H, d, J=5.0, NHCH$_2$), 4.77, 4.81 (4H, 2×s, 2×OCH$_2$), 5.53 (1H, br, NH), 6.86 (1H, d, J=8.2, H-6), 7.50 (1H, d, J=1.8, H-3), 7.57 (1H, dd, J=8.2, 1.8, H-5).

The acid compound of example 20e was obtained as a solid. Yield, (50%).

EXAMPLE 20f (4-{2-Amino-acetyl}-2-ethoxycarbonylmethoxy-phenoxy)-acetic acid ethyl ester, hydrochloride The title compound was obtained from the compound of example 20d using the procedure described in example 5b. Solvent of crystallization: MeOH-ether. Yield, 75%.

EXAMPLE 20g (4-{2-[5-Cyano-1-oxo-1,3-dihydro-isoindol-2-yl]-acetyl}-2-ethoxy carbonylmethoxy-phenoxy)-acetic acid ethyl ester The title compound was obtained from the compound of example 20e using the procedure described in example 1g. The crude product was purified using flash chromatography (silica gel, 5% $CH_3CN$—$CHCl_3$). Yield, 22%; mp, 120-21° C.; MS (ESI$^+$): 503 (M$^+$+Na); analysis: $C_{22}H_{20}N_2O_5$, 0.25$H_2O$ requires C, 66.51; H, 5.03; N, 7.05. found: C, 66.94; H, 5.14; N, 7.14%.

EXAMPLE 20h (2-Ethoxycarbonylmethoxy-4-{2-[1-oxo-5-thiocarbamoyl-1,3-dihydro-iso indol-2-yl]-acetyl}-phenoxy)-acetic acid ethyl ester The title compound was obtained from the compound of example 20g using the procedure described in example 1h. Yield, 75%; mp, 169-70° C.; MS (ESI$^+$): 537 (M$^+$+Na); analysis: $C_{25}H_{26}N_2O_8S$ requires C, 58.36; H, 5.09; N, 5.44; S, 6.23. found: C, 58.52; H, 5.08; N, 5.11; S, 6.62%.

EXAMPLE 20i (2-Ethoxycarbonylmethoxy-4-{2-[5-methylsulfanyl-carbonimidoyl-1-oxo-1,3-dihydro-isoindol-2-yl]-acetyl}-phenoxy)-acetic acid ethyl ester, hydroiodide The title compound was obtained from the compound of example 20h using the procedure described in example 1l. Yield, 79%, yellow solid; mp, 168-69° C.; MS (ESI$^+$): 551 (M$^+$+Na); analysis; $C_{26}H_{29}N_2O_8SI$ requires C, 47.56; H, 4.42; N, 4.27; S, 4.88; I, 19.36. found C, 47.72; H, 4.49; N, 4.56; S, 4.69; I, 19.54%.

EXAMPLE 21

(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 20i using the procedure described in example 4. Yield, 52%; mp, 163-64° C.; MS (ESI$^+$): 536 (M$^+$+1); analysis: $C_{25}H_{27}N_3O_9$, requires C, 58.48; H, 5.30; N, 8.18. found, C, 58.16; H, 5.19; N, 8.08%.

EXAMPLE 22

(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester The title compound was obtained from the compound of example 20 using the procedure described in example 6. Isobutyl chloroformate was used instead of methyl chloroformate. Yield, 24%. mp, 204-05° C.; MS (ESI: 598 (W+1); analysis: $C_{30}H_{35}N_3O_{10}$, requires C, 60.29; H, 5.90; N, 7.03. found, C, 60.70; H, 6.28; N, 6.96%.

EXAMPLE 23

(2-Ethoxycarbonylmethoxy-4-{2-[5-(N-hydroxycarbamimidoyl)-1-oxo-1,3-dihydro-isoindol-2-yl]-1-hydroxyimino-ethyl}-phenoxy)-acetic acid ethyl ester A mixture of the compound of example 20g (0.14 g; 0.3 mmol), hydroxylamine hydrochloride (0.07 g; 1.11 mmol) and $Na_2CO_3$ (0.053 g; 0.51 mmol) in ethanol (0.5 ml) and water (1.5 ml) was refluxed in an atmosphere of nitrogen for 1 h. The reaction mixture was cooled to room temperature, concentrated and treated with water to obtain the title compound as a white solid which was filtered, washed with cold water and dried. Yield, 0.051 g (32.2%); mp, 181-82° C.; MS (ESI$^+$): 551 (M$^+$+Na$^+$); analysis: $C_{25}H_{28}N_4O_9$, requires C, 56.81; H, 5.34; N, 10.60. found C, 56.33; H, 5.25; N, 10.16%

EXAMPLE 24

(4-{2-[5-Carbamimidoyl-1-oxo-1,3-dihydro-isoindol-2-yl]-acetyl}-2-isobutoxy carbonyl methoxy-phenoxy)acetic acid isobutyl ester, hydroiodide The title compound was obtained from the compound of example 24e using the procedure described in example 1. Isobutanol was used instead of methanol. Yield, 10%; mp, 95-96° C.; MS (ESI$^+$): 554 (M$^+$+1); analysis: $C_{29}H_{36}IN_3O_8$, requires C, 51.11; H, 5.32; N, 6.17. found: C, 51.42; H, 5.51; N, 6.05%.

EXAMPLE 24a (4-{2-tert-Butoxycarbonylamino-acetyl}-2-isobutoxycarbonylmethoxy-phenoxy)-acetic acid isobutyl ester The title compound (oil) was obtained from the compound of example 20e using the procedure described in example 5a. Isobutanol was used instead of propane-2-ol together with 2.2 equivalents of DCC. Yield, (54%); (CDCl$_3$): 0.91, 0.95 [12H, 2×d, J=8.5, 2×CH(CH$_3$)$_2$], 1.46 (9H, s, C(CH$_3$)$_3$], 1.94 (2H, m, 2×CH$_2$CHMe$_2$), 3.97 (4H, d, J=6.7, CH$_2$CHMe$_2$), 4.56 (2H, d, J=4.5, NHCH$_2$), 4.80, 4.83 (4H, 2×s, 2×OCH$_2$), 5.51 (1H, br, NH), 6.86 (1H, d, J=8.2, H-6), 7.50 (1H, d, J=2.0, H-3), 7.59 (1H, dd, J=8.2, 2.0, H-5).

EXAMPLE 24b (4-{2-Amino-acetyl}-2-isobutoxycarbonylmethoxy-phenoxy)-acetic acid isobutyl ester; hydrochloride The title compound was obtained from the compound of example 24a using the procedure described in example 5b. Yield, 95%.

EXAMPLE 24c (4-{2-[5-Cyano-1-oxo-1,3-dihydro-isoindol-2-yl]-acetyl}-2-isobutoxy carbonyl methoxy-phenoxy)-acetic acid isobutyl ester The title compound was obtained from the compound of example 24b using the procedure described in example 1g.

The crude product was purified using flash chromatography (silica gel, 5% $CH_3CN$—$CHCl_3$). Yield, 21%; mp, 140-41° C.; MS (EI): 536 ($M^+$); analysis: $C_{29}H_{32}N_2O_8$, requires C, 64.91; H, 6.01; N, 5.22. found: C, 65.15; H, 6.06; N, 4.95%.

EXAMPLE 24d (2-Isobutoxycarbonylmethoxy-4-{2-[1-oxo-5-thiocarbamoyl-1,3-dihydro-isoindol-2-yl]-acetyl}-phenoxy)-acetic acid isobutyl ester The title compound was obtained from the compound of example 24c using the procedure described in example 1h. Yield, 68%; mp, 175-76° C.; MS ($ESI^+$): 593 ($M^+$+Na); analysis: $C_{29}H_{34}N_2O_8S$ requires C, 61.04; H, 6.01; N, 4.91; S, 5.62. found: C, 60.84; H, 5.74; N, 4.87; S, 5.40%.

EXAMPLE 24e (2-Isobutoxycarbonylmethoxy-4-{2-[5-methylsulfanylcarbonimidoyl-oxo-1,3-dihydro-isoindol-2-yl]-acetyl}-phenoxy)-acetic acid isobutyl ester, hydroiodide The title compound was obtained from the compound of example 24d using the procedure described in example 11. Yield, 87%, yellow solid; MS ($ESI^+$): 608 ($M^+$+Na).

EXAMPLE 25

2-(4-{2-[5-Carbamimidoyl-1-oxo-1,3-dihydro-isoindol-2-yl]-acetyl}-phenoxy)-N,N-diethyl-acetamide, acetic acid salt The title compound was obtained from the compound of example 25e using the procedure described in example 1. Yield, 30%; mp, 194-95° C.; MS ($ESI^+$): 423 ($M^+$+1); analysis: $C_{25}H_{30}N_4O_6$ requires: C, 62.23; H, 6.27; N, 11.61. found: C, 62.49; H, 6.18; N, 11.19%.

EXAMPLE 25a (2-{4-Diethylcarbamoylmethoxy-phenyl}-2-oxoethyl)-carbamic acid tent-butyl ester Isobutyl chloroformate (0.84 ml; 6.5 mmol) was added to a stirred solution of 4-methyl-morpholine (0.72 ml; 6.5 mmol) and the compound of example 1f (2.0 g; 6.5 mmol) in DMF (10 ml) at −25° C., followed by the addition of diethyl amine (0.88 ml; 8.45 mmol). The reaction mixture was stirred for 15 min., poured into a 10% aqueous $NaHCO_3$ solution and extracted with EtOAc. The EtOAc layer was washed with brine, concentrated and crystallized using EtOAc-PE60-80° C. to obtain the title compound. Yield, 1.95 g (82%); mp, 100-01° C.; MS (EI): 364 ($M^+$), 291, 234 (100%); analysis: $C_{19}H_{28}N_2O_5$ requires C, 62.62; H, 7.74; N, 7.69. found: C, 62.43; H, 7.60; N, 7.25%.

EXAMPLE 25b 2-(4-{2-Amino-acetyl}-phenoxy)-N,N diethyl-acetamide, hydrochloride The title compound was obtained from the compound of example 25a using the procedure described in example 5b. Yield, 95%; mp, 83-84° C.; MS (ESI): 265 ($M^+$+1).

EXAMPLE 25c 2-(4-{2-[5-Cyano-1-oxo-1,3-dihydro-isoindol-2-yl]-acetyl}-phenoxy)-N,N-diethylacetamide The title compound was obtained from the compound of example 25b using the procedure described in example 1g. Yield, 25%; mp, 139-40° C.; MS (EI): 405 ($M^+$); analysis, $C_{23}H_{23}N_3O_4$ requires, C, 68.13; H, 5.72; N, 10.36. found: C, 68.48; H, 5.86; N, 10.34%.

EXAMPLE 25d

N,N-Diethyl-2-(4-{2-[1-oxo-5-thiocarbamoyl-1,3-dihydro-isoindol-2-yl]-acetyl}-phenoxy)-acetamide The title compound was obtained from the compound of example 25c using the procedure described in example 1h. The crude product was purified using flash chromatography (silica gel, 10% $CH_3CN$+0.5% MeOH in $CHCl_3$). Yield, 75%, yellow solid; mp, 191-192° C.; MS ($ESI^+$): 462 ($M^+$+Na), analysis: $C_{23}H_{25}N_2O_4S$ requires C, 62.45; H, 5.73; N, 9.56, S, 7.29. found: C, 62.22; H, 5.59; N, 9.31; S, 7.01%.

EXAMPLE 25e 2-(2-{4-Diethylcarbamoylmethoxy-phenyl}-2-oxoethyl)-1-oxo-2,3-dihydro-1H-isoindol-5-carboximidothioic acid methyl ester, hydroiodide The title compound was obtained from the compound of example 25d using the procedure described in example 11. Yield, 89%; MS (ESI): 452 (WA).

EXAMPLE 26

4-(2-{4-[2-(5-Carbamimidoyl-1-oxo-1,3-dihydroisoindol-2-yl)-acetyl]-phenoxy}-acetoxy)-piperidine-1-carboxylic acid benzyl ester, sesquihydrate The title compound was obtained from the compound of example 26e using the procedure described in example 1. Propane-2-ol was used instead of methanol. Yield, 28%, white solid; mp, 180-81° C.; MS ($ESI^+$): 585 ($M^+$+1); analysis: $C_{34}H_{36}N_4O_9 2.5H_2O$ requires: C, 59.21; H, 5.22; N, 8.12. found: C, 58.85; H, 5.23; N, 7.96.

EXAMPLE 26a 4-(2-{-4-[2-tert-Butoxycarbonylamino-acetyl]-phenoxy}-acetoxy)-piperidine-1-carboxylic acid benzyl ester The compound of example 1f was treated with 4-hydroxy-piperidine-1-carboxylic acid benzyl ester in the presence of DCC as described in the procedure of example 5a to obtain the title compound. The crude material was purified using flash chromatography (silica gel, 5% $CH_3CN$ in chloroform).

Yield, 73%; analysis: $C_{28}H_{34}N_2O_8$ requires: C, 63.87; H, 6.51; N, 5.32. found: C, 64.13; H, 6.78; N, 5.02%.

EXAMPLE 26b 4-(2-{-4-[2-Amino-acetyl]-phenoxy}-acetoxy)-piperidine-1-carboxylic acid benzyl ester, hydrochloride The title compound was obtained from the compound of example 26a using the procedure described in example 5b. Yield, 80%.

EXAMPLE 26c 4-(2-{4-[2-(5-Cyano-1-oxo-1,3-dihydro-isoindol-2-yl)-acetyl]-phenoxy}-acetoxy)-piperidine-1-carboxylic acid benzyl ester The title compound was obtained from the compound of example 26b using the procedure described in example 1g. Yield, 20%; mp, 94-95° C.; MS (ESI⁻): 566 (M−1); analysis: $C_{32}H_{29}N_3O_7$ requires: C, 67.72; H, 5.15; N, 7.40. found: C, 67.72; H, 5.25; N, 7.06%.

EXAMPLE 26d 4-(2-{4-[2-(1-Oxo-5-thiocarbamoyl-1,3-dihydro-isoindol-2-yl)-acetyl]-phenoxy}-acetoxy)-piperidine-1-carboxylic acid benzyl ester The title compound was obtained from the compound of example 26c using the procedure described in example 1h. Yield, 57%; mp, 97-98° C.; MS (ESI⁺): 624 (M⁺+Na), 602 (M⁺+1); analysis: $C_{32}H_{31}N_3O_7S$ requires: C, 63.88; H, 5.19; N, 6.98; S, 5.33. found: C, 63.58; H, 5.14; N, 6.78; S, 5.57%.

EXAMPLE 26e 4-(2-{4-[2-(5-Methylsulfanylcarbonimidoyl-1-oxo-1,3-dihydro-isoindol-2-yl)-acetyl]-phenoxy}-acetoxy)-piperidine-1-carboxylic acid benzyl ester, hydroiodide The title compound (yellow solid) was obtained from the compound of example 26d using the procedure described in example 11. Yield, 98%; MS (ESI⁺): 638 (M⁺+Na), 616 (M⁺+1); ¹H NMR (CDCl₃): 1.64, 1.89 (4H, 2×m), 3.14 (3H, s, SCH₃), 3.33, 3.67 (4H, 2×m), 4.68, 4.73, 5.05 (6H, 3×s, 3×CH₂), 5.10-5.18 (3H, m, CH₂& COOCH—), 6.99 (2H, d, J=8.6, H-2' & H-6'), 7.36 (5H̄, br, CH₂PhH̄), 8.0 (4H, m, H-6, H-7, H-3' & H-5'), 8.3 (1H, s, H-4).

EXAMPLE 27

4-Benzyloxycarbonylamino-2-(4-{2-[5-carbamimidoyl-1-oxo-1,3-dihydro-isoindol-2-yl]-acetyl}-phenoxy)-butyric acid ethyl ester, acetic acid salt The title compound was obtained from the compound of example 27j using the procedure described in example 1. Ethanol was used instead of methanol. Yield, 38%, white solid; mp, 164-65° C.; MS (ESI⁺): 573 (M⁺+1); analysis: $C_{33}H_{36}N_4O_9$ requires C, 62.36; H, 5.70; N, 8.86. found: C, 61.91; H, 5.68; N, 9.20%.

EXAMPLE 27a

2-Amino-1-(4-benzyloxy-phenyl)-ethanone, hydrochloride

Hexamine (5.6 g; 40 mmol) was added to a solution of 1-(4-benzyloxy-phenyl)-2-bromo-ethanone (12.2 g; 40 mmol) in chloroform (80 ml), and stirred for 3 h. Dry ether (80 ml) was added and the solid that separated was filtered, washed with ether, dried then suspended in methanol (100 ml) and con. HCl (20 ml) and allowed to stir for 16 h. The reaction mixture was concentrated, and treated with water (20 ml). The solid obtained was filtered, washed with cold water (2×10 ml) and dried to obtain the title compound. Yield, 10 g (89.9%); mp, 228-29° C.; MS (EI): 241, 211, 91; analysis: $C_{15}H_{16}ClNO_2$ requires: C, 64.87; H, 5.81; N, 5.04. found: C, 64.86; H, 6.11; N, 5.16%.

EXAMPLE 27b (2-{4-Benzyloxy-phenyl}-2-oxo-ethyl)-carbamic acid tert-butyl ester

The compound of example 27a (8.33 g; 30 mmol) was dissolved in water (100 ml) and dioxane (100 ml), cooled to 0° C. with stirring, and treated with NaHCO₃ (5.2 g; 65 mmol) and (Boc)₂O (7.2 g; 33 mmol). The reaction mixture was stirred at 0° C. for 1 h, subsequently at room temperature for 1 h and then concentrated. The residue was extracted with EtOAc. The organic layer was washed with brine, dried (Na₂SO₄) and concentrated to obtain the title compound which was then crystallized from EtOAc-PE 60-80° C. Yield, 9.5 g (92.8%); mp 75-76° C.; MS (EI): 341 (M⁺), 285, 268, 211, 91; analysis: $C_{20}H_{23}NO_4$ requires: C, 70.36; H 6.79; N, 4.10. found: C, 70.49; H, 7.22; N, 4.23%.

EXAMPLE 27c (2-{4-hydroxy-phenyl}-2-oxo-ethyl)-carbamic acid tert-butyl ester

The compound of example 27b (6.0 g; 17.6 mmol) was dissolved in methanol (60 ml) and hydrogenated using 10% Pd—C (50 mg) at 40 psi for 2 h. The reaction mixture was filtered, concentrated and purified using flash chromatography (silica gel, 3% CH₃CN in chloroform) to obtain the title compound. Yield, 2.6 g (59%); mp, 183-85° C.; MS (CI): 252 (M⁺+1), 196, 178, 152; analysis: $C_{13}H_{17}NO_4$ requires: C, 62.14; H, 6.82; N, 5.57. found: C, 62.23; H, 6.44; N, 5.57%.

Another polar compound was also isolated and characterized as (2-Hydroxy-{2-[4-hydroxy-phenyl]}-ethyl)-carbamic acid tert-butyl ester. Yield, 1.5 g (25%); mp, 145-46° C.; analysis: $C_{13}H_{19}NO_4$ requires: C, 61.64; H, 7.56; N, 5.53. found: C, 62.04; H, 7.91; N, 5.57%.

EXAMPLE 27d

4-Benzyloxycarbonylamino-2S-hydroxy buyric acid ethyl ester

Freshly distilled thionyl chloride (5 ml) was added drop wise over a period of 15 min with stirring to a solution of 4-Amino-2S-hydroxy-butyric acid (5 g, 42 mmol) in EtOH (100 ml) at 0° C. The reaction mixture was brought to room temperature and stirred overnight (16 h). It was concentrated under vacuum to remove all traces of thionyl chloride, treated with water (100 ml), dichloromethane (50 ml) and chilled to 0° C. NaHCO$_3$ (17.5 g) was added with stirring, followed by the addition of a solution of 50% benzyl chloroformate in toluene (14.3 ml). The reaction mixture was allowed to stir for 1 h at 0° C. and subsequently at room temperature for 30 min. The organic layer was separated, washed with brine, dried (Na$_2$SO$_4$), concentrated and. purified using flash chromatography (silica gel, 10% CH$_3$CN in CHCl$_3$) to obtain the title compound. Yield, 7.7 g (65.3%), oil; MS (EI): 281 (M$^+$), 238, 235, 208, 174; $^1$H NMR (CDCl$_3$): 1.29 (3H, t, J=7.5, CH$_2$CH$_3$), 1.86, 2.06 [2H, 2×m, CH$_2$CH(OH)], 3.18 (1H, d, J=6.40 OH), 3.4 (2H, m, NHCH$_2$), 4.22 (2H, q, J=7.7, CH$_2$CH$_3$), 5.12 (2H, s, CH$_2$Ph), 5.18 [1H, m, CH(OH)], 7.3-7.42 (5H, br, PhH).

EXAMPLE 27e

4-Benzyloxycarbonylamino-2(S)-methanesulfonyloxy-butyric acid ethyl ester

Methanesulfonyl chloride (2.79 ml; 36 mmol) was added drop wise with stirring to a solution of the compound of example 27d (8.4 g; 30 mmol) in dichloromethane (90 ml) and pyridine (3.7 ml; 45.98 mmol) at 0° C. The reaction mixture was stirred at 0° C. for 2 h and subsequently at room temperature overnight (16 h). It was processed as is routinely done and was purified using flash chromatography (silica gel, 5% CH$_3$CN in chloroform). Yield, 6.6 g (61.3%); MS (CI): 360 (M$^+$+1); $^1$H NMR (CDCl$_3$): 1.30 (3H, t, J=7.3, CH$_2$CH$_3$), 2.28 (2H, 2×m, NHCH$_2$CH$_2$), 3.18 (3H, s, SO$_2$CH$_3$), 3.15, 3.35 (2H, 2×m, NHCH$_2$), 4.25 (2H, q, J=7.3, CH$_2$CH$_3$), 5.1 (2H, s, CH$_2$Ph), 5.18 [1H, m, CH(OSO$_2$Me)], 7.3-7.4 (5H, br, PhH).

EXAMPLE 27f

4-Benzyloxycarbonylamino-2(S)-(4-{2-tert-butoxycarbonylamino-acetyl}-phenoxy)-butyric acid ethyl ester A mixture of compound of example 27c (4.0 g; 16 mmol), compound of example 27e (6.4 g; 18 mmol) and K$_2$CO$_3$ (4.5 g) in DMF (30 ml) was stirred at 65° C. for 2.5 h. The reaction mixture was brought to room temperature and acidified with 2N HCl (20 ml). It was processed as is routinely done and was purified using flash chromatography (silica gel, 8% CH$_3$CN in chloroform). Yield, 5.6 g (68%), oil; $^1$H NMR (CDCl$_3$): 1.23 (3H, t, J=7.6, CH$_2$CH$_3$), 1.5 [9H, s, C (CH$_3$)$_3$], 2.25 (2H, m, NHCH$_2$CH$_2$), 3.45 (2H, 2×m, NHCH$_2$CH$_2$), 4.22 (2H, q, J=7.6, CH$_2$CH$_3$), 4.58 (2H, d, J=5.5, NHCH$_2$), 4.80 (1H, t, J=5.5 NHCH$_2$CH$_2$), 5.1 (2H, s, CH$_2$Ph), 5.55 (1H, br, N HCH$_2$CO), 6.89 (2H, d, J=8.0, H-3 & H-5), 7.3-7.4 (5H, br, PhH). 7.92 (2H, d, J=8.0 H-2 & H-6).

EXAMPLE 27g 2-(4-{2-Amino-acetyl}-phenoxy)-4-benzyloxycarbonylamino-butyric acid ethyl ester, hydrochloride The title compound was obtained from the compound of example 27f using the procedure described in example 5b. Yield, 90%; $^1$H NMR (CD$_3$OD): 1.28 (3H, t, J=7.3, CH$_2$CH$_3$), 2.22 (2H, m, NHCH$_2$CH$_2$), 3.40 (2H, 2×m, NHCH$_2$CH$_2$), 4.25 (2H, q, J=7.3, CH$_2$CH$_3$), 4.58 (2H, d, J=5.5, NHCH$_2$), 5.03 (1H, m, —CHCOO), 5.10 (2H, s, CH$_2$Ph), 7.08 (2H, d, J=9.0, H-3 & H-5), 7.3-7.8 (5H, br, PhH), 8.05 (2H, d, J=8.0, H-2 & H-6).

EXAMPLE 27h

4-Benzyloxycarbonylamino-2-(4-{2-[5-cyano-1-oxo-1,3-dihydro-isoindol-2-yl]-acetyl}-phenoxy)-butyric acid ethyl ester The title compound was obtained from the compound of example 27g using the procedure described in example 1g. The crude product was purified using flash chromatography (silica gel, 10% CH$_3$CN in chloroform). Yield, 12%; mp, 152-54° C. (CHCl$_3$-PE 60-80° C.); analysis: C$_{31}$H$_{29}$N$_3$O$_7$ requires C, 67.03; H, 5.22; N, 7.57. found C, 66.83; H, 5.24; N, 7.52%.

EXAMPLE 27i

4-Benzyloxycarbonylamino-2-{4-[2-(1-oxo-5-thiocarbamoyl-1,3-dihydro-isoindol-2-yl)-acetyl]-phenoxy}-butyric acid ethyl ester The title compound was obtained from the compound of example 27h using the procedure described in example 1h. The crude product was purified using flash chromatography (silica gel, 10% CH$_3$CN, 2% MeOH in chloroform). Yield, 93%; mp, 80-81° C.: MS (ESI$^-$): 588 (M−1); $^1$H NMR (CDCl$_3$): 1.25 (3H, t, J=8.8, CH$_2$CH$_3$), 2.24 (2H, m, NHCH$_2$CH$_2$), 3.44 (2H, 2×m, NHCH$_2$CH$_2$), 4.22 (2H, q, J=8.8, CH$_2$CH$_3$), 4.58, 5.02, 5.18 (6H, 3×s, 3×CH$_2$), 4.80 (1H, t, NHCH$_2$), 5.04 (1H, m, —CHCOO), 6.94 (2H, d, J=8.8, H-2'& H-6'), 7.35 (5H, br, PhH), 7.50 (1H, br, CSNH$_2$), 7.75-7.78 (3H, m, CSNH$_2$, H-6 & H-7), 7.95 (2H, m, H-3' & H-5'), 8.01 (1H, br, H-4).

EXAMPLE 27j

4-Benzyloxycarbonylamino-2-(4-{2-[5-methylsulfanylcarbonimidoyl-1-oxo-1,3-dihydro-isoindol-2-yl]-acetyl}-phenoxy)-butyric acid ethyl ester, hydroiodide The title compound was obtained from the compound of example 27i using the procedure described in example 11. Yield, 95%.

EXAMPLE 28

4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester The title compound was obtained from the compound of example 27j using the procedure described in example 4. Purification was effected using flash chromatography (silica gel, 3% MeOH in chloroform). Yield, 75%; mp, 174-75° C.; MS (ESI): 611 (M$^+$+Na), 589 (M$^+$+1); analysis: C$_{31}$H$_{32}$N$_4$O$_8$ requires C, 63.26; H, 5.44; N, 9.52. found: C, 62.78; H, 5.28; N, 9.25%.

EXAMPLE 29

(4-{2-[5-(N-Hydroxycarbamimidoyl)-1-oxo-1,3-dihydro-isoindol-2-yl]-acetyl}-phenylsulfanyl)-acetic acid methyl ester The title compound was obtained from the compound of example 29g using the procedure described in example 4. Purification was effected using flash chromatography (silica gel, 3% MeOH in chloroform). Yield, 24% (white solid); mp, 193-94° C.; MS (ESI$^+$): 435 (M$^+$+Na), 414 (M$^+$+1); analysis: $C_{20}H_{19}N_3O_5$ requires C, 58.10; H, 4.63; N, 10.16; S, 7.75. found: C, 58.50; H, 4.67; N, 10.22; S, 7.66%.

EXAMPLE 29a (4-Acetyl-phenylsulfanyl)-acetic acid methyl ester

A mixture of 1-(4-bromo-phenyl)-ethanone (40 g, 201 mmol), methyloxycarbonyl methanthiolate copper (I) (40.68 g; 241 mmol), quinoline (173 ml) and pyridine (13.6 ml) was heated at 180° C. for 2 h. The reaction mixture was poured over crushed ice, acidified with conc. HCl and extracted with EtOAc. The EtOAc layer was washed with water, brine, dried ($Na_2SO_4$), concentrated and purified using flash chromatography (silica gel, 20% EtOAc-PE 60-80° C.) to obtain the title compound. Yield, 20 g (44%), oil; MS (EI): 224 (M), 209; analysis: $C_{11}H_{12}O_3S$, $0.5H_2O$ requires C, 56.65; H, 5.57. found: C, 57.10; H, 5.35%.

EXAMPLE 29b (4-{2-Bromo-acetyl}-phenylsulfanyl)-acetic acid methyl ester

The title compound was obtained from the compound of example 29a using the procedure described in example 20c. Yield, 82%; mp, 113-14° C.; MS (EI): (302,304) (M$^+$), 209; analysis: $C_{11}H_{11}BrO_3S$ requires C, 43.56; H, 3.63; S, 10.56; Br, 26.40. found: C, 43.48; H, 3.67; S, 10.82; Br, 27.82%.

EXAMPLE 29c (4-{2-tert-Butoxycarbonylamino-acetyl}-phenylsulfanyl)-acetic acid methyl ester The title compound was obtained from the compound of example 29b using the procedure described in example 27a-b. Yield, 44%, light yellow gum; MS (ESI$^+$): 362 (M$^+$+Na), 340 (M$^+$+1); analysis: $C_{16}H_{21}NO_5S$ requires C, 56.62; H, 6.24; N, 4.13; S, 9.45. found: C, 56.40; H, 6.28; N, 4.44; S, 9.88%.

EXAMPLE 29d (4-{2-Amino-acetyl}-phenylsulfanyl)-acetic acid methyl ester, hydrochloride The title compound was obtained from the compound of example 29c using the procedure described in example 5b. Yield 93%; IR (KBr): 3365, 3000, 1760, 1690, 1600; MS (ESI$^+$): 240 (M$^+$+1).

EXAMPLE 29e (4-{2-[5-Cyano-1-oxo-1,3-dihydro-isoindol-2-yl]-acetyl}-phenylsulfanyl)-acetic acid methyl ester The title compound was obtained from the compound of example 29d using the procedure described in example 1g. The crude product was purified using flash chromatography (silica gel, 3-10% $CH_3CN$ in chloroform). Yield, 17%; mp, 206-07° C.; MS (ESI$^+$): 403 (M$^+$+Na), 381 (M$^+$+1); analysis: $C_{20}H_{16}N_2O_4S$ requires C, 63.15; H, 4.24; N, 7.36; S, 8.43. found: C, 63.07; H, 4.18; N, 7.36; S, 8.84%.

EXAMPLE 29f (4-{2-[1-Oxo-5-thiocarbamoyl-1-oxo-1,3-dihydro-isoindol-2-yl]-acetyl}-phenylsulfanyl)-acetic acid methyl ester The title compound was obtained from the compound of example 29e using the procedure described in example 1h. Yield, 70%; mp, 214-15° C.; MS (ESI): 413 (M−1); analysis: $C_2H_{18}N_2O_4S$ requires C, 57.96; H, 4.38; N, 6.76, S, 15.47. found: C, 58.14; H, 4.22; N, 6.67; S, 15.61%.

EXAMPLE 29g (4-{2-[5-Methylsulfanylcarbonimidoyl-1-oxo-1,3-dihydro-isoindol-2-yl]-acetyl}-phenylsulfanyl)-acetic acid methyl ester, hydroiodide The title compound was obtained from the compound of example 29f using the procedure described in example 11. Yield, 85%, yellow solid.

EXAMPLE 30

(4-{2-[5-Carbamimidoyl-1-oxo-1,3-dihydro-isoindol-2-yl]-acetyl}-2-chloro-phenoxy)-acetic acid ethyl ester, acetic acid salt The title compound was obtained from the compound of example 30h using the procedure described in example 1. Yield, 43%, white solid; mp, 172-73° C.; MS (ESI$^+$): 452 (M$^+$+Na), 430 (M$^+$+1); analysis: $C_{23}H_{24}ClN_3O_7$, $0.5H_2O$; requires C, 55.37; H, 5.01; N, 8.42; Cl, 7.1.1. found, C, 55.38; H, 4.88; N, 8.18; Cl, 7.46%.

EXAMPLE 30a (2-Chloro-phenoxy)-acetic acid ethyl ester

The title compound was prepared by reacting 2-chloro-phenol, with ethyl 2-bromoacetate and $K_2CO_3$ in DMF. Yield, 97%, colourless oil; $^1H$ NMR (CDCl$_3$): 1.29 (3H, t, J=6.3, CH$_2$CH$_3$), 4.29 (2H, q, J=6.3, CH$_2$CH$_3$), 4.72 (2H, s, OCH$_2$), 6.76 (1H, d, J=8.2, H-6), 6.95 (1H, m, H-4), 720 (1H, m, H-5), 7.40 (1H, dd, J=8.2, H-3).

EXAMPLE 30b (4-Acetyl-2-chloro-phenoxy)-acetic acid ethyl ester

The title compound was obtained from the compound of example 30a using the procedure described in example 20b. Yield, 10%. Crude product was purified by flash chromatography with 20% EtOAc in PE 60-80° C. mp, 70-71° C.; MS (EI): 256 (M⁺), 241, 213 155; analysis: $C_{12}H_{13}ClO_4$ requires C, 56.15; H, 5.07; Cl, 13.82. found, C, 56.24; H, 5.10; Cl, 13.67%.

EXAMPLE 30c

(4-{2-Bromo-acetyl}-2-chloro-phenoxy)-acetic acid ethyl ester

The title compound was obtained from the compound of example 30b using the procedure described in example 20c. Purification was effected using flash chromatography (silica gel, 40% EtOAc in PE60-80° C.). Yield, 46%; mp, 128-30° C.; MS (EI): (334,336) (M⁺), 241; analysis:

$C_{12}H_{12}BrClO_4$ requires C, 42.95; H, 3.60. found, C, 42.69; H, 3.45%.

EXAMPLE 30d

(4-{2-tert-Butoxycarbonylamino-acetyl}-2-chloro-phenoxy)-acetic acid ethyl ester The title compound was obtained from the compound of example 30c using the procedure described in example 20d. Yield, 20%; mp, 75-76° C.; MS (EI): 371 (M⁺), 241; analysis: $C_{17}H_{22}ClNO_6$ requires C, 54.91; H, 5.92; N, 3.77; Cl, 9.54. found, C, 55.37; H, 6.00; N, 3.72; Cl, 9.94%.

EXAMPLE 30e

(4-{2-Amino-acetyl}-2-chloro-phenoxy)-acetic acid ethyl ester; hydrochloride The title compound was obtained from the compound of example 30d using the procedure described in example 5b. Yield, 78%; mp, 163-64° C.; MS (EI): 271 (M⁺), 241; analysis: $C_{12}H_{13}Cl_2NO_4$ requires C, 46.77; H, 4.87; N, 4.55; Cl, 23.03. found, C, 47.12; H, 4.97; N, 4.36; Cl, 22.67%.

EXAMPLE 30f

(2-Chloro-4-{2-[5-cyano-1-oxo-1,3-dihydro-isoindol-2-yl]-acetyl}-phenoxy)-acetic acid ethyl ester The title compound was obtained from the compound of example 30e using the procedure described in example 1g. Yield, 11%, white solid; mp, 178-80° C.; MS (EI): 412 (M⁺), 241; analysis: $C_{21}H_{17}ClN_2O_5$ requires C, 61.10; H, 4.15; N, 6.74; Cl, 8.59. found, C, 60.90; 1-1, 4.23; N, 6.59; Cl, 8.60%.

EXAMPLE 30g

(2-Chloro-4-{2-[1-oxo-5-thiocarbamoyl-1,3-dihydro-isoindol-2-yl]-acetyl}-phenoxy)-acetic acid ethyl ester The title compound was obtained from the compound of example 30F using the procedure described in example 1h. Yield, 86%, yellow solid; mp, 85-87° C.; MS (ESI⁺): 468 (M⁺+Na), 446 (M⁺+1); analysis: $C_{21}H_{19}ClN_2O_5S$ requires C, 56.44; H, 4.29; N, 6.22; Cl, 7.93; S, 7.17. found, C, 56.01; H, 4.30; N, 6.01; Cl, 7.80; S, 7.60%.

EXAMPLE 30h

(2-Chloro-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 30g using the procedure described in example 1i. Yield, 91%, yellow solid; mp, 155° C.; MS (ESI⁺): 468 (M⁺+Na), 461 (M⁺+1).

EXAMPLE 31

(2-Chloro-4-{2-[5-(imino-isobutoxycarbonylamino-methyl)-1-oxo-1,3-dihydro-isoindol-2-yl]-acetyl}-phenoxy)-acetic acid ethyl ester The title compound was obtained from the compound of example 30 using the procedure described in example 6 Isobutyl chloroformate was used instead of methyl chloroformate. Yield, 42%, white solid; mp, 178-79° C.; MS (ESI⁺): 552 (M⁺+Na), 530 (M⁺+1); analysis: $C_{26}H_{28}ClN_3O_7$ requires C, 58.93; H, 5.19; N, 7.93; Cl, 6.70. found, C, 59.37; H, 5.35; N, 7.98; Cl, 6.39%.

EXAMPLE 32

(2-Chloro-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 30h using the procedure described in example 4. Yield, 71%, white solid; mp, 201-02° C.; MS (ESI⁺): 468 (M⁺+Na), 446 (M⁺+1); analysis: $C_{21}H_{20}ClN_3O_6$ requires C, 56.57; H, 4.50; N, 9.43; Cl, 7.96. found, C, 56.53; H, 4.43; N, 9.11; Cl, 8.04%.

EXAMPLE 33

(4-{2-[5-Carbamimidoyl-1-oxo-1,3-dihydro-isoindol-2-yl]-acetyl}-2-ethyl sulfanyl-phenoxy)-acetic acid ethyl ester, acetic acid salt, monohydrate The title compound was obtained from the compound of example 33h using the procedure described in example 1. Yield, 24%, white solid; mp, 185-86° C.; MS (ESI⁺): 478 (M⁺+Na), 456 (M⁺+1); analysis: $C_{25}H_{29}N_3O_7S$, $H_2O$ requires C, 56.27; H, 5.67; N, 7.88; S, 6.01. found: C, 56.26; H, 5.58; N, 8.20; S, 6.38%.

EXAMPLE 33a

1-(3-Ethylsulfanyl-4-hydroxy-phenyl)-ethanone

The title compound was obtained from 1-(3-bromo-4-hydroxy-phenyl)-ethanone using the procedure described in example 29a. 1-Ethanethiolate Cu (I) was used instead of methyloxycarbonylmethanthiolate copper(I). It was purified using flash chromatography (silica gel, 10% EtOAc-PE60-80° C. Yield, 57%, brownish white solid; mp, 88° C.; MS (EI): 196 (M⁺), 181 (100%); analysis: $C_{10}H_{12}O_2S$ requires C, 61.22; H, 6.12; S, 16.32. found C, 61.54; H, 6.35; S, 16.28%.

EXAMPLE 33b (4-Acetyl-2-ethylsulfanyl-phenoxy)-acetic acid ethyl ester

The title compound was obtained from the compound of example 33a using the procedure described in example 20a. The crude product was purified using flash chromatography (silica gel, 10% EtOAc in PE 60-80° C.). Yield, 89%, white solid; mp, 64-65° C.; MS (ESI): 305 ($M^+$+Na), 283 ($M^+$+1); analysis: $C_{14}H_{18}O_4S$ requires C, 59.57; H, 6.38; S, 11.35. found C, 59.86; H, 6.49; S, 11.47%.

EXAMPLE 33c (4-{2-Bromo-acetyl}-2-ethylsulfanyl-phenoxy)-acetic acid ethyl ester The title compound was obtained from the compound of example 33b using the procedure described in example 20c. Yield, 45%, white solid; mp, 84° C.; MS (EI): (360,362) ($M^+$), 267 (100%); analysis: $C_{14}H_{17}BrO_4S$ requires C, 46.54; H, 4.71; Br, 22.16; S, 8.86. found: C, 46.90; H, 4.84; Br, 21.87; S, 9.31%

EXAMPLE 33d (4-{2-tert-Butoxycarbonylamino-acetyl}-2-ethylsulfanyl-phenoxy)-acetic acid ethyl ester The title compound was obtained from the compound of example 33c using the procedure described in example 20d. Yield, 29%, white solid; mp, 83° C.; MS (EI): 397 ($M^+$), 267 (100%), 253; analysis: $C_{19}H_{27}NO_6S$ requires C, 57.43; H, 6.80; N, 3.53; S, 8.06. found: C, 57.36; H, 6.80; N, 3.34; S, 8.15%.

EXAMPLE 33e (4-{2-Amino-acetyl}-2-ethylsulfanyl-phenoxy)-acetic acid ethyl ester, hydrochloride The title compound was obtained from the compound of example 33d using the procedure described in example 5b. Yield, 96%; MS (ESI): 298 ($M^+$-1-1); $^1$H NMR (DMSO-$D_6$): 1.35 (6H, t, J=7.32, 2×$CH_2CH_3$), 3.00 (2H, q, J=7.32, S$CH_2CH_3$), 4.29 (2H, q, J=7.3, $CH_2CH_3$), 4.65 (2H, d, $CH_2NH$), 4.80 (2H, s, $OCH_2$), 6.75 (1H, d, J=9.14, H-5), 7.30 (3H, br, $NH_3$), 7.75 (1H, dd, J=9.14, H-6), 7.90 (1H, br, H-2).

EXAMPLE 33f (4-{2-[5-Cyano-1-oxo-1,3-dihydro-isoindol-2-yl]-acetyl}-2-ethylsulfanyl-phenoxy)-acetic acid ethyl ester The title compound was obtained from the compound of example 33e using the procedure described in example 1g. Yield, 8%; mp, 157-60° C.; MS (ESI$^-$): 437 (M−1); analysis: $C_{23}H_{22}N_2O_5S$ requires C, 63.01; H, 5.02; N, 6.39; S, 7.31. found: C, 63.26; H, 4.64; N, 6.49; S, 7.64%.

EXAMPLE 33g (2-Ethylsulfanyl-4-{2-[1-oxo-5-thiocarbamoyl-1,3-dihydro-isoindol-2-yl]-acetyl}-phenoxy)-acetic acid ethyl ester The title compound was obtained from the compound of example 33f using the procedure described in example 1h. Yield, 83%; mp, 178-79° C.; MS (ESI$^+$): 495 ($M^+$+Na), 473 ($M^+$+1); analysis: $C_{23}H_{24}N_2O_5S_2$ requires C, 58.46; H, 5.12; N, 5.93; S, 13.57. found: C, 58.40; H, 5.17; N, 5.99; S, 13.62%.

EXAMPLE 33h (2-Ethylsulfanyl-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 33g using the procedure described in example 11. Yield, 91%; mp, 182-83° C.; MS (ESI$^+$): 508 ($M^+$+Na), 487 ($M^+$+1);

EXAMPLE 34

(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester, hemihydrate The title compound was obtained from the compound of example 33h using the procedure described in example 4. Yield, 85%, white solid; mp, 190-91° C.; MS (ESI$^+$): 494 ($M^+$+Na), 472 ($M^+$+1); analysis: $C_{23}H_{25}N_3O_6S$, 0.5$H_2O$, requires C, 57.50; H, 5.42; N, 8.75; S, 6.66. found: C, 57.88; H, 5.32; N, 9.10; S, 6.71%.

EXAMPLE 35

(4-{2-[5-Carbamimidoyl-1-oxo-1,3-dihydro-isoindol-2-yl]-acetyl}-2-ethane sulfonyl-phenoxy)-acetic acid ethyl ester; acetic acid salt, hydrate The title compound was obtained from the compound of example 35e using the procedure described in example 1. Yield, 26% (white solid); mp, 174-75° C.; MS (ESI$^+$): 488 ($M^+$+1); analysis: $C_{25}H_{29}N_3O_9S$, $H_2O$, requires C, 53.10; H, 5.49; N, 7.43; S, 5.75. found: C, 52.40; H, 5.36; N, 7.08; S, 5.68%.

EXAMPLE 35a (4-{2-tert-Butoxycarbonylamino-acetyl}-2-ethanesulfonyl-phenoxy)-acetic acid ethyl ester A mixture of compound of example 33d (2.2 g; 5.54 mmol) and 3-chloroperbenzoic acid (2.87 g; 16.62 mmol) in dichloromethane (10 ml) was stirred at room temperature until all the starting material was consumed. It was processed as is routinely done and was purified using flash chromatography (silica gel, with 5% $CH_3CN$ in chloroform). Yield, 2 g (84%), foam; MS (ESI$^+$): 430 ($M^+$+1); analysis: $C_{19}H_{27}NO_8S$, requires C, 58.14; H, 6.34; N, 3.26; S, 7.46. found: C, 58.51; H, 6.32; N, 3.25; S, 7.40%.

EXAMPLE 35b (4-{2-Amino-acetyl}-2-ethanesulfonyl-phenoxy)-acetic acid ethyl ester, hydrochloride The title compound was obtained from the compound of example 35a using the procedure described in example 5b Yield, 99%, pale yellow gum; MS (ESI$^+$): 330 ($M^+$+1); $^1$H NMR (CDCl$_3$): 1.30 (6H, t, J=7.32, 2×$CH_2CH_3$), 3.50 (2H, q, J=7.32, $SO_2CH_2CH_3$), 4.29 (2H, q, J=7.3, $OCH_2CH_3$), 4.60

(2H, d, NHCH$_2$), 4.90 (2H, s, OCH$_2$), 5.50 (1H, br, NHCH$_2$), 7.01 (1H, d, J=9.14, H-6), 8.21 (1H, dd, J=9.14, H-5), 8.60 (1H, br, H-3).

EXAMPLE 35c (4-{2-[5-Cyano-t-oxo-1,3-dihydro-isoindol-2-yl]-acetyl}-2-ethanesulfonyl-phenoxy)-acetic acid ethyl ester The title compound was obtained from the compound of example 35b using the procedure described in example 1g. Yield, 7%; mp, 194-95° C.; MS (ESI$^-$): 469 (M−1); analysis: C$_{23}$H$_{22}$N$_2$O$_7$S requires C, 58.72; H, 4.68; N, 5.96; S, 6.81. found: C, 58.97; H, 4.64; N, 5.72; S, 6.95%.

EXAMPLE 35d (2-Ethanesulfonyl-4-{2-[1-oxo-5-thiocarbamoyl-1,3-dihydro-isoindol-2-yl]-acetyl}-phenoxy)-acetic acid ethyl ester The title compound was obtained from the compound of example 35c using the procedure described in example 1h. Yield, 69%, yellow solid; mp, 117-18° C.; MS (ESI$^+$): 527 (M$^+$+Na), 505 (M$^+$+1); analysis: C$_{23}$H$_{24}$N$_2$O$_7$S$_2$, H$_2$O requires C, 52.87; H, 4.98; N, 5.36; S, 12.26. found: C, 52.61; H, 4.61; N, 5.35; S, 12.35%.

EXAMPLE 35e (2-Ethanesulfonyl-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 35d using the procedure described in example 11. Yield, 89%, yellow solid; mp, 198-200° C.; MS (ESI$^+$): 541 (M$^+$+Na), 519 (M$^+$+1).

EXAMPLE 36

(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 35e using the procedure described in example 4. Yield, 70%, white solid; mp, 196-97° C.; MS (ESI$^+$): 526 (M$^+$+Na), 504 (M$^+$+1); analysis: C$_{23}$H$_{25}$N$_3$O$_8$S requires C, 54.87; H, 4.97; N, 8.35; S, 6.36. found: C, 54.57; H, 4.84; N, 8.05; S, 6.66%.

EXAMPLE 37

(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 37h using the procedure described in example 4. Yield, 37%; mp, 183-84° C.; MS (ESI$^+$): 554 (M$^+$+Na), 532 (M$^+$+1); analysis: C$_{25}$H$_{29}$N$_3$O$_6$S$_2$ requires C, 56.50; H, 5.46; N, 7.90; S, 12.05. found C, 56.90; H, 5.46; N, 8.01; S, 12.30%.

EXAMPLE 37a 1-(3,5-Bis-ethylsulfanyl-4-hydroxy-phenyl)-ethanone

Following the procedure for the preparation of example 29a, 1-(3,5-dibromo-4-hydroxy-phenyl)-ethanone was treated with 1-ethanethiolate Cu(I) in place of methyloxycarbonylmethanthiolate copper (I) to obtain 37a. The crude product was purified by flash chromatography with 10% EtOAc in PE 60-80° C. Yield, 16%; mp, 74-75° C.; MS (EI): 256 (M$^+$), 241, 213; analysis: C$_{12}$H$_{16}$O$_2$S$_2$ requires C, 56.25; H, 6.25; S, 25.00. found C, 56.63; H, 6.47; S, 25.39%.

EXAMPLE 37b (4-Acetyl-2,6-bis-ethylsulfanyl-phenoxy)-acetic acid ethyl ester The title compound was obtained from the compound of example 37a using the procedure described in example 20a. It was purified using flash chromatography (silica gel, EtOAc in PE 60-80° C.). Yield, 80%, pale yellow liquid; MS (CI): 371 (M$^+$+29), 343 (M$^+$+1), 329; analysis: C$_{16}$H$_{22}$O$_4$S$_2$ requires C, 56.12; H, 6.47; S, 18.72. found C, 56.36; H, 6.42; S, 18.69%.

EXAMPLE 37c (4-{2-Bromo-acetyl}-2,6-bis-ethylsulfanyl-phenoxy)-acetic acid ethyl ester The title compound was obtained from the compound of example 37b using the procedure described in example 20c. The crude product was purified using flash chromatography (silica gel, 10% EtOAc in PE 60-80° C.). Yield, 80%, brown gum; MS (EI): (422, 420) (M$^+$), (319, 317); analysis: C$_{16}$H$_{21}$BrO$_4$S$_2$ requires C, 45.61; H, 5.02; Br, 18.96; S, 15.22. found C, 45.21; H, 4.98; Br, 18.60; S, 15.09%.

EXAMPLE 37d (4-{2-tert-Butoxycarbonylamino-acetyl}-2,6-bis-ethylsulfanyl-phenoxy)-acetic acid ethyl ester The title compound was obtained from the compound of example 37c using the procedure described in example 27a-b. The crude product was purified using flash chromatography (silica gel, 10% EtOAc in PE 60-80° C.). Yield, 48%, pale yellow oil; MS (EI): 457 (M$^+$), 425, 398; analysis: C$_{21}$H$_{31}$NO$_6$S$_2$ requires C, 55.12; H, 6.83; N, 3.06; S, 14.01. found C, 54.93; H, 6.49; N, 2.98; S, 13.80%.

EXAMPLE 37e (4-{2-Amino-acetyl}-2,6-bis-ethylsulfanyl-phenoxy)-acetic acid ethyl ester, hydrochloride The title compound was obtained from the compound of example 37d using the procedure described in example 5b. Yield, 72%, yellow semisolid; MS (ESI): 358 (M$^+$+1); analysis: C$_{16}$H$_{24}$ClNO$_4$S$_2$ requires C, 48.78; H, 6.14; N, 3.56; Cl, 9.00; S, 16.28. found C, 48.42; H, 6.05; N, 3.10; Cl, 8.90; S, 15.95%.

EXAMPLE 37f (4-{2-[5-Cyano-1-oxo-1,3-dihydro-isoindol-2-yl]-acetyl}-2,6-bis-ethylsulfanyl-phenoxy)-acetic acid ethyl ester The title compound was obtained from the compound of example 37e using the procedure described in example 1g. The crude was purified using flash chromatography (silica gel, 5% $CH_3CN$ in chloroform). Yield, 6%, white solid; MS (ESI): 521 ($M^+$+Na), 499 ($M^+$+1); analysis: $C_{25}H_{26}ClN_2O_5S_2$ requires C, 60.22; H, 5.26; N, 5.62; S, 12.86. found C, 60.68; H, 5.20; N, 5.70; S, 12.90%.

EXAMPLE 37g (2,6-Bis-ethylsulfanyl-4-{2-[1-oxo-5-thiocarbamoyl-1,3-dihydro-isoindol-2-yl]-acetyl}-phenoxy)-acetic acid ethyl ester The title compound was obtained from the compound of example 37f using the procedure described in example 1h. Yield, 51%, yellow solid; mp, 83-84° C.; MS (ESI): 531 (M−1); analysis: $C_{25}H_{28}N_2O_5S_3$ requires C, 58.37; H, 5.30; N, 5.26; S, 18.06. found C, 58.51; H, 5.40; N, 5.28; S, 18.10%.

EXAMPLE 37h (2,6-Bis-ethylsulfanyl-4-{2-[5-methylsulfanylcarbonimidoyl-1-oxo-1,3-dihydro-isoindol-2-yl]-acetyl}-phenoxy)-acetic acid ethyl ester hydroiodide The title compound was obtained from the compound of example 37g using the procedure described in example a Yield, 98%, yellow solid.

EXAMPLE 38

(2-Acetylamino-4-{2-[5-N-hydroxycarbamimidoyl)-1-oxo-1,3-dihydro-iso indol-2-yl]-acetyl}-phenoxy)-acetic acid ethyl ester The title compound was obtained from the compound of example 38h using the procedure described in example 1. Yield, 38%; mp, 185-86° C.; MS (ESI): 491 ($M^+$+Na), 469 ($M^+$-1-1); analysis: $C_{23}H_{24}N_4O_7$ requires C, 58.97; H, 5.16; N, 11.96. found: C, 58.85; H, 5.14; N, 11.49%.

EXAMPLE 38a

N-(5-Acetyl-2-hydroxy-phenyl)-acetamide

A solution of 1-(4-hydroxy-3-nitro-phenyl)-ethanone (10 g) in methanol, DMF (50 ml) and acetic anhydride (10 ml) was hydrogenated using 10% Pd—C (0.45 g) for 2 h at 30 psi. The catalyst was filtered off. The filtrate was concentrated (5 ml) and treated with EtOAc (100 ml) to obtain the title compound, which was filtered, washed with EtOAc (10 ml) and dried. Yield, 9.1 g (85%); mp, >215° C.; MS (EI): 193 ($M^+$), 151, 136, 108.

EXAMPLE 38b (4-Acetyl-2-acetylamino-phenoxy)-acetic acid ethyl ester

The title compound was obtained from the compound of example 38a using the procedure described in example 20a, which was purified using flash chromatography (silica gel, 5-10% $CH_3CN$ in chloroform). Yield, 60%; mp, 113-14° C.; MS (ESI): 302 ($M^+$+Na), 280 ($M^+$+1); analysis: $C_{14}H_{17}NO_5$ requires C, 60.21; H, 6.13; N, 5.02. found: C, 60.42; H, 6.24; N, 5.02%.

EXAMPLE 38c (2-Acetylamino-4-{2-bromo-acetyl}-phenoxy)-acetic acid ethyl ester The title compound was obtained from the compound of example 38b using the procedure described in example 20c. The crude product was purified using flash chromatography (silica gel, 10% $CH_3CN$ in chloroform). Yield, 64%; mp, 124-25° C. (EtOAc-PE60-80° C.); MS (ESI): 380 ($M^+$+Na), 358 ($M^+$+1); analysis: $C_{14}H_{16}BrNO_5$ requires C, 46.95; H, 4.50; N, 3.91; Br, 22.31. found: C, 46.84; H, 4.15; N, 3.54; Br, 22.80%.

EXAMPLE 38d (2-Acetylamino-4-{2-tert-butoxycarbonylamino-acetyl}-phenoxy)-acetic acid ethyl ester The title compound was obtained from the compound of example 38c using the procedure described in example 20d. The crude product was purified using flash chromatography (silica gel, 3-10% $CH_3CN$ in chloroform). Yield, 35%, oil; $^1H$ NMR ($CDCl_3$): 1.30 (3H, t, J=7.5, $CH_2CH_3$), 1.45 [9H, s, C(C$H_3)_3$], 2.27 (3H, s, $NHCOCH_3$), 4.30 (2H, q, J=7.5, C$H_2CH_3$), 4.63 (2H, d, J=5.4, $COCH_2NH$), 4.74 (2H, s, OC$H_2$), 5.5 (1H, br, $NHCH_2$), 6.97 (1H, d, J=8.8, H-6), 7.69 (1H, dd, J=8.8, 2.0, H-5), 8.20 (1H, br, J=1.8, H-3), 9.00 (1H, br, NH).

EXAMPLE 38e (2-Acetylamino-4-{2-amino-acetyl}-phenoxy)-acetic acid ethyl ester, hydrochloride The title compound was obtained from the compound of example 38d using the procedure described in example 20e. Yield, 90%

EXAMPLE 38f (2-Acetylamino-4-{2-[5-cyano-1-oxo-1,3-dihydro-isoindol-2-yl]-acetyl}-phenoxy)-acetic acid ethyl ester The title compound was obtained from the compound of example 38e using the procedure described in example 1g. The crude product was purified using flash chromatography (silica gel, 10% $CH_3CN$ in chloroform, 1% MeOH in chloroform). Yield, 16%; mp, 121-22° C.

EXAMPLE 38g (2-Acetylamino-4-{2-[1-oxo-thiocarbamoyl-1,3-dihydro-isoindol-2-yl]-acetyl}-phenoxy)-acetic acid ethyl ester The title compound was obtained from the compound of example 38f using the procedure described in example 1h.

The crude product was purified using flash chromatography (silica gel, 10% CH$_3$CN in chloroform, 1% MeOH in chloroform). Yield, 87%; mp, 110° C.

EXAMPLE 38h (2-Acetylamino-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 38g using the procedure described in example 1i. Yield, 99%.

EXAMPLE 39

(2-{Ethoxycarbonylmethyl-methanesulfonyl-amino}-4-{2-[5-(imino-iso butoxycarbonylamino-methyl)-1-oxo-1,3-dihydro-isoindol-2-yl]-acetyl}-phenoxy)-acetic acid ethyl ester, mono hydrate The title compound was obtained from the compound of example 39l using the procedure described in example 6. Isobutyl chloroformate was used instead of methyl chloroformate. Yield, 63%; mp, 80-82° C.; MS (ESI): 697 (M$^+$+Na), 675 (M$^+$+1); analysis: C$_{31}$H$_{38}$N$_4$O$_{11}$S H$_2$O requires, C, 53.75; H, 5.78; N, 8.09; S, 4.62. found C, 53.97; H, 5.57; N, 7.67; S, 4.14%.

EXAMPLE 39a 1-(4-Benzyloxy-3-nitro-phenyl)-ethanone 1-(4-hydroxy-3-nitro-phenyl)-ethanone was treated with benzyl bromide in the presence of K$_2$CO$_3$ in DMF, and processed as reported in the synthesis of example 20a to obtain the crude product which was purified using flash chromatography (silica gel, 5% CH$_3$CN in chloroform). Yield, 94%; mp, 132° C.; MS (CI): 300 (M$^+$+29), 272 (M$^+$+1), 91; analysis: C$_{15}$H$_{13}$NO$_4$ requires, C, 66.42; H, 4.83; N, 5.16. found; C, 66.58; H, 4.52; N, 5.30%.

EXAMPLE 39b 1-(3-Amino-4-benzyloxy-phenyl)-ethanone

The title compound was obtained from the compound of example 39a using a reported procedure (Boruah. R. N., Ind. J. Chem., 33B, 758, 1994). The crude product was purified using flash chromatography (silica gel, 5% CH$_3$CN in chloroform). Yield, 76.9%; mp, 124-25° C.; MS (EI): 241 (M$^+$), 150, 91; analysis: C$_{15}$H$_{15}$NO$_2$ requires C, 74.67; H, 6.27; N, 5.80. found: C, 74.89; H, 6.45; N, 5.92%.

EXAMPLE 39c

N-(5-Acetyl-2-benzyloxy-phenyl)-methanesulfonamide

Methanesulfonyl chloride (6.08 ml; 78.5 mmol) was added drop wise over a period of 30 min. with vigorous stirring to a mixture of compound of example 39b (15.5 g; 64.32 mmol) in CH$_2$Cl$_2$ (200 ml) and pyridine (13.78 ml; 165.7 mmol) at 0° C. The reaction mixture was slowly brought to room temperature and stirred overnight (~16 h). It was acidified using dil. HCl and extracted with EtOAc. The EtOAc layer was washed with water, brine, dried (Na$_2$SO$_4$), concentrated and purified using flash chromatography (silica gel, 5% CH$_3$CN in chloroform). Yield, 17.5 g (85.3%); mp, 118-19° C.; MS (EI): 319 (M$^+$), 240, 91; analysis: C$_{16}$H$_{17}$NO$_4$S requires C, 60.17; H, 5.36; N, 4.39; S, 10.04. found: C, 60.30; H, 5.40; N, 4.44; S, 10.41%.

EXAMPLE 39d

N-(5-Acetyl-2-hydroxy-phenyl)-methanesulfonamide

In an atmosphere of nitrogen 10% Pd—C (1.17 g) was added to a mixture of compound of example 39c (11.7 g; 36.67 mmol) and ammonium formate (11.56 g; 116.23 mmol) in methanol (110 mL) It was refluxed for 3 h. The catalyst was filtered and the filtrate concentrated and purified using flash chromatography (silica gel, 10% CH$_3$CN in chloroform). Yield, 8.3 g (84.2%); mp, 202° C.: MS (ESI$^-$): 228 (M−1); analysis: C$_9$H$_{11}$NO$_4$S requires C, 47.15; H, 4.84; N, 6.11; S, 13.98. found: C, 47.39; H, 4.72; N, 6.53; S, 13.53%.

EXAMPLE 39e (4-acetyl-2-{ethoxycarbonylmethyl-methansulfonyl-amino}-phenoxy)-acetic acid ethyl ester The title compound was obtained from the compound of example 39d using the procedure described in example 20a. Yield, 56%; MS (ESI): 424 (M$^+$+Na), 402 (M$^+$+1); analysis: C$_{17}$H$_{23}$NO$_8$S requires C, 50.87; H, 5.77; N, 3.49; S, 7.99. found: C, 51.29; H, 6.01; N, 3.08; S, 7.75%.

EXAMPLE 39f (4-{2-Bromoacetyl}-2-{ethoxycarbonylmethyl-methane-sulfonyl-amino}-phenoxy)-acetic acid ethyl ester The title compound was obtained from the compound of example 39e using the procedure described in example 20c. The crude product was purified using flash chromatography (silica gel, 5-10% CH$_3$CN in chloroform). Yield, 60%; MS (ESI): 504 (M$^+$+Na), 482 (M$^+$+1); $^1$H NMR (CDCl$_3$): 1.32 (6H, m, 2×CH$_2$CH$_3$), 3.16 (3H, s, SO$_2$CH$_3$), 4.18, 4.27 (4H, 2×q, J=6.8, 2×C$\overline{H_2}$CH$_3$), 4.42, 4.45, 4.8$\overline{4}$ (6H, 3×s, 3×CH$_2$), 6.90 (1H, d, J=8.$\overline{8}$, H-3), 8.03 (1H, dd, J=8.5, 1.8, H-4), $\overline{8.27}$ (1H, d, J=1.8, H-6).

EXAMPLE 39g (4-{2-tert-Butoxycarbonylamino-acetyl}-2-{ethoxycarbonylmethyl-methanesulfonyl-amino}-phenoxy)-acetic acid ethyl ester The title compound was obtained from the compound of example 39f using the procedure described in example 20d. The crude product was purified using flash chromatography (silica gel, 5% CH$_3$CN in chloroform). Yield, 28%; mp, 114-15° C.; MS (ESI): 538 (M$^+$+Na).

EXAMPLE 39h (4-{2-Amino-acetyl}-2-{ethoxycarbonylmethyl-methanesulfonyl-amino}-phenoxy)-acetic acid ethyl ester, hydrochloride The title compound was obtained from the compound of example 39g using the procedure described in example 20e.

Yield, 90%; mp, 187-90° C.; IR (KBr): 2950, 1750, 1600, 1475.

EXAMPLE 39i (4-{2-[5-Cyano-1-oxo-1,3-dihydro-isoindol-2-yl]-acetyl}-2-ethoxy carbonylmethyl-methanesulfonyl-amino)-phenoxy]-acetic acid ethyl ester The title compound was obtained from the compound of example 39h using the procedure described in example 1g. The crude product was purified using flash chromatography (silica gel, 10% $CH_3CN$ in chloroform, 1% MeOH in chloroform). Yield, 20%; mp, 170-71° C.; MS (ESI): 580 ($M^+$+Na), 558 ($M^+$+1).

EXAMPLE 39j (2-{Ethoxycarbonylmethyl-methanesulfonyl-amino}-4-{2-[1-oxo-5-thio carbamoyl-1,3-dihydro-isoindol-2-yl]-acetyl}-phenoxy)-acetic acid ethyl ester The title compound was obtained from the compound of example 39i using the procedure described in example 1h. The crude product was purified using flash chromatography (silica gel, 10% $CH_3CN$ in chloroform, 2% MeOH in chloroform). Yield, 85%; mp, 96° C.; MS (ESI): 614 ($M^+$+Na), 592 ($M^+$+1); analysis: $C_{26}H_{29}N_3O_9S_2$ requires, C, 52.78; H, 4.94; N, 7.10. found C, 52.58; H, 4.72; N, 7.49%.

EXAMPLE 39k (2-{Ethoxycarbonylmethyl-methanesulfonyl-amino}-4-{2-[5-methyl sulfanylcarbonimidoyl-1-oxo-1,3-dihydro-isoindol-2-yl]-acetyl}-phenoxy)-acetic acid ethyl ester, hydroiodide The title compound was obtained from the compound of example 39j using the procedure described in example 1i. Yield, 98%.

EXAMPLE 39l (4-{2-[5-Carbamimidoyl-1-oxo-1,3-dihydro-isoindol-2-yl]-acetyl}-2-{ethoxycarbonyl methyl-methanesulfonyl-amino}-phenoxy)-acetic acid ethyl ester, acetic acid salt The title compound was obtained from the compound of example 39k using the procedure described in example 1. Yield, 25%; $^1$H NMR (DMSO-$D_6$): 1.18, 1.23 (6H, 2×t, J=7.5, 2×$CH_2CH_3$), 1.78 (3H, s, $CH_3COO$), 3.14 (3H, s, $SO_2CH_3$), 4.10, 4.20 (4H, 2×q, J=6.8, 2×$CH_2CH_3$), 4.45, 4.63, 5.11, 5.18 (8H, 4×s, 4×$CH_2$), 7.28 (1H, d, J=8.9, H-3'), 7.92 (2H, br), 7.92, 8.08, 8.14 (5H, m).

EXAMPLE 40

(2-{Ethoxycarbonylmethyl-methanesulfonyl-amino}-4-{2-[5-(N-hydroxy carbamimidoyl)-1-oxo-1,3-dihydro-isoindol-2-yl]-acetyl}-phenoxy)-acetic acid ethyl ester The title compound was obtained from the compound of example 39k using the procedure described in example 4. Purification effected using flash chromatography (silica gel, 3% MeOH in chloroform). Yield, 45%; mp, 165-67° C.; MS (ESI): 614 ($M^+$+Na), 591 ($M^+$+1); analysis: $C_{26}H_{30}N_4O_{10}S$ requires, C, 52.88; H, 5.12; N, 9.49; S, 5.43. found C, 52.53; H, 5.09; N, 9.06; S, 5.72%.

EXAMPLE 41

(4-{2-[5-Carbamimidoyl-1-oxo-1,3-dihydro-isoindol-2-yl]-acetyl}-3-hydroxy-phenoxy)-acetic acid ethyl ester, acetic acid salt The title compound was obtained from the compound of example 41h using the procedure described in example 1. Yield, 40%, white solid; mp, 195-96° C.; MS (ESI): 412 ($M^+$+1), analysis: $C_{23}H_{25}N_3O_8$ requires C, 58.60; H, 5.31; N, 8.92. found: C, 58.87; H, 5.36; N, 8.83%.

EXAMPLE 41a (4-acetyl-3-hydroxy-phenoxy)-acetic acid ethyl ester

EXAMPLE 41b (4-acetyl-3-ethoxycarbonylmethoxy-phenoxy)-acetic acid ethyl ester 1-(2,4-dihydroxy-phenyl)-ethanone was treated with 1 equivalent of ethyl 2-bromoacetate and processed as described in the synthesis of example 20a to obtain the desired title compounds. The crude mixture was purified using flash chromatography (silica gel, 3% $CH_3CN$ in chloroform).

41a: Yield, 57%; mp, 76-78° C.; MS (EI): 238 ($M^+$), 223 (100%), 195, 165; analysis: $C_{12}H_{14}O_5$ requires C, 60.50; H, 5.92. found: C, 60.73; H, 5.89%.

41b: Yield 15.4%; mp, 84-84.5° C.; MS (EI): 324 ($M^+$), 309, 253, 223; analysis: $C_{16}H_{20}O_7$ requires C, 59.25; H, 6.22. found: C, 59.49; H, 6.21%.

EXAMPLE 41c (4-{2-Bromo-acetyl}-3-hydroxy-phenoxy)-acetic acid ethyl ester

The title compound was obtained by refluxing the compound of example 41a with $CuBr_2$ in EtOAc—$CHCl_3$ (1:1) as reported in the literature (L. C. King et. al. JOC, 1964, 29, 3459). The crude product was purified using flash chromatography (silica gel, 3% $CH_3CN$ in chloroform) and crystallisation (EtOAc-PE60-80° C.). Yield, 54%; mp, 107-08° C.; MS (EI): (316, 318) ($M^+$), 236, 223 (100%); analysis: $C_{12}H_{13}BrO_5$ requires C, 45.45; H, 4.15. found: C, 45.69; H, 4.14%.

EXAMPLE 41d (4-{2-Amino-acetyl}-3-hydroxy-phenoxy)-acetic acid ethyl ester, hydrochloride

EXAMPLE 41e (4-{2-tert-Butoxycarbonylamino-acetyl}-3-hydroxy-phenoxy)-acetic acid ethyl ester The compound of example 41c (14.88 g) was converted to the hexamine complex (21.5 g), then hydrolyzed with conc. HCl in EtOH using the procedure described in example 1e.

The solvent was removed and the residue was stirred with water (50 ml) and filtered. It was washed with cold water (2×5 ml). and dried to give compound of example 41d. Yield, 3.5 g (25.8%); mp, 189-92° C. (d); analysis: $C_{12}H_{16}ClNO_5$ requires C, 49.75; H, 5.57; N, 4.83. found: C, 49.44; H, 5.93; N, 5.10%.

The filtrate was treated with di-tert-butyldicarbonate (13 g) using the procedure described in example 16a. The crude product was purified using flash chromatography (silica gel, 2% $CH_3CN$ in chloroform) to obtain compound of example 41e. Yield, 8.5 g (51.7%); mp, 46-48° C.; analysis: $C_{17}H_{23}NO_7$ requires C, 57.78; H, 6.56; N, 3.96. found: C, 58.18; H, 6.67; N, 3.86%.

EXAMPLE 41f (4-{2-[5-Cyano-1-oxo-1,3-dihydro-isoindol-2-yl]-acetyl}-3-hydroxy-phenoxy)-acetic acid ethyl ester The title compound was obtained from the compound of example 41d using the procedure described in example 1g. The crude product was purified using flash chromatography (silica gel, 5% $CH_3CN$ in chloroform). Yield, 60%; mp, 193-95° C.; MS (EI): 394 ($M^+$), 223 (100%), 195, 171; analysis: $C_{21}H_{18}N_2O_6$ requires C, 63.96; H, 4.60; N, 7.10. found: C, 63.51; H, 4.57; N, 7.13%.

EXAMPLE 41g (3-Hydroxy-4-{2-[1-oxo-5-thiocarbamoyl-1,3-dihydro-isoindol-2-yl]-acetyl}-phenoxy)-acetic acid ethyl ester The title compound was obtained from the compound of example 41f using the procedure described in example 1h. The crude product was purified using flash chromatography (silica gel, 10% $CH_3CN$ and 2% MeOH in chloroform). Yield, 96%, yellow solid; mp, 227-29° C.; MS (ESI): 451 ($M^+$+Na), 429 ($M^+$+1); $C_{21}H_{20}N_2O_6S$ requires C, 58.88; H, 4.67; N, 6.54; S, 7.48. found: C, 59.14; H, 4.68; N, 6.29; S, 7.75%.

EXAMPLE 41h (3-Hydroxy-4-{2-[5-methylsulfanylcarbonimidoyl-1-oxo-1,3-dihydro-iso indol-2-yl]-acetyl}-phenoxy)-acetic acid ethyl ester, hydroiodide The title compound was obtained from the compound of example 41g using the procedure described in example 1I. Yield, 56%, yellow solid; mp, 167° C. (d); MS (ESI): 465 ($M^+$+Na), 443 ($M^+$+1).

EXAMPLE 42

(3-Hydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 41h using the procedure described in example 4. The crude product was purified using flash chromatography (silica gel, 8% MeOH in chloroform). Yield, 75% (white solid); mp, 197-98° C.; MS ($ESI^-$): 426 (M−1), analysis: $C_{21}H_{21}N_3O_7$ requires C, 59.02; H, 4.92; N, 9.84. found: C, 59.33; H, 4.91; N, 9.44%.

EXAMPLE 43

(3-Hydroxy-4-{2-[5-(N-hydroxycarbamimidoyl)-1-oxo-1,3-dihydro-iso indol-2-yl]-acetyl}-phenoxy)-acetic acid benzyl ester The title compound was obtained from the compound of example 43g using the procedure described in example 4. The crude product was purified using flash chromatography (silica gel, 4% MeOH in chloroform). Yield, 89%, white solid; mp, 183-84° C.; MS ($ESI^+$): 512 ($M^+$+Na), 490 ($M^+$+1); analysis: $C_{26}H_{23}N_3O_7$ requires C, 63.80; H, 4.74; N, 8.58. found: C, 64.47; H, 4.84; N, 8.63%.

EXAMPLE 43a (4-Acetyl-3-hydroxy-phenoxy)-acetic acid benzyl ester 1-(2,4-Dihydroxy-phenyl)-ethanone was treated with 1 equivalent of benzyl 2-bromoacetate and processed as described in the synthesis of example 20a to obtain the title compound. The crude was purified using flash chromatography (silica gel, 3% $CH_3CN$ in chloroform) and crystallization was effected using ether-PE 60-80° C. Yield, 75%, white solid; mp, 66-67° C.; MS (EI): 300 ($M^+$), 285, 165, 91 (100%); analysis: $C_{17}H_{16}O_5$ requires C, 67.99; H, 5.37. found: C, 67.99; H, 5.53%.

EXAMPLE 43b (4-{2-Bromo-acetyl}-3-hydroxy-phenoxy)-acetic acid benzyl ester

The title compound was obtained from the compound of example 43a using the procedure as described in the synthesis of example 41c The crude product was purified using flash chromatography (silica gel, 1% $CH_3CN$-chloroform: PE 60-80° C.) and crystallized from EtOAc-PE 60-80° C. Yield, 41%; mp, 98-99° C.; MS (EI): (380, 378) ($M^+$), 298, 285; analysis: $C_{17}H_{15}O_5Br$ requires C, 53.85; H, 3.99; Br, 21.07. found: C, 53.70; H, 4.20; Br, 21.46%.

EXAMPLE 43c (4-{2-tert-Butoxycarbonylamino-acetyl}-3-hydroxy-phenoxy)-acetic acid benzyl ester The title compound was obtained from the compound of example 43b using the procedure described in example 16a. The crude product was purified using flash chromatography (silica gel, EtOAc PE 60-80° C.) and crystallized from EtOAc-PE 60-80° C.). Yield, 7%; mp, 97-98° C.; MS (CI): 416 ($M^+$+1); analysis: $C_{22}H_{25}NO_7$ requires C, 63.61; H, 6.07; N, 3.37. found: C, 63.48; H, 6.17; N, 3.69%.

EXAMPLE 43d (4-{2-Amino-acetyl}-3-hydroxy-phenoxy)-acetic acid benzyl ester; hydrochloride, sesquihydrate The title compound was obtained from the compound of example 43c using the procedure described in example 5b. Yield, 91%, white solid; mp, 160-61° C.; MS (ESI): 316 ($M^+$+1); analysis: $C_{17}H_{18}ClNO_5$, 1.5$H_2O$ requires C, 53.86; H, 5.54; N, 3.70. found: C, 54.24; H, 5.82; N, 4.15%.

EXAMPLE 43e (4-{2-[5-Cyano-1-oxo-1,3-dihydro-isoindol-2-yl]-acetyl}-3-hydroxy-phenoxy)-acetic acid benzyl ester The title compound was obtained from the compound of example 43d using the procedure described in example 1g. The crude product was purified using flash chromatography (silica gel 5% $CH_3CN$ in chloroform). Yield, 24%; mp, 211-13° C.; MS (ESI$^-$): 455 (M−1); analysis: $C_{26}H_{20}N_2O_6$ requires C, 68.42; H, 4.42; N, 6.14. found: C, 68.20; H, 4.09; N, 6.54%.

EXAMPLE 43f (3-Hydroxy-4-{2-[1-oxo-5-thio carbamoyl-1-oxo-1,3-dihydro-isoindol-2-yl]-acetyl}-phenoxy)-acetic acid benzyl ester The title compound was obtained from the compound of example 43e using the procedure described in example 1h. The crude product was purified using flash chromatography (silica gel, 10% $CH_3CN$ and 1% MeOH in chloroform). Yield, 83%, yellow solid; mp, 152-53° C.; MS (ESI$^-$): 489 (M−1); analysis: $C_{26}H_{22}N_2O_6S$ requires C, 63.66; H, 4.52; N, 5.71; S, 6.54. found: C, 63.80; H, 4.44; N, 5.64; S, 6.28%.

EXAMPLE 43g (3-Hydroxy-4-{2-[5-methylsulfanylcarbonimidoyl-1-oxo-1,3-dihydro-isoindol-2-yl]-acetyl}-phenoxy)-acetic acid benzyl ester, hydroiodide The title compound was obtained from the compound of example 43f using the procedure described in example 1i. Yield, 94%, yellow solid; $^1$H NMR (DMSO-D$_6$): 2.85 (3H, s, SCH$_3$), 4.65, 5.0, 5.12, 5.22 (8H, 4×s, 4×CH$_2$), 6.55 (1H, br, H-2'), 6.60 (1H, dd, J=8.9, 2.0, H-6'), 7.40 (5H, br, PhH), 7.72 (1H, d, J=8.9, H-5'), 7.95 (2H, br, H-4 & H-6), 8.10 (1H, d, J=8.7, H-7), 11.60 (1H, s, OH).

EXAMPLE 44

(4-{2-[5-Carbamimidoyl-1-oxo-1,3-dihydro-isoindol-2-yl]-acetyl}-3-hydroxy-phenoxy)-acetic acid, trifluoroacetate A mixture of the compound of example 43 (0.08 g; 0.163 mmol) and acetic anhydride (0.023 ml; 0.245 mmol) in glacial acetic acid (12 ml) was subjected to hydrogenation over 10% Pd—C (0.02 g) at 15 psi for 15 min. Distilled TFA (5 ml) was added to obtain a clear solution. The catalyst was filtered off and the filtrate was evaporated to dryness. The crude product was triturated with acetonitrile and ether twice to afford the title compound as a pure white solid. Yield, 0.045 g, (56%); mp, 262° C. (d); MS (ESI$^+$): 384 (M$^+$+1); analysis: $C_{21}H_{18}N_3F_3O_8$, $2H_2O$ requires C, 47.29; H, 4.16; N, 7.88. found: C, 47.57; H, 4.06; N, 7.22%.

EXAMPLE 45

(4-{2-[5-(N-Hydroxycarbamimidoyl)-1-oxo-1,3-dihydro-isoindol-2-yl]-acetyl}-3-methoxy-phenoxy)-acetic acid ethyl ester The title compound was obtained from the compound of example 45e using the procedure described in example 4. The crude product was purified using flash chromatography (silica gel, 1-2% MeOH in chloroform). Yield, 25%, white solid; mp, 163-65° C.; MS (ESI$^+$): 464 (M$^+$+Na), 442 (M$^+$+1); analysis: $C_{22}H_{23}N_3O_7$ requires C, 59.86; H, 5.25; N, 9.52. found: C, 59.66; H, 4.92; N, 9.20%.

EXAMPLE 45a (4-{2-tert-Butoxycarbonylamino-acetyl}-3-methoxy-phenoxy)-acetic acid ethyl ester To a vigorously stirred solution of the compound of example 41e (4.5 g; 12.7 mmol) in dry DMF (20 ml) was added sequentially fused $K_2CO_3$ (3.5 g; 25.5 mmol), methyl iodide (0.96 ml; 15.3 mmol) and KF (0.45 g). The reaction mixture was stirred for 3 h, diluted with water (200 ml) and the oily residue was extracted with chloroform (3×30 ml). The organic layer was washed with brine, dried ($Na_2SO_4$), concentrated and purified using flash chromatography (silica gel, 3% $CH_3CN$ in chloroform). Yield, 3.25 g (69.5%); mp, 75° C.; MS (ESI$^+$): 390 (M$^+$+Na), 368 (M$^+$+1); analysis: $C_{18}H_{25}NO_7$ requires C, 58.85; H, 6.85; N, 3.81. found: C, 58.79; H, 7.26; N, 3.81%.

EXAMPLE 45b (4-{2-Amino-acetyl}-3-methoxy-phenoxy)-acetic acid ethyl ester, hydrochloride The title compound was obtained from the compound of example 45a using the procedure described in example 5b.

EXAMPLE 45c (4-{2-[5-Cyano-1-oxo-1,3-dihydro-isoindol-2-yl]-acetyl}-3-methoxy-phenoxy)-acetic acid ethyl ester The title compound was obtained from the compound of example 45b using the procedure described in example 1g.

The crude product was purified using flash chromatography (silica gel, 10% $CH_3CN$ in chloroform). Yield, 28%; mp, 182-83° C.; MS (CI): 437 (M$^+$+29), 409 (M$^+$+1); analysis: $C_{22}H_{20}N_2O_6$, 1.5$H_2O$ requires C, 60.63; H, 5.28; N, 6.43. found: C, 60.97; H, 4.76; N, 6.42%.

EXAMPLE 45d (3-Methoxy-4-{2-[1-oxo-5-thiocarbamoyl-1,3-dihydro-isoindol-2-yl]-acetyl}-phenoxy)acetic acid ethyl ester The title compound was obtained from the compound of example 45c using the procedure described in example 1h.

The crude product was purified using flash chromatography (silica gel, 2% MeOH in chloroform). Yield, 86%; mp, 172° C.; MS (ESI$^+$): 465 (M$^+$+Na), 443 (M$^+$+1); analysis: $C_{22}H_{22}N_2O_6S$ requires C, 59.72; H, 5.01; N, 6.33; S, 7.25. found: C, 60.19; H, 5.39; N, 6.21; S, 72%.

EXAMPLE 45e (3-Methoxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 45d using the procedure described in example 1i. Yield, 88%, crude product.

EXAMPLE 46

(4-{2-[5-(N-Hydroxycarbamimidoyl)-1-oxo-1,3-dihydro-isoindol-2-yl]-acetyl}-3-propoxy-phenoxy)-acetic acid ethyl ester, monohydrate The title compound was obtained from the compound of example 46e using the procedure described in example 4. The crude product was purified using flash chromatography (silica gel, 1% MeOH in chloroform). Yield, 58%, white solid; mp, 175-77° C.; MS (ESI$^+$): 492 (M$^+$+Na), 470 (M$^+$+1); analysis: $C_{24}H_{27}N_3O_7$, $H_2O$ requires C, 59.13; H, 5.90; N, 8.62; found: C, 59.50; H, 5.48; N, 8.98%.

EXAMPLE 46a (4-{2-tert-Butoxycarbonylamino-acetyl}-3-propoxy-phenoxy)-acetic acid ethyl ester The title compound was obtained from 1-bromopropane and the compound of example 41e using the procedure described in example 45a. The purification was carried out using flash chromatography (silica gel, 3% $CH_3CN$ in chloroform). Yield, 66%, oil; analysis: $C_{20}H_{29}NO_7$ requires C, 60.75; H, 7.39; N, 3.54;; found: C, 61.18; H, 7.86; N, 3.81%.

EXAMPLE 46b (4-{2-Amino-acetyl}-3-propoxy-phenoxy)-acetic acid ethyl ester, hydrochloride The title compound was obtained from the compound of example 46a using the procedure described in example 5b.

EXAMPLE 46c (4-{2-[5-Cyano-1-oxo-1,3-dihydro-isoindol-2-yl]-acetyl}-3-propoxy-phenoxy)-acetic acid ethyl ester The title compound was obtained from the compound of example 46b using the procedure described in example 1g. Yield, 13%; mp, 132-33° C.; MS (ESI$^+$): 459 (M$^+$+Na), 437 (M$^+$+1).

EXAMPLE 46d (4-{2-[1-Oxo-5-thiocarbamoyl-1,3-dihydro-isoindol-2-yl]-acetyl}-3-propoxy-phenoxy)-acetic acid ethyl ester The title compound was obtained from the compound of example 46c using the procedure described in example 1h. The crude product was purified using flash chromatography (silica gel, 1-2% MeOH in chloroform). Yield, 98%; mp, 205° C.; MS (ESI$^-$): 469 (M−1).

EXAMPLE 46e (4-{2-[5-Methylsulfanylcarbonimidoyl-1-oxo-1,3-dihydro-isoindol-2-yl]-acetyl}-3-propoxy-phenoxy)-acetic acid ethyl ester; hydroiodide The title compound was obtained from the compound of example 46d using the procedure described in example 1i. Yield, 98%, crude product.

EXAMPLE 47

(4-{2-[5-Carbamimidoyl-1-oxo-1,3-dihydro-isoindol-2-yl]-acetyl}-3-ethoxy carbonylmethoxy-phenoxy)-acetic acid ethyl ester, acetic acid salt, monohydrate The title compound was obtained from the compound of example 47e using the procedure described in example 1. Yield, 13%; mp, 186-88° C.; MS (ESI$^+$): 498 (M$^+$+1); analysis: $C_{29}H_{31}N_3O_{10}$, $H_2O$ requires: C, 57.19; H, 5.82; N, 7.41; found: C, 57.02; H, 5.31; N, 7.55%.

EXAMPLE 47a (4-{2-tert-Butoxycarbonylamino-acetyl}-3-ethoxy-carbonylmethoxy-phenoxy)-acetic acid ethyl ester The title compound was obtained from ethyl 2-bromoacetate and the compound of example 41e using the procedure described in example 45a. Purification was carried out using flash chromatography (silica gel, 2% $CH_3CN$ in chloroform). Yield, 83%, mp, 65-66° C.; MS (ESI$^+$): 462 (M$^+$+Na), 440 (M$^+$+1); analysis: $C_{21}H_{29}NO_7$ requires C, 57.40; H, 6.65; N, 3.19; found: C, 57.82; H, 7.04; N, 3.25%.

EXAMPLE 47b (4-{2-Amino-acetyl}-3-ethoxycarbonylmethoxy-phenoxy)-acetic acid ethyl ester, hydrochloride The title compound was obtained from the compound of example 47a using the procedure described in example 5b.

EXAMPLE 47c (4-{2-[5-Cyano-1-oxo-1,3-dihydro-isoindol-2-yl]-acetyl}-3-ethoxy carbonyl methoxy-phenoxy)-acetic acid ethyl ester The title compound was obtained from the compound of example 47b using the procedure described in example 1g. The crude product was purified using flash chromatography (silica gel, 5-10% $CH_3CN$ in chloroform). Yield, 16%; mp, 135-36° C.; MS (ESI$^+$): 503 (M$^+$+Na), 481 (M$^+$+1); analysis: $C_{25}H_{24}N_2O_8$ requires: C, 62.50; H, 5.03; N, 5.83; found: C, 62.22; H, 4.93; N, 6.33%.

EXAMPLE 47d (3-Ethoxycarbonylmethoxy-4-{2-[1-oxo-5-thiocarbamoyl-1,3-dihydro-iso indol-2-yl]-acetyl}-phenoxy)-acetic acid ethyl ester The title compound was obtained from the compound of example 47c using the procedure described in example 1h.

The crude product was purified using flash chromatography (silica gel, 1-2% MeOH in chloroform. Yield, 70%; MS (ESI$^+$): 537 (M$^+$+Na), 515 (M$^+$+1).

EXAMPLE 47e (3-Ethoxycarbonylmethoxy-4-{2-[5-methylsulfanyl-carbonimidoyl-1-oxo-1,3-dihydro-isoindol-2-yl]-acetyl}-phenoxy)-acetic acid ethyl ester, hydroiodide The title compound was obtained from the compound of example 47d using the procedure described in example 11. Yield, 98%, crude product.

EXAMPLE 48

(3-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 47e using the procedure described in example 4. Yield, 32%; mp, 139-40° C.; MS (ESI$^+$): 536 (M$^+$+Na), 514 (M$^+$+1); analysis: $C_{25}H_{27}N_3O_9$, 0.5H$_2$O, requires: C, 57.47; H, 5.17; N, 8.04; found: C, 57.42; H, 5.07; N, 8.21%.

EXAMPLE 49

(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 49g using the procedure described in example 4. Yield, 42%; mp, 182-83° C.; MS (ESI): 510 (M$^+$+Na), 488 (M$^+$+1); analysis: $C_{23}H_{25}N_3O_7S$ requires C, 56.66; H, 5.17; N, 8.62; S, 6.58; found: C, 56.37; H, 5.47; N, 9.01; S, 6.18%.

EXAMPLE 49a 1-(3-Ethylsulfanyl-2,4-dihydroxy-phenyl)-ethanone

NBS (53.4 g; 0.3 mol) was added over a period of 1 h to a solution of 1-(2,4-dihydroxy-phenyl)-ethanone (45.6 g; 0.3 mol) in acetic acid (300 ml). The reaction mixture was stirred overnight, treated with water (1.5 lit.) and extracted with EtOAc. The EtOAc layer was washed with water, dried (Na$_2$SO$_4$), concentrated and purified using flash chromatography (silica gel, 3% CH$_3$CN in chloroform) to obtain a mixture of bromo compounds viz. 3-bromo, 5-bromo and 3,5-dibromo (53 g) and 1-(2,4-dihydroxyphenyl)-1-ethanone (7 g). (Purification to separate the bromo compounds resulted in very poor yields).

The mixture was heated with CuSEt, quinoline and pyridine at 160-70° C. for 1.5 h following a reported procedure (refer R. Adams et. al., JACS, 1951, 81, 4927-31). The crude product was purified using flash chromatography (silica gel, 10% EtOAc in PE60-80° C.) to obtain the title compound. Yield, 24%; mp, 42-44° C.; MS (EI): 212 (M$^+$), 197, 137, 109; analysis: $C_{10}H_{12}O_3S$ requires C, 56.59; H, 5.70; S, 15.10; found: C, 57.07; H, 6.47; S, 14.83%.

Two other compounds were also isolated:

1-(3,5-Bis-ethylsulfanyl-2,4-dihydroxy-phenyl)-ethanone

Yield, 14%; mp, 55-56° C.; MS (EI): 272 (M$^+$), 257, 243, 143; analysis: $C_{17}H_{16}O_3S_2$ requires C, 52.12; H, 5.92; S, 23.54; found: C, 52.48; H, 6.30; S, 23.71%.

1-(5-Ethylsulfanyl-2,4-dihydroxy-phenyl)-ethanone

Yield, 10%; mp, 74-76° C.; MS (EI): 212 (M$^+$), 197, 183, 169, 113; analysis: $C_{10}H_{12}O_3S$ requires C, 56.59; H, 5.70; found: C, 56.72; H, 5.41%.

EXAMPLE 49b (4-Acetyl-2-ethylsulfanyl-3-hydroxy-phenoxy)-acetic acid ethyl ester The title compound was obtained from the compound of example 49a using the procedure described in example 20a. It was purified using flash chromatography (silica gel, 10-20% EtOAc in PE 60-80° C.). Yield, 62%; mp, 48-50° C. (EtOAc-PE 60-80° C.); MS (EI): 298 (M$^+$), 283, 265, 195 (100%); analysis: $C_{14}H_{18}O_5S$ requires C, 56.36; H, 6.08; S, 10.78; found: C, 56.64; H, 6.16; S, 11.38%.

EXAMPLE 49c (4-{2-Bromo-acetyl}-2-ethylsulfanyl-3-hydroxy-phenoxy)-acetic acid ethyl ester Compound of example 49b was treated with CuBr$_2$ following reported procedure (see example 41c) to obtain the title compound, which was purified using flash chromatography (silica gel, 20% EtOAc in PE 60-80° C., 3% CH$_3$CN in dichloromethane). Yield, 33%; mp, 121-23° C. (EtOAc-PE 60-80° C.); MS (EI): (376, 378) (M$^+$), 297, 255, 193 (100%); analysis: $C_{14}H_{17}BrO_5S$ requires C, 44.57; H, 4.54; Br, 21.18; S, 8.50; found: C, 45.22; H, 4.58; Br, 21.29; S, 8.32%.

EXAMPLE 49d (4-{2-Amino-acetyl}-2-ethylsulfanyl-3-hydroxy-phenoxy)-acetic acid ethyl ester, hydrochloride The title compound was obtained from the compound of example 49c using the procedure described in example 41d. Yield, 51%; mp, 91-92° C.; MS (ESI): 336 (M$^+$+Na), 312 (M$^+$+1).

EXAMPLE 49e (4-{2-[5-Cyano-1-oxo-1,3-dihydro-isoindol-2-yl]-acetyl}-2-ethylsulfanyl-3-hydroxy-phenoxy)-acetic acid ethyl ester The title compound was obtained from the compound of example 49d using the procedure described in example 1g. Yield, 26%; mp, 138-40° C.; MS (ESI): 477 (M$^+$+Na), 455 (M$^+$+1).

EXAMPLE 49f (2-Ethylsulfanyl-3-hydroxy-4-{2-[1-oxo-5-thiocarbamoyl-1,3-dihydro-isoindol-2-yl]-acetyl}-phenoxy)-acetic acid ethyl ester, hemihydrate The title compound was obtained from the compound of example 49e using the procedure described in example 1h. Yield, 75%; mp, 90° C.; MS (ESI): 511 ($M^+$+Na), 489 ($M^+$+1); analysis: $C_{23}H_{24}N_2O_4S_2$, 0.5$H_2O$ requires C, 55.46; H, 5.02; N, 5.62; found: C, 55.05; H, 4.84; N, 4.94; S, 12.83%.

EXAMPLE 49g (2-Ethylsulfanyl-3-hydroxy-4-{2-[5-methylsulfanyl-carbonimidoyl-1-oxo-1,3-dihydro-isoindol-2-yl]-acetyl}-phenoxy)-acetic acid ethyl ester, hydroiodide The title compound was obtained from the compound of example 49f using the procedure described in example 11. Yield, 98%.

EXAMPLE 50

(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 50g using the procedure described in example 4. Yield, 83%; mp, 218-19° C.; MS (ESI): 456 ($M^+$+1); analysis: $C_{23}H_{25}N_3O_7$ requires C, 60.65; H, 5.53; N, 9.23; found: C, 60.26; H, 5.51; N, 8.99%.

EXAMPLE 50a (4-Acetyl-2-ethyl-5-hydroxy-phenoxy)-acetic acid ethyl ester

The title compound was obtained when 1-(5-Ethyl-2,4-dihydroxy-phenyl)-ethanone was reacted with ethyl 2-bromoacetate, and processed as described in the synthesis of example 20a. Yield, 85.6%; mp, 89-90° C.; MS (EI): 266 ($M^+$), 179.

EXAMPLE 50b (4-{2-Bromo-acetyl}-2-ethyl-5-hydroxy-phenoxy)-acetic acid ethyl ester The compound of example 50a was treated with $CuBr_2$ following reported procedure (L. C. King et. al., JOC, 1964, 29, 3459-61). Yield, 57.3%; $^1$H NMR ($CDCl_3$): 1.25 (3H, t, $CH_2CH_3$), 1.30 (3H, t, $OCH_2CH_3$), 2.65 (2H, q, $CH_2CH_3$), 4.25 (2H, q, $OCH_2CH_3$), 4.40 (2H, s, $CH_2Br$), 4.7 (2H, s, $OCH_2$), 6.25 (1H, s, H-6), 7.5 (1H, s, H-3), 12.15 (1H, s, OH).

EXAMPLE 50c (4-{2-tert-Butoxycarbonylamino-acetyl}-2-ethyl-5-hydroxy-phenoxy)-acetic acid ethyl ester The title compound was obtained from the compound of example 50b using the procedure described in example 27a-b. Yield, 56.3%; $^1$H NMR ($CDCl_3$): 1.25 (3H, t, $CH_2CH_3$), 1.30 (3H, t, $OCH_2CH_3$), 1.6, [9H, s, $C(CH_3)_3$], 2.65 (2H, q, $CH_2CH_3$), 4.25 (2H, q, $OCH_2CH_3$), 4.65 (2H, s, $OCH_2$), 4.7 (2H, s, $OCH_2$), 5.5 (1H, br, NH), 6.25 (1H, s, H-6), 7.45 (1H, s, H-3), 12.0 (1H, s, OH).

EXAMPLE 50d (4-{2-Amino-acetyl}-2-ethyl-5-hydroxy-phenoxy)-acetic acid ethyl ester, hydrochloride The title compound was obtained from the compound of example 50c using the procedure described in example 5b. Yield 74%.

EXAMPLE 50e (4-{2-[5-Cyano-1-oxo-1,3-dihydro-isoindol-yl]-acetyl}-2-ethyl-5-hydroxy-phenoxy)-acetic acid ethyl ester The title compound was obtained from the compound of example 50d using the procedure described in example 1g. Yield, 28%; mp, 209-10° C.; MS (EI): 422 ($M^+$), 251 (100%).

EXAMPLE 50f (2-Ethyl-5-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 50e using the procedure described in example 1h. The crude product was purified using flash chromatography (silica gel, 1-2% MeOH in chloroform). Yield, 70%; mp, 190-92° C.; MS (ESI): 457 ($M^+$+1).

EXAMPLE 50g (2-Ethyl-5-hydroxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 50f using the procedure described in example 11. MS (ESI): 471.5 ($M^+$) $^1$H NMR ($CDCl_3$+$CD_3OD$): 1.20 (3H, t, $CH_2CH_3$), 1.25 (3H, t, $OCH_2CH_3$), 2.65 (2H, q, $CH_2CH_3$), 2.90 (3H, s, $NH_2$, OH), 3.0 (3H, s, $SCH_3$), 4.25 (2H, q, $OCH_2CH_3$), 4.65, 4.70, 5.05 (6H, 3×s, 3×$CH_2$), 6.25 (1H, s, H-6'), 7.5 (1H, s, H-3'), 7.90 (1H, dd, H-7), 8.05 (1H, d, H-6), 8.15 (1H, s, H-4).

EXAMPLE 51

(5-Hydroxy-4-{2-[5-(N-hydroxycarbamimidoyl)-1-oxo-1,3-dihydro-iso indol-2-yl]-acetyl}-2-isopropyl-phenoxy)-acetic acid ethyl ester The title compound was obtained from the compound of example 51g in two steps, using the procedures sequentially, described in example 1i and 4. The crude product was purified using flash chromatography (silica gel, 10-20% $CH_3CN$ in chloroform). Yield, 70%; mp, 207-09° C.; MS ($ES^{30}$): 492 ($M^+$+Na), 470 ($M^+$+1); analysis: $C_{24}H_{27}N_3O_7$ requires C, 61.40; H, 5.80; N, 8.95. found C, 61.80; H, 5.67; N, 8.93%.

EXAMPLE 51a 1-(2,4-Dihydroxy-5-isopropyl-phenyl)-ethanone

Dry HCl was passed through a suspension of 4-isopropyl-1,3-benzenediol (17.01 g; 112 mmol), $CH_3CN$ (8.3 ml; 158 mmol) and fused ZnCl$_2$ (14 g) in dry ether (100 ml) for 1 h at 0° C. The reaction mixture was then stirred for 1 h at room temperature and filtered. The solid obtained was hydrolyzed with boiling water as reported in the literature. The crude product was purified using flash chromatography (silica gel, 3% CH$_3$CN in chloroform). Yield, 15.2 g (69.6%); mp, 142-44° C.; MS (CI): 223 (M$^+$+29), 195 (M$^+$+1), 179; analysis: C$_{11}$H$_{14}$O$_3$ requires: C, 68.02; H, 7.26; found C, 68.40; H, 7.33%.

EXAMPLE 51b (4-Acetyl-5-hydroxy-2-isopropyl-phenoxy)-acetic acid ethyl ester The title compound was obtained from the compound of example 51a using the procedure described in example 20a. It was purified using flash chromatography (silica gel, chloroform/PE 60-80° C. (1:1) chloroform). Yield, 80%; mp, 70-72° C. (EtOAc-PE 60-80° C.); MS (EI): 280, 265 (100%), 237, 191; analysis: C$_{15}$H$_{20}$O$_5$ requires: C, 64.27; H, 7.19; found C, 64.86; H, 7.47%.

EXAMPLE 51c (4-{2-Bromo-acetyl}-5-hydroxy-2-isopropyl-phenoxy)-acetic acid ethyl ester The title compound was obtained from the compound of example 51b using the procedure described in example 50b. The crude product was purified using flash chromatography (silica gel, 0.5% CH$_3$CN in chloroform: PE 60-80° C. (4:6). Yield, 76%; mp, 94-95° C. (EtOAc-PE 60-80° C.); 1635; MS (EI): (358,360) (M$^+$), (343,345), 265 (100%), 237, 191.

EXAMPLE 51d (4-{2-tert-Butoxycarbonylamino-acetyl}-5-hydroxy-2-isopropyl-phenoxy)-acetic acid ethyl ester The title compound was obtained from the compound of example 51c using the procedure described in example 27a-b. The crude product was purified using flash chromatography (silica gel, 15% EtOAc in PE 60-80° C.). Yield, 47%; mp, 110-11° C. (EtOAc-PE 60-80° C.); MS (EI): 395 (M$^+$), 339, 265 (100%); analysis: C$_{20}$H$_{29}$NO$_7$ requires C, 60.70; H, 7.39; N, 3.54; found C, 61.11; H, 7.49; N, 2.98%.

EXAMPLE 51e (4-{2-Amino-acetyl}-5-hydroxy-2-isopropyl-phenoxy)-acetic acid ethyl ester, hydrochloride The title compound was obtained from the compound of example 51d using the procedure described in example 5b. Yield, 88%; MS (EI): 295 (M$^+$), 265 (100%), 237.

EXAMPLE 51f (4-{2-[5-Cyano-1-oxo-1,3-dihydro-isoindol-2-yl]-acetyl}-5-hydroxy-2-isopropyl-phenoxy)-acetic acid ethyl ester The title compound was obtained from the compound of example 51e using the procedure described in example 1g. The crude product was purified by flash chromatography (silica gel, 5% CH$_3$CN in chloroform). Yield, 18%; mp, 195-96° C. (MeOH-ether); MS (CI): 465 (M$^+$+29), 437 (M$^+$+1), 265, 198, 159; analysis: C$_{24}$H$_{24}$N$_2$O$_6$ requires C, 66.05; H, 5.54; N, 6.42; found C, 66.34; H, 5.83; N, 6.39%.

EXAMPLE 51g (5-Hydroxy-2-isopropyl-4-{2-[1-oxo-5-thiocarbamoyl-1,3-dihydro-iso indol-2-yl]-acetyl}-phenoxy)-acetic acid ethyl ester The title compound was obtained from the compound of example 51f using the procedure described in example 1h. The crude product was purified using flash chromatography (silica gel, 1% MeOH in chloroform). Yield, 76%; mp, 185-86° C. (MeOH-ether); MS (ES): 469 (M−1); analysis: C$_{24}$H$_{26}$N$_2$O$_6$S requires C, 61.26; H, 5.57; N, 5.95; S, 6.81; found C, 61.80; H, 5.55; N, 5.72; S, 7.26%.

EXAMPLE 52

(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 52g using the procedure described in example 4. Yield, 92%, white solid; mp, 177-78° C.; MS (ESI): 506 (M$^+$+Na), 484 (M$^+$+1); analysis: C$_{25}$H$_{29}$N$_3$O$_7$ requires C, 60.91; H, 6.09; N, 8.52; found C, 60.74; H, 6.00; N, 8.45%.

EXAMPLE 52a (4-Acetyl-2-tert-butyl)-5-hydroxy-phenoxy)-acetic acid ethyl ester The title compound was obtained when 1-(5-tert-Butyl-2,4-dihydroxy-phenyl)-ethanone was treated with ethyl 2-bromoacetate and processed as described in the synthesis of example 20a. Yield, 64%; mp, 110-11° C. (EtOAc-PE 60-80° C.); MS (CI): 323 (M$^+$+29), 295 (M$^+$+1), 279, 267, 239; analysis: C$_{16}$H$_{22}$O$_5$ requires: C, 65.29; H, 7.53; found C, 65.61; H, 7.85%.

EXAMPLE 52b (4-{2-Bromo-acetyl}-2-tert-butyl-5-hydroxy-phenoxy)-acetic acid ethyl ester The title compound was obtained from the compound of example 52a using the procedure described in example 50b. The crude product was purified using flash chromatography (silica gel, 0.5% CH$_3$CN in chloroform: PE 60-80° C. (4:6)). Yield, 71%; mp, 75-76° C. (EtOAc-PE 60-80° C.); MS (EI): (372, 374) (M$^+$), (357, 359), 277; analysis: C$_{16}$H$_{21}$BrO$_5$ requires C, 51.49; H, 5.67; Br, 21.41; found C, 51.44; H, 6.19; Br, 21.39%.

EXAMPLE 52c (4-{2-tert-Butoxycarbonylamino-acetyl}-2-tert-butyl-5-hydroxy-phenoxy)-acetic acid ethyl ester The title compound was obtained from the compound of example 52b using the procedure described in example 27a-b. The crude product was purified using flash chromatography (silica gel, 15% EtOAc in PE 60-80° C.). Yield, 50%, oil; MS (CI): 438 (M$^+$+29), 394, 382, 354 (100%); analysis: C$_{21}$H$_{31}$NO$_7$ requires C, 61.60; H, 7.63; N, 3.42; found C, 62.12; H, 7.46; N, 3.24%.

EXAMPLE 52d (4-{2-Amino-acetyl}-2-tert-butyl-5-hydroxy-phenoxy)-acetic acid ethyl ester, hydrochloride The title compound was obtained from the compound of example 52c using the procedure described in example 5b. Yield, 97%; MS (CI): 338 (M$^+$+29), 310 (M$^+$+1), 292, 279; $^1$H NMR (DMSO-D$_6$): 1.24 [3H, t, J=7.4, CH$_2$CH$_3$], 1.38 [9H, s, C(CH$_3$)$_3$], 4.22 (2H, q, J=7.4, CH$_2$CH$_3$), 4.37 (2H, d, NHCH$_2$), 4.90 (2H, s, OCH$_2$), 6.53 (1H, s, H-3), 7.68 (1H, s, H-6), 8.27 (3H, br, NH$_3$), 11.41 (1H, s, OH).

EXAMPLE 52e (2-tert-Butyl-4-{2-[5-cyano-1-oxo-1,3-dihydro-isoindol-2-yl]-acetyl}-5-hydroxy-phenoxy)-acetic acid ethyl ester The title compound was obtained from the compound of example 52d using the procedure described in example 1g. The crude product was purified using flash chromatography (silica gel, 1-3% CH$_3$CN in chloroform). Yield, 37%; mp, 192-94° C. (EtOAc-PE 60-80° C.); MS (EI): 450 (M$^+$), 279, 251, 193, 171; analysis: C$_{25}$H$_{26}$N$_2$O$_6$ requires C, 66.66; H, 5.82; N, 6.22; found C, 67.12; H, 5.76; N, 6.15%.

EXAMPLE 52f (2-tert-Butyl-5-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 52e using the procedure described in example 1h. The crude product was purified using flash chromatography (silica gel, 10% CH$_3$CN-1% MeOH in chloroform). Yield, 92%, yellow solid; mp, 203-04° C.; MS (ESI): 483 (M$^+$-1-1), 279, 251, 193, 171; analysis: C$_{25}$H$_{28}$N$_2$O$_6$S requires C, 61.97; H, 5.82; N, 5.78; S, 6.62. found C, 61.59; H, 5.96; N, 5.76; S, 6.98%.

EXAMPLE 52g (2-tert-Butyl-5-hydroxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 52f using the procedure described in example 1i. Yield, 87%, yellow solid; mp, 208-10° C.; MS (ESI$^-$): 497 (M-1).

EXAMPLE 53

(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester, hemihydrate The title compound was obtained from the compound of example 53i using the procedure described in example 4. Yield, 46%; mp, 227-28° C.; MS (ESI$^-$): 460 (M$^+$-1); analysis: C$_{21}$H$_{20}$ClN$_3$O$_7$, 0.5H$_2$O requires C, 53.52; H, 4.46; N, 8.91; found: C, 53.61; H, 4.42; N, 8.61%.

EXAMPLE 53a 1-(5-Chloro-2,4-dihydroxy-phenyl)-ethanone

EXAMPLE 53b 1-(3-Chloro-2,4-dihydroxy-phenyl)-ethanone

N-chlorosuccinimide (19.31 g; 144.5 mmol) in DMF (20 ml) was added drop wise over a period of 10 min. with stirring to a mixture of 1-(2,4-dihydroxy-phenyl)-ethanone (20 g; 131.46 mmol), glacial acetic acid (105 ml) and DMF (26 ml) at 0° C. The reaction mixture was stirred overnight (~16 h) at room temperature. It was diluted with water and extracted with EtOAc. The organic layer was washed with water, dried (Na$_2$SO$_4$), concentrated and purified using flash chromatography (silica gel, 30% EtOAc in PE 60-80° C.). Crystallization using EtOAc-PE 60-80° C. gave the pure products.

53a: Yield, 7.7 g (31%), white solid; mp, 165-67° C.; MS (CI): 187, 189 (M$^+$+1).

53b: Yield, 9.4 g (38%), white solid; MS (CI): 187, 189 (M$^+$+1).

EXAMPLE 53c (4-Acetyl-2-chloro-5-hydroxy-phenoxy)-acetic acid ethyl ester

The title compound was obtained from the compound of example 53a using the procedure described in example 20a. Yield, 39%, white solid; mp, 140° C.; MS (EI): 272 (M$^+$), 257, 208; analysis: C$_{12}$H$_{13}$ClO$_5$ requires C, 52.86; H, 4.81; Cl, 13.00; found: C, 53.33; H, 4.81; Cl, 13.17%.

EXAMPLE 53d (4-{2-Bromo-acetyl}-2-chloro-5-hydroxy-phenoxy)-acetic acid ethyl ester The title compound was obtained from the compound of example 53c using the procedure described in example 50b. Yield, 65%, white solid; mp, 112-14° C.; MS (EI): (352, 354) (M$^+$), 257 (100%), 259; analysis: C$_{12}$H$_{12}$BrClO$_5$ requires C, 41.00; H, 3.44; halogen, 32.81; found: C, 41.43; H, 3.86; halogen, 33.08%.

EXAMPLE 53e (4-{2-tert-Butoxycarbonylamino-acetyl}-2-chloro-5-hydroxy-phenoxy)-acetic acid ethyl ester The title compound was obtained from the compound of example 53d using the procedure described in example 20d (1.5N ethanolic HCl was used instead of 1.5 N aqueous HCl). Yield, 37%, white solid; mp, 109-10° C.; MS (ESI): 410 (M$^+$+Na); analysis: C$_{17}$H$_{22}$ClO$_7$ requires C, 52.65; H, 5.72; N, 3.61; Cl, 9.14; found: C, 52.26; H, 5.85; N, 3.93; Cl, 8.89%.

EXAMPLE 53f (4-{2-Amino-acetyl}-2-chloro-5-hydroxy-phenoxy)-acetic acid ethyl ester, hydrochloride The title compound was obtained from the compound of example 53e using the procedure described in example 5b. Yield, 90%, white solid; mp, 239-41° C. (d); MS (ESI): 310 ($M^+$+Na), 288 ($M^+$+1).

EXAMPLE 53g (2-Chloro-4-{2-[5-cyano-1-oxo-1,3-dihydro-isoindol-2-yl]-acetyl}-5-hydroxy-phenoxy)-acetic acid ethyl ester The title compound was obtained from the compound of example 53f using the procedure described in example 1g. Yield, 5%, white solid; mp, 214-15° C.; MS (CI): 457 ($M^+$+29), 429 ($M^+$+1).

EXAMPLE 53h (2-Chloro-5-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 53g using the procedure described in example 1h. Yield, 69%, yellow solid; mp, 227-29° C.; MS (ESI): 485 ($M^+$+Na), 463 ($M^+$+1).

EXAMPLE 53i (2-Chloro-5-hydroxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 53h using the procedure described in example 11. Yield, 96%, yellow solid; mp, 173-75° C. (d); MS (ESI): 477 ($M^+$+1).

EXAMPLE 54

(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester, hemihydrate The title compound was obtained from the compound of example 54g using the procedure described in example 4. Yield, 47%, white solid; mp, 214-15° C.; MS (ESI): 484 ($M^+$+Na), 462 ($M^+$+1); analysis: $C_{21}H_{20}ClN_3O_7$, $0.5H_2O$ requires C, 53.52; H, 4.46; N, 8.91; found: C, 53.71; H, 4.34; N, 8.74%.

EXAMPLE 54a (4-Acetyl-2-chloro-3-hydroxy-phenoxy)-acetic acid ethyl ester

The title compound was obtained from the compound of example 53b using the procedure described in example 20a. Yield, 50%, white solid; mp, 110-11° C.; MS (CI): 301 ($M^+$+29), 273 ($M^+$+1); analysis: $C_{12}H_{13}ClO_5$ requires C, 52.86; H, 4.81; Cl, 13.00; found: C, 53.42; H, 5.00; Cl, 13.19%.

EXAMPLE 54b (4-{2-Bromo-acetyl}-2-chloro-3-hydroxy-phenoxy)-acetic acid ethyl ester The title compound was obtained from the compound of example 54a using the procedure described in example 50b. Yield, 65%, white solid; mp, 137-38° C.; MS (EI): (352, 354) ($M^+$), 259, 257 (100%); analysis: $C_{12}H_{12}BrClO_5$ requires C, 41.00; H, 3.44; halogen, 32.81; found: C, 41.54; H, 3.54; halogen, 33.35%.

EXAMPLE 54c (4-{2-tert-Butoxycarbonylamino-acetyl}-2-chloro-3-hydroxy-phenoxy)-acetic acid ethyl ester The title compound was obtained from the compound of example 54b using the procedure described in example 20d (1.5N ethanolic HCl was used instead of 1.5N aqueous HCl). Yield, 37%, white solid; mp, 109-10° C.; MS (CI): 416 ($M^+$+29), 388 ($M^+$+1); analysis: $C_{17}H_{22}ClO_7$ requires C, 52.65; H, 5.72; N, 3.61; Cl, 9.14; found: C, 52.16; H, 5.85; N, 3.93; Cl, 8.89%.

EXAMPLE 54d (4-{2-Amino-acetyl}-2-chloro-3-hydroxy-phenoxy)-acetic acid ethyl ester, hydrochloride The title compound was obtained from the compound of example 54c using the procedure described in example 5b. Yield, 99%, white solid; mp, 198-200° C.; MS (ESI): 288 ($M^+$+1); analysis: $C_{12}H_{14}ClNO_5$ requires C, 43.22; H, 4.80; N, 4.20; Cl, 21.28; found C, 43.04; H, 4.70; N, 4.75; Cl, 21.23%.

EXAMPLE 54e (2-Chloro-4-{2-[5-cyano-1-oxo-1,3-dihydro-isoindol-2-yl]-acetyl}-3-hydroxy-phenoxy)-acetic acid ethyl ester The title compound was obtained from the compound of example 54d using the procedure described in example 1g. Yield, 4%, white solid; mp, 227-29° C.; MS (ESI): 451 ($M^+$+Na), 429 ($M^+$+1); analysis: $C_{21}H_{17}ClN_2O_6$ requires C, 56.38; H, 4.25; N, 6.27; found C, 56.31; H, 4.12; N, 5.87%.

EXAMPLE 54f (2-Chloro-3-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 54e using the procedure described in example 1h.

Yield, 63%, yellow solid; mp, 186-88° C.; (ESI): 485 (M$^+$+Na), 463 (M$^+$+1); analysis: C$_{21}$H$_{19}$ClN$_2$O$_6$S requires C, 54.49; H, 4.14; N, 6.05; found C, 54.09; H, 4.31; N, 5.84%.

EXAMPLE 54g (2-Chloro-3-hydroxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 54f using the procedure described in example 11. Yield, 86%, yellow solid; mp, 195-97° C.; MS (ESI): 477 (M$^+$+1).

EXAMPLE 55

(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester, hydrate The title compound was obtained from the compound of example 55f in two steps, using the procedures sequentially, described in examples 1i and 4. Yield, 22%; mp, 226-28° C.; MS (ES$^+$): 464 (M$^+$+Na), 442 (M$^+$+1); analysis: C$_{22}$H$_{23}$N$_3$O$_7$, H$_2$O requires C, 57.51; H, 5.48; N, 9.15; found C, 57.15; H, 5.11; N, 8.83%.

EXAMPLE 55a 1-(2,4-Dihydroxy-3-methyl-phenyl)-ethanone

A mixture of 2-methyl-benzene-1,3-diol, acetic anhydride and ZnCl$_2$ was heated at 150-60° C. for 3.5 h, and processed as reported in the literature. (Pearson. D. E. et. al., Synthesis, 533, 1972 and the references cited therein). The crude was purified using flash chromatography (silica gel, 0-5% CH$_3$CN in chloroform) to obtain the title compound. Yield, 73%; mp, 65-66° C. (EtOAc-PE 60-80° C.); MS (CI): 195 (M$^+$+29), 169 (M$^+$+1); analysis: C$_9$H$_{10}$O$_3$ requires C, 65.05; H, 6.07. found C, 65.44; H, 6.62%.

EXAMPLE 55b (4-Acetyl-3-hydroxy-2-methyl-phenoxy)-acetic acid ethyl ester

The title compound was obtained from the compound of example 55a using the procedure described in example 20a. The crude was purified using flash chromatography (silica gel, 3% CH$_3$CN in chloroform). Yield, 87%; mp, 58-60° C. (EtOAc-PE 60-80° C.); MS (EI): 252 (M$^+$), 237 (100%), 208, 178, 164; analysis: C$_{13}$H$_{16}$O$_5$ requires C, 61.90; H, 6.39; found C, 61.55; H, 6.60%.

EXAMPLE 55c (4-{2-Bromo-acetyl}-3-hydroxy-2-methyl-phenoxy)-acetic acid ethyl ester The title compound was obtained from the compound of example 55b using the procedure described in example 50b. The crude was purified using flash chromatography (silica gel, 1-2% CH$_3$CN in chloroform). Yield, 61%; mp, 117° C. (hot EtOAc-PE 60-80° C.); MS (EI): (332, 330) (M$^+$), 237 (100%), 208.

EXAMPLE 55d (4-{2-Amino-acetyl}-3-hydroxy-2-methyl-phenoxy)-acetic acid ethyl ester, hydrochloride The title compound was obtained from the compound of example 55c using the procedure described in example 41d. Yield, 86%; mp, 201-03° C.; MS (CI): 296 (M$^+$+29), 268 (M$^+$).

EXAMPLE 55e (4-{2-[5-cyano-1-oxo-1,3-dihydro-isoindol-2-yl]-acetyl}-3-hydroxy-2-methyl-phenoxy)-acetic acid ethyl ester, hemihydrate The title compound was obtained from the compound of example 55d using the procedure described in example 1g. The crude product was purified using flash chromatography (silica gel, 5% CH$_3$CN in chloroform). Yield, 21%; mp, 224-25° C. (EtOAc-PE60-80° C.); MS (EI): 450 (M$^+$), 279, 251, 193, 171; analysis: C$_{22}$H$_{20}$N$_2$O$_6$, 0.5H$_2$O requires C, 63.30; H, 5.07; N, 6.71; found C, 62.99; H, 4.94; N, 6.59%.

EXAMPLE 55f (3-Hydroxy-2-methyl-4-{2-[1-oxo-5-thiocarbamoyl-1,3-dihydro-isoindol-2-yl]-acetyl}-phenoxy)-acetic acid ethyl ester The title compound was obtained from the compound of example 55e using the procedure described in example 1h. The crude product was purified using flash chromatography (silica gel, 25% CH$_3$CN in chloroform). Yield, 65%; mp, 210-12° C. (EtOAc-PE60-80° C.); MS (ESI): 465 (M$^+$+Na), 443 (M$^+$+1); analysis: C$_{22}$H$_{22}$N$_2$O$_6$S requires C, 59.72; H, 5.01; N, 6.33; S, 7.25; found C, 60.05; H, 5.26; N, 6.14; S, 7.57%.

EXAMPLE 56

(3-Hydroxy-4-{2-[5-(N-hydroxycarbamimidoyl)-1-oxo-1,3-dihydro-iso indol-2-yl]-acetyl}-2-methyl-phenoxy)-acetic acid benzyl ester, hemihydrate The title compound was obtained from the compound of example 56f in two steps, using the procedures sequentially, described in examples 1i and 4. Mp, 200° C.; MS (ESI): 504 (M$^+$+1); analysis. C$_{27}$H$_{25}$N$_3$O$_7$, 0.5H$_2$O requires, C, 63.27; H, 5.11; N, 8.20; found, C, 63.50; H, 4.87; N, 8.16%.

EXAMPLE 56a (4-{2-tert-Butoxycarbonylamino-acetyl}-3-hydroxy-2-methyl-phenoxy)-acetic acid ethyl ester The title compound was obtained from the compound of example 55d using the procedure described in example 27b. The crude product was purified using flash chromatography (silica gel, 5% CH$_3$CN in chloroform). Yield, 86%; MS (ESI): 390 (M$^+$+Na), 368 (M$^+$+1).

EXAMPLE 56b (4-{2-tert-Butoxycarbonylamino-acetyl}-3-hydroxy-2-methyl-phenoxy)-acetic acid The compound of example 56a was hydrolyzed using 1N methanolic NaOH to obtain the title compound, which was purified using flash chromatography (silica gel, 5% CH$_3$CN in chloroform). Yield, 82.5%; MS (ESI): 362 (M$^+$+Na), 340 (M$^+$+1).

EXAMPLE 56c (4-{2-tert-Butoxycarbonylamino-acetyl}-3-hydroxy-2-methyl-phenoxy)-acetic acid benzyl ester The title compound was obtained from the compound of example 56b using the procedure described in example 5a (benzyl alcohol was used instead of isopropanol). The crude product was purified by flash chromatography (silica gel, 2% CH$_3$CN in chloroform). Yield, 87.4%; MS (ESI): 475 (M$^+$+Na), 452 (M$^+$+1); analysis. C$_{23}$H$_{27}$NO$_7$ requires C, 64.32; H, 6.34; N, 3.26; found, C, 63.67; H, 6.05; N, 3.32%.

EXAMPLE 56d (4-{2-Amino-acetyl}-3-hydroxy-2-methyl-phenoxy)-acetic acid benzyl ester; hydrochloride The title compound was obtained from the compound of Example 56c using the procedure described in example 5b. Yield, 71%.

EXAMPLE 56e (4-{2-[5-Cyano-1-oxo-1,3-dihydro-isoindol-2-yl]-acetyl}-3-hydroxy-2-methyl-phenoxy)-acetic acid benzyl ester The title compound was obtained from the compound of example 56d using the procedure described in example 1g. The crude product was purified using flash chromatography (silica gel, 5% CH$_3$CN in chloroform). Yield, 38.7%; mp, 212° C.; MS (CI): 499 (M$^+$+29), 471 (M$^+$+1), 407, 299, 199, 159, 91 (100%).

EXAMPLE 56f (3-Hydroxy-2-methyl-4-{2-[1-oxo-5-thiocarbamoyl-1,3-dihydro-isoindol-2-yl]-acetyl}-phenoxy)-acetic acid benzyl ester The title compound was obtained from the compound of example 56e using the procedure described in example 1h. The crude product was purified using flash chromatography (silica gel, 25% CH$_3$CN in chloroform). Yield, 67.5%, yellow solid; mp, 207° C.; analysis C$_{27}$H$_{24}$N$_2$O$_6$S requires, C, 64.27; H, 4.99; N, 5.55; found, C, 63.28; H, 4.91; N, 5.42%.

EXAMPLE 57

(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 57g using the procedure described in example 4. Yield, 72%; mp, 196-97° C.; analysis: C$_{23}$H$_{25}$N$_3$O$_7$ requires C, 60.65; H, 5.53; N, 9.23; found: C, 60.58; H, 5.75; N, 8.74%.

EXAMPLE 57a (4-Acetyl-2-ethyl-3-hydroxy-phenoxy)-acetic acid ethyl ester 1-(3-Ethyl-2,4-dihydroxy-phenyl)-ethanone was treated with 2-bromo-acetic acid ethyl ester and processed as described in the synthesis of example 20a. Yield, 96.89%; mp, 74-75° C.; MS (CI): 267 (M$^+$+1).

EXAMPLE 57b (4-{2-Bromo-acetyl}-2-ethyl-3-hydroxy-phenoxy)-acetic acid ethyl ester The title compound was obtained from the compound of example 57a using the procedure described in example 50b. Yield, 47%; $^1$H NMR (CDCl$_3$): 1.1 (3H, t, CH$_2$CH$_3$), 1.30 (3H, t, J=7.3, OCH$_2$CH$_3$), 2.75 (2H, q, J=7.3, CH$_2$CH$_3$), 4.25 (2H, q, J=7.3, OCH$_2$CH$_3$), 4.4 (2H, s, BrCH$_2$), 4.75 (2H, s, OCH$_2$CO), 6.3 (1H, d, H-6), 7.6 (1H, d, J=8.5, H-5), 12.77 (1H, s, 2

EXAMPLE 57c (4-{2-tert-Butoxcarbonylamino-acetyl}-2-ethyl-3-hydroxy-phenoxy)-acetic acid ethyl ester The title compound was obtained from the compound of example 57b using the procedure described in example 41e. Yield, 60%; MS (CI): 382 (M+1).

EXAMPLE 57d (4-{2-Amino-acetyl}-2-ethyl-3-hydroxy-phenoxy)-acetic acid ethyl ester; hydrochloride The title compound was obtained from the compound of example 57c using the procedure described in example 5b. Yield, 65%.

EXAMPLE 57e (4-{2-[5-cyano-1-oxo-1,3-dihydro-isoindol-2-yl]-acetyl}-2-ethyl-3-hydroxy-phenoxy)-acetic acid ethyl ester The title compound was obtained from the compound of example 57d using the procedure described in example 1g. The crude product was purified using flash chromatography (silica gel, 5% CH$_3$CN in chloroform). Yield, 17.4%; mp, 178-79° C.; MS (CI): 423 (M$^+$+1).

EXAMPLE 57f (2-Ethyl-3-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 57e using the procedure described in example 1h. Yield, 86.4%, yellow solid; mp, 156-57° C.; MS (ESI$^-$): 455 (M−1).

EXAMPLE 57g (2-Ethyl-3-hydroxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 57f using the procedure described in example 11. Yield, 98%, yellow solid; mp 74-75° C.

EXAMPLE 58

(3-Hydroxy-4-{2-[5-(N-hydroxycarbamimidoyl)-1-oxo-1,3-dihydro-iso indol-2-yl]-acetyl}-2-propyl-phenoxy)-acetic acid ethyl ester The title compound was obtained from the compound of example 58g using the procedure described in example 4. The crude product was purified using flash chromatography (silica gel, 3% MeOH in chloroform). Yield, 70%, white solid; mp, 211-12° C.; MS (ESI): 492 (M$^+$+Na), 470 (M$^+$4-1); analysis: $C_{24}H_{27}N_3O_7$ requires C, 61.40; H, 5.80; N, 8.95; found C, 61.60; H, 5.84; N, 8.68%.

EXAMPLE 58a (4-Acetyl-3-hydroxy-2-propyl-phenoxy)-acetic acid ethyl ester 1-(2,4-Dihydroxy-3-propyl-phenyl)-ethanone was treated with ethyl 2-bromoacetate and processed as described in the synthesis of example 20a. Yield, 80%, white solid; mp, 61-62° C.; MS (EI): 280 (M$^+$), 265, 251 (100%), 193; analysis: $C_{15}H_{20}O_5$ requires C, 64.27; H, 7.19; found: C, 64.56; H, 7.39%.

EXAMPLE 58b (4-{2-Bromo-acetyl}-3-hydroxy-2-propyl-phenoxy)-acetic acid ethyl ester The title compound was obtained from the compound of example 58a using the procedure described in example 50b. Yield, 50%, white solid; mp, 120-21° C.; MS (EI): (358, 360) (M$^+$), (231, 229), 279, 265 (100%); analysis: $C_{15}H_{19}BrO_5$ requires C, 50.16; H, 5.33; Br, 22.24; found: C, 50.47; H, 5.32; Br, 21.89%.

EXAMPLE 58c (4-{2-tert-Butoxycarbonylamino-acetyl}-3-hydroxy-2-propyl-phenoxy)-acetic acid ethyl ester The title compound was obtained from the compound of example 58b using the procedure described in example 20b (1.5N ethanolic HCl was used instead of 1.5N aqueous HCl). Yield, 40%, white solid; mp, 80-83° C.; MS (CI): 396 (M$^+$+1), 340, 296 (100%); analysis: $C_{20}H_{29}NO_7$ requires C, 60.75; H, 7.39; N, 3.54; found: C, 61.00; H, 7.52; N, 3.52%.

EXAMPLE 58d (4-{2-Amino-acetyl}-3-hydroxy-2-propyl-phenoxy)-acetic acid ethyl ester, hydrochloride The title compound was obtained from the compound of example 58c using the procedure described in example 5b.

Yield, 91%, white solid; mp, 188-190° C.; MS (ESI): 288 (M$^+$+1); analysis: $C_{15}H_{22}ClNO_5$ requires C, 54.30; H, 6.68; N, 4.22; Cl, 10.69; found: C, 54.20; H, 6.50; N, 3.98; Cl, 10.50%.

EXAMPLE 58e (4-{2-[5-Cyano-1-oxo-1,3-dihydro-isoindol-2-yl]-acetyl}-3-hydroxy-2-propyl-phenoxy)-acetic acid ethyl ester The title compound was obtained from the compound of example 58d using the procedure described in example 1g. The crude product was purified using flash chromatography (silica gel, 5% CH$_3$CN in chloroform). Yield, 39%, white solid; mp, 136-37° C.; MS (ESI): 437 (M$^+$+1); analysis: $C_{24}H_{24}N_2O_6$ requires C, 66.05; H, 5.54; N, 6.42; found C, 66.05; H, 5.49; N, 6.13%.

EXAMPLE 58f (3-Hydroxy-4-{2-[1-oxo-5-thiocarbamoyl-1,3-dihydro-isoindol-2-yl]-acetyl}-2-propyl-phenoxy)-acetic acid ethyl ester The title compound was obtained from the compound of example 58e using the procedure described in example 1h. Purification was effected using flash chromatography (silica gel, 5% MeOH in chloroform). Yield, 73%, yellow solid; mp, 194-95° C.; MS (ESI): 493 (M$^+$+Na), 471 (M$^+$+1); analysis: $C_{24}H_{26}N_2O_6S$ requires C, 61.26; H, 5.57; N, 5.95; S, 6.81; found C, 61.17; H, 5.54; N, 5.75; S, 7.09%.

EXAMPLE 58g (3-Hydroxy-4-{2-[5-methylsulfanylcarbonimidoyl-1-oxo-1,3-dihydro-isoindol-2-yl]-acetyl}-2-propyl-phenoxy)-acetic acid ethyl ester, hydroiodide The title compound was obtained from the compound of example 58f using the procedure described in example 11. Yield, 98%, yellow solid; MS (ESI): 485 (M$^+$+1); $^1$H NMR (DMSO-D$_6$): 0.90 (3H, t, J=7.6, CH$_2$CH$_2$CH$_3$), 1.25 (3H, t, J=7.6, OCH$_2$CH$_3$), 1.52 (2H, m, CH$_2$CH$_2$CH$_3$), 2.65 (2H, t, J=7.6, CH$_2$CH$_2$CH$_3$), 2.85 (3H, s, SCH$_3$), 4.2 (2H, q, J=7.6, OCH$_2$CH$_3$), 4.65, 5.05, 5.20 (6H, 3×s, 3×CH$_2$), 6.65 (1H, d, J=10.2, H-6'), 7.95 (4H, m), 8.19 (1H, br), 12.2 (1H, s, OH).

EXAMPLE 59

(3-Hydroxy-4-{2-[5-(N-hydroxycarbamimidoyl)-1-oxo-1,3-dihydro-iso indol-2-yl]-acetyl}-2-propyl-phenoxy)-acetic acid benzyl ester The title compound was obtained from the compound of example 59e using the procedure described in example 4. The crude product was purified using flash chromatography (silica gel, 3% MeOH in chloroform). Yield, 80%, white solid; mp, 199-200° C.; MS (ESI): 554 (M$^+$+Na), 532 (M$^+$+1); analysis: $C_{29}H_{29}N_3O_7$ requires C, 63.53; H, 5.50; N, 7.91; found C, 65.20; H, 5.48; N, 7.70%.

EXAMPLE 59a (4-{2-tert-Butoxycarbonylamino-acetyl}-3-hydroxy-2-propyl-phenoxy)-acetic acid benzyl ester The compound of example 58c was hydrolyzed using 1N methanolic NaOH. The acid obtained was converted into the title compound as described in the preparation of example 5a.

Benzyl alcohol was used instead of isopropanol. Yield, 81%, white solid; mp, 112-13° C.; MS (EI): 457 (M$^+$), 401, 327 (100%), 91; analysis: $C_{25}H_{31}NO_7$ requires C, 65.63; H, 6.83; N, 3.06; found: C, 66.14, H, 6.93; N, 3.07%.

EXAMPLE 59b (4-{2-Amino-acetyl}-3-hydroxy-2-propyl-phenoxy)-acetic acid benzyl ester, hydrochloride The title compound was obtained from the compound of example 59a using the procedure described in example 5b.

EXAMPLE 59c (4-{2-[5-Cyano-1-oxo-1,3-dihydro-isoindol-2-yl]-acetyl}-3-hydroxy-2-propyl-phenoxy)-acetic acid benzyl ester The title compound was obtained from the compound of example 59b using the procedure described in example 1g and was purified using flash chromatography (silica gel, 5% $CH_3CN$ in chloroform). Yield, 33% white solid; mp, 198-99° C.; MS (ESI): 521 (M$^+$+Na), 499 (M$^+$+1); analysis: $C_{24}H_{26}N_2O_6$ requires C, 69.87; H, 5.26; N, 5.62; found C, 69.97; H, 5.16; N, 5.52%.

EXAMPLE 59d (3-Hydroxy-4-{2-[1-oxo-5-thiocarbamoyl-1,3-dihydro-isoindol-2-yl]-acetyl}-2-propyl-phenoxy)-acetic acid benzyl ester The title compound was obtained from the compound of example 59c using the procedure described in example 1h. Purification was effected using flash chromatography (silica gel, 10% $CH_3CN$+5% MeOH in chloroform). Yield, 91%, yellow solid; mp, 170-71° C.; MS (ESI): 555 (M$^+$+Na), 533 (M$^+$+1); analysis: $C_{29}H_{28}N_2O_6S$ requires C, 65.40; H, 5.30; N, 5.26; S, 6.02; found C, 65.76; H, 5.08; N, 5.27; S, 6.39%.

EXAMPLE 59e (3-Hydroxy-4-{2-[5-methylsulfanylcarbonimidoyl-1-oxo-1,3-dihydro-isoindol-2-yl]-acetyl}-2-propyl-phenoxy)-acetic acid benzyl ester, hydroiodide The title compound was obtained from the compound of example 59d using the procedure described in Example 1i. Yield, 87%, yellow solid; mp, 175-76° C.; MS (ESI): 569 (M$^+$+Na), 547 (M$^+$+1); analysis: $C_{30}H_{31}IN_2O_6S$ requires C, 53.42; H, 4.63; N, 4.15; S, 4.75; I, 18.81; found C, 54.08; H, 4.65; N, 4.06; S, 5.07; I, 19.00%.

EXAMPLE 60

(4-{2-[5-Carbamimidoyl-1-oxo-1,3-dihydro-isoindol-2-yl]-acetyl}-3-hydroxy-2-propyl-phenoxy)-acetic acid, trifluoroacetic acid salt The compound of example 59 was hydrogenated using 10% Pd—C, as described in example 17. TFA was added to dissolve the precipitated compound. Filtration and concentration afforded the title compound. Yield, 80%, white solid; mp, 222-23° C.; MS (ESI): 426 (M$^+$+1); analysis: $C_{24}H_{24}F_3N_3O_8$ requires C, 53.44; H, 4.48; N, 7.79; found C, 52.89; H, 4.70; N, 7.39%.

EXAMPLE 61

(4-Hydroxy-3-{2-[5-(N-hydroxycarbamimidoyl)-1-oxo-1,3-dihydro-iso indol-2-yl]-acetyl}-phenoxy)-acetic acid ethyl ester The title compound was obtained from the compound of example 61g using the procedure described in example 4. The crude product was purified by flash chromatography (silica gel, 3% MeOH in chloroform). Yield, 34%, white solid; mp, 158-59° C.; MS (ESI): 450 (M$^+$+Na), 428 (M$^+$+1); analysis: $C_{21}H_{21}N_3O_7$ requires C, 59.01; H, 4.95; N, 9.83; found: C, 58.95; H, 5.03; N, 9.58%.

EXAMPLE 61a (3-Acetyl-4-hydroxy-phenoxy)-acetic acid ethyl ester $K_2CO_3$ (15.43 g; 112 mmol) was added in small portions over 30 min to a solution of 1-(2,5-dihydroxy-phenyl)-ethanone (11.33 g; 74.47 mmol) and ethyl 2-bromoacetate (8.29 ml; 75 mmol) in DMF (40 ml). The reaction mixture was stirred at room temperature for 2 h, and then processed. The crude product obtained was purified using flash chromatography (silica gel, 2% $CH_3CN$ in chloroform). Yield, 6.0 g (33.8%); mp, 60° C. (EtOAc-PE 60-80° C.); MS (EI): 238 (M$^a$), 223, 195, 151 (100%); analysis: $C_{12}H_{14}O_5$ requires C, 60.50; H, 5.92; found: C, 60.57; H, 6.10%.

EXAMPLE 61b (3-{2-Bromo-acetyl}-4-hydroxy-phenoxy)-acetic acid ethyl ester

The title compound was obtained from the compound of example 61a using the procedure described in example 50b. The crude product was purified using flash chromatography (silica gel, dichloromethane: PE 60-80° C.::60:40). Yield, 68%; mp, 120-22° C. (EtOAc-PE 60-80° C.); MS (EI): 316, 318 (M$^+$), 236, 223, 195, 163; analysis: $C_{12}H_{13}BrO_5$ requires C, 45.45; H, 4.13; found: C, 45.67; H, 4.16%.

EXAMPLE 61c (3-{2-tert-Butoxycarbonylamino-acetyl}-4-hydroxy-phenoxy)-acetic acid ethyl ester The title compound was obtained from the compound of example 61b using the procedure described in example 16a (1.5N alcoholic HCl was used instead of 1.5N aqueous HCl). The crude product was purified by flash chromatography (silica gel, 3% $CH_3CN$ in chloroform). Yield, 52.4%; mp, 91-93° C. (EtOAc-PE 60-80° C.); MS (ESI$^+$): 376 (M$^+$+Na), 354 (W+1); analysis: $C_{17}H_{23}NO_7$ requires C, 57.78; H, 6.56; N, 3.96; found: C, 58.87; H, 6.61; N, 3.66%.

EXAMPLE 61d (3-{2-Amino-acetyl}-4-hydroxy-phenoxy)-acetic acid ethyl ester, hydrochloride The title compound was obtained from the compound of example 61c using the procedure described in example 5b.

EXAMPLE 61e (3-{2-[5-Cyano-1-oxo-1,3-dihydro-isoindol-2-yl]-acetyl}-4-hydroxy-phenoxy)-acetic acid ethyl ester The title compound was obtained from the compound of example 61d using the procedure described in example 1g. The crude product was purified using flash chromatography (silica gel, 5% $CH_3CN$ in chloroform). Yield, 16%; mp, 182° C. (EtOAc); MS (ESI$^+$): 417 ($M^+$+Na), 395 ($M^+$+1); analysis: $C_{21}H_{18}N_2O_6$ requires C, 63.96; H, 4.60; N, 7.10; found: C, 63.83; H, 4.47; N, 7.11%.

EXAMPLE 61f (4-Hydroxy-3-{2-[1-oxo-5-thiocarbamoyl-1,3-dihydro-isoindol-2-yl]-acetyl}-phenoxy)-acetic acid ethyl ester The title compound was obtained from the compound of example 61e using the procedure described in example 1h. The crude product was purified by flash chromatography with 10% $CH_3CN$ and 1% MeOH in chloroform. Yield, 60%; MS (ESI$^+$): 451 ($M^+$+Na), 429 ($M^+$+1).

EXAMPLE 61g (4-Hydroxy-3-{2-[5-methylsulfanylcarbonimidoyl-1-oxo-1,3-dihydro-iso indol-2-yl]-acetyl}-phenoxy)-acetic acid ethyl ester, hydroiodide The title compound was obtained from the compound of example 61f using the procedure described in example 11.

EXAMPLE 62

(3-Hydroxy-4-{2-[5-(N-hydroxycarbamimidoyl)-1-oxo-1,3-dihydro-iso indol-2-yl]-acetyl}-5-methoxy-phenoxy)-acetic acid ethyl ester The title compound was obtained from the compound of example 62g using the procedure described in example 4. The crude product was purified using flash chromatography (silica gel, 3% MeOH in chloroform). Yield, 0.061 g (73%), white solid; mp, 209-10° C.; MS (ESI): 480 ($M^+$+Na), 458 ($M^+$+1), (ESI$^-$): 456 (M–1); analysis: $C_{22}H_{23}N_3O_8$ requires: C, 57.77; H, 5.07; N, 9.19; found: C, 57.36; H, 5.09; N, 9.21%.

EXAMPLE 62a

Cyanomethyl-carbamic acid benzyl ester

To a vigorously stirred solution of aminoacetonitrile (20 g; 0.216 mole), $NaHCO_3$ (50 g; 0.595 mole) in water (450 ml) and dioxane (250 ml), 50% benzyl chloroformate in toluene (67.88 ml; 0.475 mole) was added at 0° C. After stirring at room temperature for 16 h, the reaction mixture was extracted with EtOAc. The EtOAc layer was washed with water and dried over anhydrous $Na_2SO_4$. Solvent was removed and the dark brown oil was purified by flash chromatography over silica gel with 30-50% EtOAc-PE 60-80° C. Yield, 33 g (80.3%); mp, 42-43° C.; MS (EI): 190 ($M^+$), 145, 130, 117, 108, 91; analysis: $C_{10}H_{10}N_2O_2$ requires C, 63.15; H, 5.30; N, 14.73; found: C, 62.95; H, 5.05; N, 14.50%.

EXAMPLE 62b (2-{2,4-Dihydroxy-6-methoxy-phenyl}-2-oxo-ethyl)-carbamic acid benzyl ester Dry HCl gas was passed through a suspension of 5-methoxy-benzene-1,3-diol (11 g; 78.49 mmol), 62a (16.42 g; 86.36 mmol) and fused $ZnCl_2$ (1.96 g) in dry ether (40 ml), for 1 h at 0° C. The reaction mixture was kept at 0° C. overnight (~16 h). The ether was decanted and the yellow residue was hydrolyzed with water as reported in literature (J. S. H. Davies, JCS, 1950, 3206-13). The title compound obtained was purified using flash chromatography (silica gel, 5% $CH_3CN$—$CHCl_3$.) Yield, 10 g (28%); mp, 147-48° C.; MS (EI): 331 ($M^+$), 167 (100%); analysis: $C_{17}H_{17}NO_6$ requires: C, 61.63; H, 5.17; N, 4.23; found: C, 61.20; H, 4.85; N, 4.0%.

EXAMPLE 62c (4-{2-Benzyloxycarbonylamino-acetyl}-3-hydroxy-5-methoxy-phenoxy)-acetic acid ethyl ester The title compound was obtained from the compound of example 62b using the procedure described in example 20a. The crude product was purified using flash chromatography (silica gel, 30% EtOAc-PE 60-80° C.). Yield, 6.3 g (50%); mp, 113-14° C.; MS (EI): 417 (M), 253 (100%); analysis: $C_{21}H_{23}NO_8$ requires: C, 61.43; H, 5.55; N, 3.36; found: C, 61.24; H, 4.98; N, 3.63%.

EXAMPLE 62d (4-{2-Amino-acetyl}-3-hydroxy-5-methoxy-phenoxy)-acetic acid ethyl ester, hydrobromide A mixture of 62c (0.72 g, 1.725 mmol), glacial acetic acid (0.353 ml) and 33% HBr in AcOH (1.06 ml) was stirred at room temperature for 30 min. The solvent was removed and the dark brown oil obtained was triturated with dry ether to afford the title compound as a brownish white solid. Yield, 0.6 g (95%); mp, 175-76° C.; MS (EI): 283 ($M^+$), 253 (100%); analysis: $C_{13}H_{18}BrNO_8$ requires: C, 42.87; H, 4.98; N, 3.85; Br, 21.94; found: C, 42.44; H, 5.01; N, 3.68; Br, 22.02%.

EXAMPLE 62e (4-{2-[5-Cyano-1-oxo-1,3-dihydro-isoindol-2-yl]-acetyl}-3-hydroxy-5-methoxy-phenoxy)-acetic acid ethyl ester, hemihydrate The title compound was obtained from the compound of example 62d using the procedure described in example 1g. The crude product was purified using flash chromatography (silica gel, 5% $CH_3CN$ in chloroform). Yield, 0.156 g (6%); mp, 209-10° C.; MS (EI): 424 ($M^+$), 253 (100%); analysis: $C_{22}H_{20}NO_7.0.5H_2O$ requires: C, 60.91; H, 4.85; N, 6.46; found: C, 60.76; H, 4.29; N, 6.37%.

EXAMPLE 62f (3-Hydroxy-5-methoxy-4-{2-[1-oxo-5-thiocarbamoyl-1,3-dihydro-isoindol-2-yl]-acetyl}-phenoxy)-acetic acid ethyl ester, monohydrate The title compound was obtained from the compound of example 62e using the procedure described in example 1h.

The crude product was purified using flash chromatography (silica gel, 10% CH$_3$CN, 1% MeOH in chloroform). Yield, 0.143 g (91%), yellow solid; mp, 150-52° C.; MS (ESI): 457 (M−1); analysis: C$_{22}$H$_{22}$N$_2$O$_7$, H$_2$O requires: C, 55.40; H, 5.04; N, 5.88; S, 6.71; found: C, 55.81; H, 4.93; N, 6.30; S, 7.02%.

EXAMPLE 62g (3-Hydroxy-5-methoxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 62f using the procedure described in example 1i. Yield, 0.128 g (79%), yellow solid; mp; 152-54° C.; MS (ESI$^+$): 495 (M$^+$+Na), 473 (M$^+$+1); analysis: C$_{23}$H$_{25}$IN$_2$O$_7$S. requires C, 46.01; H, 4.20; N, 4.67; S, 5.34; I, 21.14; found: C, 45.98; H, 4.21; N, 4.86; S, 5.64; I, 21.10%.

EXAMPLE 63

(3,5-Dihydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 63h using the procedure described in example 4. The crude product was purified using flash chromatography (silica gel, 3-5% MeOH in CHCl$_3$). Yield, 0.03 g (33%), white solid; mp, 229-30° C.; MS (ESI$^+$): 466 (M$^+$+Na), 444 (M$^+$+1), analysis: C$_{21}$H$_{21}$N$_3$O$_8$. requires C, 56.88; H, 4.77; N, 9.48; found: C, 56.50; H, 4.77; N, 8.96%.

EXAMPLE 63a

Acetic acid 3-acetoxy-5-benzyloxy-phenyl ester

Water (4.3 ml, 236 mmol) in DMF (20 ml) was added drop wise at room temperature with stirring to a mixture of acetic acid 3,5-diacetoxy-phenyl ester (refer Kawamoto. H. et. al. Synth. Commun. M, 531, 1996) (35 g, 139 mmol), NaH (5.66 g, 236 mmol) and benzyl chloride (19.16 ml, 166 mmol) in dry DMF (300 ml). The reaction mixture was stirred overnight (~16 h), poured into chilled dil. aqueous HCl and extracted with CH$_2$Cl$_2$ to obtain the crude title compound which was purified using flash chromatography (silica ge, 20-50% CH$_2$Cl$_2$ in PE 60-80° C.). Yield, 12.5 g (30%), white solid; mp: 129-30° C.; MS (EI): 300 (M$^+$), 258, 216, 91 (100%); analysis: C$_{17}$H$_{16}$O$_5$ requires: C, 67.99; H, 5.37 found: C, 67.50; H, 5.40%.

EXAMPLE 63b

5-Benzyloxy-benzene-1,3-diol

The compound in example 63a was treated with 1N methanolic NaOH for 1 h. The reaction mixture was processed and the crude product obtained was purified using flash chromatography (silica gel, 20% EtOAc in PE 60-80° C.). Yield, 93%, white solid; mp: 85-86° C.; MS (EI): 216 (M$^+$), 91 (100%); analysis: C$_{13}$H$_{12}$O$_3$ requires: C, 72.21; H, 5.59 found: C, 72.51; H, 6.05%.

EXAMPLE 63c (2-{2-Benzyloxy-4,6-dihydroxy-phenyl}-2-oxo-ethyl)-carbamic acid benzyl ester The title compound was obtained from the compound of example 63b using the procedure described in example 62a-b. The crude product was purified using flash chromatography (silica gel, 5% CH$_3$CN in chloroform). Yield, 35%, white solid; mp: 129-31° C.; MS (ESI: 430 (M$^+$+Na), 408 (M$^+$+1), (ESI$^-$): 406 (M−1); analysis: C$_{23}$H$_{21}$NO$_6$ requires: C, 67.81; H, 5.20; N, 3.42; found: C, 67.89; H, 5.10; N, 3.09%.

EXAMPLE 63d (3-Benzyloxy-4-{2-benzyloxycarbonylamino-acetyl}-5-hydroxy-phenoxy)-acetic acid ethyl ester The title compound was obtained from the compound of example 63c using the procedure described in example 20a. It was purified using flash chromatography (silica gel, chloroform). Yield, 70%, white solid; mp, 140-41° C.; MS (CI): 522. (M$^+$+29), 494 (M$^+$+1); analysis: C$_{27}$H$_{27}$NO$_8$ requires: C, 65.71; H, 5.51; N, 2.84; found: C, 66.07; H, 6.03; N, 2.98%.

EXAMPLE 63e (4-{2-Amino-acetyl}-3,5-dihydroxy-phenoxy)-acetic acid ethyl ester, hydrochloride The compound of example 63d (3.5 g; 7.09 mmol) in glacial acetic (150 ml) was hydrogenated using 10% Pd—C (1 g) at 15 psi for 30 min. The catalyst was filtered, the filtrate was evaporated to dryness and the crude product obtained was triturated with ethereal HCl and washed with dry ether to afford the title compound as white solid. Yield, 2 g (92%); mp: 225-27° C.; MS (ESI$^-$): 268. (M−1); analysis: C$_{12}$H$_{16}$ClNO$_6$ requires: C, 47.15; H, 5.28; N, 4.58; Cl, 11.60; found: C, 46.63; H, 5.05; N, 4.29; Cl, 11.50%.

EXAMPLE 63f (4-{2-[5-Cyano-1-oxo-1,3-dihydro-isoindol-2-yl]-acetyl}-3,5-dihydroxy-phenoxy)-acetic acid ethyl ester The title compound was obtained from the compound of example 63e using the procedure described in example 1g. The crude product was purified using flash chromatography (silica gel, 10% CH$_3$CN, 2% MeOH in CHCl$_3$). Yield, 0.55 g (23%), white solid, mp, >260° C.; MS (ESI$^+$): 411 (M$^+$+1); analysis: C$_{21}$H$_{18}$N$_2$O$_7$. requires: C, 61.46; H, 4.42; N, 6.83; found: C, 62.24; H, 4.42; N, 6.83%.

EXAMPLE 63g (3,5-Dihydroxy-4-{2-[1-oxo-5-thiocarbamoyl-1,3-dihydro-isoindol-2-yl]-acetyl}-phenoxy)-acetic acid ethyl ester The title compound was obtained from the compound of example 63f using the procedure described in example 1h. The crude product was purified using flash chromatography (silica gel, 5-10% CH$_3$CN in CHCl$_3$). Yield, 97%, yellow solid; mp: 260° C. (d); MS (ESI$^+$): 467 (M$^+$+Na), 445 (M$^+$+

1); analysis: $C_{21}H_{20}N_2O_7S$ requires: C, 56.75; H, 4.54; N, 6.30; S, 7.21; found: C, 57.11; H, 4.72; N, 6.07; S, 7.02%.

EXAMPLE 63h (3,5-Dihydroxy-4-{2-[5-methylsulfanylcarbonimidoyl-1-oxo-1,3-dihydro-isoindol-2-yl]-acetyl}-phenoxy)-acetic acid ethyl ester, hydroiodide The title compound was obtained from the compound of example 63g using the procedure described in example 1i. Yield, 97%, yellow solid; mp, 95° C. (d); MS (ESI$^+$): 482 (M$^+$+Na), 459 (M$^+$+1).

EXAMPLE 64

(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester The title compound was obtained from the compound of example 64f in two steps, using the procedures sequentially, described in examples 1i and 4. The crude product was purified using flash chromatography (silica gel, 3% MeOH in chloroform). Yield, 48%, white solid; mp, 153-55° C.; MS (ESI): 552 (M$^+$+Na).

EXAMPLE 64a (4-Acetyl-2-ethoxycarbonylmethoxy-3-hydroxy-phenoxy)-acetic acid ethyl ester 1-(2,3,4-Trihydroxy-phenyl)-ethanone was treated with 2-bromo-acetic acid ethyl ester in the presence of $K_2CO_3$ and processed as described in the synthesis of example 20a. The crude product was purified using flash chromatography (silica gel, 20% EtOAc in PE 60-80° C.). Yield, 69.2%, oil; MS (EI): 341 (M$^+$+1), 279, 267, 193, 165; analysis: $C_{16}H_{20}O_8$ requires C, 56.47; H, 5.92; found: C, 56.91; H, 6.32%.

EXAMPLE 64b (4-{2-Bromo-acetyl}-2-ethoxycarbonylmethoxy-3-hydroxy-phenoxy)-acetic acid ethyl ester The title compound was obtained from the compound of example 64a using the procedure described in example 50b. The crude product was purified using flash chromatography (silica gel, 20% EtOAc in PE 60-80° C.). Yield, 61%; MS (EI): 418, 420 (M$^+$), 338, 265, 250, 191, and 165.

EXAMPLE 64c

[4-(2-tert-Butoxycarbonylamino-acetyl)-2-ethoxycarbonylmethoxy-3-hydroxy-phenoxy]-acetic acid ethyl ester The title compound was obtained from the compound of example 64b using the procedure described in example 20d (1.5N alcoholic HCl was used instead of 1.5N aqueous HCl). The crude product was purified using flash chromatography (silica gel, 20-30% EtOAc in PE 60-80° C.). Yield, 58%, oil; MS (ESI$^+$): 478 (M$^+$+Na), 456 (M$^+$+1); analysis: $C_{21}H_{29}NO_{10}$ requires C, 55.38; H, 6.42; N, 3.06; found: C, 55.78; H, 6.85; N, 3.43%.

EXAMPLE 64d

[4-(2-Amino-acetyl)-2-ethoxycarbonylmethoxy-3-hydroxy-phenoxy]-acetic acid ethyl ester, hydrochloride The title compound was obtained from the compound of example 64c using the procedure described in example 5b.

EXAMPLE 64e (4-{2-[5-Cyano-1-oxo-1,3-dihydro-isoindol-2-yl]-acetyl}-2-ethyoxy carbonylmethoxy-3-hydroxy-phenoxy)-acetic acid ethyl ester The title compound was obtained from the compound of example 64d using the procedure described in example 1g. The crude product was purified using flash chromatography (silica gel, 5% $CH_3CN$ in chloroform). Yield, 14%; mp, 136-38° C. (EtOAc); MS (ESI$^-$): 495 (M−1).

EXAMPLE 64f (2-Ethoxycarbonylmethoxy-3-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 64e using the procedure described in example 1h. The crude product was purified using flash chromatography (silica gel, 10% $CH_3CN$, 1% MeOH in chloroform). Yield 72%; mp, 76° C.; MS (ESI$^+$): 553 (M$^+$+Na); analysis: $C_{25}H_{26}N_2O_9S$ requires C, 56.60; H, 4.94; N, 5.28; found: C, 57.02; H, 4.62; N, 5.03%.

EXAMPLE 65

(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester, sesquihydrate The title compound was obtained from the compound of example 65i in two steps, using the procedures sequentially, described in examples 1i and 4. It was purified using flash chromatography with 3% MeOH in chloroform. Yield, 26%, white solid; mp, 186-88° C.; MS (ESI): 552 (M$^+$+Na), 520 (M$^+$+1); analysis: $C_{25}H_{27}N_3O_{10}$, 1.5$H_2O$ requires C, 53.90; H, 5.39; N, 7.55; found: C, 53.96; H, 5.12; N, 7.33%.

EXAMPLE 65a (2-Ethoxycarbonylmethoxy-4-formyl-phenoxy)-acetic acid ethyl ester 3,4-Dihydroxy-benzaldehyde was treated with 2-bromo-acetic acid ethyl ester in the presence of $K_2CO_3$ and processed as described in the synthesis of example 20a. The crude product was purified using flash chromatography (silica gel, 30-50% EtOAc in PE 60-80° C.). Yield, 87%; mp, 56° C. (EtOAc-PE 60-80° C.); MS (EI): 310 (M$^+$), 237, 163, 149; analysis: $C_{15}H_{18}O_7$, 0.5$H_2O$ requires C, 56.37; H, 5.95; found: C, 56.72; H, 5.79%.

EXAMPLE 65b (2-Ethoxycarbonylmethoxy-4-hydroxy-phenoxy)-acetic acid ethyl ester The compound of example 65a obtained above was treated with 3-chlorobenzoic acid in dichloromethane as reported in the literature (I. M. Godfrey et. al, JCS Perkin I, 1974, 1353,). The formyl ester obtained was purified using column chromatography (neutral alumina, 3-5% MeOH in dichloromethane) and crystallized from EtOAc-PE 60-80° C. Yield, 68%; mp, 67° C. (EtOAc-PE 60-80° C.); MS (EI): 298 ($M^+$); analysis: $C_{14}H_{18}O_7$ requires C, 56.37; H, 6.08; found: C, 56.12; H, 5.89%.

EXAMPLE 65c (4-Allyloxy-2-ethoxycarbonylmethoxy-phenoxy)-acetic acid ethyl ester Allyl bromide (25.53 ml; 302 mmol) was added slowly to a mixture of the compound of example 65b (75 g; 251.4 mmol), $K_2CO_3$ (52.04 g; 377 mmol) and KI (~1 g) in DMF (150 ml) under vigorous stirring for 15 min at room temperature. The reaction mixture was stirred overnight (~16 h), treated with water (1 lit.), and extracted with EtOAc. The EtOAc layer was washed with water, brine, dried ($Na_2SO_4$), concentrated and purified using flash chromatography (silica gel, 3% $CH_3CN$ in chloroform) to obtain the title compound as an oil. Yield, 76 g (89.7%); MS (EI): 337 ($M^+$), 136.

EXAMPLE 65d (4-Acetyl-2-ethoxycarbonylmethoxy-5-hydroxy-phenoxy)-acetic acid ethyl ester The compound of example 65c (38 g; 112.5 mmol) was heated with acetyl chloride (9.74 ml; 137 mmol) and activated Zn (7.46 g) in toluene (250 ml) for 5 h (Synth. Commun, 1998, 28, 2203). to obtain the title compound which was processed as is routinely done and purified using flash chromatography (silica gel, 3% $CH_3CN$ in chloroform). Yield, 30 g (78.3%); MS (CI): 409 ($M^++29$), 381($M^+$); analysis: $C_{16}H_{20}O_8$ requires C, 56.47; H, 5.92; found: C, 56.05; H, 5.59%.

EXAMPLE 65e (4-{2-Bromo-acetyl}-2-ethoxycarbonylmethoxy-5-hydroxy-phenoxy)-acetic acid ethyl ester The title compound was obtained from the compound of example 65d using the procedure described in example 50b. The crude product was purified using flash chromatography (silica gel, with 3% $CH_3CN$ in chloroform). Yield, 50%; MS (CI): 447 ($M^++29$), 419 ($M^++1$); analysis: $C_{16}H_{19}BrO_8$ requires C, 45.84; H, 4.57; Br, 19.06; found: C, 45.45; H, 4.26; Br, 18.91%.

EXAMPLE 65f 4-(2-tert-Butoxycarbonylamino-acetyl)-2-ethoxycarbonylmethoxy-5-hydroxy-phenoxy]-acetic acid ethyl ester The title compound was obtained from the compound of example 65e using the procedure described in example 16a (1.5N alcoholic HCl was used instead of 1.5N aqueous HCl). The crude product was purified using flash chromatography (silica gel, 3% $CH_3CN$ in chloroform). Yield, 30%; mp, 73-74° C.; MS ($ESI^+$): 478 ($M^++Na$), 456 ($M^++1$); analysis: $C_{21}H_{29}NO_{10}$ requires C, 55.38; H, 6.42; N, 3.06; found: C, 55.69; H, 6.74; N, 3.19%.

EXAMPLE 65g (4-{2-Amino-acetyl}-2-ethoxycarbonylmethoxy-5-hydroxy-phenoxy)-acetic acid ethyl ester, hydrochloride The title compound was obtained from the compound of example 65f using the procedure described in example 5b.

EXAMPLE 65h (4-{2-[5-Cyano-1-oxo-1,3-dihydro-isoindol-2-yl]-acetyl}-2-ethoxycarbonyl methoxy-5-hydroxy-phenoxy)-acetic acid ethyl ester The title compound was obtained from the compound of example 65g using the procedure described in example 1g. The crude product was purified using flash chromatography (silica gel, 10% $CH_3CN$ in chloroform, 1% MeOH in chloroform). Yield, 22%; mp 168-69° C. (EtOAc); MS ($ESI^+$): 519 ($M^++23$), 497($M^++1$); analysis: $C_{25}H_{24}N_2O_9$, $2H_2O$ requires C, 56.34; H, 5.20; N, 5.25; found: C, 56.60; H, 4.86; N, 5.19%.

EXAMPLE 65i (2-Ethoxycarbonylmethoxy-5-hydroxy-4-{2-[1-oxo-5-thiocarbamoyl-1,3-dihydro-isoindol-2-yl]-acetyl}-phenoxy)-acetic acid ethyl ester The title compound was obtained from the compound of example 65h using the procedure described in example 1h. The crude product was purified using flash chromatography (silica gel, 10% $CH_3CN$, 1% MeOH in chloroform). Yield, 94%; mp 142-43° C.; MS ($ESI^+$): 553 ($M^++Na$), 531($M^++1$); analysis: $C_{25}H_{26}N_2O_9S$ requires C, 56.60; H, 4.94; N, 5.28; found: C, 56.82; H, 4.71; N, 5.23%.

EXAMPLE 66

(4-{2-[5-Carbamimidoyl-1-oxo-1,3-dihydro-isoindol-2-yl]-acetyl}-piperazine-1-yl)-acetic acid ethyl ester; acetic acid salt The title compound was obtained from the compound of example 66f by subjecting it to hydrogenation in AcOH and ethanol over 10% Pd—C, using the procedure reported in the literature (see Gante. J. et. al. Bioorg. Med. Chem. 6, 2425, 1996). The title compound was purified using an RP-18 column (40% MeOH in water containing 0.2% AcOH). Yield, 39.5%; mp, 211-12° C.; MS ($ESI^+$): 388 ($M^++1$), analysis: $C_{21}H_{29}N_5O_6$ requires C, 56.38; H, 6.49; N, 15.66; found: C, 55.57; H, 6.34; N, 15.02%.

EXAMPLE 66a (5-Cyano-1-oxo-1,3-dihydro-isoindol-2-yl)-acetic acid ethyl ester The title compound was obtained from Glycine ethyl ester hydrochloride using the procedure described in example 1g.

It was purified using flash chromatography (silica gel, 3.5% CH$_3$CN in chloroform). Yield 88%; mp, 105° C.; MS (EI): 244 (M$^+$), 170, 114; analysis: C$_{13}$H$_{12}$N$_2$O$_3$ requires: C, 63.93; H, 4.95; N, 11.47; found: C, 63.48; H, 4.54; N, 11.35%.

EXAMPLE 66b (5-{N-Hydroxycarbamimidoyl}-1-oxo-1,3-dihydro-isoindol-2-yl)-acetic acid ethyl ester A mixture of the compound of example 66a (1.85 g; 8 mmol), hydroxylamine hydrochloride (2.21 g; 31.82 mmol) and Na$_2$CO$_3$ (1.55 g; 14.62 mmol) in methanol (14.3 ml) and water (43 ml) was refluxed in an atmosphere of nitrogen for 3 h. It was concentrated and extracted with EtOAc. The organic layer was dried (Na$_2$SO$_4$), concentrated and purified by trturation with EtOAc and PE 60-80° C. to obtain the title compound. Yield, 1 g (47%); mp, 150-51° C.; MS (ESI): 286 (M$^+$+Na), analysis: C$_{12}$H$_{13}$N$_3$O$_4$ requires C, 54.75; H, 4.98; N, 15.96; found: C, 54.70; H, 4.92; N, 15.89%.

EXAMPLE 66C (5-{5-Methyl-[1,2,4]oxadiazol-3-yl}-1-oxo-1,3-dihydro-isoindol-2-yl)-acetic acid ethyl ester The compound of example 66b (1 g; 3.8 mmol) in acetic anhydride (20 ml) was heated at 120° C. for 4 h. It was concentrated and purified using flash chromatography (silica gel, 5% CH$_3$CN in dichloromethane) to obtain the title compound. Yield, 0.6 g (55%); mp, 155° C.; MS (ESI$^-$): 286 (M−1), analysis: C$_{14}$H$_{13}$N$_3$O$_4$ requires C, 58.53; H, 4.56; N, 14.63; found: C, 58.13; H, 4.79; N, 14.14%.

EXAMPLE 66d (5-{5-Methyl-[1,2,4]oxadiazol-3-yl}-1-oxo-1,3-dihydro-isoindol-2-yl)-acetic acid A solution of the compound of example 66c (0.5 g; 1.7 mmol) in methanol (13.6 ml) was stirred with 1N NaOH (3.4 ml; 3.4 mmol) at room temperature for 1 h. It was concentrated, treated with water extracted with EtOAc. The aqueous layer was acidified with dil. HCl. The title compound precipitated as a white solid. It was filtered, washed with water and dried. Yield, 0.45 g (95%); mp, 230-31° C.; MS (ESI"): 272 (M−1), analysis: C$_{13}$H$_{11}$N$_3$O$_4$ requires C, 51.14; H, 4.06; N, 15.38; found: C, 51.10; H, 4.20; N, 14.90%.

EXAMPLE 66e (4-{2-[5-(5-Methyl-[1,2,4]oxadiazol-3-yl)-1-oxo-1,3-dihydro-isoindol-2-yl]-acetyl}-piperazin-1-yl)-acetic acid ethyl ester DCC (0.433 g; 2.1 mmol) was added with vigorous stirring to a solution of the compound of example 66d (0.53 g; 1.9 mmol) and 1-hydroxybenzotriazole (0.338 g; 2.47 mmol) in dry DMF (15 ml) at 0° C. After 10 min. piperazin-1-yl-acetic acid ethyl ester (0.43 g; 2.47 mmol) was added to the mixture It was stirred at 0° C. for 1 h and then kept in the freezer over night. The DCU was filtered off and the filtrate was washed with 1N aqueous NaHCO$_3$, water, 1N aqueous HCl, brine, dried (Na$_2$SO$_4$), concentrated and purified using flash chromatography (silica gel, 5% MeOH in chloroform) to obtain the title compound. Yield, 0.64 g (77%); mp, 189-90° C.; MS (ESI$^+$): 450 (M$^+$+Na), analysis: C$_{21}$H$_{25}$N$_5$O$_5$ requires C, 59.01; H, 5.90; N, 16.38; found: C, 58.80; H, 5.93; N, 15.80%.

EXAMPLE 67

(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester The title compound was obtained from the compound of example 67g in two steps, using the procedures sequentially, described in examples 1i and 4. It was purified using flash chromatography (silica gel, 3% MeOH in chloroform). Yield, 48%; mp, 116-18° C.; MS (ESI): 547 (M$^+$+Na), 525. (M$^+$+1), analysis: C$_{27}$H$_{32}$N$_3$O$_7$, 1.5H$_2$O requires: C, 58.74; H, 5.80; N, 10.15. found: C, 58.60; H, 5.97; N, 10.00%.

EXAMPLE 67a

4-Hydroxy-piperidine-1-carboxylic acid benzyl ester

Benzyl chloroformate (8.55 mL; 60 mmol) was added drop wise over a period of 30 min to a well stirred chilled mixture of piperidin-4-ol (5 g; 49.44 mmol), 1N aqueous NaOH (60 mL; 60 mmol) and dioxane (60 mL). The mixture was stirred for 30 min. at room temperature, treated with water, acidified with conc. HCl to pH 2 and extracted with EtOAc. The EtOAc layer was washed with water, brine, dried (Na$_2$SO$_4$), concentrated and purified using flash chromatography (silica gel, 50% CH$_2$Cl$_2$ in PE 60-80° C., 10% CH$_3$CN+2% MeOH in chloroform). Yield, 12.5 g (99%), oil; MS (CI): 236 (M$^+$+1). 218, 192, 174, 91.

EXAMPLE 67b

4-Ethoxycarbonylmethoxy-piperidine-1-carboxylic acid benzyl ester

The compound of example 67a (16 g; 70 mmol) in dioxane (25 ml) was added drop wise at 5-10° C. to (toluene washed) 55% NaH (3.84 g; 80 mmol) suspended in dioxane (25 ml) over a period of 30 min. in an atmosphere of nitrogen. The reaction mixture was stirred at room temperature for 1 h, cooled to 0° C. and treated to a drop wise addition of ethyl 2-bromoacetate (8.9 ml; 80 58 mmol) over a period of 15-20 min. It was poured over crushed ice, and extracted with EtOAc. The EtOAc layer was washed with brine, dried (Na$_2$SO$_4$), concentrated and purified using flash chromatography (silica gel, 5-10% CH$_3$CN in chloroform). Yield, 18.5 g (84.55%), oil; MS (ESI): 344 (M$^+$+Na), 322 (M$^+$+1).

EXAMPLE 67c (Piperidin-4-yloxy)-acetic acid ethyl ester, hydrochloride

The compound of example 67b (14 g, 43.56 mmol) in MeOH (150 ml) and AcOH (10 ml) was hydrogenated using 10% Pd—C (0.15 g) at 40-50 psi for 4 h. The catalyst was filtered off and treated with ethereal HCl. It was concentrated and the title compound obtained was crystallized from dry MeOH in ether. Yield, 9.5 g (97.5%).

EXAMPLE 67d (1-{2-Benzyloxycarbonylamino-3-[4-benzyloxycarbonyloxy-phenyl]-propionyl}-piperidine-4-yloxy)-acetic acid ethyl ester DCC (4.12 g; 20 mmol) in EtOAc (10 ml) was added under vigorous stirring to a solution of di-Z-L-Tyr (8.08 g; 18 mmol) and HOBt (2.7 g; 20 mmol) in EtOAc (100 ml) at 0° C. After 10 min, the compound of example 67c (4.46 g; 19.93 mmol) was neutralized with $Et_3N$ (2.8 ml; 20 mmol) in DMF (10 ml) at 0° C. and was added to the reaction mixture. The resulting mixture was stirred at 0° C. for 2 h and then kept in the freeze over night (~16 h). DCU was filtered off. The filtrate was successively washed with 1N $NaHCO_3$, water, 1N HCl and brine. It was dried over anhydrous $Na_2SO_4$. The solvent was removed. The crude product was purified by flash chromatography with 10% $CH_3CN$ in $CHCl_3$. Yield, 8.2 g (73.6%); MS (ESI): 641 ($M^+$+Na), 619 ($M^+$+1); analysis: $C_{34}H_{38}N_2O_9$ requires: C, 66.01; H, 6.19; N, 4.53; found: C, 66.39; H, 6.58; N, 4.81%.

EXAMPLE 67e (1-{2-Amino-3-[4-hydroxy-phenyl]-propionyl}-piperidin-4-yloxy)-acetic acid ethyl ester, hydrochloride The compound of example 67d in MeOH and AcOH was hydrogenated using 10% Pd—C for 2 h at 40-50 psi. The catalyst was filtered off and ethereal HCl added. It was concentrated and the title compound obtained was crystallized from dry MeOH in ether. Yield, 85%; MS (ESI): 373 ($M^+$+Na), 351 ($M^+$+1).

EXAMPLE 67f (1-{2-[5-Cyano-1-oxo-1,3-dihydro-isoindol-2-yl]-3-(4-hydroxy-phenyl)-propionyl}-piperidin-4-yloxy)-acetic acid ethyl ester The title compound was obtained from the compound of example 67e using the procedure described in example 1g. It was purified using flash chromatography (silica gel, 10% $CH_3CN$, 2% MeOH in $CHCl_3$). Yield, 22%; mp, 73-75° C.; MS (CI): 520 ($M^+$+29), 492. ($M^+$+1), 292, 188, 158; analysis: $C_{27}H_{29}N_3O_6$ requires: C, 65.98; H, 5.95; N, 8.55; found: C, 65.68; H, 5.94; N, 8.18%.

EXAMPLE 67g (1-{3-[4-Hydroxy-phenyl]-2-(1-oxo-5-thiocarbamoyl-1,3-dihydro-isoindol-2-yl)-propionyl}-piperidin-4-yloxy)-acetic acid ethyl ester The title compound was obtained from the compound of example 67f using the procedure described in example 1h. It was purified using flash chromatography (silica gel, 10% $CH_3CN$ and 1% MeOH in chloroform). Yield, 95%; mp, 110° C.; MS (ESI): 548 ($M^+$+Na), 526. ($M^+$+1), 292, 188, 158.

EXAMPLE 68

(1-{2-[5-(N-Hydroxycarbamimidoyl)-1-oxo-1,3-dihydro-isoindol-2-yl]-acetyl}-piperidin-4-yloxy)-acetic acid ethyl ester The title compound was obtained from the compound of example 68d in two steps, using the procedures sequentially, described in examples 1i and 4. It was purified using flash chromatography (silica gel, 25% $CH_3CN$ in chloroform, 2-5% MeOH in chloroform). Yield, 67%, white solid; mp, 204-06° C. (MeOH: $CHCl_3$-PE 60-80° C.); MS (ESI): 441 ($M^+$+Na), 419 ($M^+$+1); analysis: $C_{20}H_{26}N_4O_6$ requires: C, 57.41; H, 6.26; N, 13.39; found: C, 57.51; H, 6.60; N, 13.49%.

EXAMPLE 68a (1-{2-tert-Butoxycarbonylamino-acetyl}-piperidin-4-yloxy)-acetic acid ethyl ester The title compound was obtained by reaction of tert-butoxycarbonylamino-acetic acid and Piperidin-4-yloxy)-acetic acid ethyl ester, hydrochloride (67c), using mixed anhydride procedure described for compound in example 25a. The crude product was purified by flash chromatography with 1% MeOH in chloroform. Yield, 84.6%, oil; analysis: $C_{16}H_{25}N_2O_6$ requires: C, 55.80; H, 8.19; N, 8.13; found: C, 55.48; H, 8.28; N, 8.06%.

EXAMPLE 68b (1-{2-Amino-acetyl}-piperidin-4-yloxy)-acetic acid ethyl ester, hydrochloride The title compound was obtained from the compound of example 68a using the procedure described in example 5b. Yield, 98%; MS (ESI): 267 ($M^+$+Na), 245 ($M^+$+1).

EXAMPLE 68c (1-{2-[5-Cyano-1-oxo-1,3-dihydro-isoindol-2-yl]-acetyl}-piperidin-4-yloxy)-acetic acid ethyl ester The title compound was obtained from the compound of example 68b using the procedure described in example 1g. It was purified using flash chromatography (silica gel, 5% $CH_3CN$ in chloroform, 2-5% MeOH in chloroform). Yield, 38.6%; mp, 109-11° C.; MS (ESI): 408 ($M^+$+Na), 386 ($M^+$+1); analysis: $C_{20}H_{23}N_3O_5$ requires: C, 62.33; H, 6.01; N, 10.90; found: C, 62.74; H, 6.19; N, 10.99%.

Alternative Method for Example 68c:

(5-cyano-1-oxo-1,3-dihydro-isoindol-2-yl)-acetic acid: Compound of example 66a (3.0 g; 12.8 mmol) was dissolved in THF (47.3 ml) and hydrolyzed with 0.5M LiOH (27.7 ml) for 30 min. The pH of the reaction was brought to 2 by adding 1N HCl. Most of the organic solvent was removed. The solid was filtered and washed with water. After drying under vacuum for 2 h at 50° C. it was crystallized from hot EtOAc-PE 60-80° C. Yield, 2.56 g (91.8%); mp, 262° C.; MS (EI): 216 ($M^+$), 171, 115; analysis: $C_{11}H_8N_2O_3$ 0.25$H_2O$ requires: C, 59.81; H, 3.86; N, 12.71; found: C, 60.17; H, 3.67; N, 13.06%.

(5-cyano-1-oxo-1,3-dihydro-isoindol-2-yl)-acetic acid: obtained above was reacted with (Piperidin-4-yloxy)-acetic acid ethyl ester, hydrochloride (67c) by mixed anhydride method as described for the preparation of 25a to obtain 68c in 60% yield.

EXAMPLE 68d (1-{2-[1-Oxo-5-thiocarbamoyl-1,3-dihydro-isoindol-2-yl]-acetyl}-piperidin-4-yloxy)-acetic acid ethyl ester The title compound was obtained from the compound of example 68c using the procedure described in example 1h. It was purified using flash chromatography (silica gel, 25% CH$_3$CN in chloroform). Yield, 81%, yellow solid; mp, 177-80° C. (CHCl$_3$-PE 60-80° C.); MS (ESI): 442 (M$^+$+Na), 420 (M$^+$+1); analysis: C$_{20}$H$_{25}$N$_3$O$_5$S requires: C, 57.26; H, 6.01; N, 10.02; S, 7.64. found: C, 57.44; H, 6.24; N, 10.27; S, 7.96%.

EXAMPLE 69

(1-{3-[5-(N-Hydroxycarbamimidoyl)-1-oxo-1,3-dihydro-isoindol-2-yl]-propionyl}-piperidin-4-yloxy)-acetic acid ethyl ester The title compound was obtained from the compound of example 69d in two steps, using the procedures sequentially, described in examples 1i and 4. It was purified using flash chromatography (silica gel, 25% CH$_3$CN in chloroform, by 2-5% MeOH in chloroform). Yield, 44%, white solid; mp, 151-52° C.; MS (ESI): 455 (M$^+$+Na), 433 (M$^+$+1); analysis: C$_{21}$H$_{28}$N$_4$O$_6$, requires: C, 58.32; H, 6.53; N, 12.95; found: C, 57.92; H, 6.61; N, 12.89%.

EXAMPLE 69a (1-{3-tert-Butoxycarbonylamino-propionyl}-piperidin-4-yloxy)-acetic acid ethyl ester Treatment of Boc-□Ala with (Piperidin-4-yloxy)-acetic acid ethyl ester, hydrochloride (67c), by mixed anhydride procedure described for compound in example 25a. The crude product was purified by flash chromatography with 1% MeOH in chloroform. Yield, 70%, oil; MS (CI): 387 (M$^+$+29), 359 (M$^+$+1), 259 (100%); analysis: C$_{17}$H$_{30}$N$_2$O$_6$ requires: C, 56.97; H, 8.44; N, 7.82; found: C, 56.67; H, 8.56; N, 7.60%.

EXAMPLE 69b (1-{3-Amino-propionyl}-piperidin-4-yloxy)-acetic acid ethyl ester, hydrochloride The title compound was obtained from the compound of example 69a using the procedure described in example 5b; Yield, 98%; mp, 70° C.; MS (ESI): 259 (M$^F$-1-1); analysis: C$_{12}$H$_{23}$ClN$_2$O$_4$ requires: C, 48.90; H, 7.86; N, 9.50; Cl, 12.03; found: C, 48.93; H, 8.18; N, 9.61; Cl, 11.83%.

EXAMPLE 69c (1-{3-[5-Cyano-1-oxo-1,3-dihydro-isoindol-2-yl]-propionyl}-piperidine-4-yloxy)-acetic acid ethyl ester The title compound was obtained from the compound of example 69b using the procedure described in example 1g. It was purified using flash chromatography (silica gel, 5% CH$_3$CN in chloroform, 2-5% MeOH in chloroform). Yield, 35%; mp, 60° C.; MS (ESI): 422 (M$^+$+Na), 400 (M$^+$+1); analysis: C$_{21}$H$_{25}$N$_3$O$_5$, 0.5H$_2$O requires: C, 61.69; H, 6.12; N, 10.28; found: C, 62.06; H, 6.17; N, 10.62%.

EXAMPLE 69d (1-{3-[1-Oxo-5-thiocarbamoyl-1,3-dihydro-isoindol-2-yl]-propionyl}-piperidin-4-yloxy)-acetic acid ethyl ester The title compound was obtained from the compound of example 69c using the procedure described in example 1h. It was purified using flash chromatography (silica gel, 5% CH$_3$CN in chloroform, 1% MeOH in chloroform). Yield, 98%, yellow solid; mp, 190° C.; MS (ESI): 456 (M$^+$+Na), 434 (M$^+$+1); analysis: C$_{21}$H$_{27}$N$_3$O$_5$S requires: C, 58.18; H, 6.28; N, 7.69; S, 7.4; found: C, 58.61; H, 6.60; N, 9.76; S, 7.29%.

EXAMPLE 70

(1-{2-[5-(5-Methyl-isoxazol-3-yl)-1-oxo-1,3-dihydro-isoindol-2-yl]-acetyl}-piperidin-4-yloxy)-acetic acid ethyl ester A solution of the compound of example 68 (1.3 g; 3.1 mmol) in acetic anhydride (22 ml) was heated at 120-30° C., following the reported procedure (J. Gante. et. al. Bioorg Med Chem. Lett. 1995, 6, 2425). It was purified using flash chromatography (silica gel, 2% MeOH in CHCl$_3$) and crystallized from chloroform-ether to obtain the title compound as a white solid. Yield, 0.96 g (69%); rap, 126-27° C.; MS (ESI): 443 (M$^+$+1); analysis: C$_{22}$H$_{26}$N$_4$O$_6$, requires: C, 59.72; H, 5.92; N, 12.66; found: C, 59.18; H, 5.90; N, 12.30%.

EXAMPLE 71

(1-{2-[5-Carbamimidoyl-1-oxo-1,3-dihydro-isoindol-2-yl]-acetyl}-piperidin-4-yloxy)-acetic acid ethyl ester, acetic acid salt, sesquihydrate The title compound was obtained from the compound of example 69d in two steps, using the procedures sequentially, described in examples 1i and 3. It was purified using, flash chromatography (RP-18 using 30% MeOH and 0.2% AcOH in water) and triturated with MeOH-ether to obtain a white solid. Yield, 42%; mp, 189-90° C.; MS (ESI): 403 (M$^+$+1); analysis: C$_{22}$H$_{30}$N$_4$O$_7$, 1.5H$_2$O requires: C, 53.93; H, 6.74; N, 11.44; found: C, 53.73; H, 6.58; N, 11.67%.

EXAMPLE 72

(1-{2-[5-(tert-Butoxycarbonylamino-imino-methyl)-1-oxo-1,3-dihydro-iso indol-2-yl]-acetyl}-piperidin-4-yloxy)-acetic acid ethyl ester, sesquihydrate NaHCO$_3$ (0.326 g; 3.88 mmol) was added at 0° C. to a mixture of the compound of example 71 (1.2 g; 2.59 mmol), dioxane (15 ml), water (7.5 ml) and 1N aqueous NaOH (2.59 ml). Subsequently di-tert-butyl-dicarbonate (0.847 g; 3.88 mmol) in dioxane (2 ml) was added. The reaction mixture was stirred at room temperature for 1 h, stripped off dioxane and extracted with EtOAc. The EtOAc layer was washed with water, dried (Na$_2$SO$_4$), concentrated and purified using flash chromatography (silica gel, 25% CH$_3$CN in chloroform, 2% MeOH in chloroform) to afford the title compound Yield, 0.75 g, white solid, (57%); mp, 83-85° C.; MS (ESI): 503 (M$^+$+1); analysis: C$_{25}$H$_{34}$N$_4$O$_7$, 1.5H$_2$O requires: C, 56.65; H, 6.99; N, 10.60; found: C, 56.52; H, 6.87; N, 11.29%.

EXAMPLE 73

(1-{2-[5-Carbamimidoyl-1-oxo-1,3-dihydro-isoindol-2-yl]-acetyl}-piperidin-4-yloxy)-acetic acid, hydrochloride, trihydrate Aqueous 1N NaOH (1.81 ml; 1.81 mmol) was added to a well-stirred solution of the compound of example 72 (0.7 g; 1.39 mmol) in MeOH (7.2 ml) at room temperature. The reaction mixture was allowed to further stir at room temperature for 1 h. Methanol was removed under reduced and the aqueous layer was acidified with dil HCl at 0° C. The reaction mixture was evaporated to dryness. The crude material obtained was dissolved in a solution of 5% MeOH in chloroform (30 ml) and filtered. The filtrate was taken to dryness and the residue was triturated with dry ether to afford the title compound as a pure white solid. Yield, 14%, white solid; mp, 135-36° C.; MS (ESI): 373 (M$^+$-1); analysis: $C_{18}H_{23}ClN_4O_5$, $3H_2O$ requires: C, 46.50; H, 6.29; Cl, 7.63; N, 12.05; found: C, 46.63; H, 6.23; Cl, 7.43; N, 11.64%.

EXAMPLE 74

(4-{2-[5-Acetimidoylamino-1-oxo-1,3-dihydro-isoindol-2-yl]-acetyl}-3-hydroxy-phenoxy)-acetic acid ethyl ester; hydro iodide, hemi hydrate The title compound was prepared by refluxing a mixture of 74b, 74c and $NaHCO_3$ in acetonitrile for 4 h. It was concentrated and purified using flash chromatography (silica gel, 10% $CH_3CN$ and 3% MeOH in chloroform) and triturated with MeOH-ether containing a few drops of EtOAc to obtain a pure white solid. Yield, 26%; mp, 196-97° C.; MS (ESI): 426 (M$^+$+1); analysis: $C_{22}H_{24}IN_3O_6$, $0.5H_2O$, requires: C, 46.94; H, 4.95; N, 7.47; found: C, 46.56; H, 4.54; N, 7.32%.

EXAMPLE 74a (3-Hydroxy-4-{2-[5-nitro-1-oxo-1,3-dihydro-isoindol-2-yl]-acetyl}-phenoxy)-acetic acid ethyl ester The title compound was obtained from the compound of example 41d and ethyl 2-bromomethyl-4-nitrobenzoate using the procedure described in example 1g. It was purified using flash chromatography (silica gel, 5% $CH_3CN$ in chloroform) and crystallized from $CHCl_3$-EtOAc-PE 60-80° C. Yield, 16%, off white solid; mp, 224-26° C.; MS (ESI): 437 (M$^+$+Na), 415 (M$^+$+1); analysis: $C_{20}H_{18}N_2O_8$ requires: C, 57.97; H, 4.38; N, 6.76; found: C, 58.23; H, 4.38; N, 6.64%.

EXAMPLE 74b (4-{2-[5-Amino-1-oxo-1,3-dihydro-isoindol-2-yl]-acetyl}-3-hydroxy-phenoxy)-acetic acid ethyl ester A mixture of the compound of example 74a, cobalt (II) chloride and Zn powder in DMF and water was stirred to obtain the title compound, according to reported procedure (see Ind. J. Chem. 33B, 758, 1994). It was purified using flash chromatography (silica gel, 10% $CH_3CN$ and 0.5% MeOH in chloroform) and crystallized using $CHCl_3$-PE 60-80° C. Yield, 43%, white solid; mp, 193-94° C.; MS (ESI): 407 (M$^+$+Na), 385 (M$^+$+1); analysis: $C_{20}H_{20}N_2O_6$ requires: C, 62.49; H, 5.24; N, 7.29; found: C, 62.95; H, 5.42; N, 7.31%.

EXAMPLE 74c

Thioacetimidic acid methyl ester hydroiodide

The title compound was obtained from thioacetamide using the procedure described in example 1i as a white solid white solid. Yield, 72%; mp, 158-60° C.; MS (EI): 89 (M$^+$); $^1$H NMR (DMSO-D$_6$): 2.56 (3H, s, CH$_3$), 2.71 (3H, s, SCH$_3$), 11.6 (1H, br, NH).

EXAMPLE 75

(3-Ethoxy-4-{2-[5-(N-hydroxycarbamimidoyl)-1-oxo-1,3-dihydro-isoindol-2-yl]-acetyl}-phenoxy)-acetic acid ethyl ester The title compound was Obtained from the compound of example 75c using the procedure described in example 4. It was purified using flash chromatography (silica gel, 2% MeOH in chloroform). Yield, 50%, white solid; mp, 192-94° C.; MS (ESI): 478.55 (M$^+$+Na), 456.37 (M$^+$+1); analysis: $C_{23}H_{25}N_3O_7$, requires C, 60.65; H, 5.53; N, 9.23; found: C, 60.57; H, 5.42; N, 8.73%.

EXAMPLE 75a (4-{2-[5-Cyano-1-oxo-1,3-dihydro-isoindol-2-yl]-acetyl}-3-ethoxy-phenoxy)-acetic acid ethyl ester Ethyl bromide (0.662 ml; 8.87 mmol) was added to a mixture of the compound of example 41f (0.7 g; 1.77 mmol), anhydrous $K_2CO_3$ (1.23 g; 8.87 mmol) and KF (0.07 g) in DMF (60 ml), with stirring at room temperature. The reaction mixture was stirred at room temperature for 16 h, poured over ice containing dill. HCl and extracted with EtOAc. The EtOAc layer was washed with water, dried ($Na_2SO_4$.), concentrated and purified using flash chromatography (silica gel, 5% $CH_3CN$ in chloroform). Yield, 0.585 g (78%); white solid; mp, 180-81° C. ($CHCl_3$-PE 60-80° C.); MS (ESI): 445 (M$^+$+Na), 423 (M$^+$+1-1); analysis: $C_{23}H_{22}N_2O_6$, requires C, 65.40; H, 5.25; N, 6.63. found: C, 65.75; H, 5.07; N, 6.11%.

EXAMPLE 75b (3-Ethoxy-4-{2-[1-oxo-5-thiocarbamoyl-1,3-dihydro-isoindol-2-yl]-acetyl}-phenoxy)-acetic acid ethyl ester The title compound was obtained from the compound of example 75a using the procedure described in example 1h. It was purified using flash chromatography (silica gel, 2% MeOH in chloroform). Yield, 95%, yellow solid; mp, 176-77° C.; MS (ESI): 480 (M$^+$+Na), 458 (M$^+$+1); analysis: $C_{23}H_{24}N_2O_6S$, requires C, 60.51; H, 5.30; N, 6.14; S, 7.02; found: C, 60.17; H, 5.36; N, 5.66; S, 7.39%.

EXAMPLE 75c (3-Ethoxy-4-{2-[5-methylsulfanylcarbonimidoyl-1-oxo-1,3-dihydro-iso indol-2-yl]-acetyl}-phenoxy)-acetic acid ethyl ester, hydroiodide The title compound was obtained from the compound of example 75b using the procedure described in example 11. Yield, 98%, yellow solid; mp, 169-72° C.; MS (ESI): 471.5 (M$^+$+1),

EXAMPLE 76

(4-{2-[5-carbamimidoyl-1-oxo-1,3-dihydro-isoindol-2-yl]-acetyl}-3-ethoxy-phenoxy)-acetic acid ethyl ester The title compound was obtained from the compound of example 75c using the procedure described in example 1. It was purified using flash chromatography (RP-18 with 40% MeOH and 2% AcOH in water) and crystallized using MeOH-ether. Yield, 0.44 g (59%); mp, 202-03° C.; MS (ESI$^+$): 440.54 (M$^+$+1); analysis: $C_{25}H_{29}N_3O_8$, requires C, 60.11; H, 5.85; N, 8.41; found: C, 59.87; H, 5.87; N, 8.33%.

EXAMPLE 77

(4-{2-[5-Carbamimdoyl-1-oxo-1,3-dihydro-isoindol-2-yl]-acetyl}-3-ethoxy-phenoxy)-acetic acid, hydrochloride, hemihydrate Aqueous 1N NaOH (1.6 ml; 1.6 mmol) was added to a well stirred mixture of the compound of example 76 (0.4 g; 0.8 mmol) and NaHCO$_3$ (0.1 g; 1.2 mmol) in dioxane-water (1:1; 5 ml) at 0° C. Subsequently di-tert-butyldicarbonate (0.262 g; 1.2 mmol) in dioxane (2.5 ml) was added. The reaction mixture was gradually brought to room temperature, and then allowed to stir for another 1 h. Dioxane was removed under reduced pressure. The residue was treated with water and extracted with EtOAc. The aqueous layer was acidified with 6N HCl to pH 3 and kept at room temperature for 16 h. The white solid that separated was filtered, washed with water, MeOH, ethyl acetate and dried to afford the pure title compound. Yield, 0.126 g (35%); mp, 241-42° C.; MS (ESI$^+$): 413.61 (M$^+$+1); analysis: $C_{21}H_n ClN_3O_6$, 0.5H$_2$O; requires C, 55.16; H, 5.03; N, 9.19. found: C, 55.16; H, 5.43; N, 9.22%.

EXAMPLE 78

(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester A mixture of the compound of example 42 (0.3 g; 0.7 mmol) and 1,1'-carbonyldiimidazol (0.17 g; 1.05 mmol) in DMF (10 ml) was stirred at room temperature for 12 h. The reaction mixture was diluted with water (100 ml) and extracted with EtOAc. The EtOAc layer was washed with 1N HCl, water, brine, dried (Na$_2$SO$_4$), concentrated, purified using flash chromatography (silica gel, 5% MeOH in chloroform) and crystallized from MeOH-ether to obtain the title compound. Yield, 0.032 g; (10%), white solid; mp, 223-25° C.; MS (ESI): 452.59 (M−1), analysis: $C_{22}H_{19}N_3O_8$, requires C, 57.09; H, 4.32; N, 9.08; found: C, 57.74; H, 4.18; N, 8.93%.

EXAMPLE 79

(4-{2-[5-(Acetylamino-imino-methyl)-1-oxo-1,3-dihydro-isoindol-2-yl]-acetyl}-3-hydroxy-phenoxy)-acetic acid ethyl ester A mixture of the compound of example 42 (0.5 g; 1.17 mmol), KF (0.05 g), pyridine (0.189 ml; 2.34 mmol) and acetyl chloride (0.167 ml; 2.34 mmol) in DMF (10 ml) was stirred at room temperature for 3 h. The reaction mixture was diluted with ice water (100 ml) and extracted with dichloromethane. The organic layer was washed with water, brine, dried, (Na$_2$SO$_4$) and concentrated to obtain the crude product, which was purified by triturating with MeOH, CHCl$_3$ and ether to obtain the title compound as a pure white solid. Yield, 0.414 g; (75%); mp, 196-98° C.; MS (ESI$^+$): 470.61 (M$^+$+1), analysis: $C_{23}H_{23}N_3O_8$, requires C, 58.85; H, 4.94; N, 8.95; found: C, 58.47; H, 4.44; N, 8.48%.

EXAMPLE 80

(3-Acetoxy-4-{2-[5-(5-methyl-[1,2,4]oxadiazol-3-yl)-1-oxo-1,3-dihydro-isoindol-2-yl]acetyl}-phenoxy)-acetic acid ethyl ester The title compound was obtained from the compound of example 42 using the procedure described in example 79 with the exception of using 8 equivalent of acetyl chloride and three times the amount of KF used earlier. Yield, 26%; mp, 162-64° C.; MS (ESI$^+$): 494 (M$^+$+1); analysis: $C_{25}H_{23}N_3O_8$, requires C, 59.70; H, 4.78; N, 8.36; found: C, 60.08; H, 4.11; N, 7.85%.

EXAMPLE 81

(4-{2-[5-Carbamimidoyl-1-oxo-1,3-dihydro-isoindol-2-yl]-acetyl}-3-hydroxy-2-propyl-phenoxy)-acetic acid ethyl ester, acetic acid salt, hemi hydrate A mixture of the compound of example 58 (0.15 g; 0.319 mmol), glacial acetic acid (20 ml) and Ac$_2$O (0.066 ml; 0.703 mmol) was stirred at room temperature for 10 min. The mixture was filtered and the filtrate was hydrogenated using 10% Pd—C (0.02 g) at 20 psi for 15 min. The catalyst was filtered off and the filtrate was evaporated to dryness. The crude product was purified using flash chromatography (silica gel, 40% MeOH and 0.2% AcOH in water). The pure product was crystallized using MeOH-ether. Yield, 0.105 g (64%); mp, 186-88° C.; analysis: $C_{26}H_{31}N_3O_8$ 0.5H$_2$O, requires C, 59.71; H, 6.12; N, 8.04; found: C, 59.53; H, 5.94; N, 7.45%.

EXAMPLE 82

(3-Hydroxy-4-{2-[5-(N-hydroxycarbamimidoyl)-1-oxo-1,3-dihydro-iso indol-2-yl]-acetyl}-2-propyl-phenoxy)-acetic acid, sesquihydrate NaOH (0.038 g; 0.937 mmol) in absolute EtOH (1 ml) was added to a suspension of the compound of example 58 (0.1 g; 0.0.213 mmol) in absolute EtOH (5 ml), and the clear solution was stirred at room temperature till the starting material was consumed. It was concentrated treated dil. HCl. and evaporated to dryness. The crude material was purified using flash chromatography (RP-18 with 1:1 MeOH: 0.2% AcOH in water). Triturating with ether and a trace amount of methanol purified the residue. Yield, 0.35 g (37%), white solid; analysis: $C_{22}H_{23}N_3O_7$ 1.5H$_2$O, requires C, 56.35; H, 5.55; N, 8.97; found: C, 56.77; H, 4.98; N, 8.92%.

EXAMPLE 83

(3-Allyloxy-4-{2-[5-(N-hydroxycarbamimidoyl)-1-oxo-1,3-dihydro-iso indol-2-yl]-acetyl}-phenoxy)-acetic acid ethyl ester, hemihydrate The title compound was obtained from the compound of example 83c using the procedure described in example 4. It was purified using flash chromatography (silica gel, 4% CH$_3$CN in chloroform, 2% MeOH in chloroform). Yield, 77%, white solid; mp, 182-83° C.; analysis: $C_{24}H_{25}N_3O_7$, 0.5H$_2$O, requires C, 60.49; H, 5.46; N, 8.81; found: C, 60.22; H, 5.09; N, 8.59%.

EXAMPLE 83a (3-Allyloxy-4-{2-[5-cyano-1-oxo-1,3-dihydro-isoindol-2-yl]-acetyl}-phenoxy)-acetic acid ethyl ester The title compound was obtained from the compound of example 41f using the procedure described in example 75a. It was purified using flash chromatography (silica gel, 5-10% $CH_3CN$ in chloroform). Yield, 76%, white solid; mp, 126-28° C. ($CHCl_3$-PE 60-80° C.); MS (ESI): 457.523 ($M^++Na$), 435.5 ($M^++1$); analysis: $C_{24}H_{22}N_2O_6$, requires C, 66.35; H, 5.10; N, 6.45. found: C, 66.14; H, 5.81; N, 6.97%.

EXAMPLE 83b (3-Allyloxy-4-{2-[1-oxo-5-thiocarbamoyl-1,3-dihydro-isoindol-2-yl]-acetyl}-phenoxy)-acetic acid ethyl ester, hemihydrate The title compound was obtained from the compound of example 83a using the procedure described in example 1h. It was purified by flash chromatography (silica gel, 5% $CH_3CN$ in chloroform, 2% MeOH in chloroform). Yield, 76%, yellow solid; mp, 74-76° C.; analysis: $C_{24}H_{24}N_2O_6S$, $0.5H_2O$, requires C, 60.31; H, 5.24; N, 5.86; S, 6.70; found: C, 60.58; H, 4.97; N, 5.83; S, 7.03%.

EXAMPLE 83c (3-Allyloxy-4-{2-[5-methylsulfanylcarbonimidoyl-1-oxo-1,3-dihydro-iso indol-2-yl]-acetyl}-phenoxy)-acetic acid ethyl ester, hydroiodide The title compound was obtained from the compound of example 83b using the procedure described in example 11. Yield, 98%, yellow solid; mp, 130° C. (d); MS (CI): 512 ($M^++29$), 484 ($M^++1$); analysis: $C_{25}H_{27}IN_2O_6S$, requires C, 49.29; H, 4.15; N, 4.02; I, 20.18; S, 5.38; found: C, 49.19; H, 4.46; N, 4.49; I, 20.49; S, 5.25%.

The efficacy of the present compounds in antagonizing the activity of the fibrinogen receptor can be determined by a number of pharmacological assays well known in the art, such as described below. The exemplified pharmacological assays, which follow herein below, have been carried out with the compounds of the present invention and their salts.

In vitro Biological Experiments

Human blood (150 ml) was collected from the ante-cubital vein of normal healthy volunteers (who were not on any medication for the past two weeks), into a siliconized glass bottle containing 25 ml of acid-citrate-dextrose (ACD) solution and 10 units of hirudin. The blood was immediately centrifuged at 200×g for 20 min at room temperature. Platelet-rich plasma (PRP) was separated and the platelet count read using a Beckman Coulter A°T diff Counter. The tubes were centrifuged again at 2000×g for 10 min at room temperature, to get platelet-free plasma (PFP). The platelet count of PRP was adjusted to $3\times10^8$ platelets/ml by appropriate dilution with PFP. All in vitro experiments were conducted using PRP with adjusted number of platelets.

Inhibition of Platelet Aggregation in Human PRP (Born, G. V. R.; Cross, M. J., J. Physiol, 1963, 168, 175)

PRP was incubated with different concentrations of the test compound for 3 min at 37° C. Platelet aggregation was then induced by the addition of ADP (5-15 µM final concentration). Percent inhibition of platelet aggregation was then calculated by comparing test aggregation values with control values (Table 1).

TABLE 1

| Example No. | $IC_{50}$ (µM) |
|---|---|
| 3 | 0.093 |
| 20 | 0.05 |
| 24 | 0.006 |

Inhibition of Aggregation of Gel-filtered Platelets (GFP) (Charo, I. F., Nanizzi, L. et al, J. Biol. Chem, 1991, 266, 1415-1421) (Table 2).

TABLE 2

| | GFP Study % Inhib. against | |
|---|---|---|
| Example No | ADP | Thromb. |
| 3 | 0.74 | 0.45 |
| 20 | 0.62 | 0.39 |

PRP was centrifuged at 285×g for 20 min to pellet the platelets. The platelet pellet was resuspended in Tyrode's buffer containing hirudin (0.06 unit/ml) and apyrase (40 mcg/ml). The platelet suspension was layered on to a Sepharose 2B (Sigma) column, previously equilibrated with Tyrode buffer (pH 7.4). Elution of platelets was carried out with Tyrode buffer containing dextrose (5.5 mM) and BSA (0.35%). The count of GFP was adjusted to $3\times10^8$ platelets/ml with Tyrode's buffer. GFP suspension was mixed with ADP and fibrinogen and aggregation of platelets was studied in presence and in absence of the test compound. Similarly, the effect of the test compound on thrombin-induced platelet aggregation was studied.

Receptor Binding Assay: (Mousa S. A., et al. Cardiology. 1993:83:374-382. and Charo, I. F., Nanizzi, L. et al, J. Biol. Chem., 1991, 266, 1415-1421)

Biotinylation of Fibrinogen

Fibrinogen was dialyzed against 0.1 M $NaHCO_3$, 0.1 M NaCl, pH 8.2 and spun in an ultracentrifuge at 1,00000×g for 30 minutes at 4° C. to remove any particulate matter. The protein concentration was adjusted to 1 mg/ml. Solid sulfo-N-hydroxy-succinimido-biotin (0.2 mg of biotin ester/ml of adhesive protein) was added and gently mixed end-over-end for 30 minutes at room temperature. The unreacted biotin ester was removed by exhaustive dialysis against 50 mM Tris.HCl, 100 mM NaCl, 0.05% $NaN_3$, pH −7.4 at 4° C. The biotinylated fibrinogen is stored at 4° C. until use.

Method

The GP IIb/IIIa protein (1 mg/ml) was diluted 1:200 with a Triton X-100-free buffer containing 20 mM Tris-HCl, 150 mM NaCl, 1 mM $CaCl_2$, 0.02% $NaN_3$ (Buffer A). This protein was immediately added to 96-well microtiter plates (Immulon II—Dynatech) at 0.1 ml (0.5 mg) per well and incubated overnight at 4° C. The wells were washed once with 50 mM Tris, 100 mM NaCl, 2 mM $CaCl_2$, 0.02% $NaN_3$, pH 7.4 (buffer B). The unbound sites were then blocked by incubating the wells with 0.1 ml solution buffer B containing 35 mg/ml BSA, for 2 hours at 30° C. The wells were washed again with buffer B containing 1 mg/ml BSA (incubation buffer). The fibrinogen receptor antagonists were added simultaneously with biotinylated fibrinogen, so as to induce competition for binding to the gpIIb/IIIa receptor. Biotinylated fibrinogen (0.1 ml/well) was added at a final concentration of 10 nM and incubated for 3 hours at 30° C. After incubation, the wells were aspirated completely and washed once with 250 µl of binding buffer. Bound fibrinogen was quantitated by addition of 0.1 ml of Streptavidin horseradish peroxidase (1:2000 dilution). The wells were then washed with incubation buffer and 100 µl of the substrate 3,3',5,5'-tetramethyl-benzidine dihydrochloride was added. (The substrate was prepared daily following the manufacturer's instructions—1 mg/ml of substrate prepared in DMSO was added to 9 ml of citrate buffer, pH=4). The kinetics of colour development was followed at 450 nm (Ref filter—630 nm) using a microtiter plate reader.

Ex vivo Biological Experiments

Mouse ex vivo Studies: (Weller, T., Alig, L., et al J. Med. Chem., 1996, 39, 3139-3147)

Mice of either sex weighing between 25-35 g were orally fed the test compound. Blood was collected, from the abdominal aorta into ACD solution, at different time-points ranging from 15 min to 6 h. The blood samples were centrifuged at 2000×g for 10 min to get PFP. This plasma was separated and used as test sample to study its effect on ADP-induced human platelet aggregation (Table 3).

TABLE 3

| | Ex vivo in mice (1 mg/kg, p.o) | | | |
|---|---|---|---|---|
| Example No. | Peak activity (time in hours) | Activity (%) at peak | Last time point * (time in hours) | Activity (%) at last time point |
| 42 | 0.75 | 100 | 6 | 62 |
| 49 | 0.75 | 65 | 3 | 38 |
| 23 | 1 | 100 | 4 | 35 |

* Time point after which the activity fell below 30%

Guinea Pig Ex vivo Studies:

Guinea pigs of either sex weighing between 500-800 g were orally fed the test compound. Blood was collected, from the carotid artery into ACD solution, at different time-points ranging from 1 to 24 h. PRP was separated and the platelet count adjusted to $3 \times 10^8$ platelets/ml using PFP. The effect of the test compound on ADP-induced guinea pig platelet aggregation was studied (Table 4).

TABLE 4

| | Ex vivo in Guinea pigs (3.1 mg/kg, p.o) | | | |
|---|---|---|---|---|
| Example No. | Peak activity (time in hours) | Activity (%) at peak | Last time point * (time in hours) | Activity (%) at last time point |
| 42 | 7 | 100 | 15 | 78 |
| 23 | 7 | 100 | 13 | 48 |

* Time point after which the activity fell below 30%

In vivo Biological Experiments

Thrombocytopenia in Guinea Pigs: (Voelkl K-P., Dierichs, R. Thromb. Res. 1986, 42, 11-20)

Guinea pigs weighing between 500-800 g were orally fed the test compound. After a fixed time interval the guinea pigs were anaethesized and the carotid artery and jugular vein were cannulated. Blood samples were collected from the carotid artery. After collection of the control blood sample (0 min), collagenase (10 mg/kg) was administered through the jugular vein. The endothelium gets damaged by the action of collagenase and causes platelets to aggregate at this site, thereby inducing thrombocytopenia. At every minute thereafter till 10 min and at 15, 20, 25 and 30 min after the administration of collagenase, blood samples were collected. The platelet count was read using the Beckman Coulter A$^c$T diff Counter. All counts were compared with the 0 min (before administration of proaggregatory challenge) sample to determine the fall in the number of free circulating platelets. A graph of the number of platelets against time was plotted and the Area Under the Curve (AUC) was calculated for each animal. Percent protection was determined by comparing the AUCs of treated to control animals.

Thrombus Formation in Hamster:

Hamsters weighing between 150-180 g were orally fed the test compound. After a fixed time interval they were anaesthetized and the abdominal aorta exposed. A copper wire with a one-centimeter long coil was inserted through the abdominal aorta, all the way up to the thoracic aorta. After 10 min the copper wire was withdrawn and the size of the thrombus, formed on the wire, determined by estimating the protein content. Percent inhibition of thrombus formation was determined by comparing the thrombi formed in the drug-treated group with those in the control group.

The compounds of the present invention have an $IC_{50}$ below 100 nM, for ADP-induced human platelet aggregation and ~200 pM for fibrinogen binding. Efficacy studies in guinea pigs revealed that the compounds show a long duration of action. The compounds of the present invention also inhibited collagenase-induced thrombocytopenia in guinea pigs. Toxicity studies with some of these molecules revealed that the LD50 was >1000 mg/kg, p.o., in mice and rats. They did not significantly increase the bleeding time in guinea pigs.

We claim:

1. A method of inhibiting binding of fibrinogen to blood platelets, comprising administering to blood platelets effective amount of a compound of the formula (I) or a stereoisomer, a tautomer or a pharmaceutically acceptable salt thereof;

$$(I)$$

wherein
   ring A is phenyl;
   $R^A$ is a group of formula (3):

$$(3)$$

wherein p is 0;
   s is 1;
   $R^1$ is selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle;
   $R^3$ and $R^4$ are independently selected from: H, alkyl, partially or fully fluorinated alkyl, alkenyl, alkynyl, —C(=O)OR$^5$, cycloalkyl, cycloalkylalkyl, aryl, arylalkyl, heterocycle, —OR$^5$, —SR$^5$, —NR$^5$R$^6$, —S(=O)$_2$NR$^5$R$^6$, —S(=O)$_2$R$^5$, —C(=O)R$^5$, —C(=O)NR$^5$R$^6$, —C(=O)OR$^5$, —C(=O)SR$^5$, —OC(=O)R$^5$, —OC(=O)OR$^5$, —OC(=O)NR$^5$R$^6$, —OS(=O)$_2$R$^5$, —S(C=O)NR$^5$ and —OS(=O)$_2$NR$^5$R$^6$, or R$^3$ and R$^1$ or R$^4$, together with the respective nitrogen atoms to which they are attached, form an unsubstituted or substituted 5-, 6- or 7-membered partially saturated or aromatic heterocycle, optionally having one or more additional heteroatoms selected from: N, O and S, wherein the substituents are selected from: hydroxy, halogen, alkyl, alkoxy, alkenyl, alkynyl, oxo, carboxy and —C(=O)OR$^5$;

R$^5$ and R$^6$ are independently selected from: H, alkyl, alkenyl, alkynyl, cycloalkyl, cycloalkylalkyl, aryl, arylalkyl and heterocycle, wherein each of said alkyl, alkenyl, alkynyl, cycloalkyl and cycloalkylalkyl group optionally contains at least one hetero atom selected from: N, S and O anywhere in the chain, including the terminal position;

R$^B$ is H;

Y$^1$ and Y$^2$, together, are selected from: =O and =S;

Z is N;

W is CH;

R$^C$ is H;

n is 0, 1, 2 or 3;

R$^D$ and R$^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy, —C(=O)OR$^5$, —OR$^{17}$, —SR$^{17}$, —NR$^{17}$R$^{18}$, —NHC(=O)R$^{17}$, —NHC(=O)OR$^{17}$, —OC(=O)R$^{17}$, —SC(=O)R$^{17}$, —OS(=O)$_2$R$^{17}$ and —NHS(=O)$_2$R$^{17}$;

R$^{17}$ and R$^{18}$ have the same meaning as R$^5$ and R$^6$, defined above;

R$^F$ is selected from: O, S and N(OR$^{19}$);

R$^{19}$ has the same meaning as R$^5$, defined above;

R$^G$ is selected from: aryl, heteroaryl, and partially or fully saturated heterocycle, where said aryl, heteroaryl and heterocycle are substituted by one or more groups of the formula (5):

and optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$ NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$ and —S(=O)$_2$OR$^{21}$;

R$^{21}$ has the same meaning as R$^1$, defined above, and R$^{22}$ is selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle:

T is selected from: —CH$_2$, O, S and NH;

q is 0, 1, 2 or 3;

R$^{23}$ and R$^{24}$ are independently selected from: H, alkyl alkenyl, alkynyl, cycloalkyl, cycloalkylalkyl, aryl, arylalkyl, heterocycle and C(=O)R$^{25}$, wherein said alkyl and alkenyl optionally contain at least one hetero atom selected from: O, S and N, in any position of the alkyl or alkenyl chain, and said alkyl and alkenyl are unsubstituted or substituted with at least one group selected from: —OR$^1$, —OC(=O)R$^1$, —OS(=O)$_2$R$^1$, —S(=O)$_2$NR$^1$R$^2$, —OC(=O)OR$^1$, —OC(=O)SR$^1$, —OC(=O)NR$^1$R$^2$, —SR$^1$, —S(=O)R$^1$, —SC(=O)H, —SC(=O)OR$^1$, —NR$^1$(OR$^2$), —NR$^1$R$^2$, —NR$^1$C(=O)R$^2$, —N(R$^1$)C(=O)OR$^2$, —NR$^1$S(=O)$_2$R$^2$, C(=O)OR$^1$, —S(=O)$_2$R$^1$ and —S(=O)$_2$OR$^1$;

R$^{25}$ is selected from: OR$^5$, SR$^5$, —OCR$^3$R$^4$ and —NR$^5$R$^6$, wherein R$^3$, R$^4$, R$^5$ and R$^6$ are as defined above and wherein optionally, R$^3$ and R$^4$, together with the carbon to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy and —C(=O)OR$^5$; and the group NR$^5$R$^6$ is, optionally, a heterocycle containing at least one additional heteroatom selected from: O, S, and N.

2. The method according to claim 1, wherein in the compounds of formula (I), R$^G$ is selected from: phenyl, piperidinyl and piperazinyl, and said phenyl, piperidinyl and piperazinyl are substituted by one or more groups of the formula (5):

and optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$ NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$ and —S(=O)$_2$OR$^{21}$; and R$^{21}$ and R$^{22}$ are as defined in claim 1.

3. The method according to claim 1, wherein in the compounds of formula (I),

R$_1$ is hydrogen;

R$_3$ and R$_4$ are independently selected from: H, OH, —C(O)OH and —C(O)Oalkyl;

R$^B$=R$^C$=R$^D$=R$^E$=hydrogen;

Y$^1$ and Y$^2$, together are =O;

n is the integer 0 or 1;

R$^G$ is phenyl, substituted with one or more of the group of formula (5):

wherein R$^{23}$ is H and R$^{24}$ is H, and, optionally, the compound is further substituted with one or more of the groups selected from: hydroxy, halogen, alkyl, alkoxy, alkenyl, alkynyl, oxo, carboxy, —C(=O)OR$^5$, SR$^{21}$, S(=O)$_2$R$^{21}$ and —N(R$^{21}$)—C(O)CH$_3$, —CH$_2$C(O)R$^{25}$; and R$^{25}$ is selected from: OR$^5$, OCR$^3$R$^4$ and NR$^5$R$^6$, wherein R$^3$ and R$^4$, together with the carbon to which they are attached form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy, —C(=O)OR$^5$; and R$^5$, R$^6$ and R$^{21}$ are independently selected from: H, alkyl and phenyl.

4. The method according to claim 1, wherein in the compounds of formula (I)

R$_1$ is hydrogen;

R$_3$ and R$_4$ are independently selected from: H, OH, —C(O)OH and —C(O)Oalkyl;

R$^B$=R$^C$=R$^D$=R$^E$=hydrogen;

Y$^1$ and Y$^2$, together are =O;

n is the integer 0 or 1;

R$^G$ is selected from: piperidinyl and piperazinyl, wherein said piperidinyl and piperazinyl are substituted with one or more of the group of formula (5):

wherein R²³ is H and R²⁴ is H and, optionally, further substituted with one or more groups selected from: hydroxy, halogen, alkyl, alkoxy, alkenyl, alkynyl, oxo, carboxy and —C(=O)OR⁵; and R²⁵ is OR⁵, wherein R⁵ is selected from: H, alkyl and phenyl.

5. The method according to claim 1, wherein the compounds of formula (I) are selected from the group consisting of:

(4-{2-[5-Carbamimidoyl-1-oxo-1,3-dihydro-isoindol-2-yl]-acetyl}-phenoxy)-acetic acid methyl ester;
(4-{2-[5-(N-Hydroxycarbamimidoyl)-1-oxo-1,3-dihydro-isoindol-2-yl]-acetyl}-phenoxy)-acetic acid methyl ester;
(4-{2-[5-Carbamimidoyl-1-oxo-1,3-dihydro-isoindol-2-yl]-acetyl}-phenoxy)-acetic acid ethyl ester;
(4-{2-[5-(N-Hydroxycarbamimidoyl)-1-oxo-1,3-dihydro-isoindol-2-yl]-acetyl}-phenoxy)-acetic acid ethyl ester;
4-(2-{5-Carbamimidoyl-1-oxo-1,3-dihydro-isoindol-2-yl}-acetyl]-phenoxy)-acetic acid isopropyl ester;
(4-{2-[5-(Imino-methoxycarbonylamino-methyl)-1-oxo-1,3-dihydro-isoindol-2-yl]-acetyl}-phenoxy)-acetic acid isopropyl ester;
(4-{2-[5-(Imino-isobutoxycarbonylamino-methyl)-1-oxo-1,3-dihydro-isoindol-2-yl]-acetyl}-phenoxy)-acetic acid isopropyl ester;
(4-{2-[5-(Benzyloxycarbonylamino-imino-methyl)-1-oxo-1,3-dihydro-isoindol-2-yl]-acetyl}-phenoxy)-acetic acid isopropyl ester;
(4-{2-[5-(N-Hydroxycarbamimidoyl)-1-oxo-1,3-dihydro-isoindol-2-yl]-acetyl}-phenoxy)-acetic acid isopropyl ester;
(4-{2-[5-Carbamimidoyl-1-oxo-1,3-dihydro-isoindol-2-yl]-acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;
(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxy-imino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;
2-(4-{2-[5-Carbamimidoyl-1-oxo-1,3-dihydro-isoindol-2-yl]-acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-acetyl}-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;

(4-{2-[5-(N-Hydroxycarbamimidoyl)-1-oxo-1,3-dihydro-isoindol-2-yl]-acetyl}-3-methoxy-phenoxy)-acetic acid ethyl ester;

(4-{2-[5-(N-Hydroxycarbamimidoyl)-1-oxo-1,3-dihydro-isoindol-2-yl]-acetyl}-3-propoxy-phenoxy)-acetic acid ethyl ester;

(4-{2-[5-Carbamimidoyl-1-oxo-1,3-dihydro-isoindol-2-yl]-acetyl}-3-ethoxy carbonylmethoxy-phenoxy)-acetic acid ethyl ester;

(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;

(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;

(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;

(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;

(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;

(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;

(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;

(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid benzyl ester;

(4-{2-[5-Carbamimidoyl-1-oxo-1,3-dihydro-isoindol-2-yl]-acetyl}-3-hydroxy-2-propyl-phenoxy)-acetic acid;

(4-Hydroxy-3-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;

(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;

(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;

(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;

(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;

(1-{2-[5-(N-Hydroxycarbamimidoyl)-1-oxo-1,3-dihydro-isoindol-2-yl]-acetyl}-piperidin-4-yloxy)-acetic acid ethyl ester;

(1-{3-[5-(N-Hydroxycarbamimidoyl)-1-oxo-1,3-dihydro-isoindol-2-yl]-propionyl}-piperidin-4-yloxy)-acetic acid ethyl ester;

(1-{2-[5-(5-Methyl-isoxazol-3-yl)-1-oxo-1,3-dihydro-isoindol-2-yl]-acetyl}-piperidin-4-yloxy)-acetic acid ethyl ester;

(1-{2-[5-Carbamimidoyl-1-oxo-1,3-dihydro-isoindol-2-yl]-acetyl}-piperidin-4-yloxy)-acetic acid ethyl ester;

(1-{2-[5-(tert-Butoxycarbonylamino-imino-methyl)-1-oxo-1,3-dihydro-isoindol-2-yl]-acetyl}-piperidin-4-yloxy)-acetic acid ethyl ester;

(1-{2-[5-Carbamimidoyl-1-oxo-1,3-dihydro-isoindol-2-yl]acetyl}-piperidin-4-yloxy)-acetic acid;

(3-Ethoxy-4-{2-[5-(N-hydroxycarbamimidoyl)-1-oxo-1,3-dihydro-isoindol-2-yl]-acetyl}-phenoxy)-acetic acid ethyl ester;

(4-[2-(5-carbamimidoyl-1-oxo-1,3-dihydro-isoindol-2-yl)-acetyl]-3-ethoxy-phenoxy}-acetic acid ethyl ester;

(4-{2-[5-Carbamimdoyl-1-oxo-1,3-dihydro-isoindol-2-yl]-acetyl}-3-ethoxy-phenoxy)-acetic acid;

(3-Hydroxy-4-{2-[1-oxo-5-(5-oxo-2,5-dihydro-[1,2,4]oxadiazol-3-yl)-1,3-dihydro-isoindol-2-yl]acetyl}-phenoxy)-acetic acid ethyl ester;

(4-{2-[5-(Acetylamino-imino-methyl)-1-oxo-1,3-dihydro-isoindol-2-yl]-acetyl}-3-hydroxy-phenoxy)-acetic acid ethyl ester;

(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;

(4-{2-[5-Carbamimidoyl-1-oxo-1,3-dihydro-isoindol-2-yl]-acetyl}-3-hydroxy-2-propyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid; and (3-Allyloxy-4-{2-[5-(N-hydroxycarbamimidoyl)-1-oxo-1,3-dihydro-isoindol-2-yl]-acetyl}-phenoxy)-acetic acid ethyl ester.

6. The method according to claim 3, wherein the compounds of formula (I) are selected from the group consisting of (4-{2-[5-Carbamimidoyl-1-oxo-1,3-dihydro-isoindol-2-yl]-acetyl}-phenoxy)-acetic acid methyl ester;

(4-{2-[5-(N-Hydroxycarbamimidoyl)-1-oxo-1,3-dihydro-isoindol-2-yl]-acetyl}-phenoxy)-acetic acid methyl ester;

(4-{2-[5-Carbamimidoyl-1-oxo-1,3-dihydro-isoindol-2-yl]-acetyl}-phenoxy)-acetic acid ethyl ester;

(4-{2-[5-(N-Hydroxycarbamimidoyl)-1-oxo-1,3-dihydro-isoindol-2-yl]-acetyl}-phenoxy)-acetic acid ethyl ester;

4-(2-{5-Carbamimidoyl-1-oxo-1,3-dihydro-isoindol-2-yl]-acetyl]-phenoxy)-acetic acid isopropyl ester;

(4-{2-[5-(Imino-methoxycarbonylamino-methyl)-1-oxo-1,3-dihydro-isoindol-2-yl]-acetyl}-phenoxy)-acetic acid isopropyl ester;

(4-{2-[5-(Imino-isobutoxycarbonylamino-methyl)-1-oxo-1,3-dihydro-isoindol-2-yl]-acetyl}-phenoxy)-acetic acid isopropyl ester;

(4-{2-[5-(Benzyloxycarbonylamino-imino-methyl)-1-oxo-1,3-dihydro-isoindol-2-yl]-acetyl}-phenoxy)-acetic acid isopropyl ester;

(4-{2-[5-(N-Hydroxycarbamimidoyl)-1-oxo-1,3-dihydro-isoindol-2-yl]-acetyl}-phenoxy)-acetic acid isopropyl ester;

(4-{2-[5-Carbamimidoyl-1-oxo-1,3-dihydro-isoindol-2-yl]-acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;
(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxy-imino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;
2-(4-{2-[5-Carbamimidoyl-1-oxo-1,3-dihydro-isoindol-2-yl]-acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-acetyl}-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;
(4-{2-[5-(N-Hydroxycarbamimidoyl)-1-oxo-1,3-dihydro-isoindol-2-yl]-acetyl}-3-methoxy-phenoxy)-acetic acid ethyl ester;
(4-{2-[5-(N-Hydroxycarbamimidoyl)-1-oxo-1,3-dihydro-isoindol-2-yl]-acetyl}-3-propoxy-phenoxy)-acetic acid ethyl ester;
(4-{2-[5-Carbamimidoyl-1-oxo-1,3-dihydro-isoindol-2-yl]-acetyl}-3-ethoxy carbonylmethoxy-phenoxy)-acetic acid ethyl ester;
(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;
(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;
(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;
(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid benzyl ester;
(4-{2-[5-Carbamimidoyl-1-oxo-1,3-dihydro-isoindol-2-yl]-acetyl}-3-hydroxy-2-propyl-phenoxy)-acetic acid;
(4-Hydroxy-3-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;
(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;
(3-Ethoxy-4-{2-[5-(N-hydroxycarbamimidoyl)-1-oxo-1,3-dihydro-isoindol-2-yl]-acetyl}-phenoxy)-acetic acid ethyl ester;
(4-[2-(5-carbamimidoyl-1-oxo-1,3-dihydro-isoindol-2-yl)-acetyl]-3-ethoxy-phenoxy}-acetic acid ethyl ester;
(4-{2-[5-Carbamimdoyl-1-oxo-1,3-dihydro-isoindol-2-yl]-acetyl}-3-ethoxy-phenoxy)-acetic acid;
(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester;
(4-{2-[5-(Acetylamino-imino-methyl)-1-oxo-1,3-dihydro-isoindol-2-yl]-acetyl}-3-hydroxy-phenoxy)-acetic acid ethyl ester;
(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid; and
(3-Allyloxy-4-{2-[5-(N-hydroxycarbamimidoyl)-1-oxo-1,3-dihydro-isoindol-2-yl]-acetyl}-phenoxy)-acetic acid ethyl ester.

7. The method according to claim 4, wherein the compounds of formula (I) are selected from the group consisting of:
(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;
(1-{2-[5-(N-Hydroxycarbamimidoyl)-1-oxo-1,3-dihydro-isoindol-2-yl]-acetyl}-piperidin-4-yloxy)-acetic acid ethyl ester;
(1-{3-[5-(N-Hydroxycarbamimidoyl)-1-oxo-1,3-dihydro-isoindol-2-yl]-propionyl}-piperidin-4-yloxy)-acetic acid ethyl ester;
(1-{2-[5-(5-Methyl-isoxazol-3-yl)-1-oxo-1,3-dihydro-isoindol-2-yl]-acetyl}-piperidin-4-yloxy)-acetic acid ethyl ester;
(1-{2-[5-Carbamimidoyl-1-oxo-1,3-dihydro-isoindol-2-yl]-acetyl}-piperidin-4-yloxy)-acetic acid ethyl ester;
(1-{2-[5-(tert-Butoxycarbonylamino-imino-methyl)-1-oxo-1,3-dihydro-isoindol-2-yl]-acetyl}-piperidin-4-yloxy)-acetic acid ethyl ester; and
(1-{2-[5-Carbamimidoyl-1-oxo-1,3-dihydro-isoindol-2-yl]-acetyl}-piperidin-4-yloxy)-acetic acid.

8. A method for the treatment of cardiovascular and cerebrovascular thromboembolic diseases in a subject in need thereof, which comprises administering to the subject a therapeutically effective amount of the compound of formula (I); or a stereoisomer, a tautomer or a pharmaceutically acceptable salt thereof;

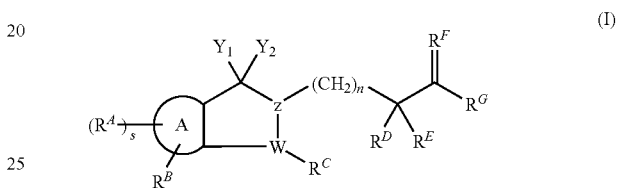

(I)

wherein
ring A is phenyl;
$R^A$ is a group of formula (3):

(3)

wherein p is 0;
s is 1;
$R^1$ is selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle;
$R^3$ and $R^4$ are independently selected from: H, alkyl, partially or fully fluorinated alkyl, alkenyl, alkynyl, —C(=O)OR$^5$, cycloalkyl, cycloalkylalkyl, aryl, arylalkyl, heterocycle, —OR$^5$, —SR$^5$, —NR$^5$R$^6$, —S(=O)$_2$NR$^5$R$^6$, —S(=O)$_2$R$^5$, —C(=O)R$^5$, —C(=O)NR$^5$R$^6$, —C(=O)OR$^5$, —C(=O)SR$^5$, —OC(=O)R$^5$, —OC(=O)OR$^5$, —OC(=O)NR$^5$R$^6$, —OS(=O)$_2$R$^5$, —S(C=O)NR$^5$ and —OS(=O)$_2$NR$^5$R$^6$, or R$^3$ and R$^1$ or R$^4$, together with the respective nitrogen atoms to which they are attached, form an unsubstituted or substituted 5-, 6- or 7-membered partially saturated or aromatic heterocycle, optionally having one or more additional heteroatoms selected from: N, O and S, wherein the substituents are selected from: hydroxy, halogen, alkyl, alkoxy, alkenyl, alkynyl, oxo, carboxy and —C(=O)OR$^5$;
$R^5$ and $R^6$ are independently selected from: H, alkyl, alkenyl, alkynyl, cycloalkyl, cycloalkylalkyl, aryl, arylalkyl and heterocycle, wherein each of said alkyl, alkenyl, alkynyl, cycloalkyl and cycloalkylalkyl group optionally contains at least one hetero atom selected from: N, S and O anywhere in the chain, including the terminal position;

137

$R^B$ is H;
$Y^1$ and $Y^2$, together, are selected from: =O and =S;
Z is N;
W is CH;
$R^C$ is H;
n is 0, 1, 2 or 3;
$R^D$ and $R^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy,
—C(=O)OR$^5$, —OR$^{17}$, —SR$^{17}$, —NR$^{17}$R$^{18}$, —NHC(=O)R$^{17}$, —NHC(=O)OR$^{17}$, —OC(=O)R$^{17}$, —SC(=O)R$^{17}$, —OS(=O)$_2$R$^{17}$ and —NHS(=O)$_2$R$^{17}$;
$R^{17}$ and $R^{18}$ have the same meaning as $R^5$ and $R^6$, defined above;
$R^F$ is selected from: O, S and N(OR$^{19}$);
$R^{19}$ has the same meaning as $R^5$, defined above;
$R^G$ is selected from: aryl, heteroaryl, and partially or fully saturated heterocycle, where said aryl, heteroaryl and heterocycle are substituted by one or more groups of the formula (5):

and optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$ NR$^{21}$R$^{22}$,
—OC(=O)OR$^{21}$, —OC(=O)SR$^{21}$, —OC(=O)NR$^{21}$R$^{22}$, —SR$^{21}$, —S(=O)R$^{21}$, —NO$_2$,
—NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$ and —S(=O)$_2$OR$^{21}$;
$R^{21}$ has the same meaning as $R^1$, defined above, and $R^{22}$ is selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle:
T is selected from: —CH$_2$, O, S and NH;
q is 0, 1, 2 or 3;
$R^{23}$ and $R^{24}$ are independently selected from: H, alkyl alkenyl, alkynyl, cycloalkyl, cycloalkylalkyl, aryl, arylalkyl, heterocycle and C(=O)R$^{25}$, wherein said alkyl and alkenyl optionally contain at least one hetero atom selected from: O, S and N, in any position of the alkyl or alkenyl chain, and said alkyl and alkenyl are unsubstituted or substituted with at least one group selected from: —OR$^1$, —OC(=O)R$^1$, —OS(=O)$_2$R$^1$, —S(=O)$_2$NR$^1$R$^2$, —OC(=O)OR$^1$, —OC(=O)SR$^1$, —OC(=O)NR$^1$R$^2$, —SR$^1$, —S(=O)R$^1$, —SC(=O)H, —SC(=O)OR$^1$, —NR$^1$(OR$^2$), —NR$^1$R$^2$, —NR$^1$C(=O)R$^2$, —N(R$^1$)C(=O)OR$^2$, —NR$^1$S(=O)$_2$R$^2$, C(=O)OR$^1$, —S(=O)$_2$R$^1$ and —S(=O)$_2$OR$^1$;
$R^{25}$ is selected from: OR$^5$, SR$^5$, —OCR$^3$R$^4$ and —NR$^5$R$^6$, wherein $R^3$, $R^4$, $R^5$ and $R^6$ are as defined above and wherein optionally, $R^3$ and $R^4$, together with the carbon to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy and —C(=O)OR$^5$; and the group NR$^5$R$^6$ is, optionally, a heterocycle containing at least one additional heteroatom selected from: O, S, and N.

138

9. The method according to claim 8, wherein in the compounds of formula (I)
$R^G$ is selected from: phenyl, piperidinyl and piperazinyl, and said phenyl, piperidinyl and piperazinyl are substituted by one or more groups of the formula (5):

and optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$ NR$^{21}$R$^{22}$,
—OC(=O)OR$^{21}$, —OC(=O)SR$^{21}$, —OC(=O)NR$^{21}$R$^{22}$, —SR$^{21}$, —S(=O)R$^{21}$, —NO$_2$,
—NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$ and —S(=O)$_2$OR$^{21}$; and $R^{21}$ and $R^{22}$ are as defined in claim 8.

10. The method according to claim 8, wherein in the compounds of formula (I),
$R_1$ is hydrogen;
$R_3$ and $R_4$ are independently selected from: H, OH, —C(O)OH and —C(O)Oalkyl;
$R^B$=$R^C$=$R^D$=$R^E$=hydrogen;
$Y^1$ and $Y^2$, together are =O;
n is the integer 0 or 1;
$R^G$ is phenyl, substituted with one or more of the group of formula (5):

wherein $R^{23}$ is H and $R^{24}$ is H, and, optionally, the compound is further substituted with one or more of the groups selected from: hydroxy, halogen, alkyl, alkoxy, alkenyl, alkynyl, oxo, carboxy, —C(=O)OR$^5$, SR$^{21}$, S(=O)$_2$R$^{21}$ and —N(R$^{21}$)—C(O)CH$_3$, —CH$_2$C(O)R$^{25}$;
and $R^{25}$ is selected from: OR$^5$, OCR$^3$R$^4$ and NR$^5$R$^6$, wherein $R^3$ and $R^4$, together with the carbon to which they are attached form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy, —C(=O)OR$^5$; and
$R^5$, $R^6$ and $R^{21}$ are independently selected from: H, alkyl and phenyl.

11. The method according to claim 8, wherein in the compounds of formula (I),
$R_1$ is hydrogen;
$R_3$ and $R_4$ are independently selected from: H, OH, —C(O)OH and —C(O)Oalkyl;
$R^B$=$R^C$=$R^D$=$R^E$=hydrogen;
$Y^1$ and $Y^2$, together are =O;
n is the integer 0 or 1;
$R^G$ is selected from: piperidinyl and piperazinyl, wherein said piperidinyl and piperazinyl are substituted with one or more of the group of formula (5):

wherein $R^{23}$ is H and $R^{24}$ is H and, optionally, further substituted with one or more groups selected from: hydroxy, halogen, alkyl, alkoxy, alkenyl, alkynyl, oxo, carboxy and —C(=O)OR$^5$;
and
$R^{25}$ is OR$^5$, wherein $R^5$ is selected from: H, alkyl and phenyl.

12. The method according to claim 8, wherein the compounds of formula (I) are selected from the group consisting of:

(4-{2-[5-Carbamimidoyl-1-oxo-1,3-dihydro-isoindol-2-yl]acetyl}-phenoxy)-acetic acid methyl ester;
(4-{2-[5-(N-Hydroxycarbamimidoyl)-1-oxo-1,3-dihydro-isoindol-2-yl]-acetyl}-phenoxy)-acetic acid methyl ester;
(4-{2-[5-Carbamimidoyl-1-oxo-1,3-dihydro-isoindol-2-yl]-acetyl}-phenoxy)-acetic acid ethyl ester;
(4-{2-[5-(N-Hydroxycarbamimidoyl)-1-oxo-1,3-dihydro-isoindol-2-yl]-acetyl}-phenoxy)-acetic acid ethyl ester;
4-(2-{5-Carbamimidoyl-1-oxo-1,3-dihydro-isoindol-2-yl}-acetyl]-phenoxy)-acetic acid isopropyl ester;
(4-{2-[5-(Imino-methoxycarbonylamino-methyl)-1-oxo-1,3-dihydro-isoindol-2-yl]-acetyl}-phenoxy)-acetic acid isopropyl ester;
(4-{2-[5-(Imino-isobutoxycarbonylamino-methyl)-1-oxo-1,3-dihydro-isoindol-2-yl]-acetyl}-phenoxy)-acetic acid isopropyl ester;
(4-{2-[5-(Benzyloxycarbonylamino-imino-methyl)-1-oxo-1,3-dihydro-isoindol-2-yl]-acetyl}-phenoxy)-acetic acid isopropyl ester;
(4-{2-[5-(N-Hydroxycarbamimidoyl)-1-oxo-1,3-dihydro-isoindol-2-yl]-acetyl}-phenoxy)-acetic acid isopropyl ester;
(4-{2-[5-Carbamimidoyl-1-oxo-1,3-dihydro-isoindol-2-yl]-acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;
(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methylbutyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxy-imino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;
2-(4-{2-[5-Carbamimidoyl-1-oxo-1,3-dihydro-isoindol-2-yl]-acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-acetyl}-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;
(4-{2-[5-(N-Hydroxycarbamimidoyl)-1-oxo-1,3-dihydro-isoindol-2-yl]-acetyl}-3-methoxy-phenoxy)-acetic acid ethyl ester;
(4-{2-[5-(N-Hydroxycarbamimidoyl)-1-oxo-1,3-dihydro-isoindol-2-yl]-acetyl}-3-propoxy-phenoxy)-acetic acid ethyl ester;

(4-{2-[5-Carbamimidoyl-1-oxo-1,3-dihydro-isoindol-2-yl]-acetyl}-3-ethoxy carbonylmethoxy-phenoxy)-acetic acid ethyl ester;
(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;
(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;
(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;
(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid benzyl ester;
(4-{2-[5-Carbamimidoyl-1-oxo-1,3-dihydro-isoindol-2-yl]-acetyl}-3-hydroxy-2-propyl-phenoxy)-acetic acid;
(4-Hydroxy-3-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;
(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;
(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;
(1-{2-[5-(N-Hydroxycarbamimidoyl)-1-oxo-1,3-dihydro-isoindol-2-yl]-acetyl}-piperidin-4-yloxy)-acetic acid ethyl ester;
(1-{3-[5-(N-Hydroxycarbamimidoyl)-1-oxo-1,3-dihydro-isoindol-2-yl]-propionyl}-piperidin-4-yloxy)-acetic acid ethyl ester;
(1-{2-[5-(5-Methyl-isoxazol-3-yl)-1-oxo-1,3-dihydro-isoindol-2-yl]-acetyl}-piperidin-4-yloxy)-acetic acid ethyl ester;
(1-{2-[5-Carbamimidoyl-1-oxo-1,3-dihydro-isoindol-2-yl]-acetyl}-piperidin-4-yloxy)-acetic acid ethyl ester;
(1-{2-[5-(tert-Butoxycarbonylamino-imino-methyl)-1-oxo-1,3-dihydro-isoindol-2-yl]-acetyl}-piperidin-4-yloxy)-acetic acid ethyl ester;
(1-{2-[5-Carbamimidoyl-1-oxo-1,3-dihydro-isoindol-2-yl]-acetyl}-piperidin-4-yloxy)-acetic acid;
(3-Ethoxy-4-{2-[5-(N-hydroxycarbamimidoyl)-1-oxo-1,3-dihydro-isoindol-2-yl]-acetyl}-phenoxy)-acetic acid ethyl ester;
(4-[2-(5-carbamimidoyl-1-oxo-1,3-dihydro-isoindol-2-yl)-acetyl]-3-ethoxy-phenoxy}-acetic acid ethyl ester;
(4-{2-[5-Carbamimdoyl-1-oxo-1,3-dihydro-isoindol-2-yl]-acetyl}-3-ethoxy-phenoxy)-acetic acid;
(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester;
(4-{2-[5-(Acetylamino-imino-methyl)-1-oxo-1,3-dihydro-isoindol-2-yl]-acetyl}-3-hydroxy-phenoxy)-acetic acid ethyl ester;
(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid; and
(3-Allyloxy-4-{2-[5-(N-hydroxycarbamimidoyl)-1-oxo-1,3-dihydro-isoindol-2-yl]-acetyl}-phenoxy)-acetic acid ethyl ester.

13. The method according to claim 10, wherein the compounds of formula (I) are selected from the group consisting of:
(4-{2-[5-Carbamimidoyl-1-oxo-1,3-dihydro-isoindol-2-yl]-acetyl}-phenoxy)-acetic acid methyl ester;
(4-{2-[5-(N-Hydroxycarbamimidoyl)-1-oxo-1,3-dihydro-isoindol-2-yl]-acetyl}-phenoxy)-acetic acid methyl ester;
(4-{2-[5-Carbamimidoyl-1-oxo-1,3-dihydro-isoindol-2-yl]-acetyl}-phenoxy)-acetic acid ethyl ester;
(4-{2-[5-(N-Hydroxycarbamimidoyl)-1-oxo-1,3-dihydro-isoindol-2-yl]-acetyl}-phenoxy)-acetic acid ethyl ester;
4-(2-{5-Carbamimidoyl-1-oxo-1,3-dihydro-isoindol-2-yl}-acetyl]-phenoxy)-acetic acid isopropyl ester;
(4-{2-[5-(Imino-methoxycarbonylamino-methyl)-1-oxo-1,3-dihydro-isoindol-2-yl]-acetyl}-phenoxy)-acetic acid isopropyl ester;
(4-{2-[5-(Imino-isobutoxycarbonylamino-methyl)-1-oxo-1,3-dihydro-isoindol-2-yl]-acetyl}-phenoxy)-acetic acid isopropyl ester;
(4-{2-[5-(Benzyloxycarbonylamino-imino-methyl)-1-oxo-1,3-dihydro-isoindol-2-yl]-acetyl}-phenoxy)-acetic acid isopropyl ester;
(4-{2-[5-(N-Hydroxycarbamimidoyl)-1-oxo-1,3-dihydro-isoindol-2-yl]-acetyl}-phenoxy)-acetic acid isopropyl ester;
(4-{2-[5-Carbamimidoyl-1-oxo-1,3-dihydro-isoindol-2-yl]-acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;

(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxyimino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;
2-(4-{2-[5-Carbamimidoyl-1-oxo-1,3-dihydro-isoindol-2-yl]-acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;
(4-{2-[5-(N-Hydroxycarbamimidoyl)-1-oxo-1,3-dihydro-isoindol-2-yl]-acetyl}-3-methoxy-phenoxy)-acetic acid ethyl ester;
(4-{2-[5-(N-Hydroxycarbamimidoyl)-1-oxo-1,3-dihydro-isoindol-2-yl]-acetyl}-3-propoxy-phenoxy)-acetic acid ethyl ester;
(4-{2-[5-Carbamimidoyl-1-oxo-1,3-dihydro-isoindol-2-yl]-acetyl}-3-ethoxy carbonylmethoxy-phenoxy)-acetic acid ethyl ester;
(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;
(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;
(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;

(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid benzyl ester;
(4-{2-[5-Carbamimidoyl-1-oxo-1,3-dihydro-isoindol-2-yl]-acetyl}-3-hydroxy-2-propyl-phenoxy)-acetic acid;
(4-Hydroxy-3-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;
(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;
(3-Ethoxy-4-{2-[5-(N-hydroxycarbamimidoyl)-1-oxo-1,3-dihydro-isoindol-2-yl]-acetyl}-phenoxy)-acetic acid ethyl ester;
(4-[2-(5-carbamimidoyl-1-oxo-1,3-dihydro-isoindol-2-yl)-acetyl]-3-ethoxy-phenoxy}-acetic acid ethyl ester;
(4-{2-[5-Carbamimdoyl-1-oxo-1,3-dihydro-isoindol-2-yl]-acetyl}-3-ethoxy-phenoxy)-acetic acid;
(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester;
(4-{2-[5-(Acetylamino-imino-methyl)-1-oxo-1,3-dihydro-isoindol-2-yl]-acetyl}-3-hydroxy-phenoxy)-acetic acid ethyl ester;
(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid; and
(3-Allyloxy-4-{2-[5-(N-hydroxycarbamimidoyl)-1-oxo-1,3-dihydro-isoindol-2-yl]acetyl}-phenoxy)-acetic acid ethyl ester.

14. The method according to claim 11, wherein the compounds of formula (I) are selected from the group consisting of:
(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;
(1-{2-[5-(N-Hydroxycarbamimidoyl)-1-oxo-1,3-dihydro-isoindol-2-yl]-acetyl}-piperidin-4-yloxy)-acetic acid ethyl ester;
(1-{3-[5-(N-Hydroxycarbamimidoyl)-1-oxo-1,3-dihydro-isoindol-2-yl]-propionyl}-piperidin-4-yloxy)-acetic acid ethyl ester;
(1-{2-[5-(5-Methyl-isoxazol-3-yl)-1-oxo-1,3-dihydro-isoindol-2-yl]-acetyl}-piperidin-4-yloxy)-acetic acid ethyl ester;
(1-{2-[5-Carbamimidoyl-1-oxo-1,3-dihydro-isoindol-2-yl]-acetyl}-piperidin-4-yloxy)-acetic acid ethyl ester;
(1-{2-[5-(tert-Butoxycarbonylamino-imino-methyl)-1-oxo-1,3-dihydro-isoindol-2-yl]-acetyl}-piperidin-4-yloxy)-acetic acid ethyl ester; and
(1-{2-[5-Carbamimidoyl-1-oxo-1,3-dihydro-isoindol-2-yl]-acetyl}-piperidin-4-yloxy)-acetic acid.

15. The method according to claim 8, wherein the cardiovascular and cerebrovascular thromboembolic diseases include: arterial thromboembolism, cerebral thromboembolism, cerebral arterial thrombosis, coronary thrombosis, deep vein thrombosis, diabetes-related thromboembolic disorders, sudden ischemic emergencies, myocardial infarction, pulmonary thromboembolisms, stroke, thrombophlebitis, transient ischemic attack, unstable angina and venous thrombosis or kidney thromboembolism.

16. A method of inhibiting aggregation of blood platelet in a subject in need thereof, which comprises administering to the subject a therapeutically effective amount of compound of general formula (I); or a stereoisomer, a tautomer or a pharmaceutically acceptable salt thereof;

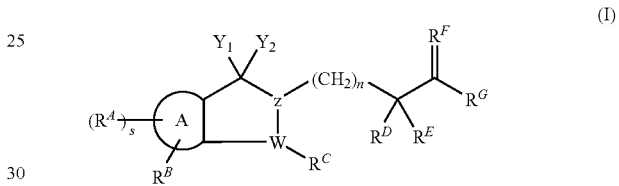

wherein
ring A is phenyl;
$R^A$ is a group of formula (3):

wherein p is 0;
s is 1;
$R^1$ is selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle;
$R^3$ and $R^4$ are independently selected from: H, alkyl, partially or fully fluorinated alkyl, alkenyl, alkynyl, —C(=O)OR$^5$, cycloalkyl, cycloalkylalkyl, aryl, arylalkyl, heterocycle, —OR$^5$, —SR$^5$, —NR$^5$R$^6$, —S(=O)$_2$NR$^5$R$^6$, —S(=O)$_2$R$^5$, —C(=O)R$^5$, —C(=O)NR$^5$R$^6$, —C(=O)OR$^5$, —C(=O)SR$^5$, —OC(=O)R$^5$, —OC(=O)OR$^5$, —OC(=O)NR$^5$R$^6$, —OS(=O)$_2$R$^5$, —S(C=O)NR$^5$ and —OS(=O)$_2$NR$^5$R$^6$, or $R^3$ and $R^1$ or $R^4$, together with the respective nitrogen atoms to which they are attached, form an unsubstituted or substituted 5-, 6- or 7-membered partially saturated or aromatic heterocycle, optionally having one or more additional heteroatoms selected from: N, O and S, wherein the substituents are selected from: hydroxy, halogen, alkyl, alkoxy, alkenyl, alkynyl, oxo, carboxy and —C(=O)OR$^5$;
$R^5$ and $R^6$ are independently selected from: H, alkyl, alkenyl, alkynyl, cycloalkyl, cycloalkylalkyl, aryl, arylalkyl and heterocycle, wherein each of said alkyl, alkenyl, alkynyl, cycloalkyl and cycloalkylalkyl group optionally contains at least one hetero atom selected from: N, S and O anywhere in the chain, including the terminal position;

$R^B$ is H;

$Y^1$ and $Y^2$, together, are selected from: =O and =S;

Z is N;

W is CH;

$R^C$ is H;

n is 0, 1, 2 or 3;

$R^D$ and $R^E$ are independently selected from: H and an unsubstituted or substituted group selected from: alkyl, alkenyl, alkynyl, cycloalkyl, cycloalkylalkyl, aryl, arylalkyl and heterocycle, wherein the substituents are selected from: hydroxy, halogen, alkyl, alkenyl, alkynyl, oxo, carboxy, —C(=O)OR$^5$, —OR$^{17}$, —SR$^{17}$, —NR$^{17}$R$^{18}$, —NHC(=O)R$^{17}$, —NHC(=O)OR$^{17}$, —OC(=O)R$^{17}$, —SC(=O)R$^{17}$, —OS(=O)$_2$R$^{17}$ and —NHS(=O)$_2$R$^{17}$;

$R^{17}$ and $R^{18}$ have the same meaning as $R^5$ and $R^6$, defined above;

$R^F$ is selected from: O, S and N(OR$^{19}$);

$R^{19}$ has the same meaning as $R^5$, defined above;

$R^G$ is selected from: aryl, heteroaryl, and partially or fully saturated heterocycle, where said aryl, heteroaryl and heterocycle are substituted by one or more groups of the formula (5):

T-(CH$_2$)$_q$—CR$^{23}$R$^{24}$—COR$^{25}$      (5)

and optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$ NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —NO$_2$, —NR$^{21}$(OR$^{22}$), —NR$^{21}$R$^{22}$, —NR$^{21}$C(=O)R$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$ and —S(=O)$_2$OR$^{21}$;

$R^{21}$ has the same meaning as $R^1$, defined above, and $R^{22}$ is selected from: H, hydroxy, alkyl, partially or fully fluorinated alkyl, alkoxy, alkenyl, alkynyl, carboxy, —C(=O)OR$^5$, cycloalkyl, cycloalkylalkyl, aryl, arylalkyl and heterocycle:

T is selected from: —CH$_2$, O, S and NH;

q is 0, 1, 2 or 3;

$R^{23}$ and $R^{24}$ are independently selected from: H, alkyl alkenyl, alkynyl, cycloalkyl, cycloalkylalkyl, aryl, arylalkyl, heterocycle and C(=O)R$^{25}$, wherein said alkyl and alkenyl optionally contain at least one hetero atom selected from: O, S and N, in any position of the alkyl or alkenyl chain, and said alkyl and alkenyl are unsubstituted or substituted with at least one group selected from: —OR$^1$, —OC(=O)R$^1$, —OS(=O)$_2$R$^1$, —S(=O)$_2$NR$^1$R$^2$, —OC(=O)OR$^1$, —OC(=O)SR$^1$, —OC(=O)NR$^1$R$^2$, —SR$^1$, —S(=O)R$^1$, —SC(=O)H, —SC(=O)OR$^1$, —NR$^1$(OR$^2$), —NR$^1$R$^2$, —NR$^1$C(=O)R$^2$, —N(R$^1$)C(=O)OR$^2$, —NR$^1$S(=O)$_2$R$^2$, C(=O)OR$^1$, —S(=O)$_2$R$^1$ and —S(=O)$_2$OR$^1$;

$R^{25}$ is selected from: OR$^5$, SR$^5$, —OCR$^3$R$^4$ and —NR$^5$R$^6$, wherein $R^3$, $R^4$, $R^5$ and $R^6$ are as defined above and wherein optionally, $R^3$ and $R^4$, together with the carbon to which they are attached, form an unsubstituted or substituted 5-, 6- or 7-membered saturated, partially saturated or aromatic heterocycle having one or more heteroatoms selected from: N, O and S, wherein the substituents are selected from: hydroxy, halogen, alkyl, alkoxy, alkenyl, alkynyl, oxo, carboxy and —C(=O)OR$^5$; and the group NR$^5$R$^6$ is, optionally, a heterocycle containing at least one additional heteroatom selected from: O, S, and N.

17. The method according to claim 16, wherein in the compounds of formula (I);

$R^G$ is selected from: phenyl, piperidinyl and piperazinyl, and said phenyl, piperidinyl and piperazinyl are substituted by one or more groups of the formula (5):

T-(CH$_2$)$_q$—CR$^{23}$R$^{24}$—COR$^{25}$      (5)

and optionally, further substituted by one or more groups selected from: —R$^5$, halogen, —CN, —SCN, —CNO, —OR$^{21}$, —OC(=O)R$^{21}$, —OS(=O)$_2$R$^{21}$, —OS(=O)$_2$ NR$^{21}$R$^{22}$, —OC(=O)OR$^{21}$, —OC(=O)SR$^{21}$, —OC(=O)NR$^{21}$R$^{22}$, —SR$^{21}$, —S(=O)R$^{21}$, —NO$_2$, —NR$^{21}$(OR$^{22}$), —NR$^{21}$R$^{22}$, —NR$^{21}$C(=O)OR$^{22}$, —N(R$^{21}$)C(=O)OR$^{22}$, —N[S(=O)$_2$R$^{21}$]R$^{23}$, C(=O)OR$^{21}$, —S(=O)$_2$R$^{21}$, and —S(=O)$_2$OR$^{21}$; and R$^{21}$ and R$^{22}$ are as defined in claim 16.

18. The method according to claim 16, wherein in the compounds of formula (I);

$R_1$ is hydrogen;

$R_3$ and $R_4$ are independently selected from: H, OH, —C(O)OH and —C(O)Oalkyl;

$R^B$=$R^C$=$R^D$=$R^E$=hydrogen;

$Y^1$ and $Y^2$, together are =O;

n is the integer 0 or 1;

$R^G$ is phenyl, substituted with one or more of the group of formula (5):

T-(CH$_2$)$_q$—CR$^{23}$R$^{24}$—COR$^{25}$      (5)

wherein $R^{23}$ is H and $R^{24}$ is H, and, optionally, the compound is further substituted with one or more of the groups selected from: hydroxy, halogen, alkyl, alkoxy, alkenyl, alkynyl, oxo, carboxy, —C(=O)OR$^5$, SR$^{21}$, S(=O)$_2$R$^{21}$ and —N(R$^{21}$)—C(O)CH$_3$, —CH$_2$C(O)R$^{25}$;

and R$^{25}$ is selected from: OR$^5$, OCR$^3$R$^4$ and NR$^5$R$^6$, wherein $R^3$ and $R^4$, together with the carbon to which they are attached form an unsubstituted or substituted 5-, 6- or 7-membered saturated, partially saturated or aromatic heterocycle having one or more heteroatoms selected from: N, O and S, wherein the substituents are selected from:

hydroxy, halogen, alkyl, alkoxy, alkenyl, alkynyl, oxo, carboxy, —C(=O)OR$^5$; and $R^5$, $R^6$ and $R^{21}$ are independently selected from: H, alkyl and phenyl.

19. The method according to claim 16, wherein in the compounds of formula (I)

$R_1$ is hydrogen;

$R_3$ and $R_4$ are independently selected from: H, OH, —C(O)OH and —C(O)Oalkyl;

$R^B$=$R^C$=$R^D$=$R^E$=hydrogen;

$Y^1$ and $Y^2$, together are =O;

n is the integer 0 or 1;

$R^G$ is selected from: piperidinyl and piperazinyl, wherein said piperidinyl and piperazinyl are substituted with one or more of the group of formula (5):

T-(CH$_2$)$_q$—CR$^{23}$R$^{24}$—COR$^{25}$      (5)

wherein $R^{23}$ is H and $R^{24}$ is H and, optionally, further substituted with one or more groups selected from: hydroxy, halogen, alkyl, alkoxy, alkenyl, alkynyl, oxo, carboxy and —C(=O)OR$^5$; and $R^{25}$ is $OR^5$, wherein $R^5$ is selected from: H, alkyl and phenyl.

20. The method according to claim 16, wherein the compounds of formula (I) are selected from the group consisting of:

(4-{2-[5-Carbamimidoyl-1-oxo-1,3-dihydro-isoindol-2-yl]-acetyl}-phenoxy)-acetic acid methyl ester;
(4-{2-[5-(N-Hydroxycarbamimidoyl)-1-oxo-1,3-dihydro-isoindol-2-yl]-acetyl}-phenoxy)-acetic acid methyl ester;
(4-{2-[5-Carbamimidoyl-1-oxo-1,3-dihydro-isoindol-2-yl]-acetyl}-phenoxy)-acetic acid ethyl ester;
(4-{2-[5-(N-Hydroxycarbamimidoyl)-1-oxo-1,3-dihydro-isoindol-2-yl]-acetyl}-phenoxy)-acetic acid ethyl ester;
4-(2-{5-Carbamimidoyl-1-oxo-1,3-dihydro-isoindol-2-yl}-acetyl]-phenoxy)-acetic acid isopropyl ester;
(4-{2-[5-(Imino-methoxycarbonylamino-methyl)-1-oxo-1,3-dihydro-isoindol-2-yl]-acetyl}-phenoxy)-acetic acid isopropyl ester;
(4-{2-[5-(Imino-isobutoxycarbonylamino-methyl)-1-oxo-1,3-dihydro-isoindol-2-yl]-acetyl}-phenoxy)-acetic acid isopropyl ester;
(4-{2-[5-(Benzyloxycarbonylamino-imino-methyl)-1-oxo-1,3-dihydro-isoindol-2-yl]-acetyl}-phenoxy)-acetic acid isopropyl ester;
(4-{2-[5-(N-Hydroxycarbamimidoyl)-1-oxo-1,3-dihydro-isoindol-2-yl]-acetyl}-phenoxy)-acetic acid isopropyl ester;
(4-{2-[5-Carbamimidoyl-1-oxo-1,3-dihydro-isoindol-2-yl]acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;
(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxy-imino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;
2-(4-{2-[5-Carbamimidoyl-1-oxo-1,3-dihydro-isoindol-2-yl]-acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-acetyl}-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;
(4-{2-[5-(N-Hydroxycarbamimidoyl)-1-oxo-1,3-dihydro-isoindol-2-yl]-acetyl}-3-methoxy-phenoxy)-acetic acid ethyl ester;
(4-{2-[5-(N-Hydroxycarbamimidoyl)-1-oxo-1,3-dihydro-isoindol-2-yl]-acetyl}-3-propoxy-phenoxy)-acetic acid ethyl ester;

(4-{2-[5-Carbamimidoyl-1-oxo-1,3-dihydro-isoindol-2-yl]-acetyl}-3-ethoxy carbonylmethoxy-phenoxy)-acetic acid ethyl ester;
(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;
(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;
(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;
(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid benzyl ester;
(4-{2-[5-Carbamimidoyl-1-oxo-1,3-dihydro-isoindol-2-yl]-acetyl}-3-hydroxy-2-propyl-phenoxy)-acetic acid;
(4-Hydroxy-3-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;
(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;
(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;
(1-{2-[5-(N-Hydroxycarbamimidoyl)-1-oxo-1,3-dihydro-isoindol-2-yl]-acetyl}-piperidin-4-yloxy)-acetic acid ethyl ester;
(1-{3-[5-(N-Hydroxycarbamimidoyl)-1-oxo-1,3-dihydro-isoindol-2-yl]-propionyl}-piperidin-4-yloxy)-acetic acid ethyl ester;
(1-{2-[5-(5-Methyl-isoxazol-3-yl)-1-oxo-1,3-dihydro-isoindol-2-yl]-acetyl}-piperidin-4-yloxy)-acetic acid ethyl ester;
(1-{2-[5-Carbamimidoyl-1-oxo-1,3-dihydro-isoindol-2-yl]-acetyl}-piperidin-4-yloxy)-acetic acid ethyl ester;
(1-{2-[5-(tert-Butoxycarbonylamino-imino-methyl)-1-oxo-1,3-dihydro-isoindol-2-yl]-acetyl}-piperidin-4-yloxy)-acetic acid ethyl ester;
(1-{2-[5-Carbamimidoyl-1-oxo-1,3-dihydro-isoindol-2-yl]-acetyl}-piperidin-4-yloxy)-acetic acid;
(3-Ethoxy-4-{2-[5-(N-hydroxycarbamimidoyl)-1-oxo-1,3-dihydro-isoindol-2-yl]-acetyl}-phenoxy)-acetic acid ethyl ester;
(4-[2-(5-carbamimidoyl-1-oxo-1,3-dihydro-isoindol-2-yl)-acetyl]-3-ethoxy-phenoxy}-acetic acid ethyl ester;
(4-{2-[5-Carbamimdoyl-1-oxo-1,3-dihydro-isoindol-2-yl]-acetyl}-3-ethoxy-phenoxy)-acetic acid;
(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester;
(4-{2-[5-(Acetylamino-imino-methyl)-1-oxo-1,3-dihydro-isoindol-2-yl]-acetyl}-3-hydroxy-phenoxy)-acetic acid ethyl ester;
(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-2-propyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-propyl-phenoxy)-acetic acid; and
(3-Allyloxy-4-{2-[5-(N-hydroxycarbamimidoyl)-1-oxo-1,3-dihydro-isoindol-2-yl]acetyl}-phenoxy)-acetic acid ethyl ester.

21. The method according to claim 18, wherein the compounds of formula (I) are selected from the group consisting of:
(4-{2-[5-Carbamimidoyl-1-oxo-1,3-dihydro-isoindol-2-yl]-acetyl}-phenoxy)-acetic acid methyl ester;
(4-{2-[5-(N-Hydroxycarbamimidoyl)-1-oxo-1,3-dihydro-isoindol-2-yl]-acetyl}-phenoxy)-acetic acid methyl ester;
(4-{2-[5-Carbamimidoyl-1-oxo-1,3-dihydro-isoindol-2-yl]-acetyl}-phenoxy)-acetic acid ethyl ester;
(4-{2-[5-(N-Hydroxycarbamimidoyl)-1-oxo-1,3-dihydro-isoindol-2-yl]-acetyl}-phenoxy)-acetic acid ethyl ester;
4-(2-{5-Carbamimidoyl-1-oxo-1,3-dihydro-isoindol-2-yl}-acetyl]-phenoxy)-acetic acid isopropyl ester;
(4-{2-[5-(Imino-methoxycarbonylamino-methyl)-1-oxo-1,3-dihydro-isoindol-2-yl]-acetyl}-phenoxy)-acetic acid isopropyl ester;
(4-{2-[5-(Imino-isobutoxycarbonylamino-methyl)-1-oxo-1,3-dihydro-isoindol-2-yl]-acetyl}-phenoxy)-acetic acid isopropyl ester;
(4-{2-[5-(Benzyloxycarbonylamino-imino-methyl)-1-oxo-1,3-dihydro-isoindol-2-yl]-acetyl}-phenoxy)-acetic acid isopropyl ester;
(4-{2-[5-(N-Hydroxycarbamimidoyl)-1-oxo-1,3-dihydro-isoindol-2-yl]-acetyl}-phenoxy)-acetic acid isopropyl ester;
(4-{2-[5-Carbamimidoyl-1-oxo-1,3-dihydro-isoindol-2-yl]-acetyl}-phenoxy)-acetic acid isobutyl ester;
(4-{2-[5-(Imino-methoxycarbonylamino-methyl)-1-oxo-1,3-dihydro-isoindol-2-yl]-acetyl}-phenoxy)-acetic acid isobutyl ester;

(4-{2-[5-(Imino-isobutoxycarbonylamino-methyl)-1-oxo-1,3-dihydro-isoindol-2-yl]-acetyl}-phenoxy)-acetic acid isobutyl ester;
(4-{2-[5-(Benzyloxycarbonylamino-imino-methyl)-1-oxo-1,3-dihydro-isoindol-2-yl]-acetyl}-phenoxy)-acetic acid isobutyl ester;
(4-{2-[5-(Imino-methanesulfonylamino-methyl)-1-oxo-1,3-dihydro-isoindol-2-yl]-acetyl}-phenoxy)-acetic acid isobutyl ester;
(4-{2-[5-(N-Hydroxycarbamimidoyl)-1-oxo-1,3-dihydro-isoindol-2-yl]-acetyl}-phenoxy)-acetic acid isobutyl ester;
(4-{2-[5-Carbamimidoyl-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-phenoxy)-acetic acid;
(4-{2-[5-(Imino-methoxycarbonylamino-methyl)-1-oxo-1,3-dihydro-isoindol-2-yl]-acetyl}-phenoxy)-acetic acid benzyl ester;
(4-{2-[5-(Imino-isobutoxycarbonylamino-methyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-2-ethoxy carbonyl methoxy-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-acetyl}-phenoxy)-acetic acid ethyl ester;
(2-Ethoxycarbonylmethoxy-4-{2-[5-(imino-{3-methyl-butyrylamino}-methyl)-1-oxo-1,3-dihydro-isoindol-2-yl]-acetyl}-phenoxy)-acetic acid ethyl ester;
(2-Ethoxycarbonylmethoxy-4-{2-[5-(N-hydroxycarbamimidoyl)-1-oxo-1,3-dihydro-isoindol-2-yl]-1-hydroxy-imino-ethyl}-phenoxy)-acetic acid ethyl ester;
(4-{2-[5-Carbamimidoyl-1-oxo-1,3-dihydro-isoindol-2-yl]-acetyl}-2-isobutoxy carbonyl methoxy-phenoxy)-acetic acid isobutyl ester;
2-(4-{2-[5-Carbamimidoyl-1-oxo-1,3-dihydro-isoindol-2-yl]acetyl}-phenoxy)-N,N-diethyl-acetamide;
4-(2-{4-[2-(5-Carbamimidoyl-1-oxo-1,3-dihydro-isoindol-2-yl)-acetyl]-phenoxy}-acetoxy)-piperidine-1-carboxylic acid benzyl ester;
4-Benzyloxycarbonylamino-2-(4-{2-[5-carbamimidoyl-1-oxo-1,3-dihydro-isoindol-2-yl]-acetyl}-phenoxy)-butyric acid ethyl ester;
4-Benzyloxycarbonylamino-2-(4-{2-[5-(N-hydroxycarbamimidoyl)-1-oxo-1,3-dihydro-isoindol-2-yl]-acetyl}-phenoxy)-butyric acid ethyl ester;
(4-{2-[5-(N-Hydroxycarbamimidoyl)-1-oxo-1,3-dihydro-isoindol-2-yl]-acetyl}-phenylsulfanyl)-acetic acid methyl ester;
(4-{2-[5-Carbamimidoyl-1-oxo-1,3-dihydro-isoindol-2-yl]-acetyl}-2-chloro-phenoxy)-acetic acid ethyl ester;
(2-Chloro-4-{2-[5-(imino-isobutoxycarbonylamino-methyl)-1-oxo-1,3-dihydro-isoindol-2-yl]-acetyl}-phenoxy)-acetic acid ethyl ester;
(2-Chloro-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethyl sulfanyl-phenoxy)-acetic acid ethyl ester;
(2-Ethylsulfanyl-4-{2-[5-(N-hydroxycarbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-2-ethane sulfonyl-phenoxy)-acetic acid ethyl ester;
(2-Ethanesulfonyl-4-{2-[5-(N-hydroxycarbamimidoyl)-1-oxo-1,3-dihydro-isoindol-2-yl]-acetyl}-phenoxy)-acetic acid ethyl ester;
(2,6-Bis-ethylsulfanyl-4-{2-[5-(N-hydroxycarbamimidoyl)-1-oxo-1,3-dihydro-isoindol-2-yl]-acetyl}-phenoxy)-acetic acid ethyl ester;
(2-Acetylamino-4-{2-[5-N-hydroxycarbamimidoyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(imino-isobutoxy carbonylamino-methyl)-1-oxo-1,3-dihydro-isoindol-2-yl]-acetyl}-phenoxy)-acetic acid ethyl ester;
(2-(Ethoxycarbonylmethyl-methanesulfonyl-amino)-4-{2-[5-(N-hydroxy carbamimidoyl)-1-oxo-1,3-dihydro-isoindol-2-yl]-acetyl}-phenoxy)-acetic acid ethyl ester;
(4-{2-[5-Carbamimidoyl-1-oxo-1,3-dihydro-isoindol-2-yl]-acetyl}-3-hydroxy-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-phenoxy)-acetic acid benzyl ester;
(4-{2-[5-Carbamimidoyl-1-oxo-1,3-dihydro-isoindol-2-yl]-acetyl}-3-hydroxy-phenoxy)-acetic acid;
(4-{2-[5-(N-Hydroxycarbamimidoyl)-1-oxo-1,3-dihydro-isoindol-2-yl]-acetyl}-3-methoxy-phenoxy)-acetic acid ethyl ester;
(4-{2-[5-(N-Hydroxycarbamimidoyl)-1-oxo-1,3-dihydro-isoindol-2-yl]-acetyl}-3-propoxy-phenoxy)-acetic acid ethyl ester;
(4-{2-[5-Carbamimidoyl-1-oxo-1,3-dihydro-isoindol-2-yl]-acetyl}-3-ethoxy carbonylmethoxy-phenoxy)-acetic acid ethyl ester;
(3-Ethoxycarbonylmethoxy-4-{2-[5-(N-hydroxycarbamimidoyl)-1-oxo-1,3-dihydro-isoindol-2-yl]-acetyl}-phenoxy)-acetic acid;
(2-Ethylsulfanyl-3-hydroxy-4-{2-[5-(N-hydroxycarbamimidoyl)-1-oxo-1,3-dihydro-isoindol-2-yl]-acetyl}-phenoxy)-acetic acid ethyl ester;
(2-Ethyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(5-Hydroxy-4-{2-[5-(N-hydroxycarbamimidoyl)-1-oxo-1,3-dihydro-isoindol-2-yl]-acetyl}-2-isopropyl-phenoxy)-acetic acid ethyl ester;
(2-tert-Butyl-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-5-hydroxy-4-{2-[5-(N-hydroxycarbamimidoyl)-1-oxo-1,3-dihydro-isoindol-2-yl]-acetyl}-phenoxy)-acetic acid ethyl ester;
(2-Chloro-3-hydroxy-4-{2-[5-(N-hydroxycarbamimidoyl)-1-oxo-1,3-dihydro-isoindol-2-yl]-acetyl}-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid ethyl ester;
(3-Hydroxy-4-{2-[5-(N-hydroxycarbamimidoyl)-1-oxo-1,3-dihydro-isoindol-2-yl]-acetyl}-2-methyl-phenoxy)-acetic acid benzyl ester;

(2-Ethyl-3-hydroxy-4-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid benzyl ester;

(4-{2-[5-Carbamimidoyl-1-oxo-1,3-dihydro-isoindol-2-yl]-acetyl}-3-hydroxy-2-propyl-phenoxy)-acetic acid;

(4-Hydroxy-3-{2-[5-(N-hydroxycarbamimidoyl)-1-oxo-1,3-dihydro-isoindol-2-yl]-acetyl}-phenoxy)-acetic acid ethyl ester;

(3-Hydroxy-4-{2-[5-(N-hydroxycarbamimidoyl)-1-oxo-1,3-dihydro-isoindol-2-yl]-acetyl}-5-methoxy-phenoxy)-acetic acid ethyl ester;

(3,5-Dihydroxy-4-{2-[5-(N-hydroxycarbamimidoyl)-1-oxo-1,3-dihydro-isoindol-2-yl]-acetyl}-phenoxy)-acetic acid ethyl ester;

(2-Ethoxycarbonylmethoxy-3-hydroxy-4-{2-[5-(N-hydroxycarbamimidoyl)-1-oxo-1,3-dihydro-isoindol-2-yl]-acetyl}-phenoxy)-acetic acid ethyl ester;

(2-Ethoxycarbonylmethoxy-5-hydroxy-4-{2-[5-(N-hydroxycarbamimidoyl)-1-oxo-1,3-dihydro-isoindol-2-yl]-acetyl}-phenoxy)-acetic acid ethyl ester;

(3-Ethoxy-4-{2-[5-(N-hydroxycarbamimidoyl)-1-oxo-1,3-dihydro-isoindol-yl]-acetyl}-phenoxy)-acetic acid ethyl ester;

(4-[2-(5-carbamimidoyl-1-oxo-1,3-dihydro-isoindol-2-yl)-acetyl]-3-ethoxy-phenoxy}-acetic acid ethyl ester;

(4-{2-[5-Carbamimidoyl-1-oxo-1,3-dihydro-isoindol-2-yl]-acetyl}-3-ethoxy-phenoxy)-acetic acid;

(3-Hydroxy-4-{2-[1-oxo-5-(5-oxo-2,5-dihydro-[1,2,4]oxadiazol-3-yl)-1,3-dihydro-isoindol-2-yl]-acetyl}-phenoxy)-acetic acid ethyl ester;

(4-{2-[5-(Acetylamino-imino-methyl)-1-oxo-1,3-dihydro-isoindol-2-yl]-acetyl}-3-hydroxy-phenoxy)-acetic acid ethyl ester;

(3-Acetoxy-4-{2-[5-(5-methyl-[1,2,4]oxadiazol-3-yl)-1-oxo-1,3-dihydro-isoindol-2-yl]-acetyl}-phenoxy)-acetic acid ethyl ester;

(4-{2-[5-Carbamimidoyl-1-oxo-1,3-dihydro-isoindol-2-yl]-acetyl}-3-hydroxy-2-propyl-phenoxy)-acetic acid ethyl ester;

(3-Hydroxy-4-{2-[5-(N-hydroxycarbamimidoyl)-1-oxo-1,3-dihydro-isoindol-2-yl]-acetyl}-2-propyl-phenoxy)-acetic acid; and (3-Allyloxy-4-{2-[5-(N-hydroxycarbamimidoyl)-1-oxo-1,3-dihydro-isoindol-2-yl]-acetyl}-phenoxy)-acetic acid ethyl ester.

22. The method according to claim 19, wherein the compounds of formula (I) are selected from the group consisting of:

(1-{2S-[5-(N-Hydroxycarbamimidoyl)-1-oxo-1,3-dihydro-isoindol-2-yl]-3-(4-hydroxy-phenyl)-propionyl}-piperidin-4-yloxy)-acetic acid ethyl ester;

(1-{2-[5-(N-Hydroxycarbamimidoyl)-1-oxo-1,3-dihydro-isoindol-2-yl]-acetyl}-piperidin-4-yloxy)-acetic acid ethyl ester;

(1-{3-[5-(N-Hydroxycarbamimidoyl)-1-oxo-1,3-dihydro-isoindol-2-yl]-propionyl}-piperidin-4-yloxy)-acetic acid ethyl ester;

(1-{2-[5-(5-Methyl-isoxazol-3-yl)-1-oxo-1,3-dihydro-isoindol-2-yl]-acetyl}-piperidin-4-yloxy)-acetic acid ethyl ester;

(1-{2-[5-Carbamimidoyl-1-oxo-1,3-dihydro-isoindol-2-yl]-acetyl}-piperidin-4-yloxy)-acetic acid ethyl ester;

(1-{2-[5-(tert-Butoxycarbonylamino-imino-methyl)-1-oxo-1,3-dihydro-isoindol-2-yl]-acetyl}-piperidin-4-yloxy)-acetic acid ethyl ester; and (1-{2-[5-Carbamimidoyl-1-oxo-1,3-dihydro-isoindol-2-yl]-acetyl}-piperidin-4-yloxy)-acetic acid.

23. The method according to claim 16, wherein the aggregation of blood platelet include: platelet thrombosis, thromboembolism and reocclusion during and after thrombolytic therapy and platelet thrombosis, thromboembolism and reocclusion after angioplasty or coronary artery bypass surgery, and blood clots after orthopedic surgery.

* * * * *